US010927362B2

(12) United States Patent
Salas et al.

(10) Patent No.: US 10,927,362 B2
(45) Date of Patent: Feb. 23, 2021

(54) PROCESSABLE SINGLE CHAIN MOLECULES AND POLYPEPTIDES MADE USING SAME

(71) Applicant: BIOVERATIV THERAPEUTICS INC., Waltham, MA (US)

(72) Inventors: Joe Salas, Wayland, MA (US); Robert T. Peters, Needham, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 390 days.

(21) Appl. No.: 15/820,172

(22) Filed: Nov. 21, 2017

(65) Prior Publication Data
US 2018/0320159 A1 Nov. 8, 2018

Related U.S. Application Data

(62) Division of application No. 13/809,287, filed as application No. PCT/US2011/043599 on Jul. 11, 2011, now Pat. No. 9,856,468.

(60) Provisional application No. 61/491,762, filed on May 31, 2011, provisional application No. 61/467,880, filed on Mar. 25, 2011, provisional application No. 61/442,150, filed on Feb. 11, 2011, provisional application No. 61/442,029, filed on Feb. 11, 2011, provisional application No. 61/442,055, filed on Feb. 11, 2011, provisional application No. 61/363,183, filed on Jul. 9, 2010, provisional application No. 61/363,186, filed on Jul. 9, 2010.

(51) Int. Cl.
*C12N 9/96* (2006.01)
*C12N 9/64* (2006.01)
*C07K 14/745* (2006.01)
*C07K 16/28* (2006.01)
*C07K 14/755* (2006.01)
*C07K 16/18* (2006.01)
*A61K 38/00* (2006.01)
*A61K 39/00* (2006.01)

(52) U.S. Cl.
CPC ............ *C12N 9/644* (2013.01); *C07K 14/745* (2013.01); *C07K 14/755* (2013.01); *C07K 16/18* (2013.01); *C07K 16/28* (2013.01); *C07K 16/2848* (2013.01); *C12N 9/647* (2013.01); *C12N 9/6432* (2013.01); *C12N 9/6437* (2013.01); *C12N 9/96* (2013.01); *C12Y 304/21021* (2013.01); *C12Y 304/21022* (2013.01); *A61K 38/00* (2013.01); *A61K 2039/505* (2013.01); *C07K 2317/622* (2013.01); *C07K 2319/00* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| 4,444,878 A | 4/1984 | Paulus |
| 4,683,195 A | 7/1987 | Mullis et al. |
| 4,683,202 A | 7/1987 | Mullis |
| 4,694,778 A | 9/1987 | Learn et al. |
| 4,704,362 A | 11/1987 | Itakura et al. |
| 4,745,055 A | 5/1988 | Schenk et al. |
| 4,800,159 A | 1/1989 | Mullis et al. |
| 4,845,075 A | 7/1989 | Murray et al. |
| 4,868,112 A | 9/1989 | Toole, Jr. |
| 4,889,919 A | 12/1989 | Murray et al. |
| 4,925,793 A | 5/1990 | Goeddel et al. |
| 4,929,554 A | 5/1990 | Goeddel et al. |
| 4,965,188 A | 10/1990 | Mullis et al. |
| 5,112,950 A | 5/1992 | Meulien et al. |
| 5,157,021 A | 10/1992 | Balschmidt et al. |
| 5,171,844 A | 12/1992 | Van Ooyen et al. |
| 5,194,596 A | 3/1993 | Tischer et al. |
| 5,227,158 A | 7/1993 | Jardieu |
| 5,304,489 A | 4/1994 | Rosen |
| 5,346,991 A | 9/1994 | Roy et al. |
| 5,349,991 A | 9/1994 | Okawa et al. |
| 5,395,760 A | 3/1995 | Smith et al. |
| 5,453,491 A | 9/1995 | Takatsu et al. |
| 5,460,950 A | 10/1995 | Barr et al. |
| 5,543,502 A | 8/1996 | Nordfang et al. |

(Continued)

FOREIGN PATENT DOCUMENTS

AU 609829 B2 5/1991
EP 0 068 763 A2 1/1983
(Continued)

OTHER PUBLICATIONS

Van Regenmortel, Structure of Antigens, volumen 3, 1995, Telford Press, pp. 49 and 50.*

(Continued)

*Primary Examiner* — Michael Szperka
(74) *Attorney, Agent, or Firm* — Lathrop GPM LLP; James H. Velema, Esq.

(57) ABSTRACT

The present invention features inter alia nucleic acid molecules which encode polypeptides comprising a single chain Fc region and the polypeptides they encode. The Fc moieties of these constructs are linked by a cleavable scFc linker which is adjacent to at least one enzymatic cleavage site, e.g., an intracellular processing site. The resulting processed molecules comprise two polypeptide chains and substantially lack the extraneous amino acid sequence found in single chain Fc linker molecule. Methods of making and using these dimeric molecules are also described.

14 Claims, 14 Drawing Sheets

Specification includes a Sequence Listing.

(56) References Cited

U.S. PATENT DOCUMENTS

| | | | |
|---|---|---|---|
| 5,589,369 A | 12/1996 | Seidman et al. |
| 5,591,669 A | 1/1997 | Krimpenfort et al. |
| 5,595,886 A | 1/1997 | Chapman et al. |
| 5,599,905 A | 2/1997 | Mosley et al. |
| 5,610,278 A | 3/1997 | Nordfang et al. |
| 5,639,605 A | 6/1997 | Kitamura et al. |
| 5,648,260 A | 7/1997 | Winter et al. |
| 5,648,273 A | 7/1997 | Bottaro et al. |
| 5,658,570 A | 8/1997 | Newman et al. |
| 5,686,292 A | 11/1997 | Schwall et al. |
| 5,726,147 A | 3/1998 | Ruf et al. |
| 5,736,137 A | 4/1998 | Anderson et al. |
| 5,739,277 A | 4/1998 | Presta et al. |
| 5,741,957 A | 4/1998 | Deboer et al. |
| 5,789,203 A | 8/1998 | Chapman et al. |
| 5,811,524 A | 9/1998 | Brams et al. |
| 5,834,250 A | 11/1998 | Wells et al. |
| 5,834,598 A | 11/1998 | Lowman et al. |
| 5,840,529 A | 11/1998 | Seidah et al. |
| 5,849,992 A | 12/1998 | Meade et al. |
| 5,869,046 A | 2/1999 | Presta et al. |
| 5,877,016 A | 3/1999 | Presta et al. |
| 5,892,019 A | 4/1999 | Schlom et al. |
| 5,910,574 A | 6/1999 | Presta et al. |
| 5,935,815 A | 8/1999 | Van De Ven et al. |
| 5,939,598 A | 8/1999 | Kucherlapati et al. |
| 5,969,108 A | 10/1999 | McCafferty et al. |
| 5,972,885 A | 10/1999 | Spira et al. |
| 6,005,079 A | 12/1999 | Casterman et al. |
| 6,015,881 A | 1/2000 | Kang et al. |
| 6,017,729 A | 1/2000 | Anderson |
| 6,030,613 A | 2/2000 | Blumberg et al. |
| 6,048,720 A | 4/2000 | Dalborg et al. |
| 6,060,447 A | 5/2000 | Chapman et al. |
| 6,075,181 A | 6/2000 | Kucherlapati et al. |
| 6,086,875 A | 7/2000 | Blumberg et al. |
| 6,096,871 A | 8/2000 | Presta et al. |
| 6,099,841 A | 8/2000 | Hillan et al. |
| 6,121,022 A | 9/2000 | Presta et al. |
| 6,159,462 A | 12/2000 | Matthews et al. |
| 6,159,730 A | 12/2000 | Reff |
| 6,193,980 B1 | 2/2001 | Efstathiou et al. |
| 6,194,551 B1 | 2/2001 | Idusogie et al. |
| 6,228,620 B1 | 5/2001 | Chapman et al. |
| 6,242,195 B1 | 6/2001 | Idusogie et al. |
| 6,271,349 B1 | 8/2001 | Dougall et al. |
| 6,277,375 B1 | 8/2001 | Ward |
| 6,281,331 B1 | 8/2001 | Kang et al. |
| 6,316,226 B1 | 11/2001 | Van Ooyen et al. |
| 6,346,513 B1 | 2/2002 | Van Ooyen et al. |
| 6,355,782 B1 | 3/2002 | Zonana et al. |
| 6,380,171 B1 | 4/2002 | Day et al. |
| 6,403,764 B1 | 6/2002 | Dubaquie et al. |
| 6,413,777 B1 | 7/2002 | Reff et al. |
| 6,458,563 B1 | 10/2002 | Lollar |
| 6,469,136 B1 | 10/2002 | Bray et al. |
| 6,479,635 B1 | 11/2002 | Anderson et al. |
| 6,485,726 B1 | 11/2002 | Blumberg et al. |
| 6,506,874 B1 | 1/2003 | Dubaquie et al. |
| 6,528,482 B1 | 3/2003 | Anderson et al. |
| 6,528,624 B1 | 3/2003 | Idusogie et al. |
| 6,537,763 B2 | 3/2003 | Dougall et al. |
| 6,538,124 B1 | 3/2003 | Idusogie et al. |
| 6,562,948 B2 | 5/2003 | Anderson |
| 6,576,608 B1 | 6/2003 | Lee et al. |
| 6,596,847 B2 | 7/2003 | Kelley et al. |
| 6,602,977 B1 | 8/2003 | Ljungqvist et al. |
| 6,673,901 B2 | 1/2004 | Koide |
| 6,686,179 B2 | 2/2004 | Fleer et al. |
| 6,703,199 B1 | 3/2004 | Koide |
| 6,737,056 B1 | 5/2004 | Presta |
| 6,740,734 B1 | 5/2004 | Nilsson et al. |
| 6,765,087 B1 | 7/2004 | Casterman et al. |
| 6,821,505 B2 | 11/2004 | Ward |
| 6,927,044 B2 | 8/2005 | Stahl et al. |
| 6,998,253 B1 | 2/2006 | Presta et al. |
| 7,041,635 B2 | 5/2006 | Kim et al. |
| 7,078,490 B2 | 7/2006 | Koide |
| 7,083,784 B2 | 8/2006 | Dall'Acqua et al. |
| 7,119,171 B2 | 10/2006 | Koide |
| 7,166,697 B1 | 1/2007 | Galanis et al. |
| 7,211,558 B2 * | 5/2007 | High .............. C07K 14/755 435/320.1 |
| 7,317,091 B2 | 1/2008 | Lazar et al. |
| 7,348,004 B2 * | 3/2008 | Peters ............. C07K 14/745 424/178.1 |
| 7,381,408 B2 | 6/2008 | Mezo et al. |
| 7,404,956 B2 | 7/2008 | Peters et al. |
| 7,417,130 B2 | 8/2008 | Stumpp et al. |
| 7,566,565 B2 | 7/2009 | Peters et al. |
| 7,566,595 B2 | 7/2009 | Steinhoff |
| 7,592,010 B2 | 9/2009 | Rosen et al. |
| 7,615,537 B2 | 11/2009 | Scaria et al. |
| 7,795,400 B2 | 9/2010 | Peters et al. |
| 7,812,136 B2 | 10/2010 | Buettner et al. |
| 7,862,820 B2 | 1/2011 | Peters et al. |
| 7,939,632 B2 | 5/2011 | Metzner et al. |
| 7,951,918 B2 | 5/2011 | Glaser et al. |
| 8,388,955 B2 | 3/2013 | Lazar et al. |
| 8,765,915 B2 | 7/2014 | Weimer et al. |
| 8,800,831 B2 | 8/2014 | Gray |
| 9,014,425 B2 | 4/2015 | Perron |
| 9,856,468 B2 | 1/2018 | Salas et al. |
| 2002/0102208 A1 | 8/2002 | Chinn et al. |
| 2003/0235536 A1 | 12/2003 | Blumberg et al. |
| 2004/0033225 A1 | 2/2004 | Browning et al. |
| 2004/0102388 A1 | 5/2004 | High et al. |
| 2004/0102440 A1 | 5/2004 | Wong |
| 2004/0132028 A1 | 7/2004 | Stumpp et al. |
| 2005/0147618 A1 * | 7/2005 | Rivera .............. A61K 47/6815 424/178.1 |
| 2005/0202527 A1 | 9/2005 | Le Bonniec et al. |
| 2006/0234299 A1 | 10/2006 | Stemmer et al. |
| 2007/0087411 A1 * | 4/2007 | Sharma .............. C07K 14/7155 435/69.1 |
| 2007/0218067 A1 | 9/2007 | Buttner et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0057056 A1 | 3/2008 | Lazar et al. |
| 2008/0193441 A1 * | 8/2008 | Trown .............. A61P 9/00 424/133.1 |
| 2008/0260738 A1 | 10/2008 | Moore et al. |
| 2009/0175828 A1 | 7/2009 | Schulte et al. |
| 2009/0291890 A1 | 11/2009 | Madison et al. |
| 2010/0330059 A1 | 12/2010 | Stafford et al. |
| 2012/0093840 A1 | 4/2012 | Ostergaard et al. |
| 2012/0178908 A1 | 7/2012 | Hilden et al. |
| 2013/0202596 A1 | 8/2013 | Salas et al. |
| 2013/0216513 A1 | 8/2013 | Salas et al. |

FOREIGN PATENT DOCUMENTS

| | | |
|---|---|---|
| EP | 0 120 694 A2 | 10/1984 |
| EP | 0 125 023 A1 | 11/1984 |
| EP | 0 240 975 A2 | 10/1987 |
| EP | 0 255 694 A1 | 2/1988 |
| EP | 0 256 654 A2 | 2/1988 |
| EP | 0 266 663 A1 | 5/1988 |
| EP | 0 295 597 A2 | 12/1988 |
| EP | 0 368 684 A1 | 5/1990 |
| EP | 0 417 014 A2 | 3/1991 |
| EP | 0 417 563 A2 | 3/1991 |
| EP | 0 455 460 A2 | 11/1991 |
| EP | 0 522 530 A2 | 1/1993 |
| EP | 0 589 877 B2 | 10/2005 |
| EP | 2 591 006 A1 | 5/2013 |
| EP | 3 560 962 A1 | 10/2019 |
| JP | H10505327 A | 5/1998 |

(56) References Cited

FOREIGN PATENT DOCUMENTS

| | | |
|---|---|---|
| WO | WO 1987/004187 A1 | 7/1987 |
| WO | WO 1988/000831 A1 | 2/1988 |
| WO | WO 1988/003559 A1 | 5/1988 |
| WO | WO 1988/003565 A1 | 5/1988 |
| WO | WO 1988/007089 A1 | 9/1988 |
| WO | WO 1990/014359 A1 | 11/1990 |
| WO | WO 1990/014425 A1 | 11/1990 |
| WO | WO 1991/009122 A1 | 6/1991 |
| WO | WO 1996/001653 A1 | 1/1996 |
| WO | WO 1996/014339 A1 | 5/1996 |
| WO | WO 1998/005787 A1 | 2/1998 |
| WO | WO 1998/023289 A1 | 6/1998 |
| WO | WO 1999/016873 A1 | 4/1999 |
| WO | WO 1999/037772 A1 | 7/1999 |
| WO | WO 1999/051642 A1 | 10/1999 |
| WO | WO 1999/058572 A1 | 11/1999 |
| WO | WO 2000/009560 A2 | 2/2000 |
| WO | WO 2000/032767 A1 | 6/2000 |
| WO | WO 2000/042072 A2 | 7/2000 |
| WO | WO 2000/063243 A1 | 10/2000 |
| WO | WO 2001/002439 A1 | 1/2001 |
| WO | WO 2001/002440 A1 | 1/2001 |
| WO | WO 2001/064942 A1 | 9/2001 |
| WO | WO 2001/070763 A1 | 9/2001 |
| WO | WO 2002/002781 A1 | 1/2002 |
| WO | WO 2002/020565 A2 | 3/2002 |
| WO | WO 2002/044215 A2 | 6/2002 |
| WO | WO 2002/060919 A2 | 8/2002 |
| WO | WO 2002/060955 A2 | 8/2002 |
| WO | WO 2002/088171 A2 | 11/2002 |
| WO | WO 2002/096948 A2 | 12/2002 |
| WO | WO 2003/074569 A2 | 9/2003 |
| WO | WO 2003/077834 A2 | 9/2003 |
| WO | WO 2004/016750 A2 | 2/2004 |
| WO | WO 2004/029207 A2 | 4/2004 |
| WO | WO 2004/035752 A2 | 4/2004 |
| WO | WO 2004/044011 A2 | 5/2004 |
| WO | WO 2004/044859 A1 | 5/2004 |
| WO | WO 2004/063351 A2 | 7/2004 |
| WO | WO 2004/074455 A2 | 9/2004 |
| WO | WO 2004/099249 A2 | 11/2004 |
| WO | WO 2004/101740 A2 | 11/2004 |
| WO | WO 2004/110472 A2 | 12/2004 |
| WO | WO 2005/001025 A2 | 1/2005 |
| WO | WO 2005/019254 A1 | 3/2005 |
| WO | WO 2005/040217 A2 | 5/2005 |
| WO | WO 2005/044859 A2 | 5/2005 |
| WO | WO 2005/047327 A2 | 5/2005 |
| WO | WO 2005/070963 A1 | 8/2005 |
| WO | WO 2005/077981 A2 | 8/2005 |
| WO | WO 2005/092925 A2 | 10/2005 |
| WO | WO 2005/123780 A2 | 12/2005 |
| WO | WO 2006/019447 A1 | 2/2006 |
| WO | WO 2006/047350 A2 | 5/2006 |
| WO | WO 2006/055689 A2 | 5/2006 |
| WO | WO 2006/083275 A2 | 8/2006 |
| WO | WO 2006/085967 A2 | 8/2006 |
| WO | WO 2006/113665 A2 | 10/2006 |
| WO | WO 2007/144173 A1 | 12/2007 |
| WO | WO-2007144173 A1 * | 12/2007 .......... C07K 14/745 |
| WO | WO 2008/012543 A1 | 1/2008 |
| WO | WO 2008/090215 A1 | 7/2008 |
| WO | WO 2008/143954 A2 | 11/2008 |
| WO | WO 2009/053368 A1 | 4/2009 |
| WO | WO 2009/140598 A1 | 11/2009 |
| WO | WO 2010/115866 A1 | 10/2010 |
| WO | WO 2010/151736 A1 | 12/2010 |
| WO | WO 2011/069164 A2 | 6/2011 |
| WO | WO 2012/006624 A2 | 1/2012 |
| WO | WO 2012/006633 A1 | 1/2012 |
| WO | WO 2012/117091 A1 | 9/2012 |

OTHER PUBLICATIONS

Culouscou et al., J Biol Chem. May 26, 1995;270(21):12857-63.*
Mohammed et al., Thromb Res. Jan. 2018; 161: 94-105. Published online Oct. 10, 2017. doi: 10.1016/j.thromres.2017.10.008.*
Adams, et al. (Mar. 2016) "Structural Transitions During Prothrombin Activation: On the Importance of Fragment 2", Biochimie, vol. 122, pp. 235-242.
Ager, et al. (1996) "Retroviral Display of Antibody Fragments; Interdomain Spacing Strongly Influences Vector Infectivity", Human Gene Therapy, vol. 7, pp. 2157-2164.
Anderson, C L., et al. (Jul. 2006) "Perspective—FcRn Transports Albumin: Relevance to Immunology and Medicine", Trends in Immunology, vol. 27, No. 7, pp. 343-348.
Armour, et al. (Aug. 1999) "Recombinant Human IgG Molecules Lacking Fc gamma Receptor I Binding and Monocyte Triggering Activities", European Journal of Immunology, vol. 29, No. 8, pp. 2613-2624.
Bajaj, et al. (Aug. 1, 1983) "Redetermination of the Rate-Limiting Step in the Activation of Factor IX by Factor XIa and by Factor VIIa/tissue Factor. Explanation for Different Electrophoretic Radioactivity Profiles Obtained on Activation of 3H- and 125I-Labeled Factor IX", Biochemistry, vol. 22, No. 17, pp. 4047-4053.
Baldassarre, et al. (Feb. 2003) "Production of Transgenic Goats by Pronuclear Microinjection of In Vitro Produced Zygotes Derived from Oocytes Recovered by Laparoscopy", Theriogenology, vol. 59, Issues 3-4, pp. 831-839.
Benard, et al. (2008) "Identification of Peptide Antagonists to Glycoprotein Ibα That Selectively Inhibit von Willebrand Factor Dependent Platelet Aggregation", Biochemistry, vol. 47, No. 16, pp. 4674-4682.
Beste, et al. (1999) "Small Antibody-like Proteins with Prescribed Ligand Specificities Derived from the Lipocalin Fold", Proceedings of the National Academy of Sciences, vol. 96, No. 5, pp. 1898-1903.
Better, et al. (May 20, 1988) "*Escherichia coli* Secretion of an Active Chimeric Antibody Fragment", Science, vol. 240 No. 4855, pp. 1041-1043.
Binz,et al. (May 2004) "High-affinity binders selected from designed ankyrin repeat protein libraries", Nature biotechnology, vol. 2, No. 5, pp. 575-582.
Bird, et al. (Oct. 21, 1988) "Single-Chain Antigen-Binding Proteins", Science, vol. 242, No. 4877, pp. 423-426.
Brandstetter, et al. (Oct. 10, 1995) "X-ray Structure of Clotting Factor IXa: Active Site and Module Structure Related to Xase Activity and Hemophilia B", Proceedings of the National Academy of Sciences of the United States of America, vol. 92, No. 21, pp. 9796-9800.
Brinster, et al. (1983) "Expression of a Microinjected Immunoglobulin Gene in the Spleen of Transgenic Mice", Nature, vol. 306, No. 5941, pp. 332-336.
Brinster, et al. (Jul. 1, 1985) "Factors Affecting the Efficiency of Introducing Foreign DNA Into Mice by Microinjecting Eggs", Proceedings of the National Academy of Sciences of the United States of America, vol. 82, No. 13, pp. 4438-4442.
Brunetti-Pierri, et al. (2009) "Bioengineered Factor IX Molecules with Increased Catalytic Activity Improve the Therapeutic Index of Gene Therapy Vectors for Hemophilia B", Human Gene Therapy, vol. 20, pp. 479-485.
Burmeister, et al. (Nov. 24, 1994) "Crystal Structure of the Complex of Rat Neonatal Fc Receptor with Fc", Nature, vol. 372, No. 6504, pp. 379-383.
Chang, et al. (May 15, 1998) "Changing Residue 338 in Human Factor IX from Arginine to Alanine Causes an Increase in Catalytic Activity", Journal of biological chemistry, vol. 273, pp. 12089-12094.
Co-pending U.S. Appl. No. 09/259,338, filed Mar. 1, 1999.
Cripe, et al. (1992) "Structure of the gene for human coagulation factor V", Biochemistry, vol. 31, No. 15, pp. 3777-3785.
Culouscou, et al. (1995) "HER4 Receptor Activation and Phosphorylation of Shc Proteins by Recombinant Heregulin-Fc Fusion Proteins", Journal of Biological Chemistry, vol. 270, No. 21, American Society for Biochemistry and Molecular Biology, United States, pp. 12857-12863.
Dall' Acqua, et al. (Nov. 1, 2002) "Increasing the Affinity of a Human IgG 1 for the Neonatal Fc Receptor: Biological Conse-

(56) References Cited

OTHER PUBLICATIONS quences", The Journal of Immunology, vol. 169, No. 9, pp. 5171-5180.
Dumoulin, et al. (Mar. 2002) "Single-Domain Antibody Fragments with High Conformational Stability", Protein Science, vol. 11, No. 3, pp. 500-515.
Eaton, et al. (Dec. 1986) "Construction and Characterization of an Active Factor VIII Variant Lacking the Central One-Third of the Molecule", Biochemistry, vol. 25, No. 26, pp. 8343-8347.
Eaton, et al. (1986.) "Proteolytic Processing of Human Factor VIII. Correlation of Specific Cleavages by Thrombin, Factor Xa, and Activated Protein C with Activation and Inactivation of Factor VIII Coagulant Activity", Biochemistry, vol. 25, No. 2, pp. 505-512.
Eigenbrot, et al. (Jul. 3, 2001) "The Factor VII Zymogen Structure Reveals Reregistration of β Strands during Activation", Structure, vol. 9, No. 7.
Ellman, et al. (1991) "Biosynthetic Method for Introducing Unnatural Amino Acids Site-Specifically into Proteins", Methods in Enzymology. vol. 202, Academic Press, 1991, pp. 301-336.
Falkner, et al. (1982) "Expression of Mouse Immunoglobulin Genes in Monkey Cells", Nature, vol. 298, No. 5871, pp. 286-288.
Fay, et al. (1991) "Human Factor VIIIa Subunit Structure. Reconstruction of Factor VIIIa from the Isolated A1/A3-C1-C2 Dimer and A2 Subunit", The Journal of Biological Chemistry, vol. 266, No. 14, pp. 8957-8962.
Friend, et al. (Dec. 15, 1999) "Phase I Study of an Engineered Aglycosylated Humanized Cd3 Antibody in Renal Transplant Rejection1", Transplantation, vol. 68, Issue 11, pp. 1632-1637.
Fuentes (Dec. 2010) "Platelet-Targeted Pro-Urokinase as a Novel Thromboprophylaxis Fibrinolytic Strategy", 52nd ASH® Annual Meeting and Exposition Poster Presentation: Poster Board III-118, American Society of Hematology, United States.
Ghetie, et al. (Jul. 1997) "Increasing the Serum Persistence of an Igg Fragment by Random Mutagenesis", Nature Biotechnology, vol. 15, No. 7, pp. 637-640.
Gitschier, et al. (Nov. 22-28, 1984) "Characterization of the Human Factor VIII Gene", Nature, vol. 312, No. 5992, pp. 326-330.
Goding (1986) "Production of Monoclonal Antibodies", Monoclonal Antibodies: Principles and Practice, Chapter 3, pp. 59-103.
Gupta, et al. (Jul. 25, 2016) "Revisiting the mechanism of coagulation factor XIII activation and regulation from a structure/functional perspective", Science Report, vol. 6, No. 30105, 16 pages.
Hamers-Casterman, et al. (Jun. 3, 1993) "Naturally Occurring Antibodies Devoid of Light Chains", Nature, vol. 363, No. 6428, pp. 446-448.
Handl, et al. (Dec. 2004) "Hitting Multiple Targets with Multimeric Ligands", Expert Opinion on Therapeutic Targets, vol. 8, No. 6, pp. 565-586.
Hanes, et al. (1999) "In Vitro Selection Methods for Screening of Peptide and Protein Libraries", Current Topics in Microbiology and Immunology, vol. 243, pp. 107-122.
Hanes, et al. (Dec. 2000) "Picomolar Affinity Antibodies from a Fully Synthetic Naïve Library Selected and Evolved by Ribosome Display", Nature biotechnology vol. 18, No. 12, pp. 1287-1292.
Hanes, et al. (Nov. 24, 1998) "Ribosome Display Efficiently Selects and Evolves High-Affinity Antibodies In Vitro From Immune Libraries", Proceedings of the National Academy of Sciences of the United States of America, vol. 95, No. 24, pp. 14130-14135.
Harrison, et al. (Apr. 1, 1998) "The Manufacturing Process for Recombinant Factor IX", Seminars in Hematology, vol. 35, Supplement 2, pp. 4-10.
He, et al. (1997) "Antibody-Ribosome-mRNA (Arm) Complexes as Efficient Selection Particles for In Vitro Display and Evolution of Antibody Combining Sites", Nucleic Acids Research, vol. 25, No. 24, pp. 5132-5134.
Hedner, U. (2000) "NovoSeven® as a Universal Haemostatic Agent", Blood Coagulation & Fibrinolysis II, Supplement 1, pp. S107-S111.

Ho, et al. (Apr. 15, 1989) "Site-Directed Mutagenesis by Overlap Extension Using the Polymerase Chain Reaction", Gene, vol. 77, No. 1, pp. 51-59.
Hoeben, et al. (1990) "Expression of Functional Factor VIII in Primary Human Skin Fibroblasts After Retrovirus-Mediated Gene Transfer", Journal of Biological Chemistry, vol. 265, No. 13, pp. 7318-7323.
Honda, et al. (Jun. 1995) "Topography of Ligand-induced Binding Sites, Including a Novel Cation-sensitive Epitope (AP5) at the Amino Terminus, of the Human Integrin Subunit", Journal of Biological Chemistry, vol. 270, No. 20, pp. 11947-11954.
Hoogenboom, et al. (Aug. 1, 2000) "Natural and Designer Binding Sites Made by Phage Display Technology", Immunology Today vol. 21, No. 8, pp. 371-378.
Horton, et al. (1993) "Gene Splicing by Overlap Extension", Methods in Enzymology, vol. 217, pp. 270-279.
Huie, et al. (Feb. 27, 2001) "Antibodies to human fetal erythroid cells from a nonimmune phage antibody library", Proceedings of the National Academy of Sciences of the United States of America, vol. 98, No. 5, pp. 2682-2687.
Huston, et al. (Aug. 1988) "Protein Engineering of Antibody Binding Sites: Recovery of Specific Activity in an Anti-Digoxin Single-Chain Fv Analogue Produced in *Escherichia coli*", Proceedings of the National Academy of Sciences of the United States of America, vol. 85, No. 16, pp. 5879-5883.
iGEM Team Freiburg (Oct. 26, 2008) "Part: BBa_K157018: Design", Registry of Standard Biological Parts, pp. 1-3.
International Search Report and Written Opinion received for PCT Patent Application No. PCT/US2011/043597, dated Nov. 11, 2011, 11 Pages.
International Search Report and Written Opinion received for PCT Patent Application No. PCT/US2011/43599, dated Dec. 1, 2011, 14 pages.
Irving, et al. (2001) "Ribosome Display and Affinity Maturation: From Antibodies to Single V Domains and Steps Towards Cancer Therapeutics", Journal of Immunological Methods, vol. 248, No. (1-2), pp. 31-45.
Israel, et al. (Sep. 1997) "Expression of the Neonatal Fc Receptor, FcRn, On Human Intestinal Epithelial Cells", Immunology, vol. 92, No. 1, pp. 69-74.
Jendreyko, et al. (Nov. 28, 2003) "Intradiabodies, Bispecific, Tetravalent Antibodies for the Simultaneous Functional Knockout of Two Cell Surface Receptors", The Journal of biological chemistry, vol. 278, No. 48, pp. 47812-47819.
Jenny, et al. (1987) "Complete eDNA and Derived Amino Acid Sequence of Human Factor V", Proceedings of the National Academy of Sciences USA, vol. 84, No. 14, pp. 4846-4850.
Jeong (2005) "Avimers Hold their Own", Nature Biotechnology, vol. 23, No. 12, pp. 1493-1494.
Jones, et al. (Jan. 1977) "Proteinase mutants of *Saccharomyces cerevisiae*", Genetics, vol. 85, No. 1, pp. 23-33.
Kane, et al. (1986) "Cloning of a cDNA Coding for Human Factor V, A Blood Coagulation Factor Homologous to Factor VIII and Ceruloplasmin", Proceedings of the National Academy of Sciences USA, vol. 83, No. 18, pp. 6800-6804.
Kang, et al. (May 15, 1991) "Linkage of Recognition and Replication Functions by Assembling Combinatorial Antibody Fab Libraries Along Phage Surfaces", Proceedings of the National Academy of Sciences of the United States of America, vol. 88, No. 10, pp. 4363-4366.
Kim, et al. (Mar. 1994) "Identifying Amino Acid Residues That Influence Plasma Clearance of Murine Igg1 Fragments by Site-Directed Mutagenesis", European Journal of Immunology, vol. 24, pp. 542-548.
Kingsman (1979) "Replication in Saccharomyces Cerevisiae of Plasmid pBR313 Carrying DNA From the Yeast trpl Region", Gene, vol. 7, No. 2, pp. 141-152.
Kobayashi, et al. (Feb. 2002) "FcRn-Mediated Transcytosis of Immunoglobulin G in Human Renal Proximal Tubular Epithelial Cells", American Journal of Physiology-Renal Physiology, vol. 282, No. 2, pp. F358-F365.

(56) References Cited

OTHER PUBLICATIONS

Kohler, et al. (Aug. 1975) "Continuous Cultures of Fused Cells Secreting Antibody of Predefined Specificity", Nature, vol. 256, No. 5517, pp. 495-497.
Kohler, Georges (Apr. 1, 1980) "Immunoglobulin Chain Loss in Hybridoma Lines", Proceedings of the National Academy of Sciences, vol. 77, No. 4, pp. 2197-2199.
Koide, et al. (1998) "The Fibronectin Type III Domain as a Scaffold for Novel Binding Proteins", Journal of Molecular Biology, vol. 284, No. 4, pp. 1141-1151.
Lai, et al. (Feb. 11, 1988) "Conserved Organization of the Human and Murine T-Cell Receptor Beta-Gene Families", Nature, vol. 331, No. 6156, pp. 543-546.
Langer, et al. (Apr. 1988) "Synthesis of biologically active deletion mutants of human factor VIII:C", Behring institute Mitteilungem, vol. 82, pp. 16-25.
Larrick, et al. (1989) "Rapid Cloning of Rearranged Immunoglobulin Genes from Human Hybridoma Cells using Mixed Primers and the Polymerase Chain Reaction", Biochemical and Biophysical Research Communications, vol. 160, No. 3, pp. 1250-1256.
Legendre, et al. (Jun. 2002) "TEM-1 β-lactamase as a scaffold for protein recognition and assay", Protein Science, vol. 11, No. 6, pp. 1506-1518.
Lin, et al. (Aug. 2010) "Generation of a Novel Factor IX with Augmented Clotting Activities in Vitro and in Vivo", Journal of Thrombosis and Haemostasis, vol. 8, No. 8, pp. 1773-1783.
Liu, et al. (Feb. 2002) "Towards Proteome-Wide Production of Monoclonal Antibody by Phage Display", Journal of Molecular Biology, vol. 315, No. 5, pp. 1063-1073.
Lollar, et al. (Jul. 5, 1991) "Structural Basis for the Deceased Procoagulant Activity of Human Factor VIII Compared to the Porcine Homolog", Journal of biological chemistry, vol. 266, Number, pp. 12481-12486.
Louvain-Quintard, et al. (2005) "Thrombin-activable factor X re-establishes an intrinsic amplification in tenase-deficient plasmas", The Journal of Biological Chemistry, vol. 280, No. 50, pp. 41352-41359.
Lusson, et al. (Jul. 15, 1993) "cDNA structure of the mouse and rat subtilisin/kexin-like PC5: a candidate proprotein convertase expressed in endocrine and nonendocrine cells", Proceedings of the National Academy of Sciences of the United States of America, vol. 90, No. 14, pp. 6991-6695.
Malassagne, et al. (Apr. 14, 2003) "Hypodermin A, a new inhibitor of human complement for the prevention of xenogeneic hyperacute rejection", Xenotransplantation, vol. 10, Issue 3, pp. 267-277.
Margaritis, et al. (Apr. 2004) "Novel Therapeutic Approach for Hemophilia Using Gene Delivery of an Engineered Secreted Activated Factor VII", Journal of Clinical Investigation, vol. 113, No. 7, pp. 1025-1031.
Marks, et al. (Jul. 1992) "By-Passing Immunization: Building High Affinity Human Antibodies by Chain Shuffling", Biotechnology, vol. 10, No. 7, pp. 779-793.
McCafferty, et al. (Dec. 6, 1990) "Phage Antibodies: Filamentous Phage Displaying Antibody Variable Domains", Nature, vol. 348, No. 6301, pp. 552-554.
McCue, et al. (Nov. 6, 2009) "Application of a Novel Affinity Adsorbent for the Capture and Purification of Recombinant Factor VIII Compounds", Journal of Chromatography A, vol. 1216, No. 45, pp. 7824-7830.
McKnight, et al. (Sep. 1983) "Expression of the Chicken Transferrin Gene in Transgenic Mice", Cell, vol. 34, Issue 2, pp. 335-341.
Meulien, et al. (1988) "A New Recombinant Procoagulant Protein Derived from the cDNA Encoding Human Factor VIII", Protein Engineering, Design and Selection, vol. 2, No. 4, pp. 301-306.
Milenic, et al. (Dec. 1991) "Construction, Binding Properties, Metabolism, and Tumor Targeting of a Single-Chain Fv Derived from the Pancarcinoma Monoclonal Antibody CC49", Cancer research, vol. 51, No. 23 part 1, pp. 6363-6371.

Morrison, et al. (1984) "Chimeric Human Antibody Molecules: Mouse Antigen-Binding Domains with Human Constant Region Domains", Proceedings of the National Academy of Sciences, vol. 81, No. 21, pp. 6851-6855.
Morrison, et al. (Aug. 1, 1979) "Sequentially Derived Mutants of the Constant Region of the Heavy Chain of Murine Immunoglobulins", The journal of immunology, vol. 123, No. 2, pp. 793-800.
Morrison, et al. (Sep. 20, 1985) "Transfectomas Provide Novel Chimeric Antibodies", Science, vol. 229, No. 4719, pp. 1202-1207.
Morrison, et al. (1984) "Transfer and Expression of Immunoglobulin Genes", Annual Review of immunology, vol. 2, pp. 239-256.
Mount, et al. (Apr. 15, 2002) "Sustained Phenotypic Correction of Hemophilia B Dogs with a Factor IX Null Mutation by Liver-Directed Gene Therapy", Blood, vol. 99, No. 8, pp. 2670-2676.
Mullinax, et al. (Oct. 1, 1990) "Identification of Human Antibody Fragment Clones Specific for Tetanus Toxoid in a Bacteriophage Lambda Immunoexpression Library", Proceedings of National Academy of Sciences of united states of America, vol. 87, No. 20, pp. 8095-8099.
Nagy, et al. (Aug. 2002) "Fully human, HLA-DR-specific monoclonal antibodies efficiently induce programmed death of malignant lymphoid cells", Nature Medicine, vol. 8, No. 8, pp. 801-807.
Nakagawa, et al. (Feb. 1993) "Identification and Functional Expression of a New Member of the Mammalian Kex2-Like Processing Endoprotease Family: Its Striking Structural Similarity to PACE4", The journal of biochemistry, vol. 113, No. 2, pp. 132-135.
Nakayama, Kazuhisa (1997) "Furin: A Mammalian Subtilisin/Kex2p-Like Endoprotease Involved in Processing of a Wide Variety of Precursor Proteins", Biochemical Journal, vol. 327, pp. 625-635.
Neumann, et al. (1982) "Gene Transfer into Mouse Lyoma Cells by Electroporation in High Electric Fields", The EMBO Journal, vol. 1, No. 7, pp. 841-845.
Noel, et al. (Mar. 11, 1990) "Nucleotide sequence of the coat protein gene and flanking regions of cucumber virus (CMV) strain 117F", Nucleic Acids Research, vol. 18, No. 5, pp. 1332.
Nord, et al. (Aug. 1997) "Binding Proteins Selected from Combinatorial Libraries of an α-Helical Bacterial Receptor Domain", Nature Biotechnology, vol. 15, Issue 8, pp. 772-777.
Noren, et al. (1989) "A General Method for Site-Specific Incorporation of Unnatural Amino Acids into Proteins", Science, vol. 244, No. 4901, pp. 182-188.
Osterlund, et al. (Dec. 2,) "Sequential coagulation factor VIIa domain binding to tissue factor", Biochemical and biophysical research communication, vol. 337, No. 4, pp. 1276-1282.
Pancer, et al. (2004) "Somatic diversification of variable lymphocyte receptors in the agnathan sea lamprey", Nature, vol. 430, No. 6996, pp. 174-180.
Panni, et al. (2002) "In Vitro Evolution of Recognition Specificity Mediated by SH3 Domains Reveals Target Recognition Rules*", Journal of biological chemistry, vol. 277, pp. 21666-21674.
Pantoliano, et al. (Oct. 22, 1991) "Conformational Stability, Folding, and Ligand-Binding Affinity of Single-Chain Fv Immunoglobulin Fragments Expressed in *Escherichia coli*", Biochemistry, vol. 30, No. 42, pp. 10117-10125.
Park, et al. (2010) "A Diagnostic Challenge: Mild Hemophilia B with Normal Activated Partial Thromboplastin Time", Blood Coagulation & Fibrinolysis, vol. 21, No. 4, pp. 368-371.
Pastan, et al. (Dec. 1994) "Cloning, Expression and Characterization of the Fv Fragments of the Anti-Carbohydrate Mabs B1 and B5 As Single-Chain Immunotoxins", Protein Engineering, vol. 7, No. 12, pp. 1509-1515.
Patra, et al. (Mar. 2000) "Optimization of Inclusion Body Solubilization and Renaturation of Recombinant Human Growth Hormone from *Escherichia coli*", Protein Expression and Purification, vol. 18, Issue 2, pp. 182-192.
Pelegrini (Nov. 2005) "Plant Gamma-Thionins: Novel Insights on the Mechanism of Action of a Multi-Functional Class of Defense Proteins", The International Journal of Biochemistry & Cell Biology, vol. 37, No. 11, pp. 2239-2253.
Pepinsky, et al. (Jun. 2001) "Improved Pharmacokinetic Properties of a Polyethylene Glycol-Modified Form of Interferon-β-1a with Preserved In Vitro Bioactivity", Journal of Pharmacology and Experimental Therapeutics, vol. 297, vol. 3, pp. 1059-1066.

(56) References Cited

OTHER PUBLICATIONS

Persson, et al. (Nov. 2001) "Rational Design of Coagulation Factor VIIa Variants with Substantially Increased Intrinsic Activity", Proceedings of the National Academy of Sciences USA, vol. 98, No. 2, pp. 13583-13588.
Persson, et al. (Jun. 1, 2001) "Substitution of Valine for Leucine 305 in Factor VIIa Increases the Intrinsic Enzymatic Activity", Journal of Biological Chemistry, vol. 276, No. 31, pp. 29195-29199.
Peterson (2003) "A Site Involving the "Hybrid" and PSI Homology Do (Beta 3-Integrin Subunit) Is a Common Target for Antibodies Associated with Mains of GpIIIa Quinine-Induced Immune Thrombocytopenia", Blood, vol. 101, No. 3, pp. 937-942.
Petrovan, et al. (Nov. 14, 2000) "Residue Met156 Contributes to the Labile Enzyme Conformation of Coagulation Factor VIIa", The Journal of Biological Chemistry, vol. 276, No. 9, pp. 6616-6620.
Raso, et al. (Jun. 1981) "Hybrid Antibodies with Dual Specificity for the Delivery of Ricin to Immunoglobulin-bearing Target Cells", Cancer research, vol. 41, pp. 2073-2078.
Rehemtulla, et al. (1993) "PACE4 Is a Member of the Mammalian Propeptidase Family That Has Overlapping but Not Identical Substrate Specificity to PACE", Biochemistry, vol. 32, No. 43, pp. 11586-11590.
Ridgway, et al. (1988) "Introduction of Vector into Host Cells", Mammalian Expression Vectors, Chapter 24.2, pp. 470-472.
Ritchie, et al. (Dec. 6, 1984) "Allelic Exclusion and Control of Endogenous Immunoglobulin Gene Rearrangement in κ Transgenic Mice", Nature, vol. 312, No. 5994, pp. 517-520.
Robl, et al. (Jan. 1, 2003) "Artificial Chromosome Vectors and Expression of Complex Proteins in Transgenic Animals", Theriogenology, vol. 59, Issue 1, pp. 107-113.
Routledge, et al. (Oct. 1, 1995) "The Effect of Aglycosylation on the Immunogenicity of a Humanized Therapeutic CD3 Monoclonal Antibody", Transplantation, vol. 60, No. 8, pp. 847-853.
Roux, et al. (1998) "Comparisons of the Ability of Human IgG3 Hinge Mutants, IgM, IgE, and IgA2, to Form Small Immune Complexes: A Role for Flexibility and Geometry", Journal of Immunology, vol. 161, 4083 Pages.
Ruberti, et al. (Jul. 12, 1994) "The Use of the RACE Method to Clone Hybridoma cDNA When V Region Primers Fail", Journal of Immunological Methods, vol. 173, No. 1, pp. 33-39.
Ruther, et al. (Oct. 1983) "Easy Identification of cDNA Clones", The EMBO Journal, vol. 2, No. 10, pp. 1791-1794.
Sarin, et al. (Oct. 1, 1988) "Inhibition of Acquired Immunodeficiency Syndrome Virus by Oligodeoxynucleoside Methylphosphonates", Proceedings of the National Academy of Sciences of the United States of America, vol. 85, No. 20, pp. 7448-7451.
Sarver, et al. (Dec. 1987) "Stable Expression of Recombinant Factor VIII Molecules Using a Bovine Papillomavirus Vector", DNA, vol. 6, No. 6, pp. 553-564.
Schellenberger, et al. (Dec. 2009) "A Recombinant Polypeptide Extends the In Vivo Half-Life of Peptides and Proteins in a Tunable Manner", Nature Biotechnology, vol. 27, No. 12, pp. 1186-1192.
Schlehuber, et al. (Jan. 1, 2005) "Lipocalins in Drug Discovery: From Natural Ligand-Binding Proteins to "Anticalins"", Drug Discovery today, vol. 10, No. 1, pp. 23-33.
Schneider, et al. (1999) "Mutagenesis and Selection of PDZ Domains That Bind New Protein Targets", Nature biotechnology, vol. 17, pp. 170-175.
Schulte, S (Mar. 2013) "Innovative Coagulation Factors: Albumin Fusion Technology and Recombinant Single-Chain Factor VIII", Thrombosis Research, vol. 131, Supplement 2, pp. S2-S6.
Schulte, Stefan (Dec. 2009) "Half-Life Extension Through Albumin Fusion Technologies", Thrombosis Research, vol. 124, Supplement 2, pp. S6-S8.
Schulte, Stefan (Dec. 2008) "Use of Albumin Fusion Technology to Prolong the Half-Life of Recombinant Factor", Thrombosis Research, vol. 122, Supplement 4, pp. S14-S19.

Schwarz, et al. (2006) "Conformation-Specific Blockade of the Integrin GPIIb/IIIa: A Novel Antiplatelet Strategy that Selectively Targets Activated Platelets", Circulation Research, vol. 99, No. 1, pp. 25-33.
Schwarz, et al. (Nov. 2004) "Single-Chain Antibodies for the Conformation-Specific Blockade of Activated Platelet Integrin αIIbβ3 Designed by Subtractive Selection from Naive Human Phage Libraries", FASEB Journal, vol. 18, No. 14, pp. 1704-1706.
Shields, et al. (Mar. 2, 2001) "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R", Journal of Biological Chemistry, vol. 276, No. 9, pp. 6591-6604.
Sichler, et al. (Feb. 7, 2003) "Physiological FIXA Activation Involves a Cooperative Conformational Rearrangement of the 99-Loop", The journal of biological chemistry, vol. 278, No. 6, pp. 4121-4126.
Silverman, et al. (2005) "Multivalent Avimer Proteins Evolved by Exon Shuffling of a Family of Human Receptor Domains", Nature Biotechnology, vol. 23, No. 12, pp. 1556-1561.
Simioni, et al. (Oct. 22, 2009) "X-Linked Thrombophilia with a Mutant Factor Ix (Factor Ix Padua)", The New England Journal of Medicine, vol. 361, No. 17, pp. 1671-1675.
Skerra, et al. (May 20, 1988) "Assembly of a Functional Immunoglobulin Fv Fragment in *Escherichia coli*", Science, vol. 240, No. 4855, pp. 1038-1041.
Soejima, et al. (Feb. 2, 2001) "Factor VIIa Modified in the 170 Loop Shows Enhanced Catalytic Activity but does not Change the Zymogen-like Property", The Journal of Biological Chemistry, vol. 276, No. 20, pp. 17229-17235.
Soejima, et al. (Oct. 2, 2002) "The 99 and 170 Loop-Modified Factor VIIa Mutants Show Enhanced Catalytic Activity Without Tissue Factor", The Journal of Biological Chemistry, vol. 277, No. 50, pp. 49027-49035.
Spitzer, et al. (Jan. 1, 1990) "Replacement of Isoleucine-397 by Threonine in the Clotting Proteinase Factor IXa (Los Angeles and Long Beach Variants) Affects Macromolecular Catalysis but not L-tosylarginine Methyl Ester Hydrolysis", Biochemical Journal, vol. 265, No. 1, pp. 219-225.
Stein, et al. (Apr. 25, 1988) "Physicochemical Properties of Phosphorothioate Oligodeoxynucleotides", Nucleic Acids Research, vol. 16, No. 8, pp. 3209-3221.
Stinchcomb, et al. (Nov. 1, 1979) "Isolation and Characterisation of a Yeast Chromosomal Replicator", Nature, vol. 282, No. 5734, pp. 39-43.
Stoop, et al. (Sep. 2003) "Engineering of a Macromolecular Scaffold to Develop Specific Protease Inhibitors", Nature Biotechnology, vol. 21, No. 9, pp. 1063-1068.
Story, et al. (Dec. 1, 1994) "A Major Histocompatibility Complex Class I-like Fc Receptor Cloned from Human Placenta: Possible Role in Transfer of Immunoglobulin G from Mother to Fetus", Journal of Experimental Medicine, vol. 180, No. 6, pp. 2377-2381.
Stubbs, et al. (1990) "CDNA Cloning of a Mouse Mammary Epithelial Cell Surface Protein Reveals the Existence of Epidermal Growth Factor-Like Domains Linked to Factor VIII-Like Sequences", Proceedings of the National Academy of Sciences, vol. 87, No. 21, pp. 8417-8421.
Sturzebecher, et al. (Jul. 28, 1997) "Dramatic enhancement of the catalytic activity of coagulation factor IXa by alcohols", The Federation of the European Biochemical Societies Letters, vol. 412, No. 2, pp. 295-300.
Takahashi, et al. (1984) "Single-Chain Structure of Human Ceruloplasmin: The Complete Amino Acid Sequence of the Whole Molecule", Proceedings of the National Academy of Sciences, vol. 81, No. 2, pp. 390-394.
Takkinen, et al. (Oct. 1, 1991) "An Active Single-Chain Antibody Containing a Cellulase Linker Domain Is Secreted by *Escherichia coli*", Protein Engineering design and selection, vol. 4, Issue 7, pp. 837-841.
Toole, et al. (Aug. 1986) "A Large Region (Approximately Equal to 95 kDa) of Human Factor VIII Is Dispensable for In Vitro Procoagulant Activity", Proceedings of the National Academy of Sciences, vol. 83, No. 16, pp. 5939-5942.

(56) References Cited

OTHER PUBLICATIONS

Toole, et al. (Nov. 22-28, 1984) "Molecular Cloning of a cDNA Encoding Human Antihaemophilic Factor", Nature, vol. 312, No. 5992, pp. 342-347.

Tschumper, et al. (Jul. 1980) "Sequence of a Yeast DNA Fragment Containing a Chromosomal Replicator and the Trp1 Gene", Gene, vol. 10, No. 2, pp. 157-166.

Tutt, et al. (Jul. 1, 1991) "Trispecific F (ab') 3 Derivatives That Use Cooperative Signaling Via the TCR/CD3 Complex and CD2 to Activate and Redirect Resting Cytotoxic T Cells", The Journal of Immunology, vol. 147, No. 1, pp. 60-69.

van den Ouweland, et al. (Jan. 1990) "Structural Homology Between the Human Fur Gene Product and the Subtilisin-Like Protease Encoded by Yeast KEX2", Nucleic Acids Research, vol. 18, No. 3, pp. 664.

Van Regenmortel (1995) "Structure of Antigens", Telford Press, vol. 3, pp. 49-50.

Vehar, et al. (Nov. 1984) "Structure of Human Factor VIII", Nature, vol. 312, No. 5992, pp. 337-342.

Venkateswarlu, Divi (Feb. 25, 2010) "Structural Investigation of Zymogenic and Activated Forms of Human Blood Coagulation Factor VIII: A Computational Molecular Dynamics Study", BMC Structural Biology vol. 10, Article No. 7.

Vita, et al. (Jul. 3, 1995) "Scorpion toxins as natural scaffolds for protein engineering", Proceedings of the National Academy of Sciences of the United States of America, vol. 92, No. 14, pp. 6404-6404.

Vysotchin, et al. (Apr. 25, 1993) "Domain Structure and Domain-Domain Interactions in Human Coagulation Factor IX*", Journal of Biological Chemistry, vol. 268, No. 12, pp. 8436-8446.

Wagner, et al. (Oct. 1, 1981) "Microinjection of a Rabbit Beta-Globin Gene into Zygotes and Its Subsequent Expression in Adult Mice and Their Offspring", Proceedings of the National Academy of Sciences of the United States of America, vol. 78, No. 10, pp. 6376-6380.

Walsh, et al. (Jul. 2001) "Roles of Platelets and Factor XI in the Initiation of Blood Coagulation by Thrombin", Thrombosis and Haemostasis, vol. 86, No. 1, Abstract, pp. 75-82.

Ward, et al. (Oct. 12, 1989) "Binding Activities of a Repertoire of Single Immunoglobulin Variable Domains Secreted from *Escherichia coli*", Nature, vol. 341, No. 6242, pp. 544-546.

Ward, et al. (Apr. 1995) "The Effector Functions of Immunoglobulins: Implications for Therapy", Therapeutic immunology, vol. 2, No. 2, pp. 77-94.

Wasley, et al. (Apr. 25, 1993) "PACE/Furin can Process the Vitamin K-Dependent Pro-Factor IX Precursor within the Secretory Pathway", The Journal of Biological Chemistry, vol. 268, No. 12, pp. 8458-8465.

Weidler, et al. (May 1991) "Pharmacokinetic Parameters as Criteria for Clinical Use of Hydroxyethyl Starch Preparations", Arzneimittelforschung/Drug Research, vol. 41, No. 5, pp. 494-498.

Weimer, et al. (Apr. 2008) "Prolonged In-Vivo Half-Life of Factor VIIa by Fusion to Albumin", Thrombosis and Haemostasis, vol. 99, No. 04, pp. 659-667.

Weisser, et al. (2009) "Applications of Single-Chain Variable Fragment Antibodies in Therapeutics and Diagnostics", Biotechnology Advances, vol. 27, pp. 502-520.

Wigler, et al. (Jul. 1978) "Biochemical Transfer of Single-Copy Eucaryotic Genes Using Total Cellular DNA As Donor", Cell, vol. 14, No. 3, pp. 725-731.

Wilson, et al. (May 22, 2006) "Multiple Functions of Notch signaling in Self-Renewing Organs and Cancer", FEBS Letters, vol. 580, No. 12, pp. 2860-2868.

Wilson, et al. (Mar. 27, 2001) "The use of mRNA display to select high-affinity protein-binding peptide", Proceedings of the National Academy of Sciences of the United States of America, vol. 98, No. 7, pp. 3750-3755.

Yang, et al. (Aug. 15, 2005) "An Ordered Sequential Mechanism for Factor IX and Factor IXa Binding to Platelet Receptors in the Assembly of the Factor X-Activating Complex", Biochemical Journal, vol. 390, Pt 1, pp. 157-167.

Zogg, et al. (Dec. 9, 2009) "Structural Basis of the Cofactor-and Substrate-Assisted Activation of Human Coagulation Factor IXa", Structure, vol. 17, No. 12, pp. 1669-1678.

\* cited by examiner

PROCESSABLE SINGLE CHAIN MOLECULES AND POLYPEPTIDES MADE USING SAME

RELATED APPLICATIONS

This application is a divisional application of U.S. application Ser. No. 13/809,287, now U.S. Pat. No. 9,856,468, which is the national phase application of International Application No. PCT/US2011/043599, filed Jul. 11, 2011 and published as WO 2012/006635, which claims the benefit of U.S. Provisional Application No. 61/363,183, filed Jul. 9, 2010, U.S. Provisional Application No. 61/363,186, filed Jul. 9, 2010, U.S. Provisional 10 Application No. 61/442,055, filed Feb. 11, 2011, U.S. Provisional Application No. 61/442,150, filed Feb. 11, 2011, U.S. Provisional Application No. 61/442,029, filed Feb. 11, 2011, U.S. Provisional Application No. 61/467,880, filed Mar. 25, 2011, and U.S. Provisional Application No. 61/491,762, filed May 31, 2011, all of which are incorporated herein by reference in their entireties.

REFERENCE TO SEQUENCE LISTING SUBMITTED ELECTRONICALLY VIA EFS-WEB

The instant application contains a Sequence Listing which has been submitted in ASCII format via EFS-Web, and is hereby incorporated by reference in its entirety. Said ASCII copy, created on Sep. 16, 2020, is named 608486_SA9-412USCON_ST25.txt and is 172,983 bytes in size. The content of the sequence listing that was originally submitted in the International Application No. PCT/US2011/043599 is incorporated herein by reference in its entirety.

BACKGROUND OF THE INVENTION

The Fc region of an immunoglobulin mediates effector functions that have been divided into two categories. In the first are functions that occur independently of antigen binding; these functions confer persistence in circulation and the ability to be transferred across cellular barriers by transcytosis (see Ward and Ghetie, *Therapeutic Immunology* 2:77-94, 1995, Capon et al. *Nature* 1989). The circulatory half-life of the IgG subclass of immunoglobulins is regulated by the affinity of the Fc region for the neonatal Fc receptor for FcRn (Ghetie et al. *Nature Biotechnol.* 15:637-640, 1997; Kim et. al., *Eur. J. Immunol.* 24:542-548, 1994; Dall'Acqua et al. (*J. Immunol.* 169:5171-5180, 2002). The second general category of effector functions include those that operate after an immunoglobulin binds an antigen. In the case of IgG, these functions involve the participation of the complement cascade or Fc gamma receptor (FcγR)-bearing cells. Binding of the Fc region to an FcγR causes certain immune effects, for example, endocytosis of immune complexes, engulfment and destruction of immunoglobulin-coated particles or microorganisms (also called antibody-dependent phagocytosis, or ADCP), clearance of immune complexes, lysis of immunoglobulin-coated target cells by killer cells (called antibody-dependent cell-mediated cytotoxicity, or ADCC), release of inflammatory mediators, regulation of immune system cell activation, and regulation of immunoglobulin production.

While it is possible to generate Fc-containing, heterodimeric polypeptides, current methods require either coexpression of the two heavy chain portions of a heterodimeric Fc region or chemical conjugation of the dimeric Fc region to one or more binding sites (e.g., a Fab domain). Coexpression of these constructs leads to production of complex mixtures representing all possible pairings of starting material in addition to aggregates and inactive protein. Consequently, yields of the desired functional polypeptide are relatively low. Recently, single chain Fc molecules have been developed which overcome many of these problems. These molecules comprise a single chain Fc region in which the component Fc moieties are genetically-fused in a single polypeptide chain such that they form a functional, dimeric Fc region. These single chain polypeptides comprise a linker which is not present in naturally occurring Fc constructs and, therefore, may create unwanted immune responses or may prevent other protein:protein interactions. These single chain Fc constructs may also have lower stability potentially due to constraints imposed by the covalent linker.

Accordingly, there is a need for Fc-containing heterodimeric polypeptides which can be produced efficiently and robustly and which minimize and preferably do not comprise extraneous amino acid sequences.

SUMMARY OF THE INVENTION

The present invention features inter alia heterodimeric polypeptides which, in unprocessed form comprise on or more genetically-fused Fc regions. In particular, unprocessed molecules of the invention comprise a single chain Fc region ("scFc") in which the component Fc moieties are genetically-fused in a single polypeptide chain such that they form a functional, single chain, dimeric Fc region. The single chain Fc molecules of the invention comprise at least two Fc moieties, F1 and F2 as numbered from the amino to the carboxy terminus in the single polypeptide chain. The component Fc moieties of an scFc are genetically fused via a polypeptide linker, a cleavable scFc (cscFc) linker. The cscFc linker is interposed between the Fc moieties that comprise the Fc region. At one terminus, the cscFc linker which forms the single chain Fc region is directly linked via a peptide bond to an enzymatic cleavage site (P1) which is linked to (e.g., adjacent to or directly linked to) an Fc moiety of the polypeptide. In one embodiment, the cleavage site is cleaved by an intracellular processing enzyme. In one embodiment, the other terminus of the cscFc linker is directly linked to a second enzymatic cleavage site (P2). In another embodiment, the other terminus of the cscFc linker is linked to a biologically active moiety or a targeting moiety.

In one embodiment, cleavage during processing of the scFc containing polypeptide by a cell allows for cleavage and/or substantial excision of the linker. Alternatively, the polypeptide comprises a cleavable scFc (cscFc) linker which can be cleaved after the polypeptide has been secreted by a cell or after it has been administered to a subject. Thus, although the polypeptides of the invention comprise a scFc region(s) in one contiguous polypeptide sequence in their unprocessed form, the cscFc linker is enzymatically cleaved (e.g., during processing in a cell, in vitro prior to administration or in vivo after administration), resulting in a processed polypeptide which comprises at least two polypeptide chains and comprises an Fc region which is not fused in a single amino acid chain.

The heterodimeric polypeptides of the invention have improved manufacturability as compared to conventional heteromeric Fc containing polypeptides because the complex mixture of molecules that result from coexpression of two or more chains is avoided. In addition, the substantial removal of the extraneous linker sequence reduces the risk of immunogenicity. This is of particular importance in the case of polypeptides which are administered repeatedly to a subject, e.g., as in the case of components of the clotting cascade. Substantial removal of the extraneous linker sequence may also relieve any steric stress or hindrance that was present in the covalently linked form. In addition, cleavage of the cscFc linker allows for biologically active moieties fused to the amino terminus of each Fc moiety to have a free N-terminus. This is particularly valuable in the case of biologically active moieties attached to the second Fc moiety such as serine protease domains which require a free N-terminus to be catalytically active or moieties which might be sterically hindered by the presence of an uncleaved polypeptide linker.

In one aspect, the instant invention pertains to a polypeptide, comprising (i) at least one biologically active moiety, (ii) an Fc region comprising at least two Fc moieties and (iii) a cleavable scFc (cscFc) linker interposed between the two Fc moieties, wherein the cscFc linker is linked (e.g., is directly linked or is adjacent to) at least one enzymatic cleavage site which results in cleavage of the cscFc linker.

In one embodiment, at least one biologically active moiety comprises a clotting factor.

In one embodiment, the clotting factor is selected from the group consisting of FVII, FVIIa, FVIII, FIX, FIXa, FX, and FXa.

In one embodiment, the polypeptide comprises the moieties A-F1-P1-L-P2-B-F2 wherein A is a biologically active moiety, F1 is a first Fc moiety or domain, P1 is an enzymatic cleavage site, L is a cscFc linker, P2 is an enzymatic cleavage site B is a biologically active moiety, F2 is a second Fc moiety or domain and "—" represents a peptide bond. Formula (I) comprises at least an A or B and optionally both. A and B, if both present, can be the same or different. Formula (I) comprises at least a P1 or P2 and optionally both. P1 and P2, if both present, can be the same or different. Formula (I) comprises at least F1 or F2. F1 and F2 can be the same or different. In one embodiment, F1 and F2 each comprise a CH2 and a CH3 domain. In one embodiment A and/or B are directly linked to F1 or F2. In another embodiment, A and/or B is linked to F1 or F2 via a spacer moiety.

In one embodiment, A is present and is selected from the group consisting of: an antigen binding portion of an antibody; a non immunoglobulin binding molecule, a binding portion of a ligand, and a binding portion of a receptor, and a clotting factor.

In one embodiment, A comprises the light chain of a clotting factor and B comprises the heavy chain of a clotting factor which when associated form an active molecule.

In one embodiment, B is present and is selected from the group consisting of: an antigen binding portion of an antibody; a non immunoglobulin binding molecule, a binding portion of a ligand, a binding portion of a receptor, and a clotting factor.

In one embodiment, F1 and F2 each comprise a CH2 and a CH3 domain.

In one embodiment, the polypeptide comprises the moieties A-F1-B-P1-L-P2-F2 or A-F1-P1-L-P2 B-F2 in linear sequence from amino to carboxy terminus.

In one embodiment, the polypeptide comprises a structure represented by the formula selected from the group consisting of: A-F1-P1-L-P2-F2; F1-P1-L-P2-B-F2; A-F1-P1-L-F2; F1-P1-L-B-F2; A-F1-L-P2-F2; F1-L-P2-B-F2, and A-F1-P1-L-P2-B-F2 in linear sequence from amino to carboxy terminus.

In one embodiment, the polypeptide comprises one biologically active moiety. In one embodiment, two biologically active moieties, e,g, A and B of formula I, are both present and are different biologically active moieties.

In one embodiment, P1 and P2 are both present and are recognized by the same or by different enzymes. In one embodiment, at least one of P1 or P2 comprises the amino acid sequence Arg-Arg-Arg-Arg (SEQ ID NO: 40). In one embodiment, at least one of P1 or P2 comprises the amino acid sequence Arg-Lys-Arg-Arg-Lys-Arg (SEQ ID NO: 39). In one embodiment, at least one of P1 or P2 comprises the amino acid sequence Arg-Arg-Arg-Arg-Ser (SEQ ID NO: 38). In one embodiment, P1 and P2 are both present and P1 comprise the sequence Arg-Arg-Arg-Arg (SEQ ID NO: 40) and P2 comprises the sequence Arg-Lys-Arg-Arg-Lys-Arg (SEQ ID NO: 39). In one embodiment, at least one of P1 or P2 comprises an amino acid sequence selected from the group consisting of: TQSFNDFTR (SEQ ID NO: 7) and SVSQTSKLTR (SEQ ID NO: 8), DFLAEGGGVR (SEQ ID NO: 9), TTKIKPR (SEQ ID NO: 10), LVPRG (SEQ ID NO:35), and ALRPR (SEQ ID NO: 94).

In one embodiment, the cscFc linker has a length of about 1 to about 50 amino acids. In one embodiment, the cscFc linker has a length of about 20 to about 30 amino acids.

In one embodiment, the cscFc linker comprises a gly/ser peptide. In one embodiment, the gly/ser peptide is of the formula (Gly$_4$Ser)n (SEQ ID NO: 4) or S(Gly$_4$Ser)n (SEQ ID NO: 26), wherein n is a positive integer selected from the group consisting of 1, 2, 3, 4, 5, 6, 7, 8, 9 and 10.

In one embodiment, the S(Gly$_4$Ser)n (SEQ ID NO: 26) linker is S(Gly$_4$Ser)$_6$ (SEQ ID NO: 5) or S(Gly$_4$Ser)$_4$ (SEQ ID NO: 6).

In another aspect, the invention pertains to a polypeptide comprising two polypeptide chains, wherein the first polypeptide chain comprises a light chain of a clotting factor linked to a first Fc moiety and a second polypeptide chain comprises a heavy chain of a clotting factor linked to a second Fc moiety, wherein the wherein the light chain and the heavy chain associate to form an enzymatically active clotting factor In one embodiment, the light chain of the clotting factor is linked to the first Fc moiety and the heavy chain of the clotting factor is linked to the second Fc moiety and wherein the clotting factor is enzymatically active upon secretion by a cell.

In one embodiment, wherein the clotting factor is selected from the group consisting of FVII, FVIIa, FIX, FIXa, FX, and FXa. In another embodiment, at least one biologically active moiety is factor VII, factor VIIa or a portion thereof. In one embodiment, at least one biologically active moiety is factor IX, factor IXa or a portion thereof. In one embodiment, at least one biologically active moiety is factor VIII, factor VIIIa or a portion thereof. In one embodiment, at least one biologically active moiety is factor X, factor Xa, or a portion thereof.

In one embodiment, a polypeptide of the invention comprises a targeting moiety.

In one embodiment, the targeting moiety binds to resting platelets.

In one embodiment, the targeting moiety selectively binds to activated platelets.

In one embodiment, the targeting moiety selectively binds to a target selected from the group consisting of: GPIba, GPVI, and the nonactive form of GPIIb/IIIa.

In one embodiment, wherein the targeting moiety selectively binds to a target selected from the group consisting of: the active form of GPIIb/IIIa, P selectin, GMP-33, LAMP-1, LAMP-2, CD40L, and LOX-1.

In one embodiment, the targeting moiety binds to the GPIb complex

In one embodiment, comprises a targeting moiety, wherein the targeting moiety is a peptide selected from the group consisting of: PS4, OS1, and OS2.

In one embodiment, the targeting moiety comprises an antibody variable region from an antibody selected from the group consisting of: SCE5, MB9, and AP3.

In one embodiment, A is the light chain of FVII and B is the heavy chain of FVII.

In another aspect, the invention pertains to a composition comprising a polypeptide of the invention In one embodiment, a composition of the invention comprises a cell culture supernatant.

In another aspect, the invention pertains to a nucleic acid molecule encoding the polypeptide of the invention. Exemplary such nucleic acid molecules are described in the instant Examples and set forth in the sequence listing.

In another aspect, the invention pertains to a nucleic acid molecule encoding a polypeptide, and the polypeptide encoded thereby, wherein the polypeptide comprises (i) at least one biologically active moiety, (ii) an Fc region comprising at least two Fc moieties and (iii) a cleavable scFc linker interposed between the two Fc moieties, wherein the cleavable scFc linker is adjacent to at least one enzymatic cleavage site, e.g., an intracellular processing site which results in cleavage of the cscFc linker. In one embodiment, the cscFc linker is adjacent to two enzymatic cleavage sites, e.g., is flanked by an enzymatic cleavage site both upstream and downstream of the cscFc linker which links the Fc moieties of the Fc region and cleavage at these two sites results in substantial removal of the cscFc linker.

In one embodiment, the invention pertains to a heterodimeric polypeptide comprising two amino acid chains which polypeptide is encoded by the nucleic acid molecule of the invention.

In another embodiment, the invention pertains to a heterodimeric polypeptide, wherein said heterodimeric polypeptide is made by expressing the vector containing a nucleic molecule of the invention in a cell cultured in cell culture medium and isolating the polypeptide from the culture medium. In one embodiment, the polypeptide is a processed polypeptide comprising at least two amino acid chains.

In one embodiment, the invention pertains to a nucleic acid molecule of the invention which is present in a vector.

In one embodiment, the vector further comprises a nucleotide sequence encoding an enzyme which cleaves at least one of the intracellular processing sites.

In another aspect, the invention pertains to a processed polypeptide comprising at least two amino acid chains which polypeptide is encoded by the nucleic acid molecule of the invention.

In one embodiment, the invention pertains to a host cell comprising the vector of the invention, wherein the host cell expresses an enzyme which cleaves the polypeptide linker.

In one embodiment, the enzyme is endogenous to the cell. In another embodiment, the enzyme is exogenous to the cell.

In another aspect, the invention pertains to a method for producing a polypeptide comprising culturing the host cell of the invention in culture such that a mature polypeptide comprising two amino acid chains is produced.

In one aspect, the invention pertains to a processed, heterodimeric polypeptide comprising two polypeptide chains, wherein said processed, heterodimeric polypeptide is made by expressing the vector of the invention in a cell cultured in cell culture medium and isolating the mature, heterodimeric polypeptide from the culture medium.

In embodiment, the invention pertains to a composition comprising a processed polypeptide of the invention and a pharmaceutically acceptable carrier.

In another embodiment, the invention pertains to a composition comprising the nucleic acid molecule of the invention a pharmaceutically acceptable carrier.

In one embodiment, the invention pertains to a method for treating or preventing a disease or disorder in a subject, comprising administering a composition of the invention to subject.

In one embodiment, the disease or disorder is selected from the group consisting of a clotting disorder, a neurological disorder, an inflammatory disorder, an autoimmune disorder, and a neoplastic disorder.

In another embodiment, the disease or disorder is a disorder affecting hemostasis. In another embodiment, the composition promotes clot formation.

In one aspect, the instant invention is directed to a polypeptide, wherein the polypeptide comprises (i) at least one biologically active moiety, (ii) an Fc region encoded in a single contiguous genetic sequence, and (iii) an scFc linker moiety, wherein the scFc linker moiety comprises at least one intracellular processing site or enzymatic cleavage site which results in cleavage and substantial removal of the scFc linker.

In another aspect, the invention pertains to a nucleic acid molecule encoding a polypeptide, wherein the polypeptide comprises (i) at least one biologically active moiety, (ii) an Fc region encoded in a single contiguous genetic sequence, and (iii) an scFc linker moiety, wherein the scFc linker moiety comprises at least one intracellular processing site or enzymatic cleavage site which results in cleavage and substantial removal of the scFc linker.

In another embodiment, the invention pertains to a mature, heterodimeric polypeptide comprising two polypeptide chains, wherein said mature, heterodimeric polypeptide is made by expressing the vector of containing a nucleic molecule of the invention in a cell cultured in cell culture medium and isolating the mature, heterodimeric polypeptide from the culture medium.

BRIEF DESCRIPTION OF THE DRAWINGS

FIG. 4 Panel B shows an SDS-PAGE gel of the purified FVIII-049 protein (after cotransfection with PC5) that demonstrates the full processing of the molecule.

FIG. 5 Panel B shows an SDS-PAGE gel of the purified FVII-064 protein (after cotransfection with PC5) that demonstrates the full processing of the molecule.

FIG. 6 Panel B shows an SDS-PAGE gel of the purified FVII-027 protein after cotransfection with PC5 that demonstrates the full processing of the molecule.

DETAILED DESCRIPTION OF THE INVENTION

The present invention advances the art by providing molecules, e.g., nucleic acid and polypeptide molecules, comprising (i) at least one biologically active moiety (e.g., an antigen binding site or binding domain, receptor binding portion of a ligand, ligand binding portion of a receptor, or moiety that modulates clotting) and (ii) at least one Fc region (i.e., single-chain Fc ("scFc") region) comprising a cleavable scFc (cscFc) linker. However, in contrast to scFc linkers of the prior art scFc molecules, the cscFc linkers of the instant invention which link the Fc moieties forming the scFc region are adjacent to at least one enzymatic cleavage site (e.g., that can be cleaved by an intracellular processing enzyme), resulting in a dimeric molecule comprising a two chain Fc region in which the csFc linker is cleaved or substantially removed. This cleavage step can occur before the polypeptide is secreted by a cell, prior to administration to a subject, or in vivo after administration.

In one embodiment, the polypeptide is represented by the formula:

Figure 1A:
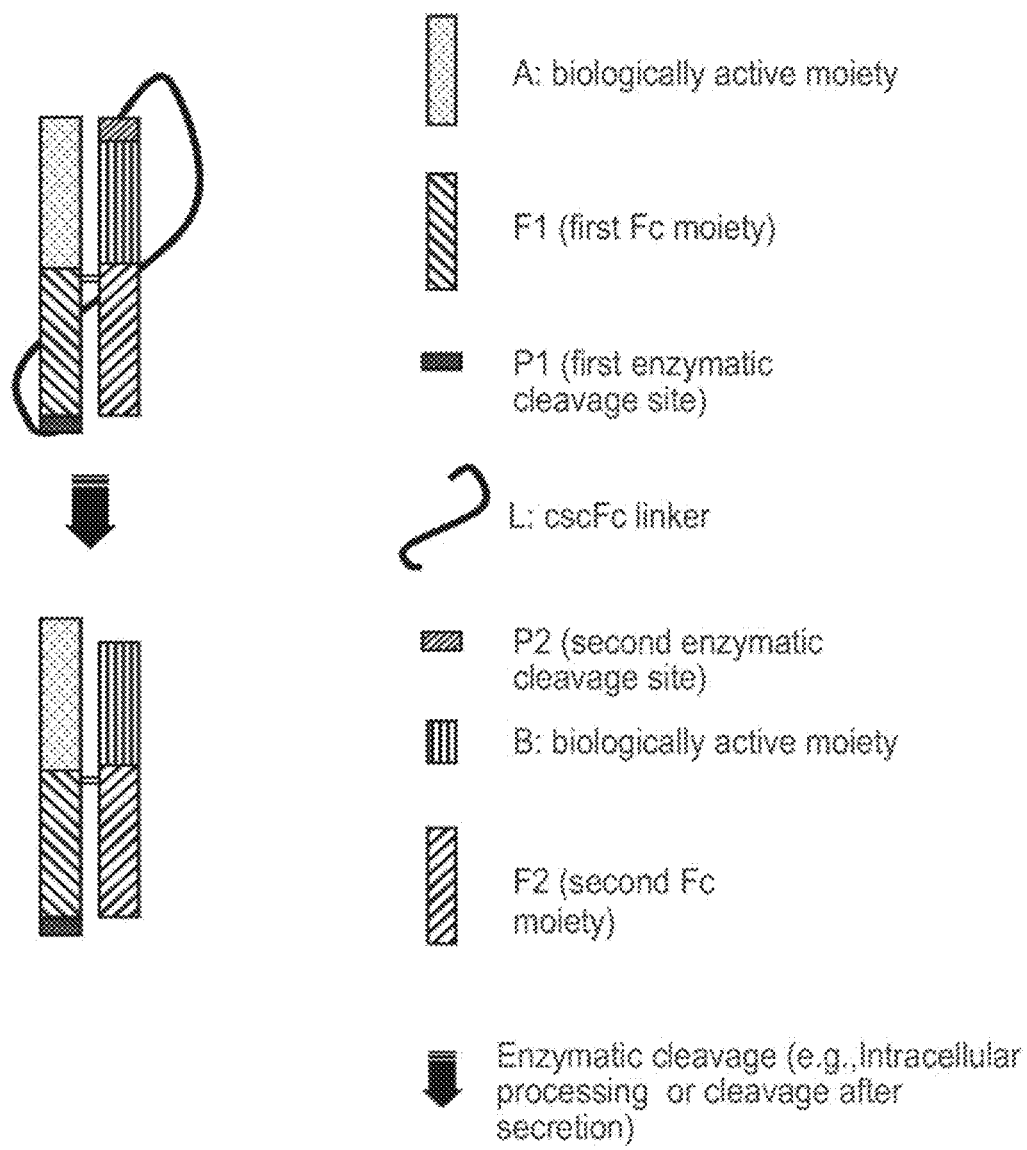
FIGS. 1A and B are illustrations of exemplary constructs of the invention with protease processing sites upstream and downstream of a polypeptide linker which links the Fc moieties.

A-F1-P1-L-P2-B-F2    (I)

in linear sequence from the amino to carboxy terminus wherein A is a biologically active moiety, F1 is a first Fc moiety or domain, P1 is an enzymatic cleavage site, L is an cscFc linker, P2 is an enzymatic cleavage site, B is a biologically active moiety, F2 is a second Fc moiety or domain and "—" represents a peptide bond. Formula (I) comprises at least an A or B and optionally both. A and B, if both present, can be the same or different. A and B can each also be subunits or chains of a molecule, such that when both present and associated with each other, they form a functional and active molecule. Formula (I) comprises at least a P1 or P2 and optionally both. P1 and P2, if both present, can be the same or different. Formula (I) comprises at least a F1 and F2. F1 and F2, if both present, can be the same or different. Exemplary polypeptide are also shown by the schematic in FIG. 1A):

Exemplary polypeptides according to formula I include: A-F1-P1-L-P2-F2; F1-P1-L-P2-B-F2; A-F1-P1-L-F2; F1-P1-L-B-F2; A-F1-L-P2-F2; and F1-L-P2-B-F2.

In one embodiment, F1 and F2 each comprise a CH2 and CH3 moiety. In another embodiment, F1 and F2 dimerize to form an Fc region and where A and B are optionally present and are biologically active moieties.

In one embodiment, P1 and P2 are both present and are recognized by the same or by different enzymes. In one embodiment, at least one of PI or P2 is an intracellular processing site which comprises a cluster of basic amino acid residues that are recognized by arginine kex2/furin enzymes. Such enzymes cleave immediately C-terminal to an arginine residue. In one embodiment, at least one of P1 or P2 intracellular processing site is an enzymatic cleavage site, which is recognized by thrombin. In another embodiment, at least one site is a cleavage site which is cleaved in vivo, for example at a cleavage site recognized, e.g., by thrombin or Factor Xa or XIa. Exemplary FXIa cleavage sites include, e.g., TQSFNDFTR (SEQ ID NO:7) and SVSQTSKLTR (SEQ ID NO:8). Exemplary thrombin cleavage sites include: DFLAEGGGVR (SEQ ID NO:9), TTKIKPR (SEQ ID NO:10), and a sequence comprising or consisting of ALRPR (SEQ ID NO: 94) (e.g., ALR-PRVVGGA (SEQ ID NO: 11)). Other cleavage sites can readily be selected by one of skill in the art, based upon the teachings herein.

The subject polypeptides comprise at least one biologically active moiety (represented as A and B in Formula I). Such biologically active moieties may be fused to either or both Fc moieties present in the Fc region of a molecule of the invention. Such fusions can be made to the C-terminus or N-terminus or to both of an Fc moiety. Such fusions can be direct (e.g., by a peptide bond) by peptide linker (e.g., a polypeptide spacer which imparts flexibility to the molecule), chemical conjugation, or other art recognized methods.

In one embodiment, a cell expressing a construct encoding a polypeptide of the invention endogenously expresses an enzyme which processes the cscFc linker (L) resulting in a multimeric molecule comprising at least two polypeptide chains, e.g., a dimeric molecule comprising two polypeptide chains. In another embodiment, a cell expressing a construct encoding a polypeptide of the invention expresses a heterologous enzyme (e.g. recombinantly expresses an enzyme) which processes, i.e., cleaves the cscFc linker at the cleavage site.

Expression of the polypeptides of the invention from a single contiguous genetic construct has numerous advantages over conventional protein expression methods which involve the co-expression of two genes (one encoding a polypeptide chain comprising a first Fc domain and a separate, second gene encoding a polypeptide chain comprising a second Fc domain with disulfide bonds linking the two polypeptide chains). The potential problems associated with such conventional constructs include significant heterogeneity within the population of resulting molecules, such that the desired molecule must be purified away from undesired molecules, inevitably resulting in a decline in total yield of the desired molecule. For example, misfolded Fc fusion proteins can be difficult to separate from properly folded, bivalent, Fc proteins since the only difference between the two is often a heterogeneous misfolding event. The subject polypeptides cannot undergo scrambling of the protein domains because this construction does not fix the molecules in close proximity to each other during the folding process. In addition, removal of the extraneous linker sequence may also relieve any steric stress or hindrance that was present in the covalently linked form. However, cleavage of the cscFc linker allows for biologically active moieties fused to the amino terminus of each Fc moiety to have a free N-terminus. This is particularly valuable in the case of biologically active moieties which are catalytically active, such as serine protease domains which require a free N-terminus to be catalytically active, or moieties or which might be sterically hindered by the presence of an uncleaved polypeptide linker.

Exemplary constructs of the invention are illustrated in the accompanying Figures and sequence listing. In one embodiment, the invention pertains to a polypeptide having the structure as set forth in the Figures. In another embodiment, the invention pertains to a polypeptide having the sequence set forth in the accompanying sequence listing or to a nucleic acid molecule encoding such a polypeptide. In one embodiment, the invention pertains to a mature form of a polypeptide having the sequence set forth in the accompanying sequence listing. It will be understood that these constructs and nucleic acid molecules encoding them can be used to improve hemostasis in a subject.

In order to provide a clear understanding of the specification and claims, the following definitions are provided below.

I. Definitions

As used herein, the term "protein" or "polypeptide" refers to a polymer of two or more of natural amino acids or non-natural amino acids.

The term "amino acid" includes alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the invention and include norleucine, ornithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions", can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

Polypeptides may be either monomers or multimers. For example, in one embodiment, a protein of the invention is a dimer. In one embodiment, the dimers of the invention are homodimers, comprising two identical monomeric subunits or polypeptides (e.g., two identical Fc moieties or two identical biologically active moieties). In another embodiment, the dimers of the invention are heterodimers, comprising two non-identical monomeric subunits or polypeptides (e.g., comprising two different biologically active moieties, one biologically active moiety only, and/or an Fc region comprising non-identical Fc moieties which dimerize to form a heteromeric Fc region). Polypeptide dimmers may comprise two polypeptide chains or may consist of one polypeptide chains.

As used herein, the term "scFc polypeptide" refers to a polypeptide comprising a single-chain Fc (scFc) region. The polypeptides of the invention comprise cscFc linkers (L of formula I) linking the Fc moieties of the scFc region. The cscFc linker is interposed between the Fc moieties that comprise the scFc region and is flanked by at least one enzymatic cleavage site, e.g., an intracellular enzymatic processing site. As used herein, the term scFc polypeptide refers to a polypeptide comprising a single-chain Fc (scFc) region. Fc moieties of the polypeptide can be linked either directly or indirectly. If the cscFc linker connects two Fc moieties contiguously in the linear polypeptide sequence, it is a "direct" linkage. In contract, the cscFc linkers may link the first Fc moiety to a different moiety (e.g., a binding moiety, a targeting moiety, or a functional moiety) which is, in turn, linked to the second Fc moiety, thereby forming an indirect linkage.

In one embodiment a polypeptide of the invention comprises additional modifications. Exemplary modifications are described in more detail below. For example, in one embodiment a polypeptide may be modified to add a functional moiety (e.g., PEG, a drug, or a label).

A "biologically active moiety" refers to a molecule, portion, fragment, derivative or component of a molecule capable of one or more of performing a function, an action or a reaction in a biological context. A biologically active moiety may comprise a complete protein or biologically active portion thereof. For example, the term "biologically active moiety" includes active and functional molecules, binding domains of molecules which bind to components of a biological system (e.g., proteins in sera or on the surface of cells or in cellular matrix) and which binding results in a biological effect (e.g., as measured by a change in the active moiety and/or the component to which it binds (e.g., a cleavage of the active moiety and/or the component to which it binds, the transmission of a signal, or the augmentation or inhibition of a biological response in a cell or in a subject)). Exemplary biologically active moieties may comprise natural molecules, e.g., a component of the clotting cascade, an antigen binding site or fragment of an antibody molecule (e.g., F(ab) or scFv) (e.g., to impart, induce or block a biological response), a ligand binding portion of a receptor or a receptor binding portion of a ligand, or a catalytic domain. In one embodiment, a biologically active moiety comprises the mature form of a protein. In another embodiment, a biologically active moiety comprises a full length protein or a portion of a full length protein which retains biological activity.

A used herein, the term "biologically active moiety" includes, for example, a first moiety which may not have activity when present alone in monomeric form, but which has a biological activity when paired with a second moiety in the context of a construct of the invention. In some such embodiments, the first moiety may be represented by A (or B) in Formula I and the second moiety may be represented by B (or A). When A and B and then associate in the polypeptide, they form a functional molecule (examples include e.g., the light and heavy chains of FVII or e.g., the subunits of FSH).

The term "biologically active moiety" includes moieties which require enzymatic activity in order to be fully biologically active. For example, clotting factors, whether in their zymogen form or in their fully activated form (e.g., FVII, FVIIa, FIX, FIXa, FX or FXa), are embraced by the term "biologically active moiety".

The term "ligand binding domain" as used herein refers to a native receptor (e.g., cell surface receptor) or a region or derivative thereof retaining at least a qualitative ligand binding ability, and preferably the biological activity of the corresponding native receptor. The term "receptor binding domain" as used herein refers to a native ligand or region or derivative thereof retaining at least a qualitative receptor binding ability, and preferably the biological activity of the corresponding native ligand.

In one embodiment, the polypeptides of the invention comprise at least one biologically active moiety which binds to a molecule targeted for reduction or elimination, e.g., a cell surface antigen or a soluble antigen. In one embodiment, the biologically active moiety comprises or consists of an antigen binding site (e.g., comprising a variable heavy chain sequence and variable light chain sequence or six CDRs from an antibody placed into alternative framework regions (e.g., human framework regions optionally comprising one or more amino acid substitutions). In another preferred embodiment, a biologically active moiety comprises a biologically active portion of a component of the clotting cascade.

The term "specificity" includes the number of potential binding sites which specifically bind (e.g., immunoreact with) a given target. A polypeptide may be monospecific and contain one or more binding sites which specifically bind the same target (e.g., the same epitope) or the polypeptide may be multispecific and contain two or more binding sites which specifically bind different regions of the same target (e.g., different epitopes) or different targets.

As used herein the term "valency" refers to the number of biologically active moieties (e.g., binding domains) in a polypeptide or protein. When a polypeptide comprises more than one biologically active moiety, each binding domain may specifically bind the same or different molecules (e.g., may bind to different ligands or different antigens, or different epitopes on the same antigen). In one embodiment, the polypeptides of the invention are monovalent. In another embodiment, the polypeptides of the invention are multivalent (e.g., bivalent).

As used herein, the term "polypeptide linkers" refers to a peptide or polypeptide sequence (e.g., a synthetic peptide or polypeptide sequence) which connects two domains in a linear amino acid sequence of a polypeptide chain. Preferred linkers include, e.g., gly-ser polypeptide linkers. The polypeptides of invention are encoded by nucleic acid molecules comprising a nucleotide sequence that encodes polypeptide linkers linking the two Fc moieties which make up the construct, either directly or indirectly. These linkers are referred to herein as "cscFc linkers". Rather than linking two Fc moieties contiguously in the linear polypeptide sequence, the cscFc linker may, for example, link the first Fc moiety to a different moiety (e.g., a biologically active moiety, targeting moiety, or functional moiety) which is, in turn, linked to the second Fc moiety. These cscFc linker (L) result in the formation of a single chain genetic construct. However, the polypeptides also comprise enzymatic cleavage sites which result in the cscFc linker being cleaved and, in one embodiment, substantially excised (e.g., during processing by a cell). Thus, the processed molecule is a dimeric molecule comprising at least two amino acid chains and substantially lacking extraneous linker amino acid sequences. In some embodiments, all or substantially all of the linker is excised, while in some embodiments, a portion of the cleavage site may remain, e.g., four arginines of the RRRR (SEQ ID NO: 40) cleavage site. In another embodiment, the linker is cleaved at one site.

In another embodiment, another type of polypeptide linker, herein referred to as a "spacer" may be used to connect different moieties, e.g., a biologically active moiety to an Fc moiety. This type of polypeptide linkers may provide flexibility to the polypeptide molecule. Spacers are not typically cleaved; however such cleavage may be desirable. Exemplary positions of spacers are shown in the accompanying drawings.

As used herein, the term "gly-ser polypeptide linker" refers to a polypeptide linker that consists of glycine and serine residues. An exemplary gly/ser polypeptide linker comprises the amino acid sequence $(Gly_4Ser)_n$. (SEQ ID NO:4) Another exemplary gly/ser polypeptide linker comprises the amino acid sequence $S(Gly_4Ser)_n$ (SEQ ID NO: 26).

In one embodiment, n=1. In one embodiment, n=2. In another embodiment, n=3, i.e., $(Gly_4Ser)_3$ (SEQ ID NO: 1). In another embodiment, n=4, i.e., $(Gly_4Ser)_4$ (SEQ ID NO:6). In another embodiment, n=5. In yet another embodiment, n=6. In another embodiment, n=7. In yet another embodiment, n=8. In another embodiment, n=9. In yet another embodiment, n=10. Another exemplary gly/ser polypeptide linker comprises the amino acid sequence Ser $(Gly_4Ser)_n$ (SEQ ID NO:26). In one embodiment, n=1. In one embodiment, n=2. In a preferred embodiment, n=3. In another embodiment, n=4. In another embodiment, n=5. In yet another embodiment, n=6.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence.

Polypeptides derived from another peptide may have one or more mutations relative to the starting polypeptide, e.g., one or more amino acid residues which have been substituted with another amino acid residue or which has one or more amino acid residue insertions or deletions. Preferably, the polypeptide comprises an amino acid sequence which is not naturally occurring. Such variants necessarily have less than 100% sequence identity or similarity with the starting antibody. In a preferred embodiment, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule. In one embodiment, there is one amino acid difference between a starting polypeptide sequence and the sequence derived therefrom. Identity or similarity with respect to this sequence is defined herein as the percentage of amino acid residues in the candidate sequence that are identical (i.e. same residue) with the starting amino acid residues, after aligning the sequences and introducing gaps, if necessary, to achieve the maximum percent sequence identity.

Preferred polypeptides of the invention comprise an amino acid sequence (e.g., at least one Fc moiety or domain) derived from a human immunoglobulin sequence. However, polypeptides may comprise one or more amino acids from another mammalian species. For example, a primate Fc domain or binding site may be included in the subject polypeptides. Alternatively, one or more amino acids derived from a non-human species may be present in a polypeptide. Preferred polypeptides of the invention are not immunogenic.

It will also be understood by one of ordinary skill in the art that the polypeptides of the invention may be altered such that they vary in amino acid sequence from the naturally occurring or native polypeptides from which they were derived, while retaining the desirable activity of the native polypeptides. For example, nucleotide or amino acid substitutions leading to conservative substitutions or changes at "non-essential" amino acid residues may be made. An isolated nucleic acid molecule encoding a non-natural variant of a polypeptide derived from an immunoglobulin (e.g., an Fc domain, moiety, or antigen binding site) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis.

The polypeptides of the invention may comprise conservative amino acid substitutions at one or more amino acid residues, e.g., at essential or non-essential amino acid residues. Thus, a nonessential amino acid residue in a polypeptide may be replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into polypeptides of the invention and screened for their ability to bind to the desired target.

In the context of polypeptides, a "linear sequence" or a "sequence" is the order of amino acids in a polypeptide in an amino to carboxyl terminal direction in which residues that flank or are adjacent to each other in the sequence are contiguous in the primary structure of the polypeptide, i.e., are linked via a peptide bond.

As used herein, the terms "linked," "fused", or "fusion" refer to linkage via a peptide bond, chemical conjugation or other means. The terms "genetically fused," "genetically linked" or "genetic fusion" are used interchangeably and refer to the co-linear, covalent linkage or attachment of two or more proteins, polypeptides, or fragments thereof via their individual peptide backbones, through genetic expression of a single polynucleotide molecule encoding those proteins, polypeptides, or fragments. Such genetic fusion results in the expression of a single contiguous genetic sequence. In one embodiment, moieties of an scFc polypeptide are genetically fused. Preferred genetic fusions are in frame, i.e., two or more open reading frames (ORFs) are fused to form a continuous longer ORF, in a manner that maintains the correct reading frame of the original ORFs. Thus, the resulting recombinant fusion protein is a single polypeptide containing two or more protein segments that correspond to polypeptides encoded by the original ORFs (which segments are not normally so joined in nature). In this case, the single polypeptide is cleaved during processing to yield dimeric molecules comprising two polypeptide chains.

As used herein, the term "Fc region" shall be defined as the portion of a polypeptide which corresponds to the Fc region of native immunoglobulin, i.e., as formed by the dimeric association of the respective Fc domains) of its two heavy chains. A native Fc region is homodimeric and comprises two polypeptide chains. In contrast, the term "genetically-fused Fc region" or "single-chain Fc region" (scFc region), as used herein, refers to a synthetic dimeric Fc region comprised of Fc domains or moieties genetically linked within a single polypeptide chain (i.e., encoded in a single contiguous genetic sequence) wherein the Fc domains or moieties of the single polypeptide chain dimerize to form an Fc region.

As used herein, the term "Fc domain" refers to the portion of a single immunoglobulin heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

As used herein, the term "Fc domain portion" or "Fc moiety" includes an amino acid sequence of an Fc domain or derived from an Fc domain. In certain embodiments, an Fc moiety comprises at least one of: a hinge (e.g., upper, middle, and/or lower hinge region) domain, a CH2 domain, a CH3 domain, a CH4 domain, or a variant, portion, or fragment thereof. In other embodiments, an Fc moiety comprises a complete Fc domain (i.e., a hinge domain, a CH2 domain, and a CH3 domain). In one embodiment, a Fc moiety comprises a hinge domain (or portion thereof) fused to a CH3 domain (or portion thereof). In another embodiment, an Fc moiety comprises a CH2 domain (or portion thereof) fused to a CH3 domain (or portion thereof). In another embodiment, an Fc moiety consists of a CH3 domain or portion thereof. In another embodiment, an Fc moiety consists of a hinge domain (or portion thereof) and a CH3 domain (or portion thereof). In another embodiment, a Fc moiety consists of a CH2 domain (or portion thereof) and a CH3 domain. In another embodiment, a Fc moiety consists of a hinge domain (or portion thereof) and a CH2 domain (or portion thereof). In one embodiment, an Fc moiety lacks at least a portion of a CH2 domain (e.g., all or part of a CH2 domain).

In one embodiment, an Fc moiety of the invention comprises at least the portion of an Fc molecule known in the art to be required for FcRn binding, referred to herein as a neonatal receptor (FcRn) binding partner. The skilled artisan will understand that portions of an immunoglobulin constant region for use in the chimeric protein of the invention can include mutants or analogs thereof, or can include chemically modified immunoglobulin constant regions (e.g. pegylated), or fragments thereof (see, e.g., Aslam and Dent 1998, Bioconjugation: Protein Coupling Techniques For the Biomedical Sciences Macmilan Reference, London). In one instance, a mutant can provide for enhanced binding of an FcRn binding partner for the FcRn. Also contemplated for use in the chimeric protein of the invention are peptide mimetics of at least a portion of an immunoglobulin constant region, e.g., a peptide mimetic of an Fc fragment or a peptide mimetic of an FcRn binding partner. In one embodiment, the peptide mimetic is identified using phage display or via chemical library screening (see, e.g., McCafferty et al. 1990, Nature 348:552, Kang et al. 1991, Proc. Natl. Acad. Sci. USA 88:4363; EP 0 589 877 B1). In another embodiment, an Fc region of the invention (an scFc region) comprises at least the portion of an Fc molecule known in the art to be required for FcγR binding.

In one embodiment, an Fc region of the invention (an scFc region) comprises at least the portion of an Fc molecule known in the art to be required for Protein A binding. In one embodiment, an Fc region of the invention (an scFc region) comprises at least the portion of an Fc molecule known in the art to be required for protein G binding.

As set forth herein, it will be understood by one of ordinary skill in the art that an Fc domain may also be modified such that it varies in other effector functions from the native Fc domain of a naturally occurring immunoglobulin molecule. In certain exemplary embodiments, the Fc moiety retains an effector function (e.g., FcγR binding).

The Fc domains or moieties of a polypeptide of the invention may be derived from different immunoglobulin molecules. For example, an Fc domain or moiety of a polypeptide may comprise a CH2 and/or CH3 domain derived from an IgG1 molecule and a hinge region derived from an IgG3 molecule. In another example, an Fc domain or moiety can comprise a chimeric hinge region derived, in part, from an IgG1 molecule and, in part, from an IgG3 molecule. In another example, an Fc domain or moiety can comprise a chimeric hinge derived, in part, from an IgG1 molecule and, in part, from an IgG4 molecule.

Amino acid positions in a heavy chain constant region, including amino acid positions in the CH1, hinge, CH2, and CH3 domains, are numbered herein according to the EU index numbering system (see Kabat et al., in "Sequences of Proteins of Immunological Interest", U.S. Dept. Health and Human Services, 5$^{th}$ edition, 1991). In contrast, amino acid positions in a light chain constant region (e.g. CL domains) are numbered herein according to the Kabat index numbering system (see Kabat et al., ibid).

As used herein, the term "$V_H$ domain" includes the amino terminal variable domain of an immunoglobulin heavy chain, and the term "$V_L$ domain" includes the amino terminal variable domain of an immunoglobulin light chain according to the Kabat index numbering system.

As used herein, the term "CH1 domain" includes the first (most amino terminal) constant region domain of an immunoglobulin heavy chain that extends, e.g., from about EU positions 118-215. The CH1 domain is adjacent to the $V_H$ domain and amino terminal to the hinge region of an immunoglobulin heavy chain molecule, and does not form a part of the Fc region of an immunoglobulin heavy chain. In one embodiment, a polypeptide of the invention comprises a CH1 domain derived from an immunoglobulin heavy chain molecule (e.g., a human IgG1 or IgG4 molecule).

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998, 161:4083).

As used herein, the term "CH2 domain" includes the portion of a heavy chain immunoglobulin molecule that extends, e.g., from about EU positions 231-340. The CH2 domain is unique in that it is not closely paired with another domain. Rather, two N-linked branched carbohydrate chains are interposed between the two CH2 domains of an intact native IgG molecule. In one embodiment, a polypeptide of the invention comprises a CH2 domain derived from an IgG1 molecule (e.g. a human IgG1 molecule). In another embodiment, a polypeptide of the invention comprises a CH2 domain derived from an IgG4 molecule (e.g., a human IgG4 molecule). In an exemplary embodiment, a polypeptide of the invention comprises a CH2 domain (EU positions 231-340), or a portion thereof.

As used herein, the term "CH3 domain" includes the portion of a heavy chain immunoglobulin molecule that extends approximately 110 residues from N-terminus of the CH2 domain, e.g., from about position 341-446b (EU numbering system). The CH3 domain typically forms the C-terminal portion of the antibody. In some immunoglobulins, however, additional domains may extend from CH3 domain to form the C-terminal portion of the molecule (e.g. the CH4 domain in the μ chain of IgM and the c chain of IgE). In one embodiment, a polypeptide of the invention comprises a CH3 domain derived from an IgG1 molecule (e.g., a human IgG1 molecule). In another embodiment, a polypeptide of the invention comprises a CH3 domain derived from an IgG4 molecule (e.g., a human IgG4 molecule).

As used herein, the term "CL domain" includes the first (most amino terminal) constant region domain of an immunoglobulin light chain that extends, e.g. from about Kabat position 107A-216. The CL domain is adjacent to the $V_L$ domain. In one embodiment, a polypeptide of the invention comprises a CL domain derived from a kappa light chain (e.g., a human kappa light chain).

Fc moieties for use in the polypeptides of the invention can be modified at art-recognized positions to alter, e.g., increase or decrease effector function. As used herein, the term "effector function" refers to the functional ability of the Fc region or portion thereof to bind proteins and/or cells of the immune system and mediate various biological effects. Effector functions may be antigen-dependent or antigen-independent. A decrease in effector function refers to a decrease in one or more effector functions, while maintaining the antigen binding activity of the variable region of the antibody (or fragment thereof). Increase or decreases in effector function, e.g., Fc binding to an Fc receptor or complement protein, can be expressed in terms of fold change (e.g., changed by 1-fold, 2-fold, and the like) and can be calculated based on, e.g., the percent changes in binding activity determined using assays the are well-known in the art.

Fc moieties for use in the polypeptides of the invention can be modified at art-recognized positions to alter, e.g., increase or decrease half life. As used herein, the term "half-life" refers to a biological half-life of a particular polypeptide in vivo. Half-life may be represented by the time required for half the quantity administered to a subject to be cleared from the circulation and/or other tissues in the animal.

As used herein, the term "antigen binding site" or "antigen binding domain" includes a site that specifically binds (immunoreacts with) an antigen such as a cell surface or soluble antigen). In one embodiment, the binding site includes an immunoglobulin heavy chain and light chain variable region and the binding site formed by these variable regions determines the specificity of the antibody. An antigen binding site is formed by variable regions (VH and VL domains) that vary from one polypeptide to another.

In certain embodiments, the polypeptides of the invention comprise at least two antigen binding domains (e.g., within the same polypeptide (e.g, at both the N- and C-terminus of a single polypeptide) or linked to each component binding polypeptide of a multimeric binding protein of the invention) that provide for the association of the polypeptide with the selected antigen. The antigen binding domains need not be derived from the same immunoglobulin molecule. In this regard, the variable region may or may not be derived from any type of animal that can be induced to mount a humoral response and generate immunoglobulins against the desired antigen. As such, the variable region may be, for example, of mammalian origin e.g., may be human, murine, non-human primate (such as cynomolgus monkeys, macaques, etc.), lupine, camelid (e.g., from camels, llamas and related species).

The term "antibody variant" or "modified antibody" includes an antibody which does not occur in nature and which has an amino acid sequence or amino acid side chain chemistry which differs from that of a naturally-derived antibody by at least one amino acid or amino acid modification as described herein or a non-naturally occurring molecule comprising at least one antigen-binding site. As used herein, the term "antibody variant" includes synthetic forms of antibodies which are altered such that they are not naturally occurring, e.g., antibodies that comprise at least two heavy chain portions but not two complete heavy chains (such as, domain deleted antibodies or minibodies); multi-specific forms of antibodies (e.g., bispecific, trispecific, etc.) altered to bind to two or more different antigens or to different epitopes on a single antigen); heavy chain molecules joined to scFv molecules; single-chain antibodies; diabodies; triabodies; and antibodies with altered effector function and the like.

As used herein the term "scFv molecule" includes binding molecules which consist of one light chain variable domain (VL) or portion thereof, and one heavy chain variable domain (VH) or portion thereof, wherein each variable domain (or portion thereof) is derived from the same or different antibodies. scFv molecules preferably comprise an scFv linker interposed between the VH domain and the VL domain. ScFv molecules are known in the art and are described, e.g., in U.S. Pat. No. 5,892,019, Ho et al. 1989. Gene 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837.

A "scFv linker" as used herein refers to a moiety interposed between the VL and VH domains of the scFv. scFv linkers preferably maintain the scFv molecule in a antigen binding conformation. In one embodiment, a scFv linker comprises or consists of an scFv linker peptide. In certain embodiments, a scFv linker peptide comprises or consists of a gly-ser polypeptide linker. In other embodiments, a scFv linker comprises a disulfide bond.

The term "glycosylation" refers to the covalent linking of one or more carbohydrates to a polypeptide. Typically, glycosylation is a posttranslational event which can occur within the intracellular milieu of a cell or extract therefrom. The term glycosylation includes, for example, N-linked glycosylation (where one or more sugars are linked to an asparagine residue) and/or O-linked glycosylation (where one or more sugars are linked to an amino acid residue having a hydroxyl group (e.g., serine or threonine). In one embodiment, a molecule of the invention is glycosylated. In another embodiment, a molecule of the invention is aglycosylated. In yet another embodiment, a molecule of the invention has reduced glycosylation as compared to that in a wild type Fc region.

As used herein the term "disulfide bond" includes the covalent bond formed between two sulfur atoms.

As used herein the term "moiety" refers to a component part or constituent of a chimeric polypeptide.

The term "functional moiety" includes moieties which, preferably, add a desirable function to the polypeptide. Preferably, the function is added without significantly altering an intrinsic desirable activity of the polypeptide, e.g., clotting activity, solubility, or half life of the molecule. A polypeptide of the invention may comprise one or more functional moieties, which may be the same or different. Examples of useful functional moieties include, but are not limited to, a detectable moiety, an functional moiety, a drug moiety, an affinity moiety, and a blocking moiety (e.g., which sterically blocks binding to an enzyme or which blocks the ability to bind to a particular receptor). Functional moieties may be linked to polypeptides using methods known in the art, e.g., via cleavable or non-cleavable linking moieties.

As used herein, the term "prodrug" refers to a precursor or derivative form of a pharmaceutically active agent that is less active, reactive or prone to side effects as compared to the parent drug and is capable of being enzymatically activated or otherwise converted into a more active form in vivo. In one embodiment, a prodrug of the invention is a polypeptide which comprises an uncleaved or unprocessed scFc region which, upon administration or prior to administration to a subject is cleaved to form a dimeric molecule comprising at least two polypeptide chains.

The term "vector" or "expression vector" is used herein to mean vectors used in accordance with the present invention as a vehicle for introducing into and expressing a desired polynucleotide in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

The constructs of the invention can be expressed in a single plasmid, avoiding the need for multiple plasmids. Numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. In one embodiment, an inducible expression system can be employed. Additional elements may also be needed for optimal synthesis of mRNA. These elements may include signal sequences, splice signals, as well as transcriptional promoters, enhancers, and termination signals. In one embodiment, a secretion signal, e.g., any one of several well characterized bacterial leader peptides (e.g., pelB, phoA, or ompA), can be fused in-frame to the N terminus of a polypeptide of the invention to obtain optimal secretion of the polypeptide. (Lei et al. (1988), *Nature*, 331:543; Better et al. (1988) *Science*, 240:1041; Mullinax et al., (1990). *PNAS*, 87:8095).

The term "host cell" refers to a cell that has been transformed with a vector constructed using recombinant DNA techniques and encoding at least one heterologous gene. In descriptions of processes for isolation of proteins from recombinant hosts, the terms "cell" and "cell culture" are used interchangeably to denote the source of protein unless it is clearly specified otherwise. In other words, recovery of protein from the "cells" may mean either from spun down whole cells, or from the cell culture containing both the medium and the suspended cells. The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature. The polypeptides of the invention can also be expressed in non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available including *Pichia pastoris*. For expression in *Saccharomyces*, the plasmid YRp7, for example, (Stinchcomb et al., (1979), *Nature*, 282:39; Kingsman et al., (1979), *Gene*, 7:141; Tschemper et al., (1980), *Gene*, 10:157) is commonly used. This plasmid already contains the TRP1 gene which provides a selection marker for a mutant strain of yeast lacking the ability to grow in tryptophan, for example ATCC No. 44076 or PEP4-1 (Jones, (1977), *Genetics*, 85:12). The presence of the trpl lesion as a characteristic of the yeast host cell genome then provides an effective environment for detecting transformation by growth in the absence of tryptophan.

As used herein the term "endogenous" refers to molecules (e.g. nucleic acid and/or protein molecules) that are naturally present in a cell. In contrast, the term "exogenous" or "heterologous" refers to such molecules that are not normally found in a given context, e.g., in a cell or in a polypeptide. For example, an exogenous or heterologous molecule may be introduced into a cell and is present after manipulation of the cell, (e.g., by transfection or other forms of genetic engineering) or a heterologous amino acid sequence may be present in a protein in which it is not naturally found As used herein, the term "cleavage site" or "enzymatic cleavage site" refers to a site recognized by an enzyme. Certain enzymatic cleavage sites comprise an intracellular processing site. In one embodiment, a polypeptide has an enzymatic cleavage site cleaved by an enzyme is one that is activated during the clotting cascade, such that cleavage of such sites occurs at the site of clot formation. Exemplary such sites include those recognized by thrombin, Factor XIa or Factor Xa. Exemplary FXIa cleavage sites include, e.g, TQSFNDFTR (SEQ ID NO: 7) and SVSQTSKLTR (SEQ ID NO: 8). Exemplary thrombin cleavage sites include, e.g, DFLAEGGGVR (SEQ ID NO: 9), TTKIKPR (SEQ ID NO: 10), LVPRG (SEQ ID NO:35) and a sequence comprising or consisting of ALRPR (SEQ ID NO: 94) (e.g. ALRPRVVGGA (SEQ ID NO: 11)). Other useful cleavage sites are known in the art.

As used herein, the term "processing site" or "intracellular processing site" refers to a type of enzymatic cleavage site in a polypeptide which is the target for enzymes that function after translation of the polypeptide. In one embodiment, such enzymes function during transport from the Golgi lumen to the trans-Golgi compartment. Intracellular processing enzymes cleave polypeptides prior to secretion of the protein from the cell.

One example of processing sites includes sites targeted by the PACE/furin (where PACE is an acronym for Paired basic Amino acid Cleaving Enzyme) family of endopeptidases. These enzymes are localized to the Golgi membrane and cleaves many proteins on the carboxyterminal side of the sequence motif Arg-[any residue]-(Lys or Arg)-Arg (SEQ ID NO: 34). As used herein the "furin" family of enzymes includes, e.g., furin, PC2, PC1/PC3, PC4, PACE4, PC5/PC6, and LPC/PC7/PC8/SPC7. Other useful processing cites are known in the art.

A "chimeric protein" or "fusion protein", as used herein, refers to any protein comprised of a first amino acid sequence derived from a first source, bonded, covalently or non-covalently, to a second amino acid sequence derived from a second source, wherein the first and second source are not the same. A first source and a second source that are not the same can include two different biological entities, or two different proteins from the same biological entity, or a biological entity and a non-biological entity. A chimeric protein can include for example, a protein derived from at least 2 different biological sources. A biological source can include any non-synthetically produced nucleic acid or amino acid sequence (e.g. a genomic or cDNA sequence, a plasmid or viral vector, a native virion or a mutant or analog, as further described herein, of any of the above). A synthetic source can include a protein or nucleic acid sequence produced chemically and not by a biological system (e.g. solid phase synthesis of amino acid sequences). A chimeric protein can also include a protein derived from at least 2 different synthetic sources or a protein derived from at least one biological source and at least one synthetic source. A chimeric protein may also comprise a first amino acid sequence derived from a first source, covalently or non-covalently linked to a nucleic acid, derived from any source or a small organic or inorganic molecule derived from any source. The chimeric protein may comprise a linker molecule between the first and second amino acid sequence or between the first amino acid sequence and the nucleic acid, or between the first amino acid sequence and the small organic or inorganic molecule. Examples of chimeric molecules include the scFc molecules of the invention.

As used herein, the term "clotting factor," refers to molecules, or analogs thereof, naturally occurring or recombinantly produced which prevent or decrease the duration of a bleeding episode in a subject. In other words, it means molecules which in their active form have pro-clotting activity, i.e., are responsible for the conversion of fibrinogen into a mesh of insoluble fibrin causing the blood to coagulate or clot.

"Clotting activity", as used herein, means the ability to participate in a cascade of biochemical reactions that culminates in the formation of a fibrin clot and/or reduces the severity, duration or frequency of hemorrhage or bleeding episode.

"Hemostasis", as used herein, means the stopping or slowing of bleeding or hemorrhage; or the stopping or slowing of blood flow through a blood vessel or body part.

"Hemostatic disorder", as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency), Von Willebrand disease, factor Xi deficiency (PTA deficiency), Factor XII deficiency, deficiencies or structural abnormalities in fibrinogen, prothrombin, Factor V, Factor VII, Factor X or factor XIII, Bernard-Soulier syndrome is a defect or deficiency in GPIb. GPIb, the receptor for vWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this may increase bleeding risk.

As used herein, the term "targeting moiety" refers to a molecule, fragment thereof or a component of a polypeptide which localizes or directs the polypeptides of the invention to a desired site or cell. In one embodiment, a construct of the invention comprises a "targeting moiety" which enhances the activity of the polypeptide, e.g., by localizing the molecule to a desired site. Such a moiety may be, e.g., an antibody or variant thereof (e.g., an scFv) or a peptide. In another embodiment, such a targeting moiety may be a polypeptide, a receptor binding portion of a ligand, or a ligand binding portion of a receptor which is linked to a polypeptide of the invention and binds to the desired target, e.g., on a cell or tissue. The targeting moiety may be genetically fused to a construct, chemically conjugated to the construct or linked to the construct via a peptide bond, e.g., a polypeptide spacer. For example, targeting moieties may be attached to a construct of the invention by formation of a bond between the targeting moiety and an Fc moiety of a construct, where the targeting moiety comprises a first functional group and the Fc moiety comprises a second functional group, and where the first and second functional groups are capable of reacting with each other to form a chemical bond (see, e.g., U.S. Pat. No. 7,381,408). In one embodiment, of the invention a targeting moiety binds to platelets as described in more detain herein.

As used herein, the phrase "subject that would benefit from administration of a polypeptide" includes subjects, such as mammalian subjects, that would benefit from administration of polypeptides of the invention, e.g., for treatment of a disorder. For example, in one embodiment, the subject may benefit from reduction or elimination of a soluble or particulate molecule from the circulation or serum (e.g., a toxin or pathogen) or from reduction or elimination of a population of cells expressing the target (e.g., tumor cells). In another embodiment, a subject may benefit from the biological activity of the imparted by the binding portion of the construct, e.g., as in the case of a polypeptide comprising a clotting factor. As discussed above, the polypeptide can be used in unconjugated form or can be chemically conjugated or linked, e.g., to a functional moiety, to form a modified polypeptide for administering to said subject.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition. In another embodiment, administration of a composition made according to the invention results in the prophylaxis of one or more symptoms associated with a disease or condition.

II. Molecules Comprising Single-Chain Fc ("scFc") Regions

In one embodiment, the invention provides for nucleic acid molecules encoding polypeptides comprising at least one genetically fused Fc region or portion thereof within a single polypeptide chain (i.e., polypeptides comprising a single-chain Fc (scFc) region). A nucleic acid molecule of the invention encodes a polypeptide in which the Fc moieties are genetically fused in a contiguous linear sequence of amino acids via a cscFc linker.

The invention also provides polypeptides specified by such nucleic acid molecules. In one embodiment, the invention provides unprocessed polypeptides in which at least two Fc moieties or domains (e.g., 2, 3, 4, 5, 6, or more Fc moieties or domains) within the same linear polypeptide chain that are capable of folding (e.g., intramolecularly or intermolecularly folding) to form one functional scFc region which is linked by an Fc polypeptide linker. For example, in one preferred embodiment, a polypeptide of the invention is capable of binding, via its scFc region, to at least one Fc receptor (e.g. an FcRn, an FcγR receptor (e.g., FcγRIII), or a complement protein (e.g. C1q)) in order to improve half life or trigger an immune effector function (e.g., antibody-dependent cytotoxicity (ADCC), phagocytosis, or complement-dependent cytotoxicity (CDCC) and/or to improve manufacturability).

In one embodiment, the invention pertains to processed (e.g., mature) polypeptides in which the at least one cleavage site adjacent to a cscFc polypeptide linker has been cleaved such that the molecule is no longer a single polypeptide chain. The resulting processed polypeptide is comprised of at least two polypeptide chains (owing to cleavage at the enzymatic cleavage site(s) P1 and/or P2).

In one embodiment, such processed polypeptides comprise a biologically active moiety linked to the second Fc moiety (i.e., the second Fc moiety when counting from the amino terminus to the carboxy terminus prior to cleavage of the polypeptide linker) which has a free amino terminus after cleavage of the polypeptide linker.

In one embodiment, a biologically active moiety attached to the N-terminus of the second Fc moiety comprises an antigen binding site (e.g., an scFv molecule). In another embodiment, a biologically active moiety attached to the N-terminus of the second Fc moiety is catalytically active, e.g., has enzymatic activity. In another embodiment, a biologically active moiety attached to the N-terminus of the second Fc moiety is secreted by a cell as a zymogen requiring further enzymatic processing of the biologically active moiety in order to be fully activated, e.g., FVII, IX, or X).

In one embodiment, the invention pertains to clotting factors which are secreted from cells in active or activated form without the need for further activation during processing. For example, Factor VII is generally produced recombinantly as a zymogen and require activation during manufacturing to produce the active form for administration. In one embodiment, a polypeptide of the invention is secreted from the cell in which it is expressed in active form to improve manufacturability. As is set forth in more detail below, such clotting factors can be produced by expressing the light chain of a clotting factor and the heavy chain of a clotting factor separately in the context of an cscFc molecule. Activation of such a construct is delayed until late in the secretory pathway during processing, e.g., when the protein colocalizes with active processing enzymes in the trans-Golgi apparatus.

A variety of polypeptides of alternative designs are within the scope of the invention. For example, in one embodiment, a nucleic acid molecule of the invention specifies a polypeptide represented by the formula:

A-F1-P1-L-P2-B-F2 (I)

in linear sequence from the amino to carboxy terminus wherein A is a biologically active moiety, F1 is a first Fc moiety or domain, P1 is an enzymatic cleavage site, L is an cscFc linker, P2 is an enzymatic cleavage site B is a biologically active moiety, F2 is a second Fc moiety or domain and "—" represents a peptide bond. Formula (I) comprises at least an A or B and optionally both. A and B, if both present, can be the same or different. Formula (I) comprises at least a P1 or P2 and optionally both. P1 and P2, if both present, can be the same or different. Formula (I) comprises at least a F1 and F2. F1 and F2, if both present, can be the same or different.

Exemplary polypeptides according to formula I include: A-F1-P1-L-P2-F2; F1-P1-L-P2-B-F2; A-F1-P1-L-F2; F1-P1-L-B-F2; A-F1-L-P2-F2; and F1-L-P2-B-F2.

In one embodiment, F1 and F2 each comprise a CH2 and CH3 moiety.

A. Fc Moieties or Domains

Fc moieties useful as F1 and F2 for producing the polypeptides of the present invention may be obtained from a number of different sources. In preferred embodiments, an Fc moiety of the polypeptide is derived from a human immunoglobulin. It is understood, however, that the Fc moiety may be derived from an immunoglobulin of another mammalian species, including for example, a rodent (e.g. a mouse, rat, rabbit, guinea pig) or non-human primate (e.g. chimpanzee, macaque) species. Moreover, the polypeptide Fc domain or portion thereof may be derived from any immunoglobulin class, including IgM, IgG, IgD, IgA and IgE, and any immunoglobulin isotype, including IgG1, IgG2, IgG3 and IgG4. In a preferred embodiment, the human isotype IgG (e.g., IgG1) is used.

A variety of Fc moiety gene sequences (e.g. human constant region gene sequences) are available in the form of publicly accessible deposits. Constant region domains comprising an Fc moiety sequence can be selected having a particular effector function (or lacking a particular effector function) or with a particular modification to reduce immunogenicity. Many sequences of antibodies and antibody-encoding genes have been published and suitable Fc moiety sequences (e.g. hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

Fc moiety sequences can be cloned, e.g., using the polymerase chain reaction and primers which are selected to amplify the domain of interest. To clone an Fc moiety sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

The polypeptides of the invention may comprise two or more Fc moieties (e.g., 2, 3, 4, 5, 6, 7, 8, 9, 10, or more Fc moieties). These two or more Fc moieties can form a Fc region. In one embodiment, the Fc moieties may be of different types. In one embodiment, at least one Fc moiety present in the polypeptide comprises a hinge domain or portion thereof. In another embodiment, the polypeptide of the invention comprises at least one Fc moiety which comprises at least one CH2 domain or portion thereof. In another embodiment, the polypeptide of the invention comprises at least one Fc moiety which comprises at least one CH3 domain or portion thereof. In another embodiment, the polypeptide of the invention comprises at least one Fc moiety which comprises at least one CH4 domain or portion thereof. In another embodiment, the polypeptide of the invention comprises at least one Fc moiety which comprises at least one hinge domain or portion thereof and at least one CH2 domain or portion thereof (e.g, in the hinge-CH2 orientation). In another embodiment, the polypeptide of the invention comprises at least one Fc moiety which comprises at least one CH2 domain or portion thereof and at least one CH3 domain or portion thereof (e.g, in the CH2-CH3 orientation). In another embodiment, the polypeptide of the invention comprises at least one Fc moiety comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, the polypeptide comprises at least one complete Fc region derived from one or more immunoglobulin heavy chains (e.g., an Fc domain including hinge, CH2, and CH3 domains, although these need not be derived from the same antibody). In other embodiments, the polypeptide comprises at least two complete Fc regions derived from one or more immunoglobulin heavy chains. In preferred embodiments, the complete Fc moiety is derived from a human IgG immunoglobulin heavy chain (e.g., human IgG1).

In another embodiment, a polypeptide of the invention comprises at least one Fc moiety comprising a complete CH3 domain (about amino acids 341-438 of an antibody Fc region according to EU numbering). In another embodiment, a polypeptide of the invention comprises at least one Fc moiety comprising a complete CH2 domain (about amino acids 231-340 of an antibody Fc region according to EU numbering). In another embodiment, a polypeptide of the invention comprises at least one Fc moiety comprising at least a CH3 domain, and at least one of a hinge region (about amino acids 216-230 of an antibody Fc region according to EU numbering), and a CH2 domain. In one embodiment, a polypeptide of the invention comprises at least one Fc moiety comprising a hinge and a CH3 domain. In another embodiment, a polypeptide of the invention comprises at least one Fc moiety comprising a hinge, a $CH_2$, and a $CH_3$ domain. In one embodiment, an Fc moiety comprises or consists of amino acids corresponding to EU numbers 221 to 447.

In preferred embodiments, the Fc moiety is derived from a human IgG immunoglobulin heavy chain (e.g., human IgG1).

In another embodiment, a polypeptide of the invention comprises at least one Fc moiety comprising an FcRn binding partner. An FcRn binding partner is a molecule or portion thereof that can be specifically bound by the FcRn receptor with consequent active transport by the FcRn receptor of the FcRn binding partner. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6 M^{-1}$, or more preferably higher than $10^8 M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

The FcRn receptor has been isolated from several mammalian species including humans. The sequences of the human FcRn, monkey FcRn rat FcRn, and mouse FcRn are known (Story et al. 1994, J. Exp. Med. 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners of the present invention encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372: 379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda, Md.

The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. As an example, one specific embodiment, incorporates the N297A mutation, removing a highly conserved N-glycosylation site. In addition to alanine other amino acids may be substituted for the wildtype amino acids at the positions specified above. Mutations may be introduced singly into Fc giving rise to more than one hundred FcRn binding partners distinct from native Fc. Additionally, combinations of two, three, or more of these individual mutations may be introduced together, giving rise to hundreds more FcRn binding partners. Moreover, one of the FcRn binding partners of a construct of the invention may be mutated and the other FcRn binding partner not mutated at all, or they both may be mutated but with different mutations. Any of the mutations described herein, including N297A, may be used to modify Fc, regardless of the biologically active molecule (e.g., EPO, IFN, Factor VII, Factor IX, T20).

Certain of the above mutations may confer new functionality upon the FcRn binding partner. For example, one embodiment incorporates N297A, removing a highly conserved N-glycosylation site. The effect of this mutation is to reduce immunogenicity, thereby enhancing circulating half life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Mutations believed to impart an increased affinity for FcRn include T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" (SEQ ID NO: 2) to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, *Therapeutic Immunology* 2:77 and Armour et al. 1999, Eur. J. Immunol. 29:2613.

In one embodiment, the FcRn binding partner is a polypeptide including the sequence PKNSSMISNTP (SEQ ID NO: 12) and optionally further including a sequence selected from HQSLGTQ (SEQ ID NO: 13), HQNLSDGK (SEQ ID NO: 14), HQNISDGK (SEQ ID NO: 24), or VISSHLGQ (SEQ ID NO: 96) (U.S. Pat. No. 5,739,277).

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the chimeric protein can be administered invasively, e.g., subcutaneously, intravenously.

The constant region domains or portions thereof making up an Fc moiety of a polypeptide of the invention may be derived from different immunoglobulin molecules. For example, a polypeptide of the invention may comprise a CH2 domain or portion thereof derived from an IgG1 molecule and a CH3 region or portion thereof derived from an IgG3 molecule. In another example, a polypeptide can comprise an Fc moiety comprising a hinge domain derived, in part, from an IgG1 molecule and, in part, from an IgG3 molecule. As set forth herein, it will be understood by one of ordinary skill in the art that an Fc moiety may be altered such that it varies in amino acid sequence from a naturally occurring antibody molecule.

In another embodiment, a polypeptide of the invention comprises an scFc region comprising one or more truncated Fc moieties that are nonetheless sufficient to confer Fc receptor (FcR) binding properties to the Fc region. For example, the portion of an Fc domain that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc moiety of a polypeptide of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In one embodiment, a polypeptide of the invention lacks one or more constant region domains of a complete Fc region, i.e., they are partially or entirely deleted. In a certain embodiments polypeptides of the invention will lack an entire CH2 domain (ΔCH2 constructs). Those skilled in the art will appreciate that such constructs may be preferred due to the regulatory properties of the CH2 domain on the catabolic rate of the antibody. In certain embodiments, polypeptides of the invention comprise CH2 domain-deleted Fc regions derived from a vector (e.g., from IDEC Pharmaceuticals, San Diego) encoding an $IgG_1$ human constant region domain (see, e.g., WO 02/060955A2 and WO02/096948A2). This exemplary vector is engineered to delete the CH2 domain and provide a synthetic vector expressing a domain-deleted $IgG_1$ constant region. It will be noted that these exemplary constructs are preferably engineered to fuse a binding CH3 domain directly to a hinge region of the respective Fc domain.

In other constructs it may be desirable to provide a spacer moiety between one or more constituent Fc moieties. For example, a spacer moiety may be placed between a hinge region and a CH2 domain and/or between a CH2 and a CH3 domains. For example, compatible constructs could be expressed wherein the CH2 domain has been deleted and the remaining CH3 domain (synthetic or unsynthetic) is joined to the hinge region with a 5-20 amino acid spacer. Such a spacer may be added, for instance, to ensure that the regulatory elements of the constant region domain remain free and accessible or that the hinge region remains flexible. Preferably, any linker peptide compatible with the instant invention will be relatively non-immunogenic and not prevent proper folding of the scFc region.

In certain embodiments, the polypeptides of the invention may comprise a dimeric Fc region comprising Fc moieties of the same, or substantially the same, sequence composition (herein termed a "homodimeric Fc region"). In other embodiments, the polypeptides of the invention may comprise a dimeric Fc region comprising at least two Fc moieties which are of different sequence composition (i.e., herein termed a "heterodimeric Fc region"). In one exemplary embodiment, the heterodimeric Fc region comprises an amino acid substitution in a first Fc moiety (e.g., an amino acid substitution of Asparagine at EU position 297), but not in a second Fc moiety.

In certain embodiments, the Fc region is hemi-glycosylated. For example, the heteromeric scFc region may comprise a first, glycosylated, Fc moiety (e.g., a glycosylated CH2 region) and a second, aglycosylated, Fc moiety (e.g., an aglycosylated CH2 region), wherein a linker is interposed between the glycosylated and aglycosylated Fc moieties. In other embodiments, the Fc region is fully glycosylated, i.e., all of the Fc moieties are glycosylated. In still further embodiments, the Fc region may be aglycosylated, i.e., none of the Fc moieties are glycosylated.

In certain embodiments, an Fc moiety employed in a polypeptide of the invention is altered, e.g., by amino acid mutation (e.g., addition, deletion, or substitution). As used herein, the term "variant Fc moiety" refers to an Fc moiety having at least one amino acid substitution as compared to the wild-type Fc from which the Fc moiety is derived. For example, wherein the Fc moiety is derived from a human IgG1 antibody, a variant comprises at least one amino acid mutation (e.g., substitution) as compared to a wild type amino acid at the corresponding position of the human IgG1 Fc region.

The amino acid substitution(s) of an Fc variant may be located at a position within the Fc moiety referred to as corresponding to the position number that that residue would be given in an Fc region in an antibody (as set forth using the EU numbering convention). One of skill in the art can readily generate alignments to determine what the EU number corresponding to a position in an Fc moiety would be.

In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

In certain embodiments, the polypeptides of the invention comprise an Fc variant comprising more than one amino acid substitution. The polypeptides of the invention may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, embodiments, the polypeptides of the invention comprise an Fc variant comprising more than one amino acid substitution. The polypeptides of the invention may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In certain embodiments, the Fc variant confers a change in at least one effector function imparted by an Fc region comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue The polypeptides of the invention may employ art-recognized Fc variants which are known to impart a change (e.g., an enhancement or reduction) in effector function and/or FcR or FcRn binding. Specifically, a binding molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

In certain embodiments, a polypeptide of the invention comprises an amino acid substitution to an Fc moiety which alters the antigen-independent effector functions of the antibody, in particular the circulating half-life of the antibody.

Such polypeptides exhibit either increased or decreased binding to FcRn when compared to polypeptides lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder (see, e.g, U.S. Pat. Nos. 7,348,004, 7,404,956, and 7,862,820). In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the polypeptides of the invention exhibit reduced transport across the epithelium of kidney glomeruli from the vasculature. In another embodiment, the polypeptides of the invention exhibit reduced transport across the blood brain barrier (BBB) from the brain, into the vascular space. In one embodiment, a polypeptide with altered FcRn binding comprises at least one Fc moiety (e.g, one or two Fc moieties) having one or more amino acid substitutions within the "FcRn binding loop" of an Fc moiety. The FcRn binding loop is comprised of amino acid residues 280-299 (according to EU numbering) of a wild-type, full-length, Fc moiety. In other embodiments, a polypeptide of the invention having altered FcRn binding affinity comprises at least one Fc moiety (e.g, one or two Fc moieties) having one or more amino acid substitutions within the 15 Å FcRn "contact zone." As used herein, the term 15 Å FcRn "contact zone" includes residues at the following positions of a wild-type, full-length Fc moiety: 243-261, 275-280, 282-293, 302-319, 336-348, 367, 369, 372-389, 391, 393, 408, 424, 425-440 (EU numbering). In preferred embodiments, a polypeptide of the invention having altered FcRn binding affinity comprises at least one Fc moiety (e.g, one or two Fc moieties) having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered FcRn binding activity are disclosed in International PCT Publication No. WO05/047327 which is incorporated by reference herein.

A polypeptide of the invention may also comprise an art recognized amino acid substitution which alters the glycosylation of the polypeptide. For example, the scFc region of the binding polypeptide may comprise an Fc moiety having a mutation leading to reduced glycosylation (e.g., N- or O-linked glycosylation) or may comprise an altered glycoform of the wild-type Fc moiety (e.g., a low fucose or fucose-free glycan).

In other embodiments, a polypeptide of the invention comprises at least one Fc moiety having engineered cysteine residue or analog thereof which is located at the solvent-exposed surface. Preferably the engineered cysteine residue or analog thereof does not interfere with an effector function conferred by the scFc region. More preferably, the alteration does not interfere with the ability of the scFc region to bind to Fc receptors (e.g. FcγRI, FcγRII, or FcγRIII) or complement proteins (e.g. C1q), or to trigger immune effector function (e.g., antibody-dependent cytotoxicity (ADCC), phagocytosis, or complement-dependent cytotoxicity (CDCC)).

In one embodiment, an unprocessed polypeptide of the invention may comprise a genetically fused Fc region (i.e., scFc region) having two or more of its constituent Fc moieties independently selected from the Fc moieties described herein. In one embodiment, the Fc moieties of a dimeric Fc region are the same. In another embodiment, at least two of the Fc moieties are different. For example, the Fc moieties of the polypeptides of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc moieties of the polypeptides of the invention may differ in sequence at one or more amino acid positions. For example, at least two of the Fc moieties may differ at about 5 amino acid positions (e.g., 1, 2, 3, 4, or 5 amino acid positions), about 10 positions, about 15 positions, about 20 positions, about 30 positions, about 40 positions, or about 50 positions).

B. Polypeptide Linkers

The genetic constructs of the instant invention encode polypeptides comprising two or more Fc domains or moieties linked via a cscFc linker to form an Fc region comprised in a single polypeptide chain. The cscFc linker is flanked by at least one enzymatic cleavage site, e.g., a site for processing by an intracellular enzyme. Cleavage of the polypeptide at the at least one enzymatic cleavage site results in a polypeptide which comprises at least two polypeptide chains. These linkers are referred to herein as "cscFc linkers" and the cscFc linker is interposed between the two Fc moieties of a polypeptide which comprises it. If the cscFc linker connects two Fc moieties contiguously in the linear polypeptide sequence, it is a "direct" linkage. In contract, the cscFc linkers may link the first Fc moiety to a binding moiety which is, in turn, linked to the second Fc moiety, thereby forming an indirect linkage.

As is set forth above, other polypeptide linkers may optionally be used in a construct of the invention, e.g., to connect a biologically active moiety to an Fc moiety. These polypeptide linkers are referred to here as spacers. Some exemplary locations of spacers that can be used in connection with the invention include, e.g., polypeptides comprising GlySer amino acids such as those set forth in the accompanying figures and described in more detail below.

In one embodiment, the polypeptide linker is synthetic, i.e., non-naturally occurring. In one embodiment, a polypeptide linker includes peptides (or polypeptides) (which may or may not be naturally occurring) which comprise an amino acid sequence that links or genetically fuses a first linear sequence of amino acids to a second linear sequence of amino acids to which it is not naturally linked or genetically fused in nature. For example, in one embodiment the polypeptide linker may comprise non-naturally occurring polypeptides which are modified forms of naturally occurring polypeptides (e.g., comprising a mutation such as an addition, substitution or deletion). In another embodiment, the polypeptide linker may comprise non-naturally occurring amino acids. In another embodiment, the polypeptide linker may comprise naturally occurring amino acids occurring in a linear sequence that does not occur in nature. In still another embodiment, the polypeptide linker may comprise a naturally occurring polypeptide sequence.

In certain embodiments, a polypeptide linker can be used to fuse identical Fc moieties, thereby forming a homomeric scFc region. In other embodiments, a polypeptide linker can be used to fuse different Fc moieties (e.g. a wild-type Fc moiety and an Fc moiety variant), thereby forming a heteromeric scFc region.

In another embodiment, a polypeptide linker comprises or consists of a gly-ser linker. In one embodiment, a cscFc linker comprises at least a portion of an immunoglobulin hinge and a gly-ser linker. As used herein, the term "gly-ser linker" refers to a peptide that consists of glycine and serine residues. An exemplary gly/ser linker comprises an amino acid sequence of the formula (Gly$_4$Ser)n (SEQ ID NO: 4), wherein is a positive integer (e.g., 1, 2, 3, 4, 5, 6, 7, 8, 9, or 10). A preferred gly/ser linker is (Gly$_4$Ser)$_2$ (SEQ ID NO:29), (Gly$_4$Ser)$_4$ (SEQ ID NO:6), or (Gly$_4$Ser)$_6$. (SEQ ID NO: 5) Another exemplary gly-ser linker is GGGSSGGGSG (SEQ ID NO: 30). In certain embodiments, said gly-ser linker may be inserted between two other sequences of the polypeptide linker (e.g., any of the polypeptide linker sequences described herein). In other embodiments, a gly-ser linker is attached at one or both ends of another sequence of the polypeptide linker (e.g., any of the polypeptide linker sequences described herein). In yet other embodiments, two or more gly-ser linkers are incorporated in series in a polypeptide linker. In one embodiment, a polypeptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule)

and a series of gly/ser amino acid residues (e.g., a gly/ser linker such as (Gly₄Ser)n) (SEQ ID NO:4)).

Polypeptide linkers of the invention are at least one amino acid in length and can be of varying lengths. In one embodiment, a polypeptide linker of the invention is from about 1 to about 50 amino acids in length. As used in this context, the term "about" indicates +/−two amino acid residues. Since linker length must be a positive integer, the length of from about 1 to about 50 amino acids in length, means a length of from 1-3 to 48-52 amino acids in length. In another embodiment, a polypeptide linker of the invention is from about 10-20 amino acids in length. In another embodiment, a polypeptide linker of the invention is from about 15 to about 50 amino acids in length. In another embodiment, a polypeptide linker of the invention is from about 20 to about 45 amino acids in length. In another embodiment, a polypeptide linker of the invention is from about 15 to about 35 or about 20 to about 30 amino acids in length. In another embodiment, a polypeptide linker of the invention is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 amino acids in length.

In one embodiment, a peptide linker of the invention is 20 or 30 amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

C. Enzymatic Cleavage Sites

In one embodiment, one or more enzymatic cleavage site(s) flanks, i.e., is adjacent to (upstream or downstream of) a cscFc linker (L) of an unprocessed polypeptide of the invention forming a cleavable scFc linker. For example, in one embodiment of a construct encoding a polypeptide of the invention, a cleavage site is fused at one or both ends of an cscFc linker (L). For example, in one embodiment, the polypeptide is represented by the formula:

A-F1-P1-L-P2-B-F2       (I)

in linear sequence from the amino to carboxy terminus wherein A is a biologically active moiety, F1 is a first Fc moiety or domain, P1 is an enzymatic cleavage site, L is an cscFc linker, P2 is an enzymatic cleavage site B is a biologically active moiety, F2 is a second Fc moiety or domain and "—" represents a peptide bond. Formula (I) comprises at least an A or B and optionally both. A and B, if both present, can be the same or different. Formula (I) comprises at least one of P1 or P2 and optionally both. P1 and P2, if both present, can be the same or different. Formula (I) comprises at least a F1 and F2. F1 and F2, if both present, can be the same or different. In one embodiment, P 1 and P2 are both present and are recognized by the same or by different enzymes.

In one embodiment, one or both of the enzymatic cleavage sites is an intracellular processing site recognized by a member of the furin family of enzymes, e.g., furin, PC2, PC1/PC3, PC4, PACE4, PC5/PC6, and LPC/PC7/PC8/SPC7. Exemplary cleavage sites for this family of enzymes include an amino acid sequence comprising the motif Arg-Xaa-Lys/Arg-Arg(SEQ ID NO:34). Other cleavage sites are known in the art.

In another embodiment, a Factor XIa or Xa cleavage site may be incorporated into a construct of the invention. Exemplary FXIa cleavage sites include, e.g, TQSFNDFTR (SEQ ID NO: 7) and SVSQTSKLTR (SEQ ID NO: 8). Exemplary thrombin cleavage sites include, e.g, DFLAE-GGGVR (SEQ ID NO: 9), TTKIKPR (SEQ ID NO: 10), LVPRG (SEQ ID NO:35) and a sequence comprising or consisting of ALRPR (SEQ ID NO: 94) (e.g. ALRPRVVGGA (SEQ ID NO: 11)).

In one embodiment, an scFc linker is cleaved at one site (e.g., when P1 is present). In another embodiment, an scFc linker is cleaved at two sites (e.g., when P1 and P2 are present). In one embodiment, some portion of the linker may remain after cleavage at the at least one enzymatic cleavage site. In order to minimize the presence of extraneous amino acid sequences, two cleavage sites may be included in a polypeptide of the invention. In some embodiments, all or substantially all of the linker is excised, while in some embodiments, a portion of the cleavage site may remain, e.g., four arginines of the RRRR (SEQ ID NO: 40) cleavage site.

D. Biologically Active Moieties

The polypeptides of the invention comprise at least one biologically active moiety. Such a moiety can be biologically active as a single chain, or may require association with another polypeptide chain (e.g., by dimerization), or may need to be enzymatically cleaved to impart biological activity.

The polypeptides of the invention can comprise only one biologically active moiety (creating a molecule which is monovalent with regard to the biologically active moiety, but which is multimeric (e.g., dimeric) with regard to the number of polypeptide chains present after processing or cleavage). Examples of such molecules are shown in U.S. Pat. No. 7,404,956, which is incorporated in its entirety by reference.

In one embodiment, a biologically active moiety is operably linked (e.g. via a polypeptide linker) or directly by a peptide bond to the C-terminus and/or N terminus of an Fc moiety. In certain embodiments, the polypeptides of the invention may comprise two or more biologically active moieties. In one embodiment, the biologically active moieties are identical. In another embodiment, the biologically active moieties are different or are each separate subunits or chains of one functional molecule.

In certain aspects, a polypeptide of the invention comprises more than one biologically active moiety and is multivalent, i.e., has at least one biologically active moiety having a first biological activity and at least one second biologically active moiety having a second biological activity. In certain embodiments, at least one biologically active moiety of the invention is an antigen binding region of an antibody or an antigen binding fragment thereof (e.g. an antibody or antigen binding fragment described supra).

In other embodiments, two or more same or different biologically active moieties are linked to each other (e.g., via a polypeptide linker) in series, and the tandem array of biologically active moieties is operably linked (e.g., chemically conjugated or genetically fused (e.g., either directly or via a polypeptide linker)) to either the C-terminus or the N-terminus of a single genetically-fused Fc region (i.e., a single scFc region) or a tandem array of genetically-fused Fc regions (i.e., tandem scFc regions). In other embodiments, the tandem array of biologically active moieties is operably linked to both the C-terminus and the N-terminus of a single genetically-fused Fc region or a tandem array of genetically-fused Fc regions.

In one embodiment, a polypeptide of the invention comprises at least one of a biologically active moiety that is an antigen binding site (e.g., an antigen binding site of an antibody, antibody variant, or antibody fragment), a receptor binding portion of ligand, or a ligand binding portion of a receptor.

In one embodiment, the biologically active moiety modulates cellular activation or inhibition (e.g., by binding to a cell surface receptor and resulting in transmission of an activating or inhibitory signal). In one embodiment, the biologically active moiety is capable of initiating transduction of a signal which results in death of the cell (e.g., by a cell signal induced pathway, by complement fixation or exposure to a payload (e.g., a toxic payload) present on the binding molecule), or which modulates a disease or disorder in a subject (e.g., by mediating or promoting cell killing, by promoting lysis of a fibrin clot or promoting clot formation, or by modulating the amount of a substance which is bioavailable (e.g., by enhancing or reducing the amount of a ligand such as TNFα in the subject)). In another embodiment, the polypeptides of the invention have at least one binding site specific for an antigen targeted for reduction or elimination, e.g., a cell surface antigen or a soluble antigen, together with at least one genetically-fused Fc region (i.e., scFc region).

In another embodiment, binding of a biologically active moiety of the invention to a target molecule (e.g. antigen) results in the reduction or elimination of the target molecule or a cell expressing the target molecule, e.g., from a tissue or from circulation. In another embodiment, the a biologically active moiety has at least one binding site specific for a target molecule that can be used to detect the presence of the target molecule (e.g., to detect a contaminant or diagnose a condition or disorder). Exemplary biologically active moieties are discussed further below.

i. Antigen Binding Portions

In certain embodiments, a polypeptide of the invention comprises at least one biologically active moiety which is a binding site, e.g, an antigen binding portion of an antibody.

In other embodiments, a binding site of a polypeptide of the invention may comprise an antigen binding portion of an antibody. The term "antigen-binding portion" refers to a polypeptide fragment of an immunoglobulin, antibody, or antibody variant which binds antigen or competes with intact antibody (i.e., with the intact antibody from which they were derived) for antigen binding (i.e., specific binding). For example, said antigen binding portions can be derived from any of the antibodies or antibody variants known in the art. Antigen binding portions can be produced by recombinant or biochemical methods that are well known in the art. Exemplary antigen-binding fragments include VH and VL regions, Fv, Fab, Fab', and (Fab')$_2$.

In exemplary embodiments, a genetic construct encoding a polypeptide of the invention comprises a nucleotide sequence encoding at least one antigen binding fragment that is operably linked (e.g., chemically conjugated or genetically-fused (e.g., directly fused or fused via a polypeptide linker)) to the C-terminus and/or N-terminus of a genetically-fused Fc region (i.e., a scFc region). In one exemplary embodiment, an immature polypeptide of the invention comprises an antigen binding fragment (e.g, a Fab) which is operably linked to the N-terminus (or C-terminus) of at least one genetically-fused Fc region via a hinge domain or portion thereof (e.g., an IgG1 hinge or portion thereof, e.g., a human IgG1 hinge). An exemplary hinge domain portion comprises the sequence DKTHTCPPCPAPELLGG (SEQ ID NO: 28).

In other embodiments, a biologically active moiety of the invention may comprise a binding site from a single chain binding molecule (e.g., a singe chain variable region or scFv). Techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain molecules. Single chain antibodies are formed by linking the heavy and light chain fragments of the Fv region via an amino acid bridge, resulting in a single chain antibody. Techniques for the assembly of functional Fv fragments in *E. coli* may also be used (Skerra et al., *Science* 242:1038-1041 (1988)).

Single chain variable region sequences comprise a single polypeptide having one or more antigen binding sites, e.g., a $V_L$ domain linked by a flexible linker to a $V_H$ domain. The VL and/or VH domains may be derived from any of the antibodies or antibody variants described supra. ScFv molecules can be constructed in a $V_H$-linker-$V_L$ orientation or $V_L$-linker-$V_H$ orientation. The flexible linker that links the $V_L$ and $V_H$ domains that make up the antigen binding site preferably comprises from about 10 to about 50 amino acid residues. In one embodiment, the polypeptide linker is a gly-ser polypeptide linker. An exemplary gly/ser polypeptide linker is of the formula (Gly$_4$Ser)n (SEQ ID NO:4), wherein n is a positive integer (e.g., 1, 2, 3, 4, 5, or 6). Other polypeptide linkers are known in the art. Antibodies having single chain variable region sequences (e.g. single chain Fv antibodies) and methods of making said single chain antibodies are well-known in the art (see e.g., Ho et al. 1989. Gene 77:51; Bird et al. 1988 Science 242:423; Pantoliano et al. 1991. Biochemistry 30:10117; Milenic et al. 1991. Cancer Research 51:6363; Takkinen et al. 1991. Protein Engineering 4:837).

In certain embodiments, a scFv molecule employed in a polypeptide of the invention is a stabilized scFv molecule. In one embodiment, the stabilized cFv molecule may comprise a scFv linker interposed between a $V_H$ domain and a $V_L$ domain, wherein the $V_H$ and $V_L$ domains are linked by a disulfide bond between an amino acid in the $V_H$ and an amino acid in the $V_L$ domain. In other embodiments, the stabilized scFv molecule may comprise a scFv linker having an optimized length or composition. In yet other embodiments, the stabilized scFv molecule may comprise a $V_H$ or $V_L$ domain having at least one stabilizing amino acid substitution(s). In yet another embodiment, a stabilized scFv molecule may have at least two of the above listed stabilizing features.

Stabilized scFv molecules have improved protein stability or impart improved protein stability to the polypeptide to which they are operably linked. Preferred scFv linkers of the invention improve the thermal stability of a polypeptide of the invention by at least about 2° C. or 3° C. as compared to a conventional polypeptide. Comparisons can be made, for example, between the scFv molecules of the invention. In certain preferred embodiments, the stabilized scFv molecule comprises a (Gly$_4$Ser)$_4$ (SEQ ID NO: 6) scFv linker and a disulfide bond which links $V_H$ amino acid 44 and $V_L$ amino acid 100. Other exemplary stabilized scFv molecules which may be employed in the polypeptides of the invention are described in U.S. Provisional Patent Application No. 60/873,996, filed on Dec. 8, 2006 or U.S. patent application Ser. No. 11/725,970, filed on Mar. 19, 2007, each of which is incorporated herein by reference in its entirety.

In certain exemplary embodiments, the polypeptides of the invention comprise at least one scFv molecule that is operably linked (e.g., chemically conjugated or genetically-fused (e.g., directly fused or fused via a polypeptide linker) to the C-terminus and/or N-terminus of a genetically-fused Fc region (i.e., a scFc region). In one exemplary embodiment, a polypeptide of the invention comprises at least one scFv molecule (e.g, one or more stabilized scFv molecules) which are operably linked to the N-terminus (or C-terminus) of at least one genetically-fused Fc region via a gly/ser linker.

Polypeptides of the invention may comprise a variable region or portion thereof (e.g. a VL and/or VH domain) derived from an antibody using art recognized protocols or may be obtained from an art-recognized antibody using standard molecular biology techniques.

Those skilled in the art will also appreciate that DNA encoding antibody variable domains may also be derived from antibody libraries expressed in phage, yeast, or bacteria using methods known in the art. Exemplary methods are set forth, for example, in EP 368 684 B1; U.S. Pat. No. 5,969,108; Hoogenboom et al., (2000) Immunol. Today 21:371; Nagy et al. (2002) Nat. Med. 8:801; Huie et al. (2001), PNAS, 98:2682; Lui et al. (2002), J. Mol. Biol. 315:1063, each of which is incorporated herein by reference. Several publications (e.g., Marks et al. (1992), Bio/Technology 10:779-783) have described the production of high affinity human antibodies by chain shuffling, as well as combinatorial infection and in vivo recombination as a strategy for constructing large phage libraries. In another embodiment, ribosomal display can be used to replace bacteriophage as the display platform (see, e.g., Hanes, et al. (1998), PNAS 95:14130; Hanes and Pluckthun. (1999), Curr. Top. Microbiol. Immunol. 243:107; He and Taussig. (1997), Nuc. Acids Res., 25:5132; Hanes et al. (2000), Nat. Biotechnol. 18:1287; Wilson et al. (2001), PNAS, 98:3750; or Irving et al. (2001) J. Immunol. Methods 248:31).

Moreover, variable region sequences useful for producing the biologically active moieties of the present invention may be obtained from a number of different sources. For example, as discussed above, a variety of human gene sequences are available in the form of publicly accessible deposits. Many sequences of antibodies and antibody-encoding genes have been published and suitable variable region sequences (e.g. VL and VH sequences) can be chemically synthesized from these sequences using art recognized techniques.

Further, a biologically active moiety of the invention may comprise a variable domain or CDR derived from a fully murine, fully human, chimeric, humanized, deimmunized, non-human primate or primatized antibody.

Exemplary antibodies from which binding sites can be derived for use in the molecules of the invention are known in the art. For example, antibodies currently approved by the FDA can be used to derive binding sites.

In one embodiment, a polypeptide of the invention binds to a molecule which is useful in treating cancer.

In still other embodiments, a biologically active moiety of the invention binds to a molecule which is useful in treating an autoimmune or inflammatory disease or disorder.

For example, a polypeptide may bind to an antigen present on an immune cell (e.g., a B or T cell) or an autoantigen responsible for an autoimmune disease or disorder. The antigen associated with an autoimmune or inflammatory disorder may be a tumor-associated antigen described supra. Thus, a tumor associated antigen may also be an autoimmune or inflammatory associated disorder. As used herein, the term "autoimmune disease or disorder" refers to disorders or conditions in a subject wherein the immune system attacks the body's own cells, causing tissue destruction. Autoimmune diseases include general autoimmune diseases, i.e., in which the autoimmune reaction takes place simultaneously in a number of tissues, or organ specific autoimmune diseases, i.e., in which the autoimmune reaction targets a single organ. Examples of autoimmune diseases that can be diagnosed, prevented or treated by the methods and compositions of the present invention include, but are not limited to, Crohn's disease; Inflammatory bowel disease (IBD); systemic lupus erythematosus; ulcerative colitis; rheumatoid arthritis; Goodpasture's syndrome; Grave's disease; Hashimoto's thyroiditis; pemphigus vulgaris; myasthenia gravis; scleroderma; autoimmune hemolytic anemia; autoimmune thrombocytopenic purpura; polymyositis and dermatomyositis; pernicious anemia; Sjögren's syndrome; ankylosing spondylitis; vasculitis; type I diabetes mellitus; neurological disorders, multiple sclerosis, and secondary diseases caused as a result of autoimmune diseases.

In other embodiments, a biologically active moiety of the invention that binds to a target molecule associated with an inflammatory disease or disorder. As used herein the term "inflammatory disease or disorder" includes diseases or disorders which are caused, at least in part, or exacerbated by inflammation, e.g., increased blood flow, edema, activation of immune cells (e.g., proliferation, cytokine production, or enhanced phagocytosis). For example, a polypeptide of the invention may bind to an inflammatory factor (e.g., a matrix metalloproteinase (MMP), TNFα, an interleukin, a plasma protein, a cytokine, a lipid metabolite, a protease, a toxic radical, a mitochondrial protein, an apoptotic protein, an adhesion molecule, etc.) involved or present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, e.g., lasting only a few days. If it is longer lasting however, then it may be referred to as chronic inflammation.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or even longer, and are associated histologically with the presence of lymphocytes and macrophages and with proliferation of blood vessels and connective tissue. Recurrent inflammatory disorders include disorders which recur after a period of time or which have periodic episodes. Examples of recurrent inflammatory disorders include asthma and multiple sclerosis. Some disorders may fall within one or more categories. Inflammatory disorders are generally characterized by heat, redness, swelling, pain and loss of function. Examples of causes of inflammatory disorders include, but are not limited to, microbial infections (e.g., bacterial, viral and fungal infections), physical agents (e.g., burns, radiation, and trauma), chemical agents (e.g., toxins and caustic substances), tissue necrosis and various types of immunologic reactions. Examples of inflammatory disorders include, but are not limited to, osteoarthritis, rheumatoid arthritis, acute and chronic infections (bacterial, viral and fungal); acute and chronic bronchitis, sinusitis, and other respiratory infections, including the common cold; acute and chronic gastroenteritis and colitis; acute and chronic cystitis and urethritis; acute respiratory distress syndrome; cystic fibrosis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; and burns (thermal, chemical, and electrical).

In yet other embodiments, a biologically active moiety of the invention binds to a molecule which is useful in treating a neurological disease or disorder. For example, a polypeptide may bind to an antigen present on a neural cell (e.g., a neuron, a glial cell, or a). In certain embodiments, the antigen associated with a neurological disorder may be an autoimmune or inflammatory disorder described supra. As used herein, the term "neurological disease or disorder" includes disorders or conditions in a subject wherein the nervous system either degenerates (e.g., neurodegenerative disorders, as well as disorders where the nervous system fails to develop properly or fails to regenerate following injury, e.g., spinal cord injury. Examples of neurological disorders that can be diagnosed, prevented or treated by the methods and compositions of the present invention include, but are not limited to, Multiple Sclerosis, Huntington's Disease, Alzheimer's Disease, Parkinson's Disease, neuropathic pain, traumatic brain injury, Guillain-Barré syndrome and chronic inflammatory demyelinating polyneuropathy (CIDP).

In other aspects, the biologically active moieties of the invention may comprise antigen binding sites, or portions thereof, derived from modified forms of antibodies. Exemplary such forms include, e.g., minibodies, diabodies, triabodies, nanobodies, camelids, Dabs, tetravalent antibodies, intradiabodies (e.g., Jendreyko et al. 2003. J. Biol. Chem. 278:47813), fusion proteins (e.g., antibody cytokine fusion proteins, proteins fused to at least a portion of an Fc receptor), and bispecific antibodies. Other modified antibodies are described, for example in U.S. Pat. No. 4,745,055; EP 256,654; Faulkner et al., Nature 298:286 (1982); EP 120, 694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229: 1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In another embodiment, a biologically active moiety of the invention comprises an antigen binding site or region which is a diabody or an antigen binding site derived therefrom. Diabodies are dimeric, tetravalent molecules each having a polypeptide similar to scFv molecules, but usually having a short (e.g., less than 10 and preferably 1-5) amino acid residue linker connecting both variable domains, such that the $V_L$ and $V_H$ domains on the same polypeptide chain cannot interact. Instead, the $V_L$ and $V_H$ domain of one polypeptide chain interact with the $V_H$ and $V_L$ domain (respectively) on a second polypeptide chain (see, for example, WO 02/02781). In one embodiment, an immature polypeptide of the invention comprises a diabody which is operably linked to the N-terminus and/or C-terminus of at least one genetically-fused Fc region (i.e., scFc region).

In certain embodiments, a biologically active moiety of the invention comprises a single domain binding molecule (e.g. a single domain antibody) linked to an scFc. Exemplary single domain molecules include an isolated heavy chain variable domain ($V_H$) of an antibody, i.e., a heavy chain variable domain, without a light chain variable domain, and an isolated light chain variable domain ($V_L$) of an antibody, i.e., a light chain variable domain, without a heavy chain variable domain. Exemplary single-domain antibodies employed in the molecules of the invention include, for example, the Camelid heavy chain variable domain (about 118 to 136 amino acid residues) as described in Hamers-Casterman, et al., Nature 363:446-448 (1993), and Dumoulin, et al., Protein Science 11:500-515 (2002). Other exemplary single domain antibodies include single VH or VL domains, also known as Dabs® (Domantis Ltd., Cambridge, UK). Yet other single domain antibodies include shark antibodies (e.g., shark Ig-NARs). Shark Ig-NARs comprise a homodimer of one variable domain (V-NAR) and five C-like constant domains (C-NAR), wherein diversity is concentrated in an elongated CDR3 region varying from 5 to 23 residues in length. In camelid species (e.g., llamas), the heavy chain variable region, referred to as VHH, forms the entire antigen-binding domain. The main differences between camelid VHH variable regions and those derived from conventional antibodies (VH) include (a) more hydrophobic amino acids in the light chain contact surface of VH as compared to the corresponding region in VHH, (b) a longer CDR3 in VHH, and (c) the frequent occurrence of a disulfide bond between CDR1 and CDR3 in VHH. Methods for making single domain molecules are described in U.S. Pat. Nos. 6,005,079 and 6,765,087, both of which are incorporated herein by reference. Exemplary single domain antibodies comprising VHH domains include Nanobodies® (Ablynx Nev., Ghent, Belgium).

In one embodiment, biologically active moiety comprises an antigen binding portion of an antibody that binds to a TNF receptor family member. The nucleotide and amino acid sequences of several TNF receptors family members are known in the art and include at least 29 human genes: TNFRSF1A (TNFR1, also known as DR1, CD120a, TNF-R-I p55, TNF-R, TNFRI, TNFAR, TNF-R55, p55TNFR, p55R, or TNFR60, GenBank GI No. 4507575; see also U.S. Pat. No. 5,395,760)), TNFRSF1B (CD120b, also known as p'75, TNF-R, TNF-R-II, TNFR80, TNFR2, TNF-R75, TNFBR, or p75TNFR; GenBank GI No. 4507577), TNFRSF3 (Lymphotoxin Beta Receptor (LTβ), also known as TNFR2-RP, CD18, TNFR-RP, TNFCR, or TNF-R-III; GI Nos. 4505038 and 20072212), TNFRSF4 (OX40, also known as ACT35, TXGP1L, or CD134 antigen; GI Nos. 4507579 and 8926702), TNFRSF5 (CD40, also known as p50 or Bp50; GI Nos. 4507581 and 23312371), TNFRSF6 (FAS, also known as FAS-R, DcR-2, DR2, CD95, APO-1, or APT1; GenBank GI Nos. 4507583, 23510421, 23510423, 23510425, 23510427, 23510429, 23510431, and 23510434)), TNFRSF6B (DcR3, DR3; GenBank GI Nos. 4507569, 23200021, 23200023, 23200025, 23200027, 23200029, 23200031, 23200033, 23200035, 23200037, and 23200039), TNFRSF7 (CD27, also known as Tp55 or S152; GenBank GI No. 4507587), TNFRSF8 (CD30, also known as Ki-1, or D1S166E; GenBank GI Nos. 4507589 and 23510437), TNFRSF9 (4-1-BB, also known as CD137 or ILA; GI Nos. 5730095 and 728738), TNFRSF10A (TRAIL-R1, also known as DR4 or Apo2; GenBank GI No. 21361086), TNFRSF10B (TRAIL-R2, also known as DR5, KILLER, TRICK2A, or TRICKB; GenBank GI Nos. 22547116 and 22547119), TNFRSF10C (TRAIL-R3, also known as DcR1, LIT, or TRID; GenBank GI No. 22547121), TNFRSF10D (TRAIL-R4, also known as DcR2 or TRUNDD), TNFRSF11A (RANK; GenBank GI No. 4507565; see U.S. Pat. Nos. 6,562,948; 6,537,763; 6,528, 482; 6,479,635; 6,271,349; 6,017,729), TNFRSF11B (Osteoprotegerin (OPG), also known as OCIF or TR1; GI Nos.

38530116, 22547122 and 33878056), TNFRSF12 (Translocating chain-Association Membrane Protein (TRAMP), also known as DR3, WSL-1, LARD, WSL-LR, DDR3, TR3, APO-3, Fn14, or TWEAKR; GenBank GI No. 7706186; US Patent Application Publication No. 2004/0033225A1), TNFRSF12L (DR3L), TNFRSF13B (TACI; GI No. 6912694), TNFRSF13C (BAFFR; GI No. 16445027), TNFRSF14 (Herpes Virus Entry Mediator (HVEM), also known as ATAR, TR2, LIGHTR, or HVEA; GenBank GI Nos. 23200041, 12803895, and 3878821), TNFRSF16 (Low-Affinity Nerve Growth Factor Receptor (LNGFR), also known as Neurotrophin Receptor or p75(NTR); GenBank GI Nos. 128156 and 4505393), TNFRSF17 (BCM, also known as BCMA; GI No. 23238192), TNFRSF18 (AITR, also known as GITR; GenBank GI Nos. 4759246, 23238194 and 23238197), TNFRSF19 (Troy/Trade, also known as TAJ; GenBank GI Nos. 23238202 and 23238204), TNFRSF20 (RELT, also known as FLJ14993; GI Nos. 21361873 and 23238200), TNFRSF21 (DR6), TNFRSF22 (SOBa, also known as Tnfrh2 or 2810028K06Rik), and TNFRSF23 (mSOB, also known as Tnfrh1). Other TNF family members include EDAR1 (Ectodysplasin A Receptor, also known as Downless (DL), ED3, ED5, ED1R, EDA3, EDA1R, EDA-A1R; GenBank GI No. 11641231; U.S. Pat. No. 6,355,782), XEDAR (also known as EDA-A2R; GenBank GI No. 11140823); and CD39 (GI Nos. 2135580 and 765256).

ii. Non-Immunoglobulin Binding Molecules

In certain other embodiments, a biologically active moiety of the invention comprises one or more binding sites derived from a non-immunoglobulin binding molecule. As used herein, the term "non-immunoglobulin binding molecules" are binding molecules whose binding sites comprise a portion (e.g., a scaffold or framework) which is derived from a polypeptide other than an immunoglobulin, but which may be engineered (e.g., mutagenized) to confer a desired binding specificity.

Other examples of biologically active moieties not derived from antibody molecules include receptor binding sites and ligand binding sites which are discussed in more detail infra.

Non-immunoglobulin biologically active moieties can comprise binding site portions that are derived from a member of the immunoglobulin superfamily that is not an immunoglobulin (e.g. a T-cell receptor or a cell-adhesion protein (e.g., CTLA-4, N-CAM, telokin)). Such binding molecules comprise a binding site portion which retains the conformation of an immunoglobulin fold and is capable of specifically binding an IGF1-R epitope. In other embodiments, non-immunoglobulin binding molecules of the invention also comprise a binding site with a protein topology that is not based on the immunoglobulin fold (e.g. such as ankyrin repeat proteins or fibronectins) but which nonetheless are capable of specifically binding to a target (e.g. an IGF-1R epitope).

Non-immunoglobulin biologically active moieties may be identified by selection or isolation of a target-binding variant from a library of binding molecules having artificially diversified binding sites. Diversified libraries can be generated using completely random approaches (e.g., error-prone PCR, exon shuffling, or directed evolution) or aided by art-recognized design strategies. For example, amino acid positions that are usually involved when the binding site interacts with its cognate target molecule can be randomized by insertion of degenerate codons, trinucleotides, random peptides, or entire loops at corresponding positions within the nucleic acid which encodes the binding site (see e.g., U.S. Pub. No. 20040132028). The location of the amino acid positions can be identified by investigation of the crystal structure of the binding site in complex with the target molecule. Candidate positions for randomization include loops, flat surfaces, helices, and binding cavities of the binding site. In certain embodiments, amino acids within the binding site that are likely candidates for diversification can be identified by their homology with the immunoglobulin fold. For example, residues within the CDR-like loops of fibronectin may be randomized to generate a library of fibronectin binding molecules (see, e.g., Koide et al., J. Mol. Biol., 284: 1141-1151 (1998)). Other portions of the binding site which may be randomized include flat surfaces. Following randomization, the diversified library may then be subjected to a selection or screening procedure to obtain binding molecules with the desired binding characteristics, e.g. specific binding to an IGF-1R epitope described supra. For example, selection can be achieved by art-recognized methods such as phage display, yeast display, or ribosome display.

In one embodiment, a biologically active moiety is derived from a fibronectin binding molecule. Fibronectin binding molecules (e.g., molecules comprising the Fibronectin type I, II, or III domains) display CDR-like loops which, in contrast to immunoglobulins, do not rely on intra-chain disulfide bonds. Methods for making fibronectin polypeptides are described, for example, in WO 01/64942 and in U.S. Pat. Nos. 6,673,901, 6,703,199, 7,078,490, and 7,119,171, which are incorporated herein by reference. In one exemplary embodiment, the fibronectin polypeptide is as AdNectin® (Adnexus Therapeutics, Waltham, Mass.).

In another embodiment, a biologically active moiety of the invention comprises a binding site from an Affibody® (Abcam, Cambridge, Mass.). Affibodies are derived from the immunoglobulin binding domains of staphylococcal Protein A (SPA) (see e.g., Nord et al., Nat. Biotechnol., 15: 772-777 (1997)). Affibody binding sites employed in the invention may be synthesized by mutagenizing an SPA-related protein (e.g., Protein Z) derived from a domain of SPA (e.g., domain B) and selecting for mutant SPA-related polypeptides having binding affinity for an IGF-1R epitope. Other methods for making affibody binding sites are described in U.S. Pat. Nos. 6,740,734 and 6,602,977 and in WO 00/63243, each of which is incorporated herein by reference.

In another embodiment, a biologically active moiety of the invention comprises a binding site from an Anticalin® (Pieris AG, Friesing, Germany). Anticalins (also known as lipocalins) are members of a diverse β-barrel protein family whose function is to bind target molecules in their barrel/loop region. Lipocalin binding sites may be engineered to bind an IGF-1R epitope by randomizing loop sequences connecting the strands of the barrel (see e.g., Schlehuber et al., Drug Discov. Today, 10: 23-33 (2005); Beste et al., PNAS, 96: 1898-1903 (1999). Anticalin binding sites employed in the binding molecules of the invention may be obtainable starting from polypeptides of the lipocalin family which are mutated in four segments that correspond to the sequence positions of the linear polypeptide sequence comprising amino acid positions 28 to 45, 58 to 69, 86 to 99 and 114 to 129 of the Bilin-binding protein (BBP) of *Pieris brassica*. Other methods for making anticalin binding sites are described in WO99/16873 and WO 05/019254, each of which is incorporated herein by reference.

In another embodiment, a biologically active moiety of the invention comprises a binding site from a cysteine-rich polypeptide. Cysteine-rich domains employed in the practice of the present invention typically do not form a α-helix, a β sheet, or a β-barrel structure. Typically, the disulfide bonds promote folding of the domain into a three-dimensional structure. Usually, cysteine-rich domains have at least two disulfide bonds, more typically at least three disulfide bonds. An exemplary cysteine-rich polypeptide is an A domain protein. A-domains (sometimes called "complement-type repeats") contain about 30-50 or 30-65 amino acids. In some embodiments, the domains comprise about 35-45 amino acids and in some cases about 40 amino acids. Within the 30-50 amino acids, there are about 6 cysteine residues. Of the six cysteines, disulfide bonds typically are found between the following cysteines: C1 and C3, C2 and C5, C4 and C6. The A domain constitutes a ligand binding moiety. The cysteine residues of the domain are disulfide linked to form a compact, stable, functionally independent moiety. Clusters of these repeats make up a ligand binding domain, and differential clustering can impart specificity with respect to the ligand binding. Exemplary proteins containing A-domains include, e.g., complement components (e.g., C6, C7, C8, C9, and Factor I), serine proteases (e.g., enteropeptidase, matriptase, and corin), transmembrane proteins (e.g., ST7, LRP3, LRP5 and LRP6) and endocytic receptors (e.g., Sortilin-related receptor, LDL-receptor, VLDLR, LRP1, LRP2, and ApoER2). Methods for making A domain proteins of a desired binding specificity are disclosed, for example, in WO 02/088171 and WO 04/044011, each of which is incorporated herein by reference.

In other embodiments, a biologically active moiety of the invention comprises a binding site from a repeat protein. Repeat proteins are proteins that contain consecutive copies of small (e.g., about 20 to about 40 amino acid residues) structural units or repeats that stack together to form contiguous domains. Repeat proteins can be modified to suit a particular target binding site by adjusting the number of repeats in the protein. Exemplary repeat proteins include Designed Ankyrin Repeat Proteins (i.e., a DARPins®, Molecular Partners, Zurich, Switzerland) (see e.g., Binz et al., Nat. Biotechnol., 22: 575-582 (2004)) or leucine-rich repeat proteins (ie., LRRPs) (see e.g., Pancer et al., Nature, 430: 174-180 (2004)). All so far determined tertiary structures of ankyrin repeat units share a characteristic composed of a β-hairpin followed by two antiparallel α-helices and ending with a loop connecting the repeat unit with the next one. Domains built of ankyrin repeat units are formed by stacking the repeat units to an extended and curved structure. LRRP binding sites from part of the adaptive immune system of sea lampreys and other jawless fishes and resemble antibodies in that they are formed by recombination of a suite of leucine-rich repeat genes during lymphocyte maturation. Methods for making DARpin or LRRP binding sites are described in WO 02/20565 and WO 06/083275, each of which is incorporated herein by reference.

Other non-immunoglobulin binding sites which may be employed in molecules of the invention include binding sites derived from Src homology domains (e.g. SH2 or SH3 domains), PDZ domains, beta-lactamase, high affinity protease inhibitors, or small disulfide binding protein scaffolds such as scorpion toxins. Methods for making binding sites derived from these molecules have been disclosed in the art, see e.g., Silverman et al., Nat. Biotechnol., 23(12): 1493-4 (2005); Panni et al, J. Biol. Chem., 277: 21666-21674 (2002); Schneider et al., Nat. Biotechnol., 17: 170-175 (1999); Legendre et al., Protein Sci., 11:1506-1518 (2002); Stoop et al., Nat. Biotechnol., 21: 1063-1068 (2003); and Vita et al., PNAS, 92: 6404-6408 (1995). Yet other binding sites may be derived from a binding domain selected from the group consisting of an EGF-like domain, a Kringle-domain, a PAN domain, a Gla domain, a SRCR domain, a Kunitz/Bovine pancreatic trypsin Inhibitor domain, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an Immunoglobulin-like domain, a C-type lectin domain, a MAM domain, a von Willebrand factor type A domain, a Somatomedin B domain, a WAP-type four disulfide core domain, a F5/8 type C domain, a Hemopexin domain, a Laminin-type EGF-like domain, a C2 domain, a CTLA-4 domain, and other such domains known to those of ordinary skill in the art, as well as derivatives and/or variants thereof. Additional non-immunoglobulin polypeptides include Avimers® (Avidia, Inc., Mountain View, Calif.—see International PCT Publication No. WO 06/055689 and US Patent Pub 2006/0234299), Telobodies® (Biotech Studio, Cambridge, Mass.), Evibodies® (Evogenix, Sydney, Australia—see U.S. Pat. No. 7,166,697), and Microbodies® (Nascacell Technologies, Munich, Germany).

iii. Binding Portions of Receptors or Ligands

In other aspects, a polypeptide of the invention comprises a ligand binding site of a receptor and/or a receptor binding portion of a ligand which is operably linked to at least one genetically-fused Fc region.

In certain embodiments, transmembrane regions or lipid or phospholipid anchor recognition sequences of the ligand binding receptor are preferably inactivated or deleted prior to fusion. DNA encoding the ligand or ligand binding partner is cleaved by a restriction enzyme at or proximal to the 5' and 3'ends of the DNA encoding the desired ORF segment. The resultant DNA fragment can be readily inserted (e.g., ligated in-frame) into DNA encoding a genetically-fused Fc region. The precise site at which the fusion is made may be selected empirically to optimize the secretion or binding characteristics of the soluble fusion protein. DNA encoding the fusion protein can then subcloned into an appropriate expression vector than can be transfected into a host cell for expression.

Exemplary binding portions of receptors or ligands that can be present in a polypeptide of the invention are set forth below:

a. Cytokines and Cytokine Receptors

Cytokines have pleiotropic effects on the proliferation, differentiation, and functional activation of lymphocytes. Various cytokines, or receptor binding portions thereof, can be utilized in the fusion proteins of the invention as biologically active molecules, binding sites and/or domains. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, cytotoxic T lymphocyte antigen 4 (CTLA-4), and interferons such as interferon-α, β, or γ (U.S. Pat. Nos. 4,925,793 and 4,929, 554).

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IL10 receptor, IFNγ (EP0240975), and the TNF family of receptors (e.g., TNFα (e.g. TNFR-1 (EP 417, 563), TNFR-2 (EP 417,014) lymphotoxin beta receptor).

b. Adhesion Proteins

Adhesion molecules are membrane-bound proteins that allow cells to interact with one another. Various adhesion proteins, including leukocyte homing receptors and cellular adhesion molecules, or receptor binding portions thereof, can be incorporated in a fusion protein of the invention as biologically active molecules, binding sites and/or domains. Leukocyte homing receptors are expressed on leukocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

c. Chemokines

Chemokines, chemotactic proteins which stimulate the migration of leukocytes towards a site of infection, can also be incorporated into a fusion protein of the invention. Exemplary chemokines include Macrophage inflammatory proteins (MIP-1-α and MIP-1-β), neutrophil chemotactic factor, and RANTES (regulated on activation normally T-cell expressed and secreted).

d. Hormones

Exemplary growth hormones for use as biologically active moieties in the fusion proteins of the invention include renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576,608); follicle stimulating hormone (FSH); calcitonin, luteinizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

e. Receptors and Ligands

In one embodiment, a polypeptide of the invention combines the binding site(s) of the ligand or receptor (e.g. the extracellular domain (ECD) of a receptor) with at least one genetically-fused Fc region (i.e., scFc region). In certain embodiments, the binding site or domain of the ligand-binding portion of a receptor may be derived from a receptor bound by an antibody or antibody variant described supra. In other embodiments, the ligand binding portion of a receptor is derived from a receptor selected from the group consisting of a receptor of the Immunoglobulin (Ig) superfamily (e.g., a soluble T-cell receptor, e.g., mTCR® (Medigene AG, Munich, Germany), a receptor of the TNF receptor superfamily described supra (e.g., a soluble TNFα receptor of an immunoadhesin), a receptor of the Glial Cell-Derived Neurotrophic Factor (GDNF) receptor family (e.g., GFRα3), a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily.

In other embodiments, the binding site or domain of the receptor-binding portion of a ligand may be derived from a ligand bound by an antibody or antibody variant described supra. For example, the ligand may bind a receptor selected from the group consisting of a receptor of the Immunoglobulin (Ig) superfamily, a receptor of the TNF receptor superfamily, a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily. In one exemplary embodiment, the binding site of the receptor-binding portion of a ligand is derived from a ligand belonging to the TNF ligand superfamily described supra (e.g., CD40L).

Growth factors or their receptors (or receptor binding or ligand binding portions thereof) may be incorporated in the fusion proteins of the invention. Exemplary growth factors include Vascular Endothelial Growth Factor (VEGF) and its isoforms (U.S. Pat. No. 5,194,596); Fibroblastic Growth Factors (FGF), including aFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), glial cell derived neurotrophic factor ligands (e.g., GDNF, neuturin, artemin, and persephin), neurotrophin-3, -4, -5, or -6 (NT-3, NT-4, NT-5, or NT-6), or a nerve growth factor such as NGF-β platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and -II (IGF-I and IGF-II; U.S. Pat. Nos. 6,403,764 and 6,506,874); Erythropoietin (EPO); Thrombopoeitin (TPO); stem-cell factor (SCF), thrombopoietin (TPO, c-Mpl ligand), and the Wnt polypeptides (U.S. Pat. No. 6,159,462).

Exemplary growth factor receptors which may be used as biologically active moieties of the invention include EGF receptors; VEGF receptors (e.g. Flt1 or Flk1/KDR), PDGF receptors (WO 90/14425); HGF receptors (U.S. Pat. Nos. 5,648,273, and 5,686,292), and neurotrophic receptors including the low affinity receptor (LNGFR), also termed as $p75^{NTR}$ or p75, which binds NGF, BDNF, and NT-3, and high affinity receptors that are members of the trk family of the receptor tyrosine kinases (e.g. trkA, trkB (EP 455,460), trkC (EP 522,530)).

f. Heterodimeric Receptors

In one embodiment, antagonists to cytokines that utilize an α specificity determining component which, when combined with the cytokine, binds to a first β signal transducing component to form a nonfunctional intermediate which then binds to a second β signal transducing component causing β-receptor dimerization and consequent signal transduction can be made using the methods of the invention. Such molecules are described in the art (see e.g., U.S. Pat. No. 6,927,044). In one example, a soluble specificity determining component of the receptor and the extracellular domain of the first b signal transducing component of the cytokine receptor are combined to form a heterodimer that binds the cytokine to form a nonfunctional complex. Exemplary cytokines that can be inhibited using such heterodimeric receptors include: ILL IL-2, IL-3, IL-4, IL-5, IL-3, IL-4, IL-5, IL-11, IL-15, GMCSF, LIF, INFγ, and TGFβ.

E. Clotting Factors

Exemplary clotting factors (blood coagulation factors) for use as biologically active moieties in the fusion proteins of the invention include the clotting factors (e.g., factors V, VII, VIII, IX, X, XI, XII and XIII, von Willebrand factor); tissue factor (U.S. Pat. Nos. 5,346,991, 5,349,991, 5,726,147, and 6,596,84); thrombin and prothrombin; fibrin and fibrinogen; plasmin and plasminogen; plasminogen activators, such as urokinase or human urine or tissue-type plasminogen activator (t-PA). Variants and biologically active portions of such clotting factors may also be used as biologically active molecules. Exemplary molecules that can be made using the scFc regions of the invention are also set forth in, e.g., U.S. Pat. Nos. 7,404,956 and 7,348,004.

Factors VII, IX, and X are all structurally related in that in each the amino terminal end of the light chain is not amenable to the incorporation of additional moieties, due to the requirement for the propeptide sequence that provides a docking site for the vitamin K-dependent gamma-glutamyl carboxylase. Similarly, the amino terminal end of the heavy chain of these three clotting factors is not amenable to the incorporation of additional moieties, with the exception of cleaveable moieties, i.e., moieties linked via a cleavage site or moieties which consist of a cleavage site, due to the requirement for a free N-terminus in order to form a catalytically active protease domain. Although factor VII is often shown to illustrate exemplary embodiments of the invention, the subject constructs may be made using factor IX, or X. For example, one of skill in the art would understand that the FVII portion of a construct of the invention could be substituted with a FIX or FX portion.

Exemplary clotting factor constructs of the invention are set forth in the accompanying Figures. Although the Figures generally illustrate the clotting Factor as a single chain (in its zymogen form) it will be understood that the clotting factor may also be present in its active form in a construct of the invention, e.g. as a two chain, disulfide bonded form.

In one embodiment, a clotting factor of the invention is expressed by a cell in active form. In another embodiment, a clotting factor is expressed in inactive form and is subsequently activated under appropriate conditions in vitro such that the active form of the clotting factor is present in the construct. In another embodiment, a clotting factor of the invention comprises a clotting factor in inactive form and the clotting factor is activated in vivo after administration.

In one embodiment, a clotting factor of the invention is a mature form of Factor VII or a variant thereof. Factor VII (FVII, F7; also referred to as Factor 7, coagulation factor VII, serum factor VII, serum prothrombin conversion accelerator, SPCA, proconvertin and eptacog alpha) is a serine protease that is part of the coagulation cascade. FVII includes a Gla domain, two EGF domains (EGF-1 and EGF-2), and a serine protease domain (or peptidase 51 domain) that is highly conserved among all members of the peptidase 51 family of serine proteases, such as for example with chymotrypsin. FVII occurs as a single chain zymogen, an activated zymogen-like two-chain polypeptide and a fully activated two-chain form. As used herein, a "zymogen-like" protein or polypeptide refers to a protein that has been activated by proteolytic cleavage, but still exhibits properties that are associated with a zymogen, such as, for example, low or no activity, or a conformation that resembles the conformation of the zymogen form of the protein. For example, when it is not bound to tissue factor, the two-chain activated form of FVII is a zymogen-like protein; it retains a conformation similar to the uncleaved FVII zymogen, and, thus, exhibits very low activity. Upon binding to tissue factor, the two-chain activated form of FVII undergoes conformational change and acquires its full activity as a coagulation factor.

Exemplary FVII variants include those with increased specific activity, e.g., mutations that increase the activity of FVII by increasing its enzymatic activity (Kcat or Km). Such variants have been described in the art and include, e.g., mutant forms of the molecule as described for example in Persson et al. 2001. PNAS 98:13583; Petrovan and Ruf. 2001. J. Biol. Chem. 276:6616; Persson et al. 2001 J. Biol. Chem. 276:29195; Soejima et al. 2001. J. Biol. Chem. 276:17229; Soejima et al. 2002. J. Biol. Chem. 247:49027. In one embodiment, a variant form of FVII includes the mutations V158D-E296V-M298Q Exemplary mutations include V158D-E296V-M298Q. In another embodiment, a variant form of FVII includes a replacement of amino acids 608-619 (LQQSRKVGDSPN (SEQ ID NO:98), corresponding to the 170-loop) from the FVII mature sequence with amino acids EASYPGK (SEQ ID NO: 99) from the 170-loop of trypsin. High specific activity variants of FIX are also known in the art. Fir example, Simioni et al. (2009 N. E. Journal of Medicine 361:1671) describe an R338L mutation. Chang et al. (1988 JBC 273:12089) and Pierri et al. (2009 Human Gene Therapy 20:479) describe an R338A mutation. Other mutations are known in the art and include those described, e.g., in Zogg and Brandstetter. 2009 Structure 17:1669; Sichler et al. 2003. J. Biol. Chem. 278:4121; and Sturzebecher et al. 1997. FEBS Lett 412:295. Another version of factor IX (the triple mutatnt V86A/E277A/R338A) with augmented clotting activities has been described by Lin et al. 2010. Journal of Thrombosis and Haemostasis 8: 1773). The contents of these references are incorporated herein by this reference.

Full activation, which occurs upon conformational change from a zymogen-like form, occurs upon binding to is co-factor tissue factor. Also, mutations can be introduced that result in the conformation change in the absence of tissue factor. Hence, reference to FVIIa includes both two-chain forms thereof, the zymogen-like form and the fully activated two-chain form.

In one embodiment, a clotting factor of the invention is a mature form of Factor VIII or a variant thereof. FVIII functions in the intrinsic pathway of blood coagulation as a cofactor to accelerate the activation of factor X by factor IXa, a reaction that occurs on a negatively charged phospholipid surface in the presence of calcium ions. FVIII is synthesized as a 2351 amino acid single-chain polypeptide having the domain structure A1-A2-B-A3-C1-C2. Wehar, G. A. et al., Nature 312:337-342 (1984) and Toole, J. J. et al., Nature 312:342-347 (1984). The domain structure of FVIII is identical to that of the homologous coagulation factor, factor V (FV). Kane, W. H. et al., PNAS (USA) 83:6800-6804 (1986) and Jenny, R. J. et al., PNAS (USA) 84:4846-4850 (1987). The FVIII A-domains are 330 amino acids and have 40% amino acid identity with each other and to the A-domain of FV and the plasma copper-binding protein ceruloplasmin. Takahashi, N. et al., PNAS (USA) 81:390-394 (1984). Each C-domain is 150 amino acids and exhibits 40% identity to the C-domains of FV, and to proteins that bind glycoconjugates and negatively charged phospholipids. Stubbs, J. D. et al., PNAS (USA) 87:8417-8421 (1990). The FVIII B-domain is encoded by a single exon and exhibits little homology to any known protein including FV B-domain. Gitschier, J. et al., Nature 312:326-330 (1984) and Cripe, L. D. et al., Biochemistry 31:3777-3785 (1992).

FVIII is secreted into plasma as a heterodimer of a heavy chain (domains A1-A2-B) and a light chain (domains A3-C1-C2) associated through a noncovalent divalent metal ion linkage between the A1- and A3-domains. In plasma, FVIII is stabilized by binding to von Willebrand factor. More specifically, the FVIII light chain is bound by noncovalent interactions to a primary binding site in the amino terminus of von Willebrand factor. Upon proteolytic activation by thrombin, FVIII is activated to a heterotrimer of 2 heavy chain fragments (A1, a 50 kDa fragment, and A2, a 43 kDa fragment) and the light chain (A3-C1-C2, a 73 kDa chain). The active form of FVIII (FVIIIa) thus consists of an A1-subunit associated through the divalent metal ion linkage to a thrombin-cleaved A3-C1-C2 light chain and a free A2 subunit associated with the A1 domain through an ion association. Eaton, D. et al., Biochemistry 25: 505 (1986); Lollar, P. et al., J. Biol. Chem. 266: 12481 (1991); and Fay, P. J. et al., J. Biol. Chem. 266: 8957 (1991). This FVIIIa heterotrimer is unstable and subject to rapid inactivation through dissociation of the A2 subunit under physiological conditions.

In one embodiment, a clotting factor comprises a B-domain deleted version of factor VIII. "B-domain" of Factor VIII, as used herein, is the same as the B-domain known in the art that is defined by internal amino acid sequence identity and sites of proteolytic cleavage, e.g., residues Ser741-Arg1648 of full-length human Factor VIII. The other human Factor VIII domains are defined by the following amino acid residues: A1, residues Ala1-Arg372; A2, residues Ser373-Arg740; A3, residues Ser1690-Asn2019; C1, residues Lys2020-Asn2172; C2, residues Ser2173-Tyr2332. The A3-C1-C2 sequence includes residues Ser1690-Tyr2332. The remaining sequence, residues Glu1649-Arg1689, is usually referred to as the a3 acidic region. The locations of the boundaries for all of the domains, including the B-domains, for porcine, mouse and canine Factor VIII are also known in the art. In one embodiment, the B domain of Factor VIII is deleted ("B-domain-deleted factor VIII" or "BDD FVIII"). An example of a BDD FVIII is REFACTO® (recombinant BDD FVIII with S743/Q1638 fusion), which is known in the art.

A "B-domain-deleted Factor VIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B-domain-deleted Factor VIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In another embodiment, a B-domain deleted Factor VIII is the 5743/Q1638 B-domain deleted Factor VIII (SQ version Factor VIII) (e.g., Factor VIII having a deletion from amino acid 744 to amino acid 1637, e.g., Factor VIII having amino acids 1-743 and amino acids 1638-2332 of SEQ ID NO: 6, i.e., SEQ ID NO: 2). In some embodiments, a B-domain-deleted Factor VIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B-domain-deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B-domain-deleted Factor VIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some embodiments, a B-domain-deleted Factor VIII is constructed with a deletion of amino acids 747-1638, i.e., virtually a complete deletion of the B domain. Hoeben R. C., et al. J. Biol. Chem. 265 (13): 7318-7323 (1990), incorporated herein by reference in its entirety. A B-domain-deleted Factor VIII may also contain a deletion of amino acids 771-1666 or amino acids 868-1562 of Factor VIII. Meulien P., et al. Protein Eng. 2(4): 301-6 (1988), incorporated herein by reference in its entirety. Additional B domain deletions that are part of the invention include: deletion of amino acids 982 through 1562 or 760 through 1639 (Toole et al., Proc. Natl. Acad. Sci. U.S.A. (1986) 83, 5939-5942)), 797 through 1562 (Eaton, et al. Biochemistry (1986) 25:8343-8347)), 741 through 1646 (Kaufman (PCT published application No. WO 87/04187)), 747-1560 (Sarver, et al., DNA (1987) 6:553-564)), 741 though 1648 (Pasek (PCT application No. 88/00831)), or 816 through 1598 or 741 through 1648 (Lagner (Behring Inst. Mitt. (1988) No 82:16-25, EP 295597)), each of which is incorporated herein by reference in its entirety. Each of the foregoing deletions may be made in any Factor VIII sequence.

In one embodiment, a clotting factor of the invention is a mature form of Factor IX or a variant thereof. Factor IX circulates as a 415 amino acid, single chain plasma zymogen (A. Vysotchin et al., J. Biol. Chem. 268, 8436 (1993)). The zymogen of FIX is activated by FXIa or by the tissue factor/FVIIa complex. Specific cleavages between arginine-alanine 145-146 and arginine-valine 180-181 result in a light chain and a heavy chain linked by a single disulfide bond between cysteine 132 and cysteine 289 (S. Bajaj et al., Biochemistry 22, 4047 (1983)). The structural organization of FIX is similar to that of the vitamin K-dependent blood clotting proteins FVII, FX and protein C (B. Furie and B. Furie, supra). The approximately 45 amino acids of the amino terminus comprise the gamma-carboxyglutamic acid, or gla, domain. This is followed by two epidermal growth factor homology domains (EGF), an activation peptide and the catalytic "heavy chain" which is a member of the serine protease family (A. Vysotchin et al., J. Biol. Chem. 268, 8436 (1993); S. Spitzer et al., Biochemical Journal 265, 219 (1990); H. Brandstetter et al., Proc. Natl. Acad Sci. USA 92, 9796 (1995)).

In one embodiment, a clotting factor of the invention is a mature form of Factor X. Factor X is a vitamin-K dependent glycoprotein of a molecular weight of 58.5 kDa, which is secreted from liver cells into the plasma as a zymogen. Initially factor X is produced as a prepropeptide with a signal peptide consisting in total of 488 amino acids. The signal peptide is cleaved off by signal peptidase during export into the endoplasmatic reticulum, the propeptide sequence is cleaved off after gamma carboxylation took place at the first 11 glutamic acid residues at the N-terminus of the mature N-terminal chain. A further processing step occurs by cleavage between Arg182 and Ser183. This processing step also leads concomitantly to the deletion of the tripeptide Arg180-Lys181-Arg182. The resulting secreted factor X zymogen consists of an N-terminal light chain of 139 amino acids ($M_r$ 16,200) and a C-terminal heavy chain of 306 amino acids ($M_r$ 42,000) which are covalently linked via a disulfide bridge between Cys172 and Cys342. Further posttranslational processing steps include the .beta.-hydroxylation of Asp103 as well as N- and O-type glycosylation.

It will be understood that in addition to wild type (WT) versions of these clotting factors or biologically active portions thereof, the present invention may also employ precursor truncated forms thereof that have activity, allelic variants and species variants, variants encoded by splice variants, and other variants, including polypeptides that have at least 40%, 45%, 50%, 55%, 65%, 70%, 75%, 80%, 85%, 90%, 95%, 96%, 97%, 98%, 99% or more sequence identity to the mature form of the clotting factor and which retain the ability to promote clot formation. For example, modified FVII polypeptides and variants thereof which retain at least one activity of a FVII, such as TF binding, factor X binding, phospholipid binding, and/or coagulant activity of a FVII may be employed. By retaining activity, the activity can be altered, such as reduced or increased, as compared to a wild-type clotting factor so long as the level of activity retained is sufficient to yield a detectable effect. Exemplary sequences of clotting factors that can be used in the constructs of the invention are found in the accompanying sequence listing.

Exemplary modified polypeptides include, but are not limited to, tissue-specific isoforms and allelic variants thereof, synthetic molecules prepared by translation of nucleic acids, proteins generated by chemical synthesis, such as syntheses that include ligation of shorter polypeptides, through recombinant methods, proteins isolated from human and non-human tissue and cells, chimeric polypeptides and modified forms thereof.

Other variants of clotting factors include versions that are modified to alter activity. For example, high specific activity versions of clotting factors are known in the art and can be used to make a polypeptide of the invention. Exemplary such high specific activity variants are described, e.g., in Persson et al. PNAS. 2001. 98:13583 and Soejima et al. Journal of Biological Chemistry. 2002. 277:49027. For example, in one embodiment, a high specific activity version of Factor VII, removes amino acids 311 to 322 of the FVII mature sequence (LQQSRKVGDSPN (SEQ ID NO: 98), corresponding to the 170-loop) and replaces them with amino acids EASYPGK (SEQ ID NO: 99) from the 170-loop of trypsin. This substitution has been shown to confer high specific activity. An additional high specific activity version of Factor VII contains three point mutations in the heavy chain of FVII, V158D, E296V and M298Q.

The instant clotting factors may also consist of fragments or portions of WT molecules that are of sufficient length or include appropriate regions to retain at least one activity (upon activation if needed) of a full-length mature polypeptide. Exemplary clotting factor variants are known in the art.

Exemplary clotting factors are those of mammalian, e.g., human, origin. The sequences of exemplary clotting factors are presented in the accompanying sequence listing, e.g., alone or in the context of an clotting factor construct.

In one embodiment, more than one clotting factor may be present in a polypeptide of the invention. In another embodiment, a polypeptide of the invention comprises a light chain of a clotting factor genetically fused to one Fc moiety of a construct of the invention and a heavy chain of a clotting factor genetically fused to the second Fc moiety of a construct of the invention, or vise versa.

Exemplary constructs comprising clotting factors as biologically active moieties are shown in the working examples. For example, in one embodiment, a clotting factor zymogen (e.g., factor VII heavy and light chain) is attached via an optional linker (e.g., 6×($G_4$S)) linker or directly to the amino terminus of a first Fc moiety (comprising CH1, CH2, and CH3 domains). The carboxy terminus of the first Fc moiety has a cscFc linker (e.g., a 6×($G_4$S) linker or 4×($G_4$S) linker) which comprises a first processing site (e.g., RRRS (SEQ ID NO: 38) processing site). The other end of the cscFc linker comprises a second processing site (e.g., an RKRRKR (SEQ ID NO: 39) or RRRR (SEQ ID NO: 40) processing site) and is optionally linked via a spacer to a targeting moiety (e.g., a platelet targeting moiety) or is directly linked to a second Fc moiety. Where a targeting moiety is present, it may be linked to the second Fc moiety via a spacer (e.g., 6×($G_4$S)). The FVII-027, FVII-064 and FIX-044 molecules described herein are examples of such constructs.

Other exemplary constructs result in the secretion of an activated clotting factor rather than a zymogen following processing of the linker by proteases. For example, in one embodiment, the light chain of a clotting factor is fused via a spacer (e.g., a 4×($G_4$S) linker) to the amino terminus of a first Fc moiety (comprising CH1, CH2, and CH3 domains). The carboxy terminus of the first Fc moiety is linked to a linker (e.g., a 6×($G_4$S) cscFc linker) which comprises a first processing site (e.g., RRRR (SEQ ID NO: 40)) processing site). The other end of the linker comprises a second processing site, e.g., an RKRRKR (SEQ ID NO: 39) processing site and is genetically fused to the heavy chain of the clotting factor (e.g., FVII heavy chain) which is in turn fused to the amino terminus of the second Fc moiety via a second spacer (e.g., a 4×($G_4$S) linker). An example of such a construct is the FVII-024 construct described herein and shown in FIG. 2.

Figure 7:
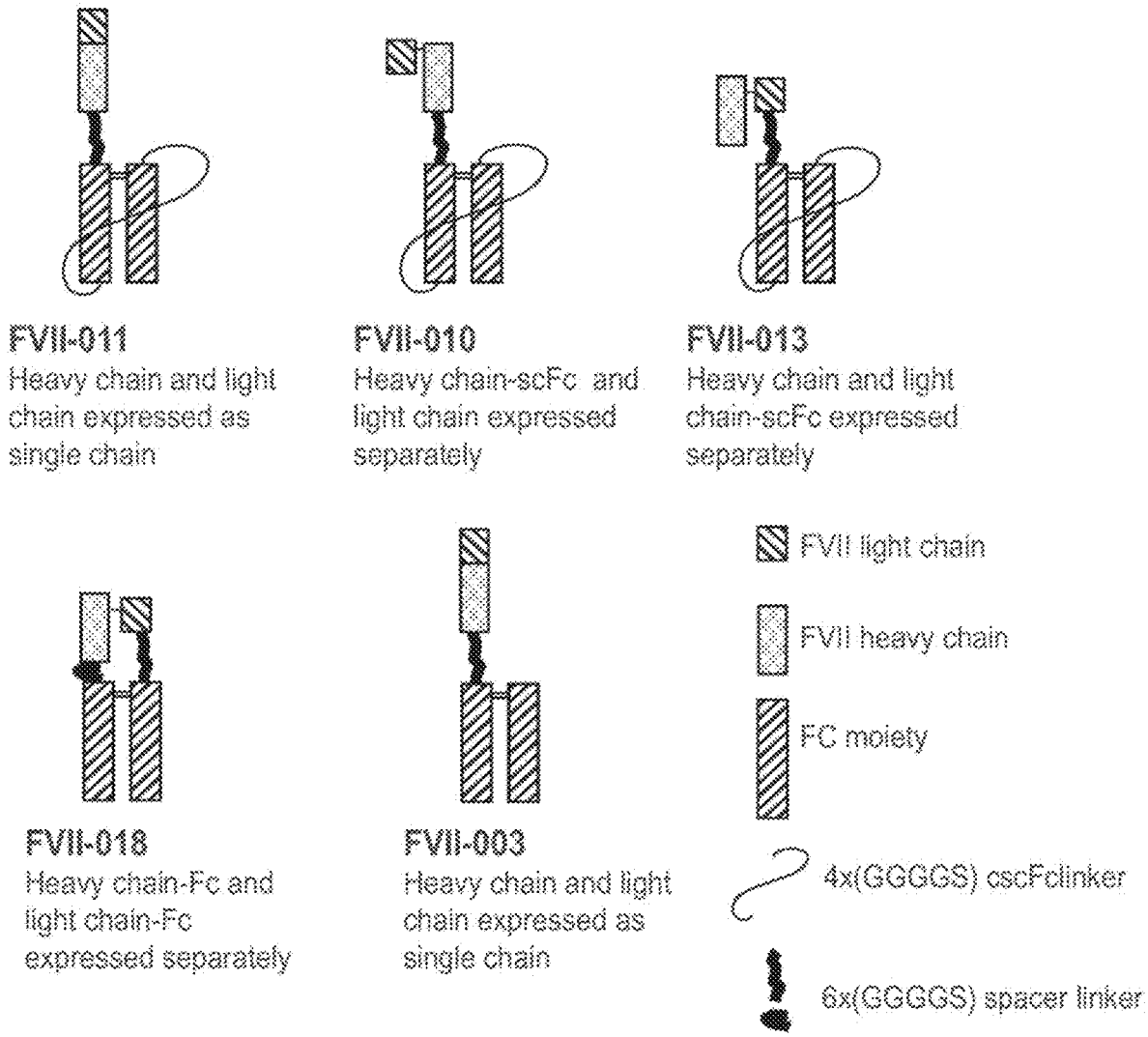
FIG. 7 illustrates several additional constructs that were made in which FVII heavy and light chains were expressed separately or as a single chain.

Additional constructs were made to vary the way in which the heavy and light chains of a clotting factor are expressed. As shown in FIG. 7, the heavy and light chain can be expressed as a single chain (FV-011 and FV-003) or separately (FV-010, FVII-013, or FVII-018).

Figure 9:
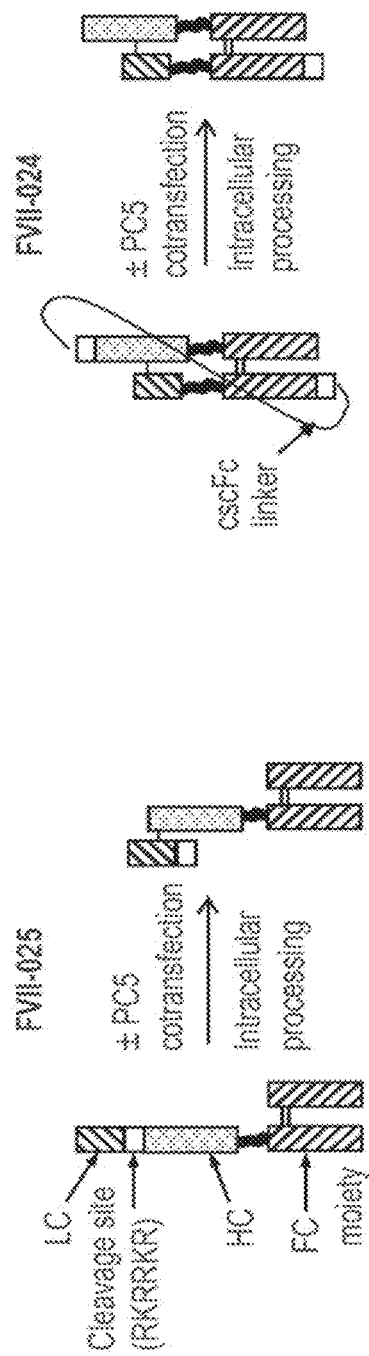
FIG. 9 illustrates a heterodimeric scFc construct and a monomeric Fc construct. These constructs were made and Western blots were performed. The data show intracellular activation is more efficient in the context of the heterodimer (FVII-024) than the monomer (FVII-025), and required cotransfection of PC5 for full processing. These FVII-024 data are the same as shown in FIG. 2, but show a direct comparison between FVII-024 and FVII-025.
Figure 9:
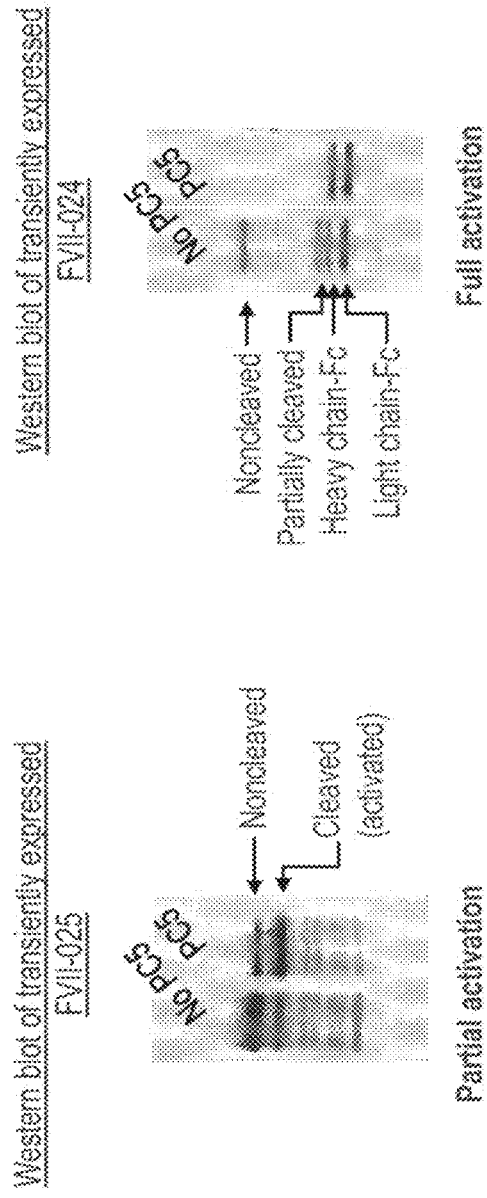

An additional construct was made to test the ability of FVII to be expressed in activated form. The FVII-025 construct is set forth in FIG. 9.

Figure 10:
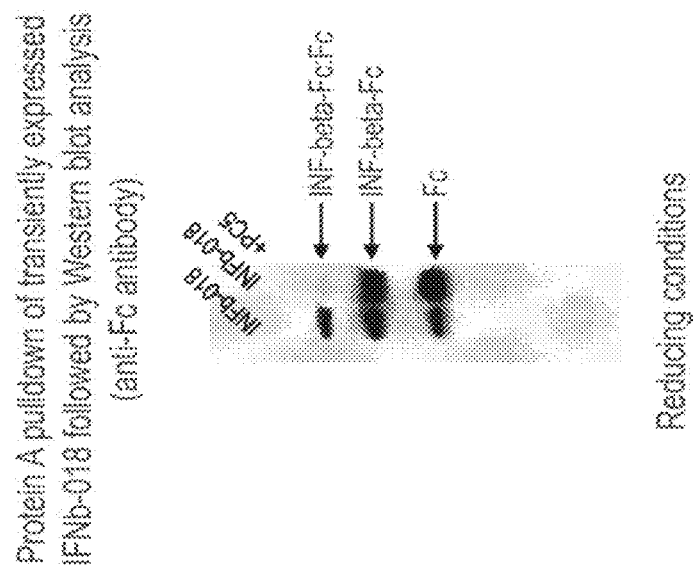
FIG. 10 shows an scFc molecule comprising IFN-β as the biologically active moiety. The Figure also shows a Western blot which illustrates partial cleavage of the processable linker in the absence of PC5 cotransfection, but full cleavage with cotransfection.
Figure 10:
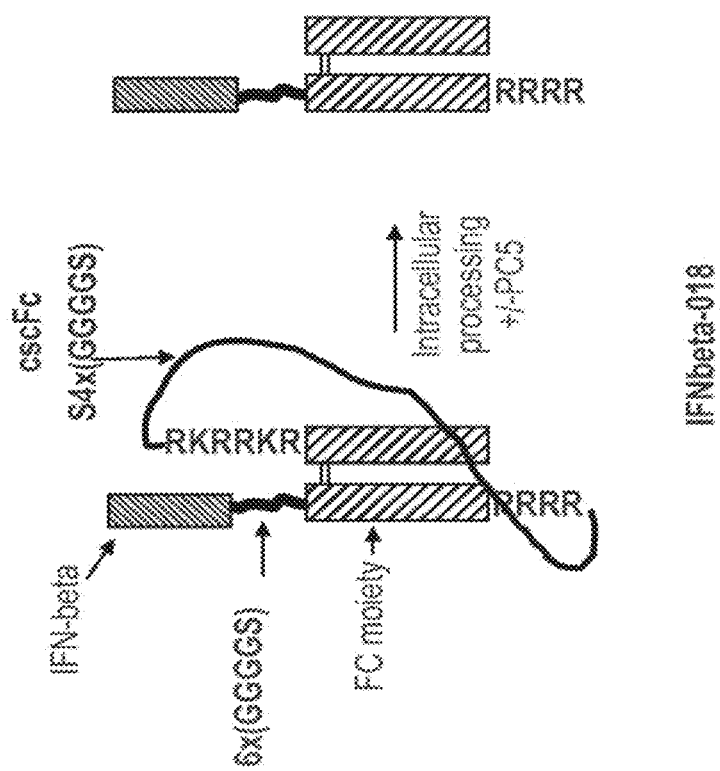

Another construct in which a different biologically active moiety, IFNβ, was employed is set forth in FIG. 10 to show that not only clotting factors can be made using the methods of the invention. In making this construct, IFNβ was linked to a first Fc moiety using a spacer molecule.

Figure 11:
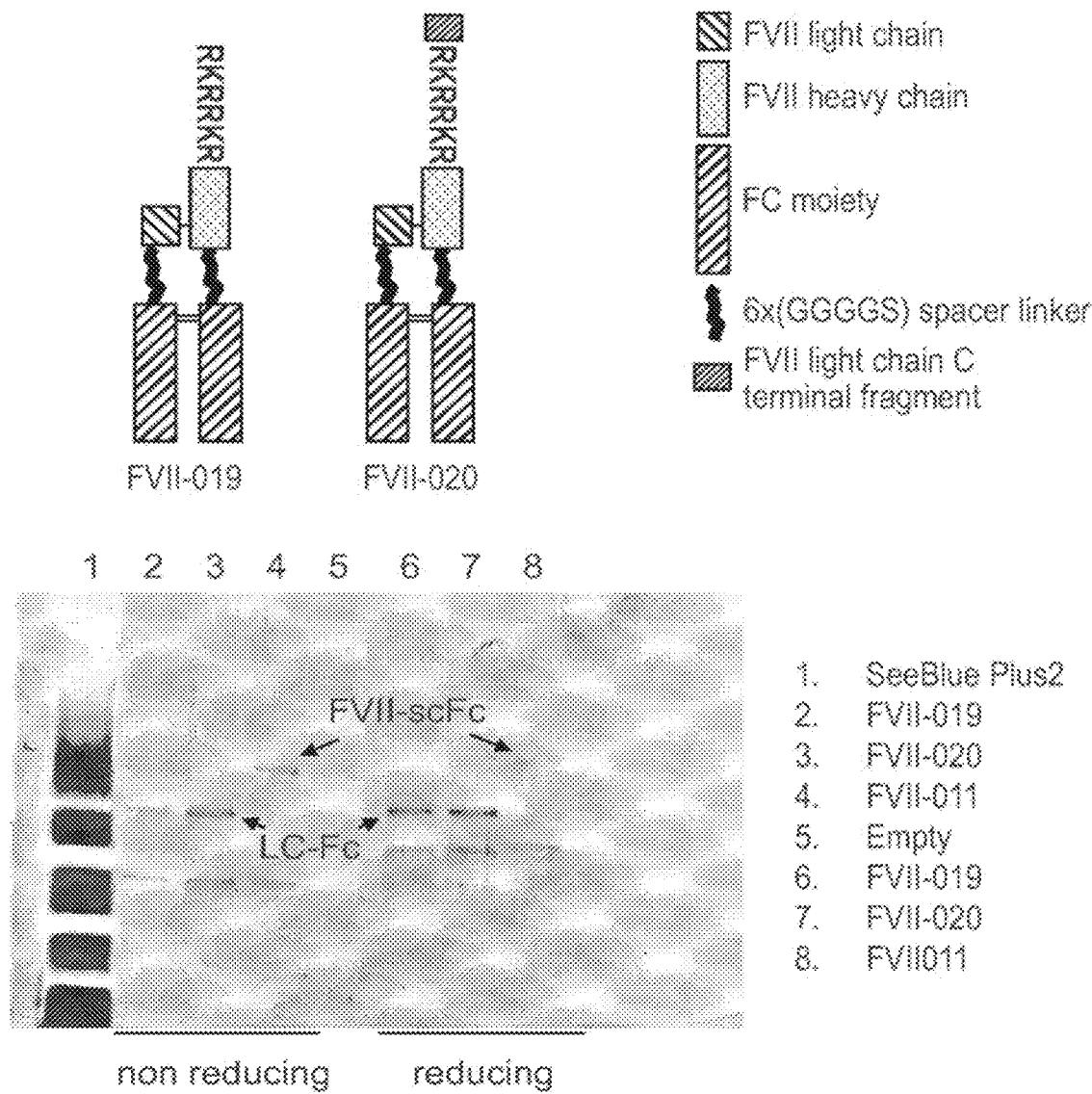
FIG. 11 shows Western blot analysis (Fc western) of FVIIFc species following transient transfection of HEK 293 cells and protein A pulldown.

Failure to express the FVII heavy chain with a free N terminus led to generation of the constructs described in FIG. 11. In these constructs, FVIIFc 15 expressed as a heterodimer where one subunit comprises the FVII light chain and an Fc moiety, and the other subunit comprises the heavy chain preceded by an RKRRKR (SEQ ID NO: 39) processing site (FVII-019) or by a light chain C terminal fragment and an RKRRKR (SEQ ID NO: 39)_processing site (FVII-020).

F. Targeting Moieties

In one embodiment, the antigen binding portion targets the composition to a particular cell type or tissue. Such targeting moieties may comprise, e.g., an antigen binding site, a ligand binding portion of a receptor, or a receptor binding portion of a ligand. In another embodiment, a targeting moiety is a peptide.

In one embodiment, a clotting factor of the invention is targeted to platelets to enhance its efficacy by localizing the clotting factor to the site of coagulation using a "targeting moiety" which binds to a molecule expressed on platelets. Preferably the targeted molecules are not expressed on cells or tissues other than platelets, i.e., the targeting moieties specifically bind to platelets.

In one embodiment, receptors/conformations found on resting platelets are targeted. By doing so, sites for coagulation could be primed for enhanced efficacy. Targeting such molecule may also extend half life of the clotting factor and/or prevent clearance. Examples of such targets include, e.g., GpIb of the GpIb/V/IX complex, and GpVI and non-active form of GPIIb/IIIa.

In one embodiment, receptors/conformations only found on activated platelets are targeted in order to localize the clotting factor to site of active coagulation. Examples of such targets include, e.g., the active form of GpIIb/IIIa as well as CD62P.

In one embodiment, a polypeptide of the invention comprises a "targeting moiety" which has affinity for and binds to platelets. For example, in one embodiment, a targeting moiety binds to the GPIb complex, e.g, GPIb-alpha. Examples of such targeting moieties include the peptides PS4, OS1, and OS2 which bind to both active and nonactive platelets (Benard et al. 2008 Biochemistry 47:4674); In another embodiment, a targeting moiety binds to the active conformation of GPIIbIIIa. Examples of such targeting moieties include SCE5 and MB9 variable regions which bind active platelets only (Schwarz et al. 2004 FASEB Journal express article 10.1096/fj.04-151fje; Schwarz et al. 2006 Circulation Research. 99:25-33; U.S. Patent publication 20070218067). In another embodiment, a targeting moiety binds to both the active/nonactive conformation of GPIIbIIIa. An example of such a targeting moiety is the variable region of the AP3 antibody (Peterson et al. 2003. Hemostasis, Thrombosis, and Vascular Biology 101:937; WO 2010115866).

Other platelet targets or targeting moieties which bind to such targets could be readily selected by one of ordinary skill in the art.

The polypeptides of the invention can comprise one or more than one targeting moiety. Exemplary configurations are set forth in the accompanying Figures. Additionally, two or more targeting moieties may be linked to each other (e.g., via a spacer) in series, and the tandem array operably linked to a construct of the invention. When two or more targeting moieties are present in a clotting factor of the invention, the moieties may be the same or different.

In one embodiment, a targeting moiety is fused to a polypeptide of the invention by a cleaveable linker or alternatively, in other embodiment, the polypeptide further comprises a cleavage site. Either of the cleavable linker or the cleavage site may be cleaved to remove the targeting moiety at the site of a clot. In another embodiment, a targeting moiety is attached via a spacer which is not cleaveable and, therefore, is not cleaved at the site of a clot.

In one embodiment, the targeting moiety is located on the N- or C-terminus of factor VIII. In another embodiment, a targeting moiety is located on the C-terminus of FVII, FIX, FX, or the C-terminus of either or both chains of FVIIa, FIXa, of FXa. In one embodiment the targeting moiety may be positioned at the N or C terminus of the second Fc moiety (F2), or the C-terminus of either or both Fc moieties (F1 and/or F2). The targeting moiety may be linked to the biologically active moiety or Fc moiety via a spacer.

In one embodiment, a targeting moiety is not fused to a construct via a peptide bond, but rather is chemically conjugated to the construct. For example, targeting moieties may be attached to a construct of the invention by formation of a bond between the targeting moiety and an Fc moiety of a construct, where the targeting moiety comprises a first functional group and the Fc moiety comprises a second functional group, and where the first and second functional groups are capable of reacting with each other to form a chemical bond (see, e.g., U.S. Pat. No. 7,381,408).

Exemplary formats of targeted clotting factors are also set forth in the accompanying Figures.

In one embodiment, a polypeptide of the invention comprises at least one of an antigen binding site (e.g., an antigen binding site of an antibody, antibody variant, or antibody fragment), a polypeptide, a receptor binding portion of ligand, or a ligand binding portion of a receptor which specifically binds to platelets, e.g., resting or activated platelets. Exemplary targeting moieties include scFv molecules or peptides which bind to molecules to be targeted. Examples of targeting moieties are found in the instant examples.

For example, in certain embodiments, a polypeptide of the invention comprises at least one antigen binding portion (e.g., binding site) of an antibody. In one embodiment, the antigen binding portion targets the composition to platelets. Such an antibody may bind to an epitope expressed by all platelets (e.g., activated and inactivated) or may bind to an epitope expressed specifically by activated platelets).

Exemplary antibodies from which binding sites can be derived or exemplary antibody binding sites for use in the polypeptide molecules of the invention are known in the art. As set forth above, antibodies known to bind to platelets can be used to derive binding sites, for example, the AP3 antibody or the MB9 scFv described in US 2007/0218067 or the variable region or an scFv molecule comprising the variable region can be used as a targeting moiety in a construct of the invention. Other exemplary antibody binding sites include SCE5 which targets a confirmation found on activated platelets. Other useful antibodies can be readily selected from those known in the art.

In certain other embodiments, the polypeptides of the invention comprise one or more binding sites derived from a non-immunoglobulin binding molecule. As used herein, the term "non-immunoglobulin binding molecules" are binding molecules whose binding sites comprise a portion (e.g., a scaffold or framework) which is derived from a polypeptide other than an immunoglobulin, but which may be engineered (e.g., mutagenized) to confer a desired binding specificity.

Other examples of binding molecules comprising binding sites not derived from antibody molecules include receptor binding sites and ligand binding sites which bind to platelets.

Non-immunoglobulin binding molecules may be identified by selection or isolation of a target-binding variant from a library of binding molecules having artificially diversified binding sites. Diversified libraries can be generated using completely random approaches (e.g., error-prone PCR, exon shuffling, or directed evolution) or aided by art-recognized design strategies. For example, amino acid positions that are usually involved when the binding site interacts with its cognate target molecule can be randomized by insertion of degenerate codons, trinucleotides, random peptides, or entire loops at corresponding positions within the nucleic acid which encodes the binding site (see e.g., U.S. Pub. No. 20040132028). The location of the amino acid positions can be identified by investigation of the crystal structure of the binding site in complex with the target molecule. Candidate positions for randomization include loops, flat surfaces, helices, and binding cavities of the binding site. In certain embodiments, amino acids within the binding site that are likely candidates for diversification can be identified using techniques known in the art. Following randomization, the diversified library may then be subjected to a selection or screening procedure to obtain binding molecules with the desired binding characteristics, e.g. specific binding platelets using methods known in the art. Selection can be achieved by art-recognized methods such as phage display, yeast display, or ribosome display. In one embodiment, molecules known in the art to bind to platelets may be employed in the constructs of the invention. For example, peptides which bind to GPIba as described in the art (e.g., PS4, OS1, or OS2) may be used (Benard et al. 2008. *Biochemistry* 47:4674-4682).

III. Preparation of Polypeptides

A variety of methods are available for producing a polypeptide of the invention. In one embodiment, the invention relates to a nucleic acid construct comprising a nucleic acid sequence encoding a polypeptide molecule of the invention. It will be understood that because of the degeneracy of the code, a variety of nucleic acid sequences will encode the amino acid sequence of the polypeptide. The desired polynucleotide can be produced by de novo solid-phase DNA synthesis or by PCR mutagenesis of an earlier prepared polynucleotide encoding the target polypeptide.

Nucleic acids encoding a biologically active molecule can be readily synthesized using recombinant techniques well known in the art. Alternatively, the peptides themselves can be chemically synthesized. Nucleic acids of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. 1988, Nucl. Acids Res. 16:3209, methylphosphonate oligonucleotides can be prepared by use of controlled pore glass polymer supports as described in Sarin et al. 1988, Proc. Natl. Acad. Sci. USA 85:7448. Additional methods of nucleic acid synthesis are known in the art. (see, e.g., U.S. Pat. Nos. 6,015,881; 6,281,331; 6,469,136).

Methods for linking desired biologically active moieties, whether derived from antibodies or other molecules, to cleavable scFc scaffolds are known in the art.

Oligonucleotide-mediated mutagenesis is one method for preparing a substitution, in-frame insertion, or alteration (e.g., altered codon) to introduce a codon encoding an amino acid substitution (e.g., into an Fc variant moiety). For example, the starting polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide encoding a polypeptide of the invention.

For recombinant production, a polynucleotide sequence encoding the polypeptide is inserted into an appropriate expression vehicle, i.e., a vector which contains the necessary elements for the transcription and translation of the inserted coding sequence, or in the case of an RNA viral vector, the necessary elements for replication and translation.

In one embodiment, a nucleic acid molecule encoding the protein is inserted into the vector in proper reading frame. The expression vector is then transfected into a suitable target cell which will express the polypeptide. Transfection techniques known in the art include, but are not limited to, calcium phosphate precipitation (Wigler et al. 1978, Cell 14: 725) and electroporation (Neumann et al. 1982, EMBO, J. 1: 841). A variety of host-expression vector systems may be utilized to express the proteins described herein in eukaryotic cells. In one embodiment, the eukaryotic cell is an animal cell, including mammalian cells (e. g. 293 cells, PerC6, CHO, BHK, Cos, HeLa cells). When the protein is expressed in a eukaryotic cell the DNA encoding the protein may also code for a signal sequence that will permit the protein to be secreted. One skilled in the art will understand that while the protein is translated the signal sequence is cleaved by the cell to form the mature protein. Various signal sequences are known in the art e. g., native factor V11 signal sequence, native factor IX signal sequence and the mouse IgK light chain signal sequence. Alternatively, where a signal sequence is not included the protein can be recovered by lysing the cells.

The protein of the invention can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, Proc. Natl. Acad. Sci. USA 82: 4438). Methods of producing transgenic animals are known in the art. including transgenics that produce immunoglobulin molecules (Wagner et al. 1981, Proc. Natl. Acad. Sci. USA 78: 6376; McKnight et al. 1983, Cell 34: 335; Brinster et al. 1983, Nature 306: 332; Ritchie et al. 1984, Nature 312: 517; Baldassarre et al. 2003, Theriogenology 59: 831; Robl et al. 2003, Theriogenology 59: 107; Malassagne et al. 2003, Xenotransplantation 10 (3): 267).

The expression vectors can encode for tags that permit for easy purification or identification of the recombinantly produced protein. Examples include, but are not limited to, vector pUR278 (Ruther et al. 1983, EMBO J. 2: 1791) in which the protein described herein coding sequence may be ligated into the vector in frame with the lac z coding region so that a hybrid protein is produced; pGEX vectors may be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e. g. PreCission Protease (Pharmacia, Peapack, N.J.)) for easy removal of the tag after purification.

For the purposes of this invention, numerous expression vector systems may be employed. These expression vectors are typically replicable in the host organisms either as episomes or as an integral part of the host chromosomal DNA. Expression vectors may include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors may also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

An exemplary expression vector is NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the polypeptides of the invention of the instant invention may be expressed using polycistronic constructs. In these expression systems, multiple gene products of interest such as multiple polypeptides of multimer binding protein may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems may be used to effectively produce the full range of polypeptides disclosed in the instant application.

More generally, once the vector or DNA sequence encoding a polypeptide has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, CHO, e.g., DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte), PerC6, and 293 (human kidney). Host cell lines are typically available from commercial services, the American Tissue Culture Collection or from published literature.

In one embodiment, a host cell endogenously expresses an enzyme (or the enzymes) necessary to cleave the polypeptide linker (L) during processing to form the mature polypeptide. During this processing, the polypeptide linker (L) is substantially removed to reduce the presence of extraneous amino acids. In another embodiment of the invention, a host cell is transformed to express one or more enzymes which are heterologous or exogenous to the cell such that processing of the polypeptide linker (L) occurs or is improved.

In one embodiment an enzyme which may be endogenously or exogenously expressed by a cell is a member of the furin family of enzymes. Complete cDNA and amino acid sequences of human furin (i.e., PACE) were published in 1990. Van den Ouweland A M et al. (1990) Nucleic Acids Res. 18:664; Erratum in: Nucleic Acids Res. 18:1332 (1990).

U.S. Pat. No. 5,460,950, issued to Barr et al., describes recombinant PACE and the coexpression of PACE with a substrate precursor polypeptide of a heterologous protein to improve expression of active, mature heterologous protein.

U.S. Pat. No. 5,935,815, issued to van de Ven et al., likewise describes recombinant human furin (i.e., PACE) and the coexpression of furin with a substrate precursor polypeptide of a heterologous protein to improve expression of active, mature heterologous protein. Possible substrate precursors disclosed in this patent include a precursor of Factor IX. Other family members in the mammalian furin/subtilisin/Kex2p-like proprotein convertase (PC) family in addition to PACE are reported to include PC1/PC3, PC2, PC4, PC5/6 (hereinafter referred to simply as PC5), PACE4, and LPC/PC7/PC8/SPC7. While these various members share certain conserved overall structural features, they differ in their tissue distribution, subcellular localization, cleavage specificities, and preferred substrates. For a review, see Nakayama K (1997) Biochem J. 327:625-35. Similar to PACE, these proprotein convertases generally include, beginning from the amino terminus, a signal peptide, a propeptide (that may be autocatalytically cleaved), a subtilisin-like catalytic domain characterized by Asp, His, Ser, and Asn/Asp residues, and a Homo B domain that is also essential for catalytic activity and characterized by an Arg-Gly-Asp (RGD) sequence. PACE, PACE4, and PC5 also include a Cys-rich domain, the function of which is unknown. In addition, PC5 has isoforms with and without a transmembrane domain; these different isoforms are known as PC5B and PC5A, respectively. Comparison between the amino acid sequence of the catalytic domain of PACE and the amino acid sequences of the catalytic domains of other members of this family of proprotein convertases reveals the following degrees of identity: 70 percent for PC4; 65 percent for PACE4 and PC5; 61 percent for PC1/PC3; 54 percent for PC2; and 51 percent for LPC/PC7/PC8/SPC7. Nakayama K (1997) Biochem J. 327:625-35.

PACE and PACE4 have been reported to have partially overlapping but distinct substrates. In particular, PACE4, in striking contrast to PACE, has been reported to be incapable of processing the precursor polypeptide of FIX. Wasley L C et al. (1993) J Biol Chem. 268:8458-65; Rehemtulla A et al. (1993) Biochemistry. 32:11586-90.

U.S. Pat. No. 5,840,529, issued to Seidah et al., discloses nucleotide and amino acid sequences for human PC7 and the notable ability of PC7, as compared to other PC family members, to cleave HIV gp160 to gp120 and gp41.

Nucleotide and amino acid sequences of rodent PC5 were first described as PC5 by Lusson J et al. (1993) Proc Natl Acad Sci USA 90:6691-5 and as PC6 by Nakagawa T et al. (1993) J Biochem (Tokyo) 113:132-5. U.S. Pat. No. 6,380,171, issued to Day et al., discloses nucleotide and amino acid sequences for human PC5A, the isoform without the transmembrane domain (see, e.g., U.S. Pat. Nos. 7,795,400 and 7,566,595).

Genes encoding the polypeptides of the invention can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan. Other yeast hosts such *Pichia* may also be employed. Yeast expression vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Alternatively, polypeptide-coding nucleotide sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for polypeptides in operable linkage with a promoter and enhancer from a mammary gland specific gene, such as casein or beta lactoglobulin.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein. An affinity tag sequence (e.g. a His(6) tag) may optionally be attached or included within the polypeptide sequence to facilitate downstream purification.

In one embodiment, a host cell of the invention can comprise a genetic construct encoding a scFc polypeptide and one or more enzymes that can cleave a cscFc linker (L). The construct and the enzyme(s) can be expressed using a single vector or two vectors. When the polypeptides are cloned on separate expression vectors, the vectors are co-transfected to obtain expression and assembly of intact whole proteins.

The subject methods result in a population of mature proteins that is substantially enriched for the desired heterodimeric two chain mature protein as compared to prior art methods. In one embodiment, a mature polypeptide composition of the invention substantially lacks unprocessed (i.e., single chain forms of the polypeptide). In one embodiment, the cell culture medium in which host cells expressing the polypeptides of the invention comprises a population of polypeptide which substantially lacks unprocessed (i.e., single chain forms) of the polypeptide, thereby simplifying purification. In another embodiment, the cell culture medium in which host cells expressing the polypeptides of the invention comprises a population of polypeptide which is enriched for active forms of a biologically active forms of a molecule. For example, in one embodiment, expression of a heterodimeric polypeptide of the invention using a cscFc linker allows for expression of active forms of molecules, e.g., clotting factors, without the need to activate them in an additional step.

Once expressed, the mature two chain protein can be purified according to standard procedures of the art, including ammonium sulfate precipitation, affinity column chromatography, HPLC purification, gel electrophoresis and the like (see generally Scopes, Protein Purification (Springer-Verlag, N.Y., (1982)). Substantially pure proteins of at least about 90 to 95% homogeneity are preferred, and 98 to 99% or more homogeneity most preferred, for pharmaceutical uses.

In vitro production allows scale-up to give large amounts of the desired altered polypeptides of the invention. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, hydrophobic interaction chromatography (HIC, chromatography over DEAE-cellulose or affinity chromatography.

IV. Purification of Polypeptides

In one embodiment, the invention pertains to a method of purification of mature polypeptide molecules of the invention which are expressed as double-chain (i.e., dimeric) comprising an Fc region that is not genetically-fused Fc. Such molecules can be separated from unprocessed molecules comprising a genetically-fused Fc region as well as other contaminants. Methods for purification are known in the art and include, e.g., size-exclusion chromatography, gel filtration column, SDS-PAGE, etc. The invention also pertains to purified populations of double-chain molecules.

V. Labeling or Conjugation of Functional Moieties to Polypeptides

The polypeptides of the present invention may be used in non-conjugated form or may be conjugated to at least one of a variety of functional moieties, e.g., to facilitate target detection or for imaging or therapy of the patient. The polypeptides of the invention can be labeled or conjugated either before or after purification, when purification is performed. In particular, the polypeptides of the present invention may be conjugated (e.g., via an engineered cysteine residue) to a functional moiety. Functional moieties are preferably attached to a portion of the polypeptide other than a binding site (e.g., a polypeptide linker or an Fc moiety of a genetically-fused Fc region (i.e., a cscFc region)).

Exemplary functional moieties include cytotoxins (such as radioisotopes, cytotoxic drugs, or toxins) therapeutic agents, cytostatic agents, biological toxins, prodrugs, peptides, proteins, enzymes, viruses, lipids, and biological response modifiers,

VI. Methods of Administering Polypeptides of the Invention

Methods of preparing and administering polypeptides of the invention to a subject are well known to or are readily determined by those skilled in the art.

Compositions for administration to a subject include nucleic acid molecules which comprise a nucleotide sequence encoding a molecule of the invention whether processed or unprocessed (for gene therapy applications) as well as polypeptide molecules.

The route of administration of the polypeptides of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338 each of which is incorporated herein by reference. Such articles of manufacture will preferably have labels or package inserts indicating that the associated compositions are useful for treating a subject suffering from, or predisposed to autoimmune or neoplastic disorders.

Effective doses of the compositions of the present invention, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

In one embodiment, the dose of a biologically active moiety (e.g., comprising FIX) can range from about 25 to 100 IU/kg, e.g., 0.417 mg/kg to 1.67 mg/kg. In another embodiment, the dose of a biologically active moiety (e.g., comprising FVIII) can range from about 25 to 65 IU/kg, e.g., 0.003125 mg/kg to 0.008125 mg/kg. In another embodiment, the dose of a biologically active moiety (e.g., comprising FVII), can range from about 90 to 270 ug/kg or 0.090 to 0.270 mg/kg.

In another embodiment, the dosage can range, e.g., from about 1000 ug/kg to 0.1 ng/kg body weight. In one embodiment, the dosing range is 1 ug/kg to 100 ug/kg. In another embodiment, doses can range from. 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg.

Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. In one embodiment, additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more polypeptides with different binding specificities are administered simultaneously, in which case the dosage of each polypeptide administered falls within the ranges indicated.

Polypeptides of the invention can be administered on multiple occasions. Intervals between single dosages can be weekly, monthly or yearly. Intervals can also be irregular as indicated by measuring blood levels of modified polypeptide or antigen in the patient. In some methods, dosage is adjusted to achieve a plasma modified polypeptide concentration of 1-1000 μg/ml and in some methods 25-300 μg/ml. Alternatively, polypeptides can be administered as a sustained release formulation, in which case less frequent administration is required. Dosage and frequency vary depending on the half-life of the polypeptide in the patient.

The dosage and frequency of administration can vary depending on whether the treatment is prophylactic or therapeutic. In prophylactic applications, compositions containing the polypeptides of the invention or a cocktail thereof are administered to a patient not already in the disease state to enhance the patient's resistance or reduce symptoms associated with a disease or disorder. Such an amount is defined to be a "prophylactic effective dose." In therapeutic applications, a relatively high dosage (e.g., from about 1 to 400 mg/kg of polypeptide per dose, with dosages of from 5 to 25 mg being more commonly used for radio-immunoconjugates and higher doses for cytotoxin-drug modified polypeptides) at relatively short intervals is sometimes required until progression of the disease is reduced or terminated, and preferably until the patient shows partial or complete amelioration of symptoms of disease. Thereafter, the patient can be administered a prophylactic regime.

Polypeptides of the invention can optionally be administered in combination with other agents that are effective in treating the disorder or condition in need of treatment (e.g., prophylactic or therapeutic).

While the polypeptides of the invention may be administered as described immediately above, it must be emphasized that, in other embodiments, polypeptides may be administered to otherwise healthy patients as a first line therapy. In such embodiments the polypeptides may be administered to patients having normal or average red marrow reserves and/or to patients that have not, and are not, undergoing. As used herein, the administration of polypeptides of the invention in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen may be timed to enhance the overall effectiveness of the treatment. For example, chemotherapeutic or biologic agents could be administered in standard, well known courses of treatment in conjunction with the subject molecules. A skilled artisan (e.g. a physician) would be readily be able to discern effective combined therapeutic regimens without undue experimentation based on the selected adjunct therapy and the teachings of the instant specification.

In this regard it will be appreciated that the combination of the polypeptide and the agent may be administered in any order and within any time frame that provides a therapeutic benefit to the patient. That is, the agent and polypeptide may be administered in any order or concurrently. In selected embodiments the polypeptides of the present invention will be administered to patients that have previously undergone chemotherapy. In yet other embodiments, the polypeptides and the chemotherapeutic treatment will be administered substantially simultaneously or concurrently. For example, the patient may be given the polypeptide while undergoing a course of chemotherapy. In preferred embodiments the polypeptide will be administered within 1 year of any agent or treatment. In other preferred embodiments the polypeptide will be administered within 10, 8, 6, 4, or 2 months of any agent or treatment. In still other preferred embodiments the polypeptide will be administered within 4, 3, 2 or 1 week of any agent or treatment. In yet other embodiments the polypeptide will be administered within 5, 4, 3, 2 or 1 days of the selected agent or treatment. It will further be appreciated that the two agents or treatments may be administered to the patient within a matter of hours or minutes (i.e. substantially simultaneously).

In one embodiment, a polypeptide of the invention can be administered as a nucleic acid molecule. Nucleic acid molecules can be administered using techniques known in the art, including via vector, plasmid, liposome, DNA injection, electroporation, gene gun, intravenously injection or hepatic artery infusion. Vectors for use in gene therapy embodiments are known in the art.

It will further be appreciated that the molecules of the instant invention may be used in conjunction or combination with an agent or agents (e.g. to provide a combined therapeutic regimen). Exemplary agents with which a molecule of the invention may be combined include agents that represent the current standard of care for a particular disorder being treated. Such agents may be chemical or biologic in nature. The term "biologic" or "biologic agent" refers to any pharmaceutically active agent made from living organisms and/or their products which is intended for use as a therapeutic.

The amount of agent to be used in combination with the polypeptides of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9$^{th}$ ed. 1996). In another embodiment, an amount of such an agent consistent with the standard of care is administered.

As previously discussed, the polypeptides of the present invention, may be administered in a pharmaceutically effective amount for the in vivo treatment of mammalian disorders. In this regard, it will be appreciated that the molecule of the invention can be formulated to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of a polypeptide of the invention, conjugated or unconjugated to a therapeutic agent, shall be held to mean an amount sufficient to achieve a benefit, e.g., to ameliorate symptoms of a disease or disorder or to detect a substance or a cell. Of course, the pharmaceutical compositions of the present invention may be administered in single or multiple doses to provide for a pharmaceutically effective amount of the polypeptide.

The polypeptides of the invention have many uses as will be recognized by one skilled in the art, including, but not limited to methods of treating a subject with a disease or condition. In keeping with the scope of the present disclosure, the molecule of the invention may be administered to a human or other animal in accordance with the aforementioned methods of treatment in an amount sufficient to produce a therapeutic or prophylactic effect. It will be understood that the type of disorders that can be treated depend upon the biologically active moiety present in the polypeptide and the known biological effects of the biologically active moiety. Given the modular nature of the disclosed polypeptides, biologically active moieties can be selected by those of skill in the art and placed into a scFc scaffold with a cscFc linker according to the claimed invention.

In one embodiment, when the polypeptide comprises a clotting factor as a biologically active moiety, the invention relates to a method of treating a subject having a hemostatic disorder comprising administering a therapeutically effective amount of at least one polypeptides of the invention.

Polypeptides of the invention which comprise a clotting factor can be used to treat or prevent a hemostatic disorder by promoting the formation of a fibrin clot. The polypeptides of the invention can be used to treat hemostatic disorders, e.g., those known to be treatable with the particular clotting factor present in the polypeptide. The hemostatic disorders that may be treated by administration of the chimeric protein of the invention include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII.

In one embodiment, the hemostatic disorder is an inherited disorder. In one embodiment, the subject has hemophilia A, and the polypeptides comprises Factor VII or Factor VIIIa. In another embodiment, the subject has hemophilia A and the chimeric protein comprises Factor VII or Factor VIIa. In another embodiment, the subject has hemophilia B and the chimeric protein comprises Factor IX or Factor IXa. In another embodiment, the subject has hemophilia B and the polypeptides comprises Factor VII or Factor VIIa. In another embodiment, the subject has inhibitory antibodies to Factor VII or Factor VIIIa and the polypeptides comprises Factor VII or Factor VIIa. In yet another embodiment, the subject has inhibitory antibodies against Factor IX or Factor IXa and the polypeptides comprises Factor VII or Factor VIIa.

The polypeptides of the invention can be used to prophylactically treat a subject with a hemostatic disorder. The polypeptides of the invention can be used to treat an acute bleeding episode in a subject with a hemostatic disorder.

In one embodiment, the hemostatic disorder is the result of a deficiency in a clotting factor, e.g., Factor IX, Factor VIII. In another embodiment, the hemostatic disorder can be the result of a defective clotting factor.

In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g. cancer chemotherapy).

The invention also relates to methods of treating a subject that does not have a hemostatic disorder or a secondary disease or condition resulting in acquisition of a hemostatic disorder. The invention thus relates to a method of treating a subject in need of a general hemostatic agent comprising administering a therapeutically effective amount of at least one polypeptide of the invention. For example, in one embodiment, the subject in need of a general hemostatic agent is undergoing, or is about to undergo, surgery. The polypeptides factor of the invention can be administered prior to or after surgery as a prophylactic. The polypeptides of the invention can be administered during or after surgery to control an acute bleeding episode. The surgery can include, but is not limited to, liver transplantation, liver resection, or stem cell transplantation.

In another embodiment, the polypeptides of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

This invention is further illustrated by the following examples which should not be construed as limiting. The contents of all references, patents and published patent applications cited throughout this application are incorporated herein by reference.

EXAMPLES

Throughout the examples, the following materials and methods were used unless otherwise stated.

Example 1: Cloning of pSYN-FVII-024

The coding sequence of FVII was obtained by reverse transcription coupled to polymerase chain reaction from a human liver mRNA library (Ambion, Austin, Tex.) using the following primers:

FVII-F1
(SEQ ID NO: 41)
GGGAATGTCAACAGGCAGGG

FVII-R1
(SEQ ID NO: 42)
CTTGGCTTTCTCTCCACAGGC

A 50 µl reaction was carried out with 10 pmol of each primer using the Superscript One-step RT-PCR with Platinum Taq system (Invitrogen, Carlsbad, Calif.) according to the manufacturer's standard protocol in a MJ thermocycler. The cycle used was 50° C. for 30 minutes for the reverse transcription followed by denaturing at 94° C. for 2 minutes and 30 cycles of (94° C. 30 seconds, 53° C. 30 seconds, 72° C. 90 seconds) followed by 10 minutes at 72° C. The expected sized band (~1400 bp) was gel-purified with a Gel Extraction kit (Qiagen, Valencia, Calif.) and cloned in pCR2.1 TOPO using the TOPO TA Cloning kit (Invitrogen, Carlsbad, Calif.) to produce the intermediate plasmid pSYN-FVII-001. To construct a plasmid for the expression of a two-chain FVII-Fc and Fc heterodimer, the FVII coding sequence was PCR-amplified using the following primers:

HindIII-Kozak-FVII-F
(SEQ ID NO: 43)
CGACAAGCTTGCCGCCACCATGGTCTCCCAGGCCCTCAGG

BspeI-Fc-FVII-R
(SEQ ID NO: 44)
CGACTCCGGAGCTGGGCACGGTGGGCATGTGTGAGTTTTGTCGGGAAATG
GGGCTCGCAGG The forward primer HindIII-Kozak-FVII-F adds a HindIII restriction site followed by a Kozak sequence immediately upstream of the FVII coding region. The reverse primer BspeI-Fc-FVII-R adds a fragment of the constant region of IgG1 (the Fc region) comprising amino acids 221-233 (EU numbering). This process also incorporates a BspEI restriction site at amino acids 231-233 using the degeneracy of the genetic code to preserve the correct amino acid sequence (EU numbering). A 50 ul reaction was carried out with 15 pmol of each primer and template pSYN-FVII-001 using Platinum Pfx DNA Polymerase system according to manufacturer's protocol in a MJ Thermocycler using the following cycles: 95° C. 2 minutes; 30 cycles of (95° C. 15 seconds, 49° C. 30 seconds, 68° C. 90 seconds); 68° C. 10 minutes. Plasmid pSYN-FIX-027 (pBUD FIXFc/Fc) was digested with HindIII and BspEI and the expected sized band for the vector (approximately 5800 bp) was purified away from the FIX insert (expected size band approximately 1480 bp) with a Gel Extraction kit (Qiagen, Valencia, Calif.). Next, the PCR-amplified FVII sequence was subcloned into HindIII and EcoRI sites of the vector derived from pSYN-FIX-027 after removing the FIX insert. This generated pSYN-FVII-002 (pBUD FVIIFc/Fc). Next, A (GGGGS)$_{6x}$ (SEQ ID NO: 36) polypeptide linker was added between FVII and the Fc region coding sequences in pSYN-FVII-002 using the following primers:

FVII-linker-F:
(SEQ ID NO: 45)
CATCCCCAGCACGTACGTCC

FVII-Linker-R:
(SEQ ID NO: 46)
GGGCATGTGTGAGTTTTGTCTGATCCCCCGCCACCGGAACCTCCACCGCC
TGATCCACCCCCACCTGATCCGCCGCCACCGGACCCACCTCCGCCGGAGC
CACCGCCACCGGGAAATGGGGCTCGCAGGAGG Fc-linker-F:
(SEQ ID NO: 47)
GACAAAACTCACACATGCCCACC Fc-linker-R:
(SEQ ID NO: 48)
GCAGAATTCTCATTTACCCGGAG Two 12 µl PCR reactions were carried out with either 12 pmol of FVII-linker-F and FVII-Linker-R (reaction 1) or Fc-linker-F and Fc-linker-R (reaction 2) using Expand High Fidelity System (Boehringer Mannheim, Indianapolis, Ind.) according to manufacturer's standard protocol in a MJ Thermocycler. The first and second reactions were carried out with 1 µg of pSYN-FVII-002 as template using the following cycle: 94° C. 2 minutes; 14 cycles of (94° C. 30 seconds, 55° C. 30 seconds, 72° C. 2 minutes); 72° C. 10 minutes. The expected sized bands (532 bp for reaction 1 and 670 bp for reaction 2) were gel purified with a Gel Extraction kit (Qiagen, Valencia, Calif.), then combined in a PCR reaction with 25 pmol of FVII-linker-F and Fc-linker-R as before, but with 30 rounds of amplification. The expected sized band (1200 bp) was gel purified with a Gel Extraction kit (Qiagen, Valencia, Calif.) and digested with restriction enzymes KpnI and EcoRI. The expected sized band (920 bp) was gel purified as before and cloned into the KpnI/EcoRI sites of pSYN-FVII-002 to generate pSYN-FVII-003 (pBUD FVIIFc/6×(GGGGS) (SEQ ID NO: 36)/Fc).

Cloning of pSYN-FVII-024 to Express a Two-Chain Heterodimer

Plasmid (pSYN-FVII-024) was generated for the expression of a two-chain heterodimer where one chain consists of the FVII light chain (residues 1-152) followed by a (GGGGS)$_{6x}$ (SEQ ID NO: 36) linker followed by the Fc region, while the other chain contains a FVII heavy chain (residues 153 to 406) followed by a (GGGGS)$_{6x}$ (SEQ ID NO: 36) linker followed by the Fc region. The plasmid is designed to express the heterodimer as a single polypeptide where the C-terminus of the FVII heavy chain-linker-Fc chain is connected to the N-terminus of the heavy chain-linker-Fc chain by the following polypeptide sequence: RRRRS-(GGGGS)$_{6x}$-RKRRKR (SEQ ID NO: 50), where the RRRRS (SEQ ID NO: 38) and RKRRKR (SEQ ID NO: 39) sequences are proprotein convertase cleavage sites. Intracellular cleavage by proprotein convertases following the last Arg at each cleavage site can result in removal of the polypeptide linker. Consequently, cells will express a 2 chain heterodimer where the FVII light chain-linker-Fc chain has a RRRRS (SEQ ID NO: 38) sequence at the C-terminus, but the remainder of the linker and the RKRRKR (SEQ ID NO: 39) sequence have otherwise been removed. Construction of the pSYN-FVII-024 and several intermediate plasmids required the use of the following primers:

HindIII-SalI-BpEI-Fc-F
(SEQ ID NO: 51)
AGTCAAGCTTGTCGACTCCGGAACTCCTGGGCGGACC

```
                            -continued
BamHI-linker(PACE1)-Fc-R
                                           (SEQ ID NO: 52)
CATCGGATCCCCCGCCACCGGAACCTCCACCGCCTGATCCACCCCCACCT

GATCCGCCGCCACCGCTCCGGCGGCGCCGTTTACCCGGAGACAGGGAGAG

G

HindIII-Kozak-FVII-F
                                           (SEQ ID NO: 43)
CGACAAGCTTGCCGCCACCATGGTCTCCCAGGCCCTCAGG BspEI-Fc-linker-FVIILC-R
                                           (SEQ ID NO: 53)
GAGTTCCGGAGCTGGGCACGGTGGGCATGTGTGAGTTTTGTCTGATCCCC

CGCCACCGGAACCTCCACCGCCTGATCCACCCCCACCTGATCCGCCGCCA

CCGGACCCACCTCCGCCGGAGCCACCGCCACCTCGGCCTTGGGGTTTGCT

GG

BamHI-2xlink-pace-HC-F
                                           (SEQ ID NO: 54)
CAGTCTGGATCCGGCGGTGGAGGTTCCGGTGGGGGTGGATCAAGGAAGAG

GAGGAAGAGGATTGTGGGGGGCAAGGTGTGCC

Fc-EcoRI-R
                                           (SEQ ID NO: 55)
ATGTCTGAATTCTCATTTACCCGGAGACAGGGAGAGG
```

To generate the first intermediate plasmid, a PCR reaction was performed with 25 pmol of primers HindIII-SalI-BpEI-Fc-F and BamHI-linker (PACE1)-Fc-R and template pSYN-Fc-001 using Expand High Fidelity System (Boehringer Mannheim, Indianapolis, Ind.) according to manufacturer's standard protocol in a MJ Thermocycler. The following cycles were used: 95° C. 2 minutes; 30 cycles of (95° C. 30 seconds, 58° C. 30 seconds, and 72° C. 1 minute); 72° C. 10 minutes. The correct sized band (approximately 730 bp) was gel purified as above and cloned into the HindIII/BamHI sites of pBUDCE4 vector (Invitrogen, Carlsbad, Calif.), generating pSYN-FVII-014. PCR amplification with primers HindIII-SalI-BpEI-Fc-F and BamHI-linker (PACE1)-Fc-R generated a DNA fragment encoding a portion of the Fc region (Amino A X-Y) followed by an RRRRS (SEQ ID NO: 38) sequence and (GGGGS)$_{2x}$ (SEQ ID NO: 29) polypeptide linker. Primer HindIII-SalI-BpEI-Fc-F introduces a HindIII and SalI restriction site at the 5' end of the molecule, while primer BamHI-linker (PACE1)-Fc-R introduces a BamHI at the 3' end that overlaps the codons encoding the last 2 residues of the GGGGS (SEQ ID NO: 56) linker (residues GS with codons GGA TCC)

Next, another PCR reaction was performed as above with primers HindIII-Kozak-FVII-F and BspEI-Fc-linker-FVIILC-R and template pSYN-FVII-002 using the same conditions described for cloning of pSYN-FVII-014, but with an annealing temperature of 57° C. The expected sized band (approximately 700 bp) was gel purified and cloned into the HindIII and BspEI sites of pSYN-FVII-014 to generate pSYN-FVII-023. Primers HindIII-Kozak-FVII-F and BspEI-Fc-linker-FVIILC-R amplified a DNA fragment encoding the FVII light chain followed by a (GGGGS)$_{6x}$ (SEQ ID NO: 36) polypeptide linker and a portion of the Fc region up to amino acid 232 (EU numbering). Primer HindIII-Kozak-FVII-F introduces a HindIII restriction site at the 5' end of the molecule followed by a Kozak sequence while primer BspEI-Fc-linker-FVIILC-R adds a BspeI site at the 3' end of the molecule.

Figure 1B:
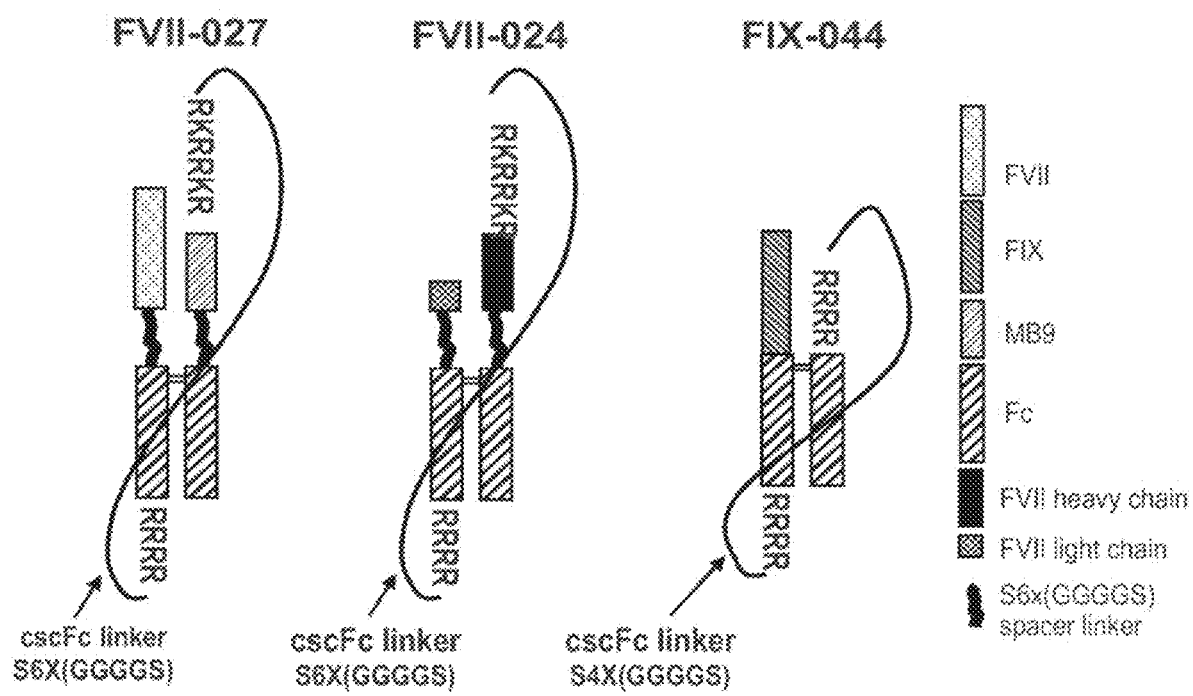

In the final step a PCR reaction was carried out as above with primers BamHI-2xlink-pace-HC-F and Fc-EcoRI-R and template pSYN-FVII-003 with the following cycles: 95° C. 2 minutes; 30 cycles of (95° C. 30 seconds, 55° C. 30 seconds, and 72° C. 2 minute); 72° C. 7 minutes. This PCR reaction generated a DNA molecule encoding a (GGGGS)$_{2x}$ (SEQ ID NO: 29) polypeptide linker followed by a RKRRKR (SEQ ID NO: 39) sequence followed by the FVII heavy chain. Primers BamHI-2xlink-pace-HC-F and Fc-EcoRI-R introduce a BamHI site and an EcoRI site at the 5' and 3' end of the molecule, respectively. The expected sized band (approximately 1600 bp) was cloned into the BamHI and EcoRI sites of pSYN-FVII-023 to generate pSYN-FVII-024. The final structure of translation of pSYN-FVII-024 is illustrated in FIG. 1B.

Example 2. Heterodimeric Constructs Comprising FIX-Fc

Cloning of pSYN-FIX-044

Plasmid pSYN-FIX-044 was constructed for the expression of a 2-chain FIX-Fc and Fc heterodimer produced in the cell as a single chain protein where the FIX-Fc coding DNA region is linked to the second Fc coding region by a DNA fragment encoding the following polypeptide sequence: RRRRS-(GGGGS)$_{4x}$-RRRR (SEQ ID NO: 57), where the RRRR (SEQ ID NO: 40) sequence is a proprotein convertase cleavage site. Proprotein convertases then cleave 5' of the last Arg in the RRRRS (SEQ ID NO: 38) and RRRR (SEQ ID NO: 40) sequences intracellularly. Consequently, cells express a 2 chain FIX-Fc/Fc heterodimer where the FIX-Fc chain has a RRRRS (SEQ ID NO: 38) sequence at the C-terminus, but the remainder of the linker and the 3' RRRR (SEQ ID NO: 40) sequence have otherwise been removed. For this purpose, the synthesis of a DNA fragment (Genscript-FIX-044) was outsourced (Genscript, Piscataway, N.J.). This fragment consisted of a DNA sequence encoding a portion of the Fc region from residues 231-447 (EU numbering) followed by a RRRRS (SEQ ID NO: 38) sequence followed by (GGGGS)$_{4x}$ (SEQ ID NO: 6) polypeptide linker and a RRRR (SEQ ID NO: 40) sequence upstream of another portion of the Fc region (residues 221-230, EU numbering). The DNA region encoding residues 231-233 of the Fc region at the 5' of the molecule overlaps a BspEI site, while the region encoding residues 236-238 of the Fc region at the 3' of the molecule include an RsrII restriction site. Genscript-FIX-044 was designed so that the RsrII site of the 5' Fc region and the BspEI site of the 3' Fc region were removed using the degeneracy of the genetic code to preserve the correct amino acid sequence. Genscript-FIX-044 was cleaved with restriction enzymes BspEI and RsrII and cloned into the same sites of pSYN-FIX-029 to generate pSYN-FIX-044. The final structure of translation of pSYN-FIX-044 is illustrated in FIG. 1B.

Example 3. Heterodimeric Constructs Comprising FVII-Fc and MB9-Fc

Cloning of pSYN-FVII-027

Plasmid (pSYN-FVII-027) was generated for the expression FVII-Fc and MB9-Fc heterodimer, where MB9 is a scFv previously shown to bind to receptor GPIIb/IIIa on activated platelets. Protein from pSYN-FVII-027 is expressed in the cell as a single polypeptide where the C-terminus of the FVII-Fc subunit is linked to the N-terminus of the MB9-Fc subunit by a (GGGGS)$_{6x}$ (SEQ ID NO: 36) polypeptide linker. Furthermore, RRRRS (SEQ ID NO: 38) and RKRRKR (SEQ ID NO: 39) sequences were inserted at the 5' and 3' end of the polypeptide linker, respectively, for intracellular cleavage by proprotein convertases following the last Arg at each sequence. Consequently, cells will express a 2 chain FVII-Fc/MB9-Fc heterodimer where the FVII-Fc chain has a RRRRS (SEQ ID NO: 38) sequence at the C-terminus, but the remainder of the linker and the RKRRKR (SEQ ID NO: 39) sequence have otherwise been removed.

As a first step a series of intermediate plasmid were generated using the following primers:

```
HindIII-SalI-BpsEI-Fc-F
                                    (SEQ ID NO: 51)
AGTCAAGCTTGTCGACTCCGGAACTCCTGGGCGGACC BamHI-linker-Fc-R
                                    (SEQ ID NO: 58)
CATCGGATCCCCGCCACCGGAACCTCCACCGCCTGATCCACCCCCACCT

GATCCGCCGCCACCTTTACCCGGAGACAGGGAGAGG

BclI-Fc-F
                                    (SEQ ID NO: 59)
CAGTCTTGATCAGACAAAACTCACACATGCCCACC scFc-EcoRI-R
                                    (SEQ ID NO: 60)
ACTGACGAATTCTCATTTACCCGGAGACAGGGAG

HindIII-Kozak-FVII-F:
                                    (SEQ ID NO: 43)
CGACAAGCTTGCCGCCACCATGGTCTCCCAGGCCCTCAGG FVII-HC-BspEI-R:
                                    (SEQ ID NO: 61)
AGGAGTTCCGGAGCTGGGCACGGTGGGCATGTGTGAGTTTTGTCGGATCC

CCCGCCACCGGAACCTCCACCGCCTGATCCACCCCCACCTGATCCGCCGC

CACCGGACCCACCTCCGCCGGAGCCACCGCCACCGGGAAATGGGGCTCGC

AGGAGG
```

A 50 ul PCR reaction was carried out with 25 pmol of HindIII-SalI-BpEI-Fc-F and BamHI-linker-Fc-R and template pSYN-Fc-001 using the following cycle: 95° C. 2 minutes; 30 cycles of (95° C. 30 seconds, 54° C. 30 seconds, 72° C. 1 minute). The expected sized band (~700 bp) was gel purified with a Gel Extraction kit (Qiagen, Valencia, Calif.) and cloned into the HindIII and BamHI restriction sites of pBUDCE4 (Invitrogen, Carlsbad, Calif.) to generate intermediate pSYN-FVII-007. Primers HindIII-SalI-BpEI-Fc-F and BamHI-linker-Fc-R amplify the Fc region starting at amino acid 221 (EU numbering) and add a HindIII and a SalI restriction enzyme site immediately upstream of site Fc region, as well as a DNA fragment encoding a (GGGGS)$_{4x}$ (SEQ ID NO: 6) linker followed by a BamHI site immediately downstream of the Fc coding region. Next, a 50 ul reaction was carried out with 25 pmol of BclI-Fc-F and scFc-EcoRI-R, and template pSYN-Fc-011 using the same cycles as above. The expected sized band (~700 bp) was gel purified as above, cut with restriction enzymes BamHI and EcoRI, and cloned in the BclI/EcoRI restriction sites of pSYN-FVII-007 to generate the intermediate plasmid pSYN-FVII-008. The primer pair BclI-Fc-F and scFc-EcoRI-R amplifies the Fc region while adding a BclI and EcoRI restriction sites immediately upstream and downstream of the Fc coding region, respectively. To generate the last intermediate plasmid, a 50 ul PCR reaction was carried out with 25 pmol of HindIII-Kozak-FVII-F and FVII-HC-BspEI-R and template pSYN-FVII-001 using the following cycle: 95° C. 2 minutes; 30 cycles of (95° C. 30 seconds, 55° C. 30 seconds, 72° C. 90 seconds). The primer pair amplifies the FVII coding region while adding a DNA fragment at the 3' end of the molecule encoding a (GGGGS)$_{6x}$ (SEQ ID NO: 36)polypeptide linker followed by a fragment of the Fc region ending at amino acid 221 (EU numbering). Primer HindIII-Kozak-FVII-F generates a HindIII restriction site at the 5' of the molecule followed by a Kozak sequence directly upstream of the FVII coding region. The FVII-HC-BspEI-R primer introduces DNA encoding the polypeptide linker as well as the Fc portion. The expected sized band (~1500 bp) was gel purified as above and cloned into the HindIII/BspEI sites of pSYN-FVII-008 to generate pSYN-FVII-011.

Next, 2 DNA fragments were synthesized: Genescript-FVII-027-1 and Genscript-FVII-026-2. Genescript-FVII-027-1 consists of a DNA fragment encoding a portion of the Fc region (starting at nucleotide 1306, EU numbering) followed by the sequence RRRRS-(GGGGS)$_{6x}$-RKRRKR (SEQ ID NO: 50) followed by a portion of the MB9 scFv (residues 1-142). An EcoRI site was introduced in the coding sequence of MB9 using the degeneracy of the genetic code to preserve the proper amino acid sequence and overlaps the last 6 bases of Genescript-FVII-027-1. In addition, the first 6 bases at the 5' include a SapI site found within the Fc region. Genscript-FVII-026-2 consists of a DNA fragment encoding a portion of the MB9 (residues 143-273) followed by a (GGGGS)$_{6x}$ (SEQ ID NO: 36) polypeptide linker followed by the Fc region and an EcoRI site. An EcoRI site was introduced in the coding sequence of MB9 using the degeneracy of the genetic code to preserve the proper amino acid sequence and overlaps the first 6 bases of Genescript-FVII-026-2.

Genescript-FVII-027-1 was cloned into the SapI and EcoRI sites of pSYN-FVII-011 to generate pSYN-FVII-036. Next, Genscript-FVII-026-2 was cloned into the EcoRI site of pSYN-FVII-036 to generate pSYN-FVII-027. Correct orientation of the last cloning step was confirmed by restriction enzyme analysis and DNA sequencing. The final structure of translation of pSYN-FVII-027 is illustrated in FIG. 1B.

Example 4. Transient Transfections of Cells

HEK-293-F cells were grown in suspension in Freestyle media (Invitrogen) supplemented with vitamin K3 (Sigma Aldrich, St. Louis, Mo.) to 2 µg/liter (growth media) as suspension cells at 37° C./10% $CO_2$. Cells we subcultured every three to four days by seeding at cell density of $5 \times 10^5$ cells/ml.

Twenty-four hours prior to transfection cells were seeded at a density of $7 \times 10^5$ cells/ml in growth media supplemented with LONG™ R3IGF-1 (Sigma Aldrich, St. Louis, Mo.) to 20 µg/liter (transfection media). On the day of transfection, a transfection solution was made with a volume equal to 5% of the total volume of the cell culture to be transfected. In the transfection solution DNA was added (final concentration 20 mg/L) to a freshly made solution of PEI (60 mg/L) in transfection media. The solution was swirled for 30 seconds and incubated for five minutes at room temperature before adding directly to the cell culture. Four hours later a volume equal to the cell culture volume of OptiCHO (Invitrogen) supplemented with vitamin K3 (when transfecting FIX or FVII constructs) (, LONG™ R3IGF-1 and 200 mM L-glutamine was added to the cells. The cell culture was allowed to grow as shown above and daily media samples were taken to assess protein expression.

Example 5. Analysis of Protein Generated from Transient Transfections

For analysis of protein from transient transfections, conditioned media from transfections were subjected to protein A immunoprecipitation. Briefly, cell culture supernatant was mixed with approximately 50 ul of protein A-Sepharose 50% slurry and incubated at 4° C. with rocking for 1 hour, then centrifuged to pellet the protein A beads. Beads were washed twice by resuspending in 1 ml of PBS, spinning and aspirating. The beads were resuspended with sodium dodecylsulfate-polyacrylamide gel electrophoresis (SDS-PAGE) under reducing or nonreducing conditions, heated for 5 minutes at 100° C., spun down and loaded on SDS-PAGE gels and run according to standard protocols. Gels were transferred to nitrocellulose membranes and Western blots were performed to detect the Fc region or the FVII light chain. For Fc detection, the antibody used was a goat anti-human IgG (Fc specific)-horseradish peroxidase conjugate (Pierce ImmunoPure antibody, catalog #31413). For FVII light chain detection an anti light chain monoclonal antibody was used (Green Mountain, clone 6MA-219). The antibodies were diluted 1:15,000 (for Fc detection) or 1:200 (for light chain detection) in PBST (PBS with 0.1% Tween-20) with 5% nonfat dry milk and incubated with the membrane for 1 hour at room temperature. The membrane was then washed in PBST 3 times for 10 minutes and signal was detected by a chemiluminescent method for Fc detection. For FVII light chain detection, the membrane was further incubated for one hour in a solution containing HRP-labeled goat anti-mouse antibody (Southern Biotech, #1010-05) diluted 1:5000 in PBST. The membrane was also washed in PBST 3 times for 10 minutes and the signal was detected by a chemiluminescent method. Chemiluminescent detection was performed using ECL Plus Western Blotting Detection System (Amersham Biosciences catalog #RPN2132) according to manufacturer's protocol. Signal was visualized in a Storm 840 Phosphorimager (Molecular Devices). Alternatively, protein gels could be analyzed by Coomassie Blue staining Example 6. The Generation of Constructs Comprising Alternate Processing Sites Cloning of pSYN-FIX-056 Intermediate:

Synthesis of DNA fragment Genscript-FVII-043 was outsourced (Genscript). This fragment consisted of a DNA molecule encoding a portion of the Fc region (residues 232 to 447, EU numbering) followed by a (GGGGS)4× (SEQ ID NO: 6) polypeptide linker and another portion of the Fc region (residues 221 to 238, EU numbering). This DNA fragment was digested with BspEI and RsrII and subcloned into the BspEI/RsrII sites of pSYN-FIX-044 to generate pSYN-FIX-049. HindIII/EcoRI fragment from pSYN-FIX-049 comprising the FIX coding region followed by the single chain Fc coding region was subcloned in to the HindIII/EcoRI sites of pBUDCE4.1 (Invitrogen) to generate pSYN-FIX-056.

Cloning of pSYN-FIX-050, -052 and -053:

Synthesis of DNA fragments Genscript-FIX-050, -052, -053 was outsourced (Genscript). These fragments comprise a portion of the Fc region (from SalI site in pSYN-FIX-056), an RRRRS (SEQ ID NO: 38) sequence, a (GGGGS)4× (SEQ ID NO: 6) polypeptide, a variable propeptide convertase cleavage site and a portion of the Fc region (up to the RsrII in the second Fc of pSYN-FIX-056). Each DNA fragment encodes for a different variable propeptide convertase cleavage site: genscript-FIX-050, RAGR (SEQ ID NO: 100); genscript-FIX-052 RSKR (SEQ ID NO: 101); and genscript-FIX-053, RKRRKR (SEQ ID NO: 39) (thus, they are identical to 044 with the exception of these sequences; 044 comprises the RRRR(SEQ ID NO: 40) site). SalI/RsrII fragments from Genscript-FIX-050, -052, and -053 were subcloned into SalI/RsrII sites of pSYN-FIX-056 to generate pSYN-FIX-050, -052, and -053, respectively.

Example 7: FIXFc Constructs with cscFc Linker

Figure 3A:
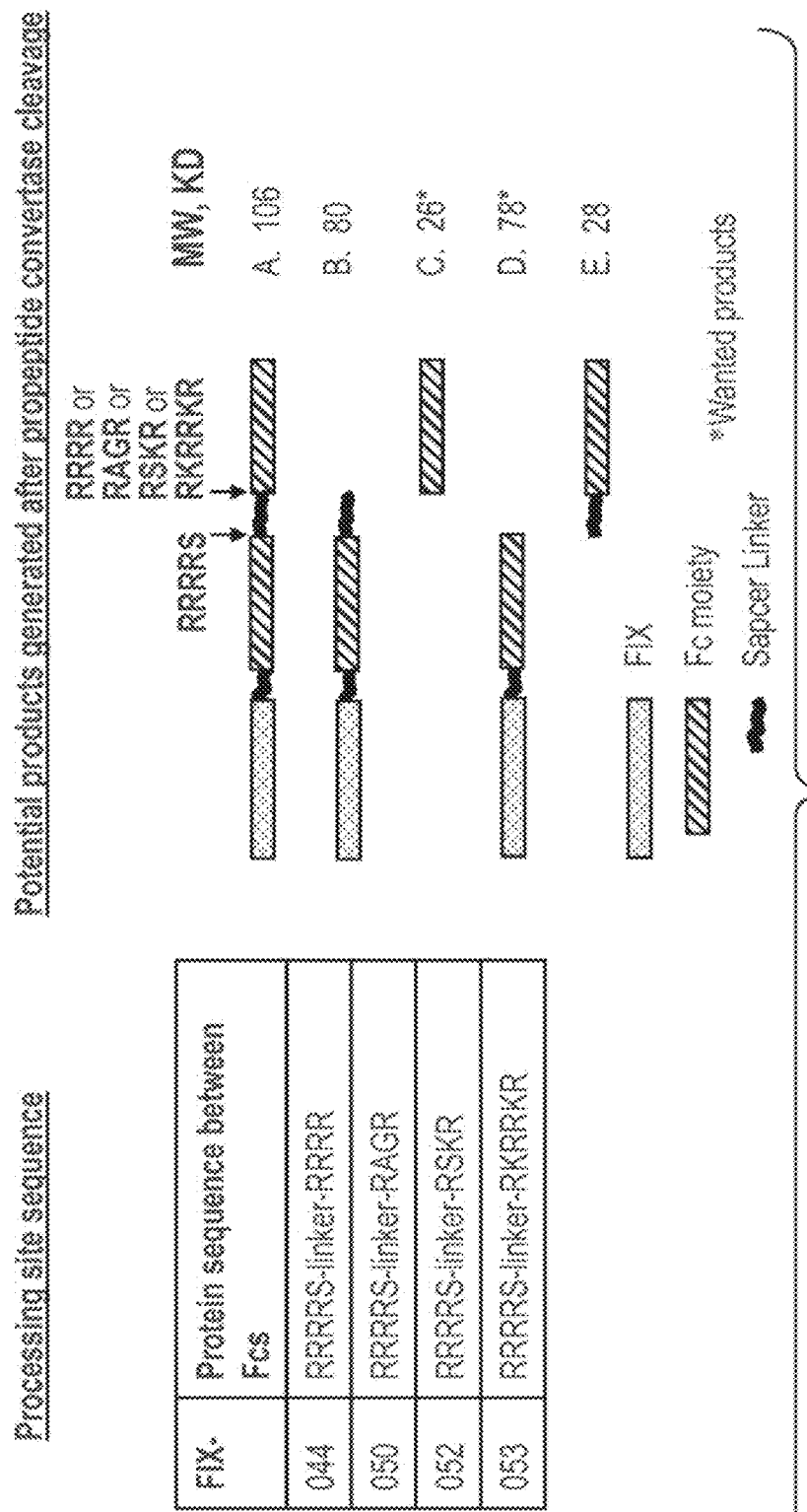
FIG. 3A illustrates propeptide convertase cleavage of processing sites in FIX-Fc proteins for the removal of a polypeptide linker connecting both Fc moieties in an cscFc.
Figure 3B:
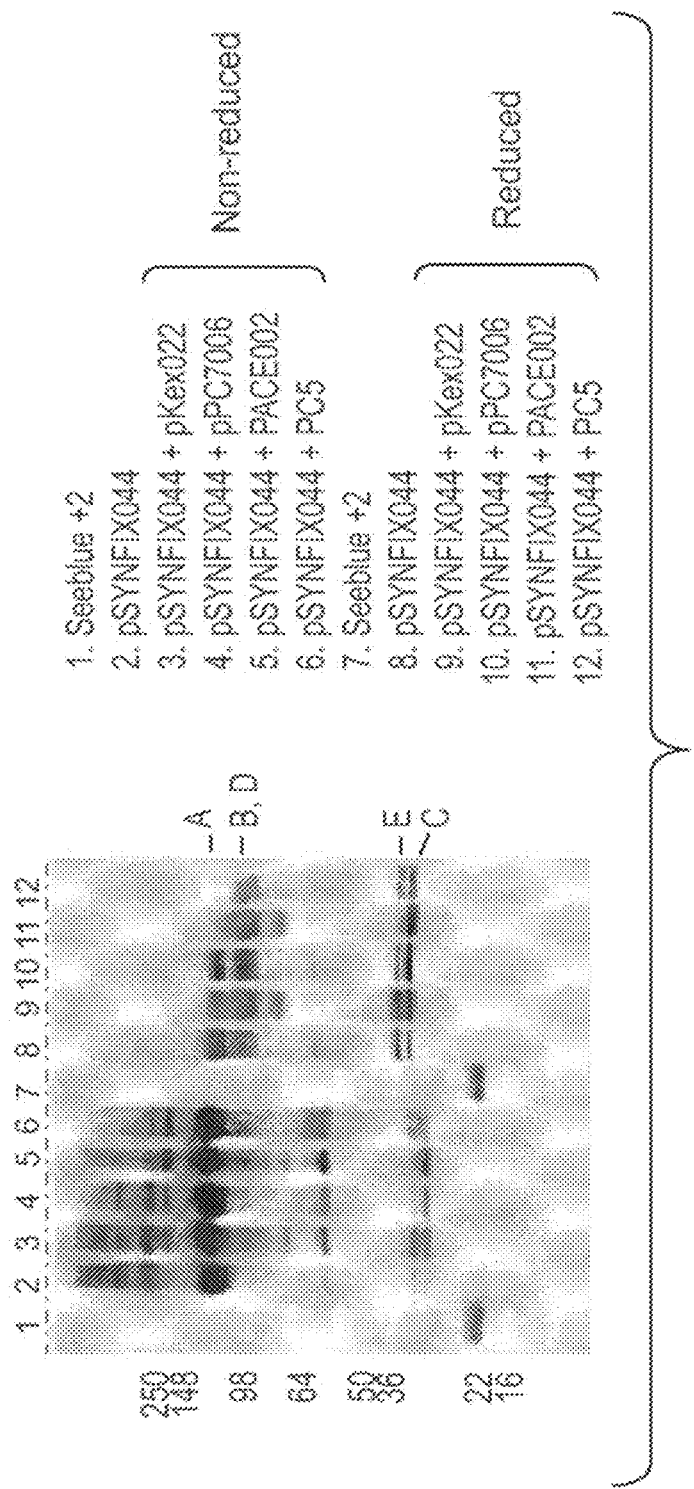
FIG. 3B illustrates that full cleavage of processing sites in FIX-044 was achieved with PACE, but not Kex2, PC5 or PC7, however, PACE cleavage results in extra cleavage of the protein (see band below B,D).

Construct FIX-044 (FIG. 3A) was made comprising a FIX molecule followed by an Fc region with a cscFc linker connecting both Fc moieties as described in FIG. 3A. FIG. 3B shows western blot data (Fc western) for FIX-044 following transfection and protein A pulldown. FIX-044 was cotransfected the Kex2, PC7, PACE or PC5.

Cloning of PC5

The coding sequence for human PC5 was obtained by RT-PCR. The following primers were used (areas that anneal to the cDNA are indicated in bold):

| Primers | SEQ ID NO | Sequences |
|---------|-----------|-----------|
| PACE-F1: | 93 | 5'-GGTAAGCTTGCCATGGAGCTGAGGCCCTGG TTGC-3' |
| PACE-R1: | 92 | 5'-GTTTTCAATCTCTAGGACCCACTCGCC-3' |
| PACE-F2: | 83 | 5'-GCCAGGCCACATGACTACTCCGC-3' |
| PACE-R2: | 82 | 5'-GGTGAATTCTCACTCAGGCAGGTGTGAGGG CAGC-3' |

Coding sequence for human PC5 (GenBank accession no. NM-006200) was obtained in two pieces. The 3' 1750 bp were obtained using the primers PC5-KpnI-F and PC5-NotI-R with the Invitrogen SUPERSCRIPT™ RT-PCR with PLATINUM™ Taq kit according to the manufacturer's standard protocol, from human liver mRNA. The cycle used for the reverse transcription was 30 min at 50° C. followed by denaturing at 94° C. for 2 min and 35 cycles of 94° C. for 15 sec, 54° C. for 30 sec, 72° C. for 3 min, followed by 10 min extension at 72° C. and then storage at 4° C. This produced a fragment from the internal KpnI site in the PC5 coding sequence through the stop codon, with a NotI site added at the 3' end. This fragment was then cloned into pCR2.1 TOPO according to manufacturer's protocol to generate pSYN-PC5-001 (pCR2.1/PC5 (KpnI-NotI)). This fragment was then subcloned into pcDNA3.1/hygro using the KpnI and NotI restriction sites to generate pSYN-PC5-002 (pcDNA3.1/hygro/PC5 (KpnI-NotI)).

The 5'~1100 bp of PC5 was obtained in two steps. It was first amplified by RT-PCR using the primers PC5-UTR-F and PC5-HindIII-R to amplify a ~1520 bp fragment from human liver mRNA, using similar conditions as above, with an annealing temperature of 57° C. These primers have complete homology to the native PC5 sequence, in the untranslated 5' sequence and sequence 3' from the internal unique HindIII site, respectively. Note that this HindIII site is not present in the final construct due to a silent nucleotide substitution. This DNA fragment was then gel purified and used as a template for a second PCR reaction with PC5-Afl2-F, which adds an AflII cloning site followed by a Kozak sequence to the N-terminal coding sequence at the 5' end, and PC5-KpnI-R, which anneals 3' to the internal unique KpnI site, to generate an 1100 bp fragment. The reaction was carried out with the EXPAND™ High Fidelity System according to the manufacturer's standard protocol in a MJ Thermocycler using the following cycles: 94° C., 2 min; 14 cycles of (94° C., 30 sec, 57° C., 30 sec, 72° C., 2 min), followed by 72° C., 10 min. This fragment was then subcloned into pSYN-PC5-002 using the AflII and KpnI restriction sites to generate pSYN-PC5-003 (pcDNA3.1/hygro/PC5).

The nucleotide sequence encoding PC5 in pSYN-PC5-003 has the following sequence (SEQ ID NO: 95):

```
atgggctggg ggagccgctg ctgctgcccg ggacgtttgg acctgctgtg cgtgctggcg
ctgctcgggg gctgcctgct ccccgtgtgt cggacgcgcg tctacaccaa ccactgggca
gtcaaaatcg ccgggggctt cccggaggcc aaccgtatcg ccagcaagta cggattcatc
aacataggac agatagggc cctgaaggac tactaccact tctaccatag caggacgatt
aaaaggtcag ttatctcgag cagagggacc cacagtttca tttcaatgga accaaaggtg
gaatggatcc aacagcaagt ggtaaaaaag cggacaaaga gggattatga cttcagtcgt
gcccagtcta cctatttcaa tgatcccaag tggcccagta tgtggtatat gcactgcagt
gacaatacac atccctgcca gtctgacatg aatatcgaag gagcctggaa gagaggctac
acgggaaaga acattgtggt cactatcctg gatgacggaa ttgagagaac ccatccagat
ctgatgcaaa actacgatgc tctggcaagt tgcgacgtga atgggaatga cttggaccca
atgcctcgtt atgatgcaag caacgagaac aagcatggga ctcgctgtgc tggagaagtg
gcagccgctg caaacaattc gcactgcaca gtcggaattg ctttcaacgc caagatcgga
ggagtgcgaa tgctggacgg agatgtcacg gacatggttg aagcaaaatc agttagcttc
aacccccagc acgtgcacat ttacagcgcc agctggggcc cggatgatga tggcaagact
gtggacggac cagcccccct cacccggcaa gcctttgaaa acggcgttag aatggggcgg
agaggcctcg gctctgtgtt tgtttgggca tctggaaatg gtggaaggag caaagaccac
tgctcctgtg atggctacac caacagcatc tacaccatct ccatcagcag cactgcagaa
agcggaaaga aaccttggta cctggaagag tgttcatcca cgctggccac aacctacagc
agcggggagt cctacgataa gaaaatcatc actacagatc tgaggcagcg ttgcacggac
aaccacactg ggacgtcagc ctcagccccc atggctgcag catcattgc gctggccctg
gaagccaatc cgtttctgac ctggagagac gtacagcatg ttattgtcag gacttcccgt
gcgggacatt tgaacgctaa tgactggaaa accaatgctg ctggttttaa ggtgagccat
ctttatggat ttggactgat ggacgcagaa gccatggtga tggaggcaga gaagtggacc
accgttcccc ggcagcacgt gtgtgtggag agcacagacc gacaaatcaa gacaatccgc
cctaacagtg cagtgcgctc catctacaaa gcctcaggct gctcagataa ccccaaccgc
catgtcaact acctggagca cgtcgttgtg cgcatcacca tcacccaccc caggagagga
gacctggcca tctacctgac ctcgcccttct ggaactaggt ctcagctttt ggccaacagg
ctatttgatc actccatgga aggattcaaa aactgggagt tcatgacaat tcattgctgg
ggagaaagag ctgctggtga ctgggtcctt gaagtttatg atactccctc tcagctaagg
aactttaaga ctccaggtaa attgaaagaa tggtctttgg tcctctacgg cacctccgtg
cagccatatt caccaaccaa tgaatttccg aaagtggaac ggttccgcta tagccgagtt
gaagacccca cagacgacta tggcacagag gattatgcag gtccctgcga ccctgagtgc
agtgaggttg gctgtgacgg gccaggacca gaccactgca atgactgttt gcactactac
tacaagctga aaaacaatac caggatctgt gtctccagct gcccccctgg ccactaccac
gccgacaaga agcgctgcag gaagtgtgcc cccaactgtg agtcctgctt tgggagccat
ggtgaccaat gcatgtcctg caaatatgga tactttctga tgaagaaac caacagctgt
gttactcact gccctgatgg gtcatatcag gataccaaga aaatctttg ccggaaatgc
agtgaaaact gcaagacatg tactgaattc cataactgta cagaatgtag ggatgggtta
agcctgcagg gatcccggtg ctctgtctcc tgtgaagatg gacggtattt caacggccag
gactgccagc cctgccaccg cttctgcgcc acttgtgctg gggcaggagc tgatgggtgc
attaactgca cagagggcta cttcatggag gatgggagat gcgtgcagag ctgtagtatc
```

-continued

```
agctattact ttgaccactc ttcagagaat ggatacaaat cctgcaaaaa atgtgatatc agttgtttga cgtgcaatgg cccaggattc aagaactgta caagctgccc tagtgggtat ctcttagact taggaatgtg tcaaatggga gccatttgca aggatgcaac ggaagagtcc tgggcggaag gaggcttctg tatgcttgtg aaaaagaaca atctgtgcca acggaaggtt cttcaacaac tttgctgcaa aacatgtaca tttcaaggc
```

SEQ ID NO: 108 contains substitutions from the GenBank sequence that do not affect the amino acid coding sequence. Specifically, the nucleotide at position 399 (corresponding to position 876 of GenBank accession no. NM-006200) is a T instead of a C, but preserves the amino acid Ser 133 (corresponding to amino acid numbering in GenBank accession no. NP-006191); nucleotide position 1473 (GenBank position 1950) is a C instead of a T, but preserves the amino acid Ala 491; and nucleotide position 1485 (GenBank position 1962) is an A instead of a G, but preserves the amino acid Ser 496. The nucleotide change at position 1473 eliminates a HindIII restriction site.

Cloning of PACE-SOL

The coding sequence for human PACE was obtained by RT-PCR. The following primers were used (areas that anneal to the cDNA are indicated in bold):

| | SEQ ID NO | |
|---|---|---|
| PACE-F1: | 109 | 5'-GGTAAGCTTGCCATGGAGCTGAGGCCCTGG TTGC-3' |
| PACE-R1: | 110 | 5'-GTTTTCAATCTCTAGGACCCACTCGCC-3' |
| PACE-F2: | 111 | 5'-GCCAGGCCACATGACTACTCCGC-3' |
| PACE-R2: | 112 | 5'-GGTGAATTCTCACTCAGGCAGGTGTGAGGG CAGC-3' |

The primer PACE-F1 adds a HindIII site to the 5' end of the PACE sequence beginning with 3 nucleotides before the start codon, while the primer PACE-R2 adds a stop codon after amino acid 715, which occurs at the end of the extracellular domain of PACE, as well as adding an EcoRI site to the 3' end of the stop codon. The PACE-R1 and PACE-F2 primers anneal on the 3' and 5' sides of an internal BamHI site, respectively. Two RT-PCR reactions were then set up using 25 pmol each of the primer pairs of PACE-F1/R1 or PACE-F2/R2 with 20 ng of adult human liver RNA (Clontech; Palo Alto, Calif.) in a 50 µl RT-PCR reaction using the SUPERSCRIPT™ One-Step RT-PCR with PLATINUM® Taq system (Invitrogen, Carlsbad, Calif.) according to manufacturer's protocol. The reaction was carried out in a MJ Thermocycler using the following cycles: 50° C. 30 minutes; 94° C. 2 minutes; 30 cycles of (94° C. 30 seconds, 58° C. 30 seconds, 72° C. 2 minutes), followed by 72° C. 10 minutes. Each of these fragments was ligated into the vector pGEM T-Easy (Promega, Madison, Wis.) and sequenced fully. The F2-R2 fragment was then subcloned into pcDNA6 V5/His (Invitrogen, Carlsbad, Calif.) using the BamHI/EcoRI sites, and then the F1-R1 fragment was cloned into this construct using the HindIII/BamHI sites. The final plasmid, pcDNA6-PACE, produces a soluble form of PACE (amino acids 1-715), as the transmembrane region has been deleted. The sequence of PACE in pcDNA6-PACE is essentially as described in Harrison S et al., (1998) *Semin Hematol* 35(2 Suppl 2):4-10.

Cloning of Kex2-SOL

The coding sequence for the yeast endoprotease, KEX2, was obtained by RT-PCR from *Saccharomyces cerevisiae* polyA+ mRNA (BD Clontech, cat #6999-1) using the following primers (areas that anneal to the cDNA are indicated in bold):

| Primers | SEQ ID NO | Sequences |
|---|---|---|
| KEX2-F: | 37 | 5'-GCGCTAGCCGTACGGCCGCCA CCATGAAAGTGAGGAAATATATTAC-TTTATGC-3' |
| KEX2-BglII-F: | 81 | 5'-GCTATTGATCACAAAGATCTA CATCCTCC-3' |
| KEX2-BglII-R: | 80 | 5'-GGAGGATGTAGATCTTTGTG ATCAATAGC-3' |
| KEX2-675-R: | 79 | 5'-GCGAATTCCGGTCCGTCATT GCCTAGGGCTCGAGAGTTTTTT AGGA-GTGTTTGGATCAG-3' |

These primers were used to obtain coding sequence for KEX2 (amino acids 1-675), the yeast homolog to PACE, in two pieces in a manner similar to that used for PACE-SOL, Example 3 above; similarly, the transmembrane region was removed to generate the soluble form of the protein.

Cloning of PC7-SOL

The coding sequence for PC7 was obtained by RT-PCR from human adult liver mRNA using the following primers (areas that anneal to the cDNA are indicated in bold):

| | SEQ ID NO | |
|---|---|---|
| PC7-BamMut-F: | 78 | 5'-GCATGGACTCCGATCCCAACG-3' |
| PC7-BamMut-R: | 77 | 5'-CGTTGGGATCGGAGTCCATGC-3' |
| PC7-F: | 49 | 5'-GGTAAGCTTGCCGCCACCATGCCGAAGG GGAGGCAGAAAG-3' |
| PC7-SOL-R: | 33 | 5'-TTTGAATTCTCAGTTGGGGGTGATGGTG TAACC-3' |
| PC7-Xma-F: | 32 | 5'-GGCACCTGAATAACCGACGG-3' |
| PC7-Xma-R: | 31 | 5'-CGTCACGTTGATGTCCCTGC-3' |

These primers were used to obtain coding sequence for PC7 (amino acids 1-663) in three pieces in a manner similar to that used for PACE-SOL, above; similarly, the transmembrane region was removed to generate the soluble form of the protein.

Figure 2:
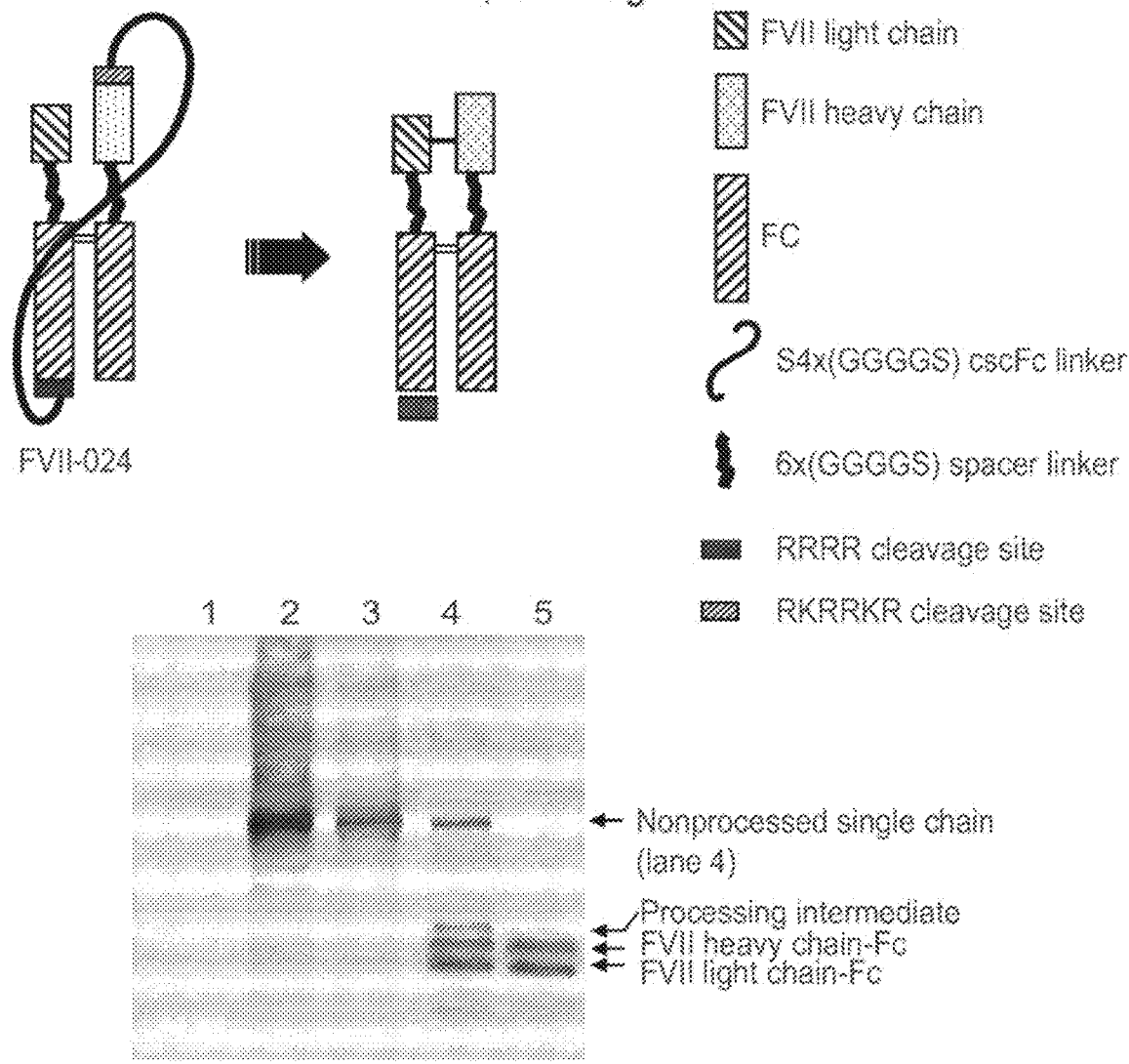
FIG. 2 illustrates a Factor VIIa Fc heterodimer in which the FVII light chain-Fc and heavy chain-Fc are expressed as a single chain and secreted as an activated protein dimer following processing of the linker by proteases. The figure includes a Western blot of a protein A pulldown of cells transiently transfected with FVII-024+/−PC5
Figure 3C:
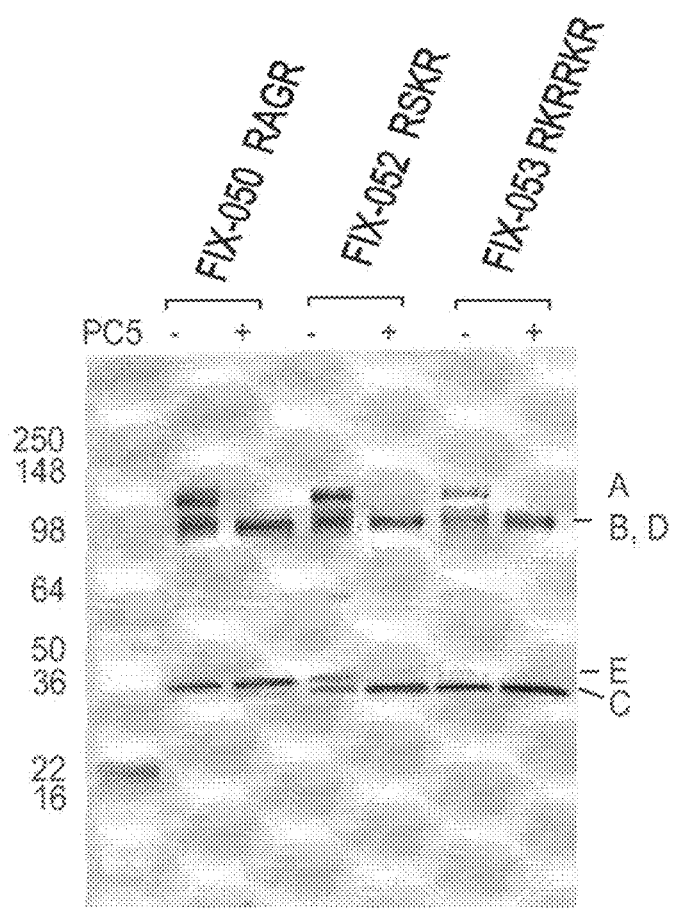
FIG. 3 panel C illustrates that optimal processing by PC5 was observed with the cleavable linkers incorporated in FIX-052 and -053.
Figure 4:
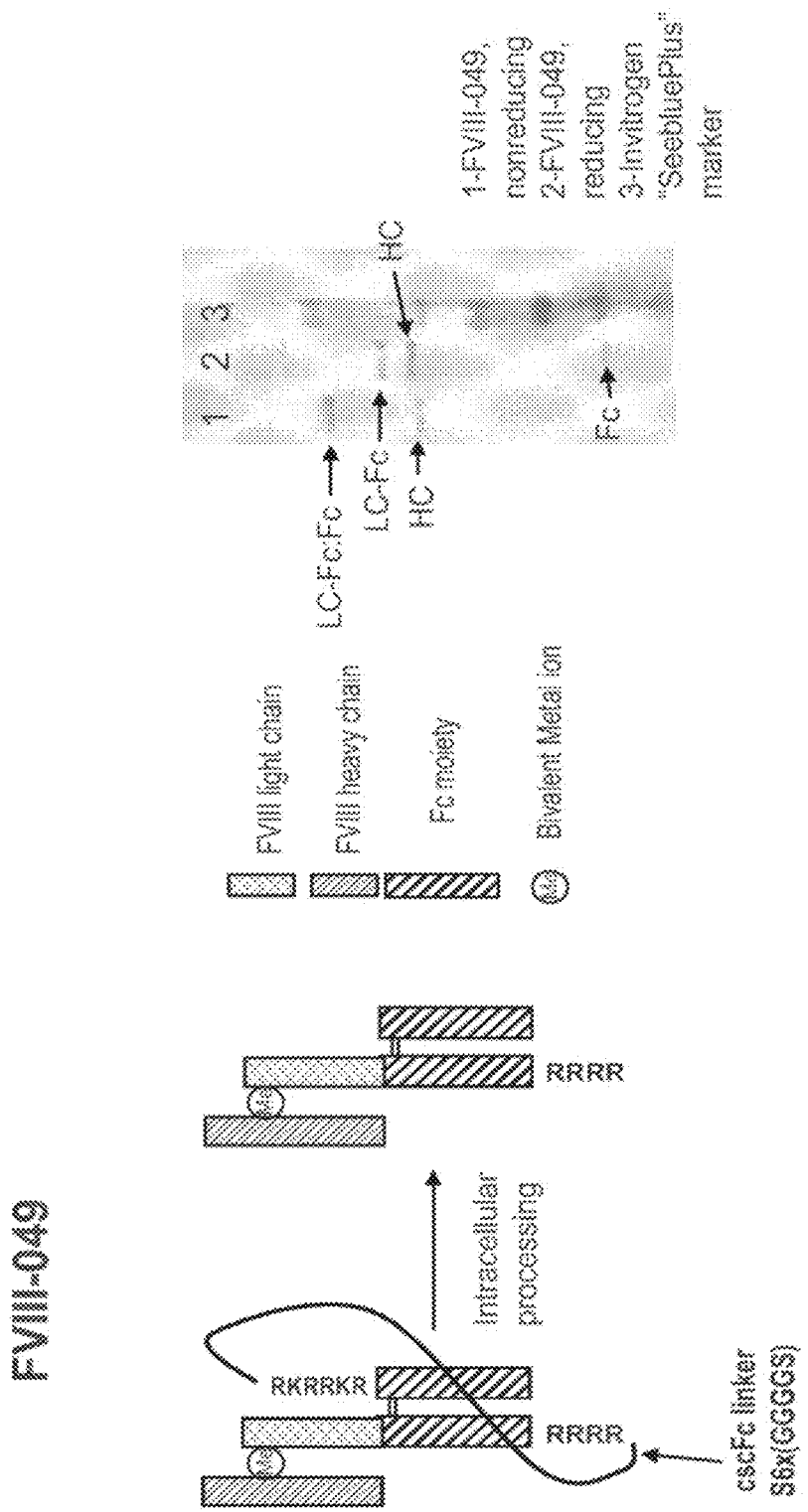
FIG. 4 panel A shows a schematic that illustrates a FVIII cleavable scFc molecule and the processed form of the molecule.

The most efficient cleavage of the cscFc linker was observed when cotransfected with PC5 and PACE (reducing conditions, lanes 11 and 12). A series of constructs were generated (FIX-050, FIX-052 and FIX-053) where the second processing site was modified as shown in FIG. 3A. These constructs we transiently transfected (with or without PC5 cotransfection) and the proteins analyzed by Fc western blot following a protein A pulldown as shown in FIG. 3C. Optimal cleavage of the cscFc was observed for FIX-052 and -053 with PC5 cotransfection Example 7: Intracellular Processing of cscFc Linker in FVIIaFc Heterodimer that Results in Expression of Active Protease FIG. 2 reveals a FVIIFc construct (FVII-024) expressed as two-chain heterodimer where one chain consists of the FVII light chain followed by a $(GGGGS)_{6x}$ (SEQ ID NO: 36) linker followed by the first Fc moiety, while the other chain contains a FVII heavy chain followed by a $(GGGGS)_{6x}$ (SEQ ID NO: 36) linker followed by the second Fc moiety. The plasmid is designed to express the heterodimer as a single polypeptide where the C-terminus of the FVII heavy chain-linker-Fc chain is connected to the N-terminus of the heavy chain-linker-Fc chain by the following polypeptide sequence: RRRRS-$(GGGGS)_{6x}$-RKRRKR where the RRRRS (SEQ ID NO: 38) and RKRRKR (SEQ ID NO: 39) sequences are proprotein convertase cleavage sites. FVII-024 was cloned, transiently expressed and analyzed by western blot analysis as described herein. The plasmid expressing FVII-024 was cotransfected with PC5 to fully process the cscFc linker, described in the protein sequence, connecting the C-terminus of the first Fc moiety to the N-terminus of the heavy chain. The effect of PC5 on the processing of the proprotein convertase cleavage sites in the FVII-024 linker was tested as shown in FIG. 2. Under nonreducing conditions the effect of PC5 on cleavage site processing cannot be detected because the FVII light chain-Fc and FVII heavy chain-Fc subunits remain linked via 2 disulfide bonds in the Fc region (lanes 2 and 3). Under reducing conditions we observed partial processing of FVII-024 generated from cells not cotransfected with PC5 (lane 4), but full processing when the cells were cotransfected with PC5 (lane 5). Full cleavage of the processing sites results in generation of the active form of FVIIa, which requires a free N-terminus of the heavy chain to adopt an active conformation Example 8: Processing of cscFc Linker in FVIIIFc The FVIIIFc construct illustrated in FIG. 4 was cloned and purified. Briefly, the coding sequence of human recombinant B-domain deleted FVIII was obtained by reverse transcription-polymerase chain reaction (RT-PCR) from human liver poly A RNA (Clontech) using FVIII-specific primers. The FVIII sequence includes the native signal sequence for FVIII. The B-domain deletion starts after serine 743 (S743; 2287 bp) and ends before glutamine 1638 (Q1638; 4969 bp) for a total deletion of 2682 bp (SQ version).

The coding sequence for human recombinant Fc was obtained by RT-PCR from a human leukocyte cDNA library (Clontech) using Fc specific primers. Primers were designed such that the B-domain deleted FVIII sequence was fused directly to the N-terminus of the Fc sequence with no intervening linker. The FVIIIFc DNA sequence was cloned into the mammalian dual expression vector pBUDCE4.1 (Invitrogen) under control of the CMV promoter.

A second identical Fc sequence including the mouse Igk signal sequence was obtained by RT-PCR and cloned downstream of the second promoter, EF1α, in the expression vector pBUDCE4.1. This final construct was designated pSYN-FVIII-013.

A second plasmid was created from similar constructs using PCR and standard molecular biology techniques, in order to express rFVIIIBDD-Fc-Fc in which the rFVIIIBDDFc coding sequence was fused to the second Fc sequence with a $(GGGGS)4$ (SEQ ID NO: 6) linker, allowing for production of only the rFVIIIBDD-Fc monomer-dimer hybrid in transient transfection. This construct was designated pSYN-FVIII-041. To make pSYN-FVIII-049, intermediate pSYN-FVIII-048 was generated by cloning NheI/XhoI fragment from pBUD-CE4.1 into pSYN-FVIII-013. The synthesis of a DNA fragment comprising the region from RsrII to XbaI sites of pSYN-FVIII-049 was outsourced. This fragment was subcloned into the RsrII/XbaI sites of pSYN-FVIII-048 to generate pSYN-FVIII-049.

The protein was expressed by transient transfection as described herein. PC5 was cotransfected to fully process the cscFc linker, described in the protein sequence, connecting the C-terminus of the first Fc moiety to the N-terminus of the second Fc moiety. SDS PAGE analysis in FIG. 4 reveals 3 distinct bands for purified FVIII-049 under reducing conditions: light chain-Fc (LC-Fc), heavy chain (HC) and Fc. This shows that the linker connecting both Fc moieties has been processed.

Example 9 Processing of cscFc Linker in FVII-Fc

Figure 5:
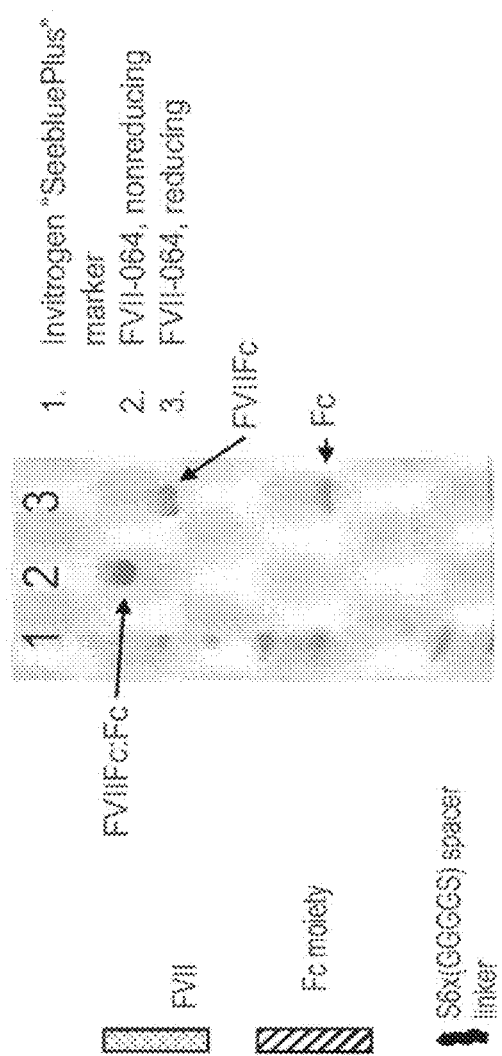
FIG. 5 panel A shows a schematic that illustrates the FVII cleavable scFc (FVII-064) construct and the processed form of the molecule. In this construct the biologically active moiety comprises FVII as a single chain.
Figure 5:
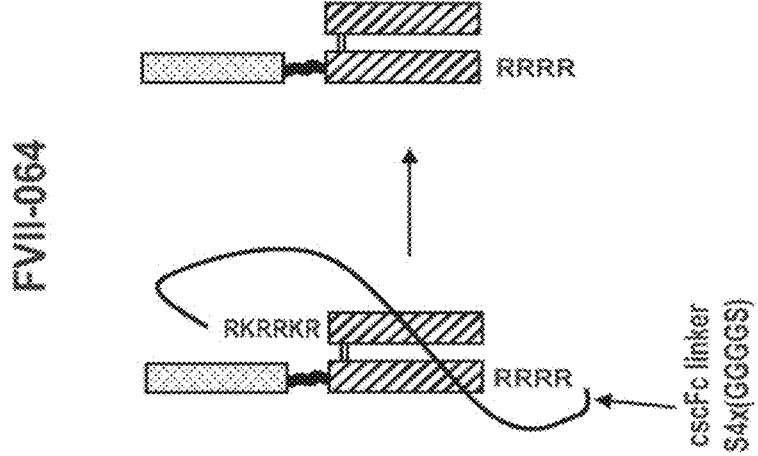
Figure 6:
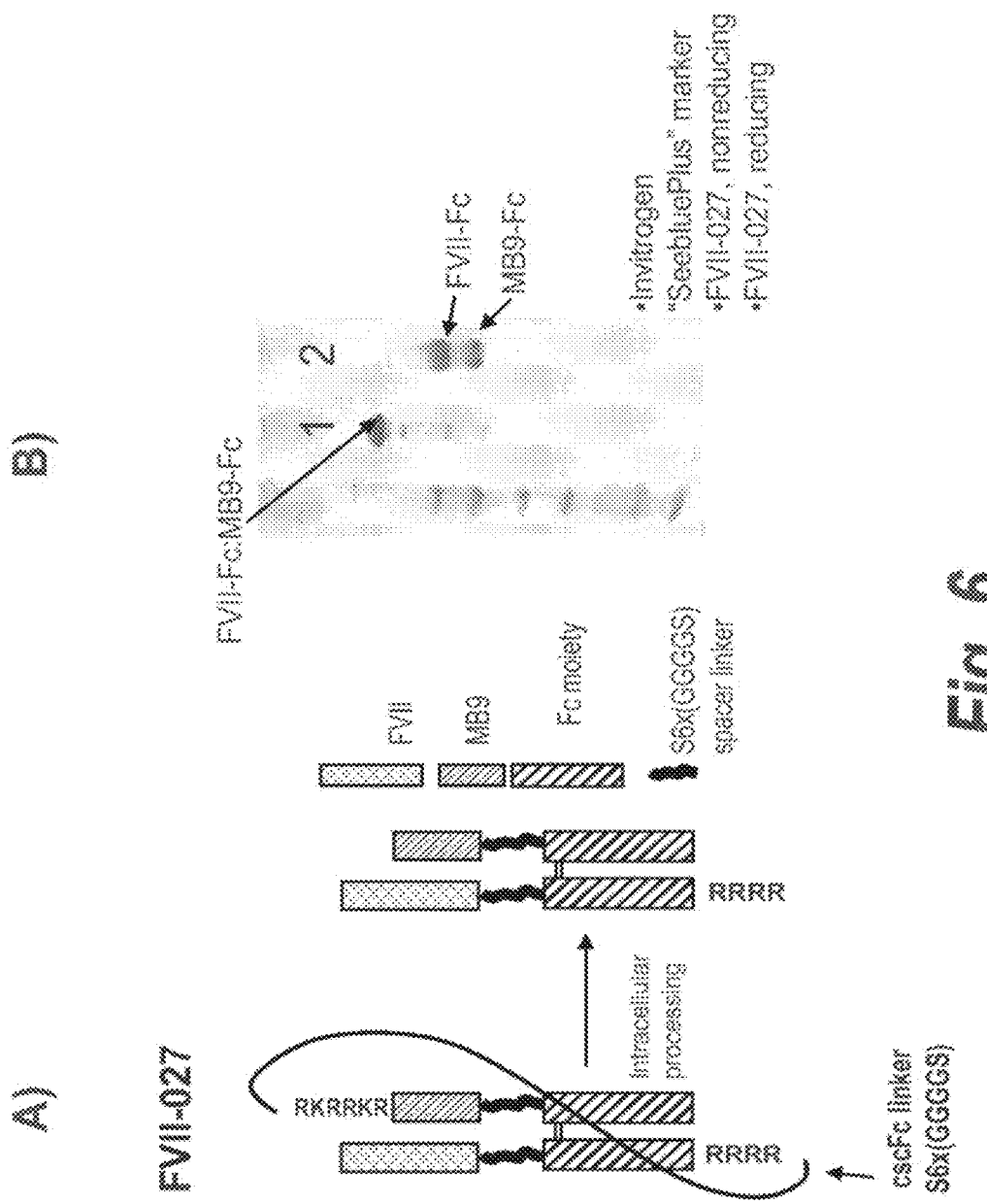
FIG. 6 panel A illustrates the FVIIFc-027 construct, which comprises a FVII cscFc fusion with a targeting moiety, MB9.

Cloning of pSYN-FVII-064
Synthesis of DNA sequence from HindIII to EcoRI of pSYN-FVII-064 was outsourced and cloned into HindIII/EcoRI sites of pBUDCE4.1 (Invitrogen)
Expression and Purification of FVII-064
DNA was transiently transfected as described herein. The transfection DNA contained PC5 to fully process the cscFc linker, described in the protein sequence, connecting the C-terminus of the first Fc moiety to the N-terminus of the second Fc moiety
Characterization of Cleavage of cscFc Linker of FVII-064
FVII-064 was purified using Ion Exchange: Q sepharose 4FF from GE healthcare. Secondary capture was performed using shFcRn (soluble human FcRn) affinity (NHS-coupled shFcRn with sepharose 4FF beads). All steps were performed at 150 cm/hrs linear Flow Rate. FIG. 5 illustrates SDS PAGE analysis of FVII-064 following transient expression (cotransfected with PC5) and purification. Under reducing conditions we observe 2 distinct bands for FVII-Fc and Fc, demonstrating full cleavage of the cscFc linker Example 10. Processing of cscFc of a FVIIFc Protein with a Platelet Targeting Construct In this example FVII-027 (FIG. 6) was transiently expressed with PC5 cotransfection to remove the cscFc linker described in the protein sequence. The construct was cloned, expressed and purified as described herein. SDS PAGE analysis of the purified protein in FIG. 6 revealed two distinct bands for FVII-Fc and MB9-Fc under reducing conditions, showing that the cscFc linker was fully processed.

Example 11 Processing of cscFc of a Interferon-Beta Fc Fusion Protein

In this example we generated a construct (IFN-beta-018) expressing interferon-beta followed by a linker and an Fc region where both Fc moieties are connected by a cscFc linker. The construct was cloned as follows: synthesis of a DNA fragment from BsiWI/BspEI of pSYN-IFN-b-018 was outsourced and subcloned into BsiWI/BspEI sites of pSYN-FIX-053 to generate pSYN-IFN-b-018. FIG. 10 illustrates Western Blot analysis of IFN-beta-018 species following transient transfection of HEK 293 cells (with or without PC5 cotransfection) and protein A pulldown. Western blot data revealed complete cleavage of the cscFc linkers when cotransfected with PC5.

Example 12. Additional Attempts at Expression of Activated Constructs

Several other constructs were made with the goal of expressing activated FVII, and are illustrated in FIG. 7. However, these constructs did not successfully express activated molecules.

Cloning of pSYN-FVII-010

The FVII-010 construct is one in which the heavy chain of factor VII was expressed in the context of an scFc scaffold and the light chain was expressed separately.

PCR-amplify with primer pairs FVII-HC-Hind3-IggKss-F/FVII-HC-BspEI-R, using pSYN-FVII-001. Clone in BspEI/HindIII sites of pSYN-FVII-008 (see supra), generating pSYN-FVII-009.

PCR amplify FVII light chain from pSYN-FVII-003 (refer to P0830) with primers FVII-LC-NotI-F/FVII-LC-XhoI-R and clone in pSYN-FVII-009 to generate pSYN-FVII-010.

FVII-HC-BspEI-R
                                        (SEQ ID NO: 27)
AGGAGTTCCGGAGCTGGGCACGGTGGGCATGTGTGAGTTTTGTCGGATCC

CCCGCCACCGGAACCTCCACCGCCTGATCCACCCCCACCTGATCCGCCGC

CACCGGACCCACCTCCGCCGGAGCCACCGCCACCGGGAAATGGGGCTCGC

AGGAGG

FVII-HC-Hind3-IggKss-f
                                        (SEQ ID NO: 25)
ACTGACAAGCTTGCCGCCACCATGGAGACAGACACACTCCTGCTATGGGT

ACTGCTGCTCTGGGTTCCAGGTTCCACTGGTATTGTGGGGGGCAAGGTGT

GC

FVII-LC-NotI-F
                                        (SEQ ID NO: 23)
ACTGACGCGGCCGCGCCGCCACCATGGTCTCCCAGG

FVII-LC-XhoI-R
                                        (SEQ ID NO: 22)
ACTGACCTCGAGTTATCGGCCTTGGGGTTTGCTGG

Cloning of pSYN-FVII-013

The FVII-013 construct is one in which the light chain was expressed in the context of an scFc scaffold and the heavy chain was expressed separately.

PCR-amplify with primer pair FVII-LC-linker-BamHI-R/HindIII-Kozak-FVII-F from pSYN-FVII-001. The coding sequence of FVII was obtained by reverse transcription coupled to polymerase chain reaction from a human liver mRNA library (Ambion, Austin, Tex.) using the following primers:

FVII-F1
                                        (SEQ ID NO: 21)
GGGAATGTCAACAGGCAGGG

FVII-R1
                                        (SEQ ID NO: 20)
CTTGGCTTTCTCTCCACAGGC

A 50 μl reaction was carried out with 10 pmol of each primer using the Superscript One-step RT-PCR with Platinum Taq system (Invitrogen, Carlsbad, Calif.) according to the manufacturer's standard protocol in a MJ thermocycler. The cycle used was 50° C. for 30 minutes for the reverse transcription followed by denaturing at 94° C. for 2 minutes and 30 cycles of (94° C. 30 seconds, 53° C. 30 seconds, 72° C. 90 seconds) followed by 10 minutes at 72° C. The expected sized band (1400 bp) was gel-purified with a Gel Extraction kit (Qiagen, Valencia, Calif.) and cloned in pCR2.1 TOPO using the TOPO TA Cloning kit (Invitrogen, Carlsbad, Calif.) to produce the intermediate plasmid pSYN-FVII-001 and cloned in BamHI/HindIII sites of pSYN-FVII-011, generating pSYN-FVII-012. PCR-amplify FVII-HC from pSYN-FVII-009 using primer pair FVII—HC-NotI-F/FVII—HC-XhoI-R ad subclone in pSYN-FVII-012 to generate pSYN-FVII-013.

Primers

FVII-LC-6xlinker-BamHI-R
                                        (SEQ ID NO: 19)
ACTGACGGATCCCCCGCCACCGGAACCTCCACCGCCTGATCCACCCCCAC

CTGATCCGCCGCCACCGGACCCACCTCCGCCGGAGCCACCGCCACCTCGG

CCTTGGGGTTTGCTGGC

HindIII-Kozak-FVII-F
                                        (SEQ ID NO: 18)
CGACAAGCTTGCCGCCACCATGGTCTCCCAGGCCCTCAGG FVII-HC-NotI-F
                                        (SEQ ID NO: 17)
ACTGACGCGGCCGCGCCGCCACCATGGAGACAGAC FVII-HC-XhoI-R
                                        (SEQ ID NO: 16)
ACTGACCTCGAGTTAGGGAAATGGGGCTCGCAGGAG Cloning of pSYN-FVII-018

For the FVII-018 construct, the heavy chain of FVII was expressed as an Fc fusion protein and the light chain of FVII was separately expressed as a separate Fc fusion protein.

Primers FVII—HC-Hind3-IggKss-F/scFc-EcoRI-R were used to PCR amplify HCFVII-linker-Fc, using pSYN-FVII-010 as template. Subclone in HindIII/EcoRI sites of pBUDCE4. This makes pSYN-FVII-017. Next, PCR-amplify from 30 pSYN-FVII-013 with primers FVII-LC-NotI-F/FC—XHOI—R and subclone in XhoI/NotI sites of FVII-017. This makes PSYN-FVII-018

Figure 8:
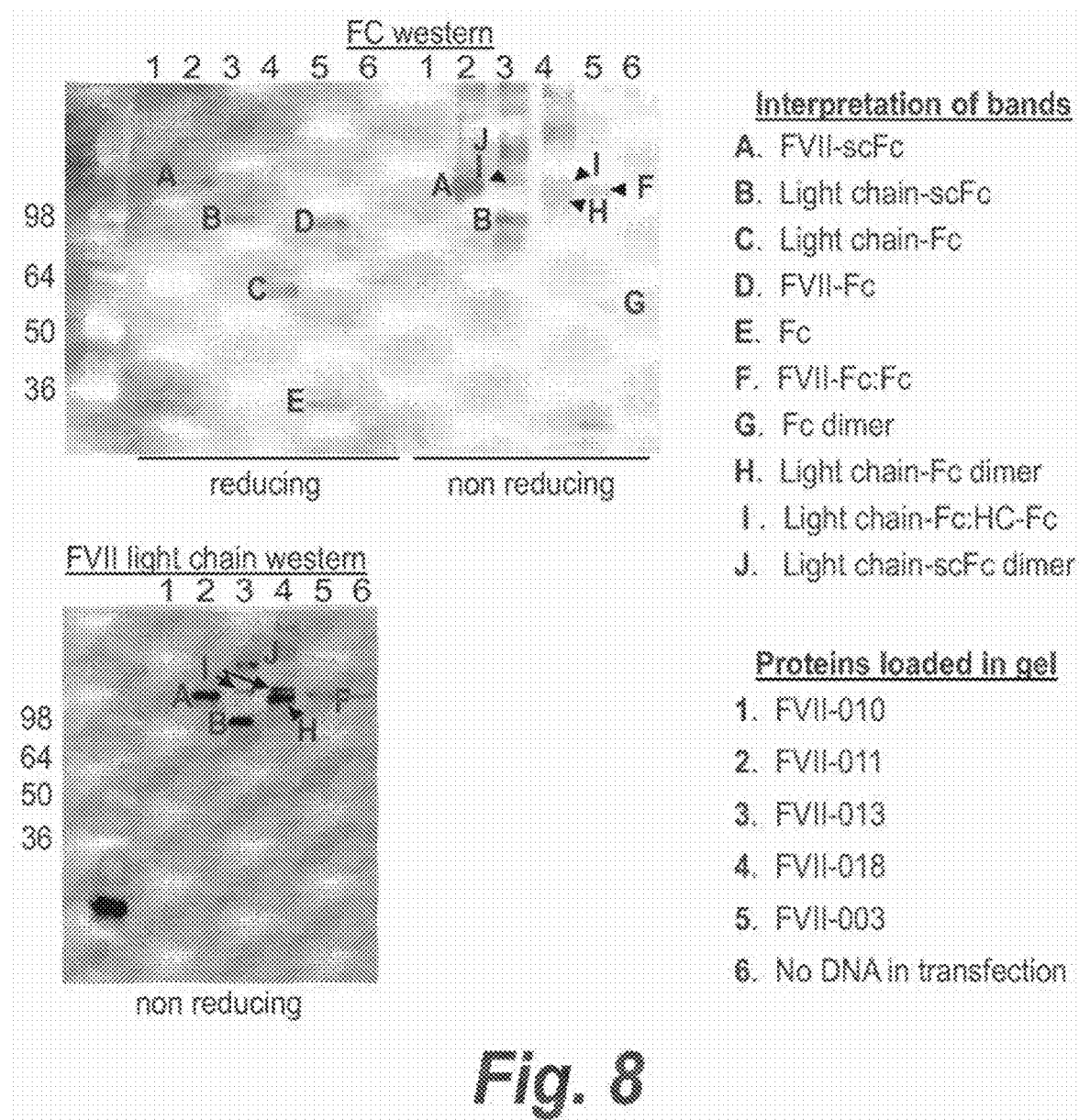
FIG. 8 illustrates Western Blot analysis of FVIIFc species following transient transfection of HEK 293 cells and protein A pulldown of the molecules illustrated in FIG. 7.

Primers scFc-EcoRI-R
                                        (SEQ ID NO: 15)
ACTGACGAATTCTCATTTACCCGGAGACAGGGAG Fc-XhoI-R
                                        (SEQ ID NO: 3)
AGCTCTCGAGTCATTTACCCGGAGACAGGG FIG. 8 illustrates Western Blot analysis of FVIIFc species following transient transfection of HEK 293 cells and protein A pulldown of the molecules illustrated in FIG. 7. Western blot data show that the FVII heavy chain cannot be expressed with a free N terminus using a common method of fusing a heterologous signal peptide to the N-terminus of the heavy chain.

Example 13. Alternative Attempts to Express Activated FVII-Fc Constructs

Failure to express the FVII heavy chain with a free N terminus led us to generate the constructs described in FIG. 11. Here FVIIFc is expressed as a heterodimer where one subunit comprises the FVII light chain and an Fc moiety, and the other subunit comprises the heavy chain preceded by an RKRRKR (SEQ ID NO: 39) processing site (FVII-019) or by a light chain C terminal fragment and an RKRRKR (SEQ ID NO: 39) processing site (FVII-020). We hypothesized that this may facilitate expression the heavy chain-Fc moiety subunit since the heavy chain would not adopt the active conformation until cleavage of the processing site in the Golgi. These constructs were analyzed by Fc western blot following a protein A pulldown of transiently transfected material. FVII-011 (FVIIFc with a single chain Fc) was used as a control. Only light chain-Fc was observed, suggesting that heavy chain Fc can not be expressed from FVII-019 or FVII-020

Example 14. Expression of Activated FVIIFc Proteins in the Monomer and Heterodimer Structures Cloning of pSYN-FVII-025.
Synthesis of a DNA fragment comprising the FVII coding region from XbaI to BsiWI with an RKRRKR (SEQ ID NO: 39) amino acid insertion between R152 and 1153 (mature sequence numbering) was outsourced. The DNA fragment was subcloned in the XbaI/BsiWI sites of pSYN-FVII-011 (the sequence of which is included herein) to generate pSYN-FVII-025

FIG. 9 illustrates a heterodimeric cscFc construct (FVII-024) and a monomeric Fc construct (FVII-025). These constructs were made and Western blots were performed following protein A pulldown and transient expression with or without PC5 cotransfection. The data show intracellular activation in the context of either the heterodimer or the monomer enabled expression of the separate heavy chain, but that the intracellular activation is more efficient in the context of the heterodimer (FVII-024) than the monomer (FVII-025).

Example 15: Protein Purification

Protein Purification of FVII-064
FVII-064 molecules were purified from conditioned media 1) Anion exchange chromatography with pseudo-affinity elution (e.g. Q sepharose 4FF (GE Healthcare) followed by elution with varying levels of CaCl2 to selectively elute the most active species), followed by 2) shFcRn (soluble human FcRn) affinity (NHS-coupled shFcRn with sepharose 4FF beads) chromatography, binding Fc-containing proteins at low pH (e.g. pH 6.2) and eluting at neutral pH (e.g. pH 8.0). These purification steps utilized standard methods known to those in the art to generate purified proteins of >95% purity by SEC analysis and SDS-PAGE.
Purification of FVIII-049
FVIII-049 was purified from clarified and chemically defined harvest media using a two column purification process, including a FVIII-specific affinity purification step (McCue 2009 Journal of Chromatography A. 1216:7824) followed by anion exchange with standard NaCl elution. These purification steps utilized standard methods known to those in the art to generate purified proteins of >95% purity by SEC analysis and SDS-PAGE.

INFORMAL SEQUENCE LISTING

```
pSYN-FVII-024 nucleotide sequencen
                                                    (SEQ ID NO: 62)
atggtctccc aggccctcag gctcctctgc cttctgcttg ggcttcaggg ctgcctggct gcagtcttcg taacccagga ggaagcccac ggcgtcctgc accggcgccg gcgcgccaac gcgttcctgg aggagctgcg gccgggctcc ctggagaggg agtgcaagga ggagcagtgc tccttcgagg aggcccggga gatcttcaag gacgcggaga ggacgaagct gttctggatt tcttacagtg atggggacca gtgtgcctca agtccatgcc agaatggggg ctcctgcaag gaccagctcc agtcctatat ctgcttctgc ctccctgcct tcgagggccg gaactgtgag acgcacaagg atgaccagct gatctgtgtg aacgagaacg gcggctgtga gcagtactgc agtgaccaca cgggcaccaa gcgctcctgt cggtgccacg aggggtactc tctgctggca gacggggtgt cctgcacacc cacagttgaa tatccatgtg gaaaaatacc tattctagaa aaaagaaatg ccagcaaacc ccaaggccga ggtggcggtg gctccggcgg aggtgggtcc ggtggcggcg gatcaggtgg gggtggatca ggcggtggag gttccggtgg cgggggatca gacaaaactc acacatgccc accgtgccca gctccggaac tcctgggcgg accgtcagtc ttcctcttcc ccccaaaacc caaggacacc ctcatgatct cccggacccc tgaggtcaca tgcgtggtgg tggacgtgag ccacgaagac cctgaggtca agttcaactg gtacgtggac ggcgtggagg tgcataatgc caagacaaag ccgcgggagg agcagtacaa cagcacgtac cgtgtggtca gcgtcctcac cgtcctgcac caggactggc tgaatggcaa ggagtacaag
```

```
tgcaaggtct ccaacaaagc cctcccagcc cccatcgaga aaaccatctc caaagccaaa gggcagcccc gagaaccaca ggtgtacacc ctgcccccat cccgggatga gctgaccaag aaccaggtca gcctgacctg cctggtcaaa ggcttctatc ccagcgacat cgccgtggag tgggagagca atgggcagcc ggagaacaac tacaagacca cgcctcccgt gttggactcc gacggctcct tcttcctcta cagcaagctc accgtggaca gagcaggtg gcagcagggg aacgtcttct catgctccgt gatgcatgag gctctgcaca accactacac gcagaagagc ctctccctgt ctccgggtaa acggcgccgc cggagcggtg gcggcggatc aggtgggggt ggatcaggcg gtggaggttc cggtggcggg ggatccggcg gtggaggttc cggtgggggt ggatcaagga agaggaggaa gaggattgtg gggggcaagg tgtgccccaa aggggagtgt ccatggcagg tcctgttgtt ggtgaatgga gctcagttgt gtgggggggac cctgatcaac accatctggg tggtctccgc ggcccactgt ttcgacaaaa tcaagaactg gaggaacctg atcgcggtgc tgggcgagca cgacctcagc gagcacgacg gggatgagca gagccggcgg gtggcgcagg tcatcatccc cagcacgtac gtcccgggca ccaccaacca cgacatcgcg ctgctccgcc tgcaccagcc cgtggtcctc actgaccatg tggtgcccct ctgcctgccc gaacggacgt tctctgagag gacgctggcc ttcgtgcgct tctcattggt cagcggctgg ggccagctgc tggaccgtgg cgccacggcc ctggagctca tggtcctcaa cgtgccccgg ctgatgaccc aggactgcct gcagcagtca cggaaggtgg gagactcccc aaatatcacg gagtacatgt tctgtgccgg ctactcggat ggcagcaagg actcctgcaa gggggacagt ggaggcccac atgccaccca ctaccggggc acgtggtacc tgacgggcat cgtcagctgg ggccagggct gcgcaaccgt gggccacttt ggggtgtaca ccagggtctc ccagtacatc gagtggctgc aaaagctcat gcgctcagag ccacgcccag gagtcctcct gcagccccca tttcccggtg gcggtggctc cggcggaggt gggtccggtg gcggcggatc aggtgggggt ggatcaggcg gtggaggttc cggtggcggg ggatcagaca aaactcacac atgcccaccg tgcccagcac ctgaactcct gggaggaccg tcagtcttcc tcttcccccc aaaacccaag gacaccctca tgatctcccg gacccctgag gtcacatgcg tggtggtgga cgtgagccac gaagaccctg aggtcaagtt caactggtac gtggacggcg tggaggtgca taatgccaag acaaagccgc gggaggagca gtacaacagc acgtaccgtg tggtcagcgt cctcaccgtc ctgcaccagg actggctgaa tggcaaggag tacaagtgca aggtctccaa caaagccctc ccagccccca tcgagaaaac catctccaaa gccaagggc agccccgaga accacaggtg tacaccctgc ccccatcccg ggatgagctg accaagaacc aggtcagcct gacctgcctg gtcaaaggct tctatcccag cgacatcgcc gtggagtggg agagcaatgg gcagccggag aacaactaca agaccacgcc tcccgtgttg gactccgacg gctccttctt cctctacagc aagctcaccg tggacaagag caggtggcag caggggaacg tcttctcatg ctccgtgatg catgaggctc tgcacaacca ctacacgcag aagagcctct ccctgtctcc gggtaaatga
```

FVII-024 amino acid sequence (SEQ ID NO: 63). Signal sequence is shown in dotted underline, propeptide is double underlined, linker region connecting FVII light chain or heavy chain to Fc region is underlined, Fc region is shown in italics and linker with proprotein convertase processing sites is shown in bold.

MVSQALRLLC LLLGLQGCLA AVFVTQEEAH GVLHRRRRAN
AFLEELRPGS LERECKEEQC SFEEAREIFK DAERTKLFWI
SYSDGDQCAS SPCQNGGSCK DQLQSYICFC LPAFEGRNCE
THKDDQLICV NENGGCEQYC SDHTGTKRSC RCHEGYSLLA
DGVSCTPTVE YPCGKIPILE KRNASKPQGR GGGGSGGGGS
GGGGSGGGGS GGGGSGGGGS DKTHTCPPCP APELLGGPSV
FLFPPKPKDT LMISRTPEVT CVVVDVSHED PEVKFNWYVD
GVEVHNAKTK PREEQYNSTY RVVSVLTVLH QDWLNGKEYK
CKVSNKALPA PIEKTISKAK GQPREPQVYT LPPSRDELTK
NQVSLTCLVK GFYPSDIAVE WESNGQPENN YKTTPPVLDS
DGSFFLYSKL TVDKSRWQQG NVFSCSVMHE ALHNHYTQKS
LSLSPGKRRR RSGGGGSGGG GSGGGGSGGG GSGGGGSGGG
GSRKRRKRIV GGKVCPKGEC PWQVLLLVNG AQLCGGTLIN
TIWVVSAAHC FDKIKNWRNL IAVLGEHDLS EHDGDEQSRR
VAQVIIPSTY VPGTTNHDIA LLRLHQPVVL TDHVVPLCLP
ERTFSERTLA FVRFSLVSGW GQLLDRGATA LELMVLNVPR
LMTQDCLQQS RKVGDSPNIT EYMFCAGYSD GSKDSCKGDS
GGPHATHYRG TWYLTGIVSW GQGCATVGHF GVYTRVSQYI
EWLQKLMRSE PRPGVLLRAP FPGGGGSGGG GSGGGGSGGG
GSGGGGSGGG GSDKTHTCPP CPAPELLGGP SVFLFPPKPK
DTLMISRTPE VTCVVVDVSH EDPEVKFNWY VDGVEVHNAK
TKPREEQYNS TYRVVSVLTV LHQDWLNGKE YKCKVSNKAL
PAPIEKTISK AKGQPREPQV YTLPPSRDEL TKNQVSLTCL
VKGFYPSDIA VEWESNGQPE NNYKTTPPVL DSDGSFFLYS
KLTVDKSRWQ QGNVFSCSVM HEALHNHYTQ KSLSLSPGK* pSYN-FVII-027 DNA sequence
(SEQ ID NO: 64)
atggtctccc aggccctcag gctcctctgc cttctgcttg
ggcttcaggg ctgcctggct gcagtcttcg taacccagga
ggaagcccac ggcgtcctgc accggcgccg gcgcgccaac
gcgttcctgg aggagctgcg gccgggctcc ctggagaggg
agtgcaagga ggagcagtgc tccttcgagg aggcccggga
gatcttcaag gacgcggaga ggacgaagct gttctggatt
tcttacagtg atggggacca gtgtgcctca gtccatgcc
agaatggggg ctcctgcaag gaccagctcc agtcctatat
ctgcttctgc ctcccctgcct tcgagggccg gaactgtgag
acgcacaagg atgaccagct gatctgtgtg aacgagaacg gcggctgtga gcagtactgc agtgaccaca cgggcaccaa
gcgctcctgt cggtgccacg aggggtactc tctgctggca
gacggggtgt cctgcacacc cacagttgaa tatccatgtg
gaaaaatacc tattctagaa aaaagaaatg ccagcaaacc
ccaaggccga attgtggggg gcaaggtgtg cccaaaggg
gagtgtccat ggcaggtcct gttgttggtg aatggagctc
agttgtgtgg ggggaccctg atcaacacca tctgggtggt
ctccgcggcc cactgtttcg acaaaatcaa gaactggagg
aacctgatcg cggtgctggg cgagcacgac ctcagcgagc
acgacgggga tgagcagagc cggcgggtgg cgcaggtcat
catccccagc acgtacgtcc cgggcaccac caaccacgac
atcgcgctgc tccgcctgca ccagcccgtg gtcctcactg
accatgtggt gcccctctgc ctgcccgaac ggacgttctc
tgagaggacg ctggccttcg tgcgcttctc attggtcagc
ggctggggcc agctgctgga ccgtggcgcc acggccctgg
agctcatggt cctcaacgtg cccggctga tgacccagga
ctgcctgcag cagtcacgga aggtgggaga ctcccaaat
atcacggagt acatgttctg tgccggctac tcggatggca
gcaaggactc ctgcaagggg gacagtggag ccccacatgc
cacccactac cggggcacgt ggtacctgac gggcatcgtc
agctgggcc agggctgcgc aaccgtgggc cactttgggg
tgtacaccag ggtctcccag tacatcgagt ggctgcaaaa
gctcatgcgc tcagagccac gcccaggagt cctcctgcga
gccccatttc ccggtggcgg tggctccggc ggaggtgggt
ccggtggcgg cggatcaggt ggggtggat caggcggtgg
aggttccggt ggcgggggat ccgacaaaac tcacacatgc
ccaccgtgcc cagctccgga actcctgggc ggaccgtcag
tcttcctctt ccccccaaaa cccaaggaca ccctcatgat
ctcccggacc cctgaggtca catgcgtggt ggtggacgtg
agccacgaag accctgaggt caagttcaac tggtacgtgg
acggcgtgga ggtgcataat gccaagacaa agccgcggga
ggagcagtac aacagcacgt accgtgtggt cagcgtcctc
accgtcctgc accaggactg gctgaatggc aaggagtaca
agtgcaaggt ctccaacaaa gccctcccag cccccatcga
gaaaaccatc tccaaagcca aagggcagcc ccgagaacca
caggtgtaca ccctgccccc atcccgggat gagctgacca
agaaccaggt cagcctgacc tgcctggtca aaggcttcta
tcccagcgac atcgccgtga gtgggagag caatgggcag
ccggagaaca actacaagac cacgcctccc gtgttggact
ccgacggctc cttcttcctc tacagcaagc tcaccgtgga
caagagcagg tggcagcagg ggaacgtctt ctcatgctcc -continued

```
gtgatgcatg aggctctgca caaccactac acgcagaaga
gcctctccct gtctccgggt aaacggcgcc gccggagcgg
tggcggcgga tcaggtgggg gtggatcagg cggtggaggt
tccggtggcg ggggatccgg cggtggaggt tccggtgggg
gtggatcaag gaagaggagg aagagggcgg aagtgcagct
ggtgcagtct ggagctgagg tgaataagcc tggggcctca
gtgaaggtct cctgcaaggc ttctggatac accttcaccg
gctactatat gcactgggtg cgacaggccc ctggacaagg
gcttgagtgg atgggatgga tcaaccctaa cagtggtggc
acaaactatg cacagaagtt tcagggctgg gtcaccatga
ccagggacac gtccatcagc accgcctaca tggagctgag
caggctgaga tctgacgaca cggccgtgta ttactgtgcg
agaggccgtg ctttgtataa ccggaacgac cggtccccca
actggttcga cccctggggc cagggaaccc tggtcaccgt
ctcctcaggg agtgcatccg ccccaaccct aagcttgaa
gaaggtgaat ctcagaagca cgcgtacg gctgtgctga
ctcagccgcc ctcggtgtca gtggcccag gacagacggc
caggattacc tgtggggaa acaacattgg aagtaaaagt
gtgcagtggt accagcagaa gccaggccag gcccctgtgc
tggtcgtcta tgatgatagc gaccggccct cagggatccc
tgagcgattc tctggctcca actctgggaa catggccacc
ctgaccatca gcagggtcga agccggggat gaggccgact
attactgtca ggtgtgggat agtagtagtg atcatgtggt
attcggcgga gggaccaagc tgaccgtcct aggtcagccc
aaggctgccc cctcggtcac tctgttcccg ccgtccgcgg
ccgctggtgg cggtggctcc ggcggaggtg ggtccggtgg
cggcggatca ggtgggggtg atcaggcgcg tggaggttcc
ggtggcgggg gatcagacaa aactcacaca tgcccaccgt
gcccagcacc tgaactcctg ggaggaccgt cagtcttcct
cttccccca aaacccaagg acaccctcat gatctcccgg
accctgagg tcacatgcgt ggtgtggac gtgagccacg
aagaccctga ggtcaagttc aactggtacg tggacggcgt
ggaggtgcat aatgccaaga caaagccgcg ggaggagcag
tacaacagca cgtaccgtgt ggtcagcgtc ctcaccgtcc
tgcaccagga ctggctgaat ggcaaggagt acaagtgcaa
ggtctccaac aaagccctcc cagcccccat cgagaaaacc
atctccaaag ccaaaggca gccccgagaa ccacaggtgt
acaccctgcc cccatcccgc gatgagctga ccaagaacca
ggtcagcctg acctgcctgg tcaaaggctt ctatcccagc
gacatcgccg tggagtggga gagcaatggg cagccggaga
acaactacaa gaccacgcct cccgtgttgg actccgacgg
ctccttcttc ctctacagca agctcaccgt ggacaagagc
aggtggcagc aggggaacgt cttctcatgc tccgtgatgc
atgaggctct gcacaaccac tacacgcaga gagcctctc
cctgtctccg ggtaaatga
```

FVII-027 amino acid sequence (SEQ ID NO: 65). Signal sequence is shown in dotted underline, propeptide is double underlined, linker region connecting FVII or MB9 to Fc region is underlined, and linker with proprotein convertase processing sites is shown in bold

```
MVSQALRLLC LLLGLQGCLA AVFVTQEEAH GVLHRRRRAN

AFLEELRPGS LERECKEEQC

SFEEAREIFK DAERTKLFWI SYSDGDQCAS SPCQNGGSCK

DQLQSYICFC LPAFEGRNCE

THKDDQLICV NENGGCEQYC SDHTGTKRSC RCHEGYSLLA

DGVSCRPTVE YPCGKIPILE

KRNASKPQGR IVGGKVCPKG ECPWQVLLLV NGAQLCGGTL

INTIWVVSAA HCFDKIKNWR

NLIAVLGEHD LSEHDGDEQS RRVAQVIIPS TYVPGTTNHD

IALLRLHQPV VLTDHVVPLC

LPERTFSERT LAFVRFSLVS GWGQLLDRGA TALELMVLNV

PRLMTQDCLQ QSRKVGDSPN

ITEYMFCAGY SDGSKDSCKG DSGGPHATHY RGTWYLTGIV

SWGQGCATVG HFGVYTRVSQ

YIEWLQKLMR SEPRPGVLLR APFPGGGGSG GGGSGGGGSG

GGGSGGGGSG GGGSDKTHTC

PPCPAPELLG GPSVFLFPPK PKDTLMISRT PEVTCVVVDV

SHEDPEVKFN WYVDGVEVHN

AKTKPREEQY NSTYRVVSVL TVLHQDWLNG KEYKCKVSNK

ALPAPIEKTI SKAKGQPREP

QVYTLPPSRD ELTKNQVSLT CLVKGFYPSD IAVEWESNGQ

PENNYKTTPP VLDSDGSFFL

YSKLTVDKSR WQQGNVFSCS VMHEALHNHY TQKSLSLSPG

KRRRRSGGGG SGGGGSGGGG

SGGGGSGGGG SGGGGSRKRR KRAEVQLVQS GAEVNKPGAS

VKVSCKASGY TFTGYYMHWV

RQAPGQGLEW MGWINPNSGG TNYAQKFQGW WTMTRDTSIS

TAYMELSRLR SDDTAVYYCA

RGRALYNRND RSPNWFDPWG QGTLVTVSSG SASAPTLKLE

EGEFSEARVQ AVLTQPPSVS

VAPGQTARIT CGGNNIGSKS VQWYQQKPGQ APVLVVYDDS
```

DRPSGIPERF SGSNSGNMAT
LTISRVEAGD EADYYCQVWD SSSDHVVFGG GTKLTVLGQP
KAAPSVTLFP PSAAAGGGGS
GGGGSGGGGS GGGGSGGGGS GGGGSDKTHT CPPCPAPELL
GGPSVFLFPP KPKDTLMISR
TPEVTCVVVD VSHEDPEVKF NWYVDGVEVH NAKTKPREEQ
YNSTYRVVSV LTVLHQDWLN
GKEYKCKVSN KALPAPIEKT ISKAKGQPRE PQVYTLPPSR
DELTKNQVSL TCLVKGFYPS
DIAVEWESNG QPENNYKTTP PVLDSDGSFF LYSKLTVDKS
RWQQGNVFSC SVMHEALHNH
YTQKSLSLSP GK* pSYN-FIX-044 DNA sequence
(SEQ ID NO: 66)
atgcagcgcg tgaacatgat catggcagaa tcaccaggcc
tcatcaccat ctgcctttta
ggatatctac tcagtgctga atgtacaggt ttgtttcctt
ttttaaaata cattgagtat
gcttgccttt tagatataga aatatctgat gctgtcttct
tcactaaatt ttgattacat
gatttgacag caatattgaa gagtctaaca gccagcacgc
aggttggtaa gtactgtggg
aacatcacag attttggctc catgccctaa agagaaattg
gctttcagat tatttggatt
aaaaacaaag actttcttaa gagatgtaaa attttcatga
tgttttcttt tttgctaaaa
ctaagaatt attcttttac atttcagttt ttcttgatca
tgaaaacgcc aacaaaattc
tgaatcggcc aaagaggtat aattcaggta aattggaaga
gtttgttcaa gggaatctag
agagagaatg tatggaagaa aagtgtagtt ttgaagaagc
acgagaagtt tttgaaaaca
ctgaaagaac aactgaattt tggaagcagt atgttgatgg
agatcagtgt gagtccaatc
catgttttaaa tggcggcagt tgcaaggatg acattaattc
ctatgaatgt tggtgtccct
ttgatttga aggaaagaac tgtgaattag atgtaacatg
taacattaag aatggcagat
gcgagcagtt ttgtaaaaat agtgctgata caaggtggt
ttgctcctgt actgagggat
atcgacttgc agaaaaccag aagtcctgtg aaccagcagt
gccatttcca tgtggaagag tttctgtttc acaaacttct aagctcaccc gtgctgagac
tgttttttcct gatgtggact
atgtaaattc tactgaagct gaaaccattt tggataacat
cactcaaagc acccaatcat
ttaatgactt cactcgggtt gttggtggag aagatgccaa
accaggtcaa ttcccttggc
aggttgtttt gaatggtaaa gttgatgcat tctgtggagg
ctctatcgtt aatgaaaaat
ggattgtaac tgctgcccac tgtgttgaaa ctggtgttaa
aattacagtt gtcgcaggtg
aacataatat tgaggagaca gaacatacag agcaaaagcg
aaatgtgatt cgaattattc
ctcaccacaa ctacaatgca gctattaata gtacaaacca
tgacattgcc cttctggaac
tggacgaacc cttagtgcta aacagctacg ttacacctat
ttgcattgct gacaaggaat
acacgaacat cttcctcaaa tttggatctg gctatgtaag
tggctgggga agagtcttcc
acaaagggag atcagcttta gttcttcagt accttagagt
tccacttgtt gaccgagcca
catgtcttcg atctacaaag ttcaccatct ataacaacat
gttctgtgct ggcttccatg
aaggaggtag agattcatgt caaggagata gtgggggacc
ccatgttact gaagtggaag
ggaccagttt cttaactgga attattagct ggggtgaaga
gtgtgcaatg aaaggcaaat
atggaatata taccaaggta tcccggtatg tcaactggat
taaggaaaaa acaaagctca
ctgacaaaac tcacacatgc ccaccgtgcc cagctccgga
actcctggga ggaccgtcag
tcttcctctt ccccccaaaa cccaaggaca ccctcatgat
ctcccggacc cctgaggtca
catgcgtggt ggtggacgtg agccacgaag accctgaggt
caagttcaac tggtacgtgg
acggcgtgga ggtgcataat gccaagacaa agccgcggga
ggagcagtac aacagcacgt
accgtgtggt cagcgtcctc accgtcctgc accaggactg
gctgaatggc aaggagtaca
agtgcaaggt ctccaacaaa gccctcccag cccccatcga
gaaaaccatc tccaaagcca

```
aagggcagcc ccgagaacca caggtgtaca ccctgccccc
atcccgggat gagctgacca
agaaccaggt cagcctgacc tgcctggtca aaggcttcta
tcccagcgac atcgccgtgg
agtgggagag caatgggcag ccggagaaca actacaagac
cacgcctccc gtgttggact
ccgacggctc cttcttcctc tacagcaagc tcaccgtgga
caagagcagg tggcagcagg
ggaacgtctt ctcatgctcc gtgatgcatg aggctctgca
caaccactac acgcagaaga
gcctctccct gtctccgggt aaacggcgcc gccggagcgg
tggcggcgga tcaggtgggg
gtggatcagg cggtggaggt tccggtggcg ggggatcccg
ccggcggcgc gacaaaactc
acacatgccc accgtgccca gcaccggaac tcctgggcgg
accgtcagtc ttcctcttcc
ccccaaaacc caaggacacc ctcatgatct cccggacccc
tgaggtcaca tgcgtggtgg
tggacgtgag ccacgaagac cctgaggtca agttcaactg
gtacgtggac ggcgtggagg
tgcataatgc caagacaaag ccgcgggagg agcagtacaa
cagcacgtac cgtgtggtca
gcgtcctcac cgtcctgcac caggactggc tgaatggcaa
ggagtacaag tgcaaggtct
ccaacaaagc cctcccagcc cccatcgaga aaaccatctc
caaagccaaa gggcagcccc
gagaaccaca ggtgtacacc ctgccccat cccgggatga
gctgaccaag aaccaggtca
gcctgacctg cctggtcaaa ggcttctatc ccagcgacat
cgccgtggag tgggagagca
atgggcagcc ggagaacaac tacaagacca gcctcccgt
gttggactcc gacggctcct
tcttcctcta cagcaagctc accgtggaca gagcaggtg
gcagcagggg aacgtcttct
catgctccgt gatgcatgag gctctgcaca accactacac
gcagaagagc ctctccctgt
ctccgggtaa atga
```

FIX-044 amino acid sequence (SEQ ID NO: 67). Signal sequence is shown in dotted underline, propeptide is double underlined, and linker with proprotein convertase processing sites is shown in bold.

```
MQRVNMIMAE SPGLITICLL GYLLSAECTV FLDHENANKI
LNRPKRYNSG KLEEFVQGNL
ERECMEEKCS FEEAREVFEN TERTTEFWKQ YVDGDQCESN
PCLNGGSCKD DINSYECWCP
FGFEGKNCEL DVTCNIKNGR CEQFCKNSAD NKVVCSCTEG
YRLAENQKSC EPAVPFPCGR
VSVSQTSKLT RAETVFPDVD YVNSTEAETI LDNITQSTQS
FNDFTRVVGG EDAKPGQFPW
QVVLNGKVDA FCGGSIVNEK WIVTAAHCVE TGVKITVVAG
EHNIEETEHT EQKRNVIRII
PHHNYNAAIN KYNHDIALLE LDEPLVLNSY VTPICIADKE
YTNIFLKFGS GYVSGWGRVF
HKGRSALVLQ YLRVPLVDRA TCLRSTKFTI YNNMFCAGFH
EGGRDSCQGD SGGPHVTEVE
GTSFLTGIIS WGEECAMKGK YGIYTKVSRY VNWIKEKTKL
TDKTHTCPPC PAPELLGGPS
VFLFPPKPKD TLMISRTPEV TCVVVDVSHE DPEVKFNWYV
DGVEVHNAKT KPREEQYNST
YRVVSVLTVL HQDWLNGKEY KCKVSNKALP APIEKTISKA
KGQPREPQVY TLPPSRDELT
KNQVSLTCLV KGFYPSDIAV EWESNGQPEN NYKTTPPVLD
SDGSFFLYSK LTVDKSRWQQ
GNVFSCSVMH EALHNHYTQK SLSLSPGK**RR RRSGGGGSGG
GGSGGGGSGG GGSRRRR**DKT
HTCPPCPAPE LLGGPSVFLF PPKPKDTLMI SRTPEVTCVV
VDVSHEDPEV KFNWYVDGVE
VHNAKTKPRE EQYNSTYRVV SVLTVLHQDW LNGKEYKCKV
SNKALPAPIE KTISKAKGQP
REPQVYTLPP SRDELTKNQV SLTCLVKGFY PSDIAVEWES
NGQPENNYKT TPPVLDSDGS
FFLYSKLTVD KSRWQQGNVF SCSVMHEALH NHYTQKSLSL
SPGK*

Genscript-FIX-044 DNA sequence
                        (SEQ ID NO: 68)
tccggaactc ctgggaggac cgtcagtctt cctcttcccc
ccaaaaccca aggacaccct
catgatctcc cggacccctg aggtcacatg cgtggtggtg
gacgtgagcc acgaagaccc
tgaggtcaag ttcaactggt acgtggacgg cgtggaggtg
cataatgcca agacaaagcc
```

```
gcgggaggag cagtacaaca gcacgtaccg tgtggtcagc gtcctcaccg tcctgcacca ggactggctg aatggcaagg agtacaagtg caaggtctcc aacaaagccc tcccagcccc catcgagaaa accatctcca agccaaagg gcagccccga gaaccacagg tgtacaccct gcccccatcc cgggatgagc tgaccaagaa ccaggtcagc ctgacctgcc tggtcaaagg cttctatccc agcgacatcg ccgtggagtg ggagagcaat gggcagccgg agaacaacta caagaccacg cctcccgtgt tggactccga cggctccttc ttcctctaca gcaagctcac cgtggacaag agcaggtggc agcagggaa cgtcttctca tgctccgtga tgcatgaggc tctgcacaac cactacacg agaagagcct ctccctgtct ccgggtaaac ggcgccgccg gagcggtggc ggcggatcag gtggggtgg atcaggcggt ggaggttccg gtggcggggg atcccgccgg cggcgcgaca aaactcacac atgcccaccg tgcccagcac cggaactcct gggcggaccg
```

Genscript-FVII-027-1 DNA sequence
(SEQ ID NO: 69)
```
gaagagcctc tccctgtctc cgggtaaacg gcgccgccgg agcggtggcg gcggatcagg tgggggtgga tcaggcggtg gaggttccgg tggcggggga tccggcggtg gaggttccgg tgggggtgga tcaaggaaga ggaggaagag ggcggaagtg cagctggtgc agtctggagc tgaggtgaat aagcctgggg cctcagtgaa ggtctcctgc aaggcttctg gatacacctt caccggctac tatatgcact gggtgcgaca ggcccctgga caagggcttg agtggatggg atggatcaac cctaacagtg gtggcacaaa ctatgcacag aagtttcagg gctgggtcac catgaccagg gacacgtcca tcagcaccgc ctacatggag ctgagcaggc tgagatctga cgacacggcc gtgtattact gtgcgagagg ccgtgctttg tataaccgga acgaccggtc ccccaactgg ttcgaccct ggggccaggg aaccctggtc accgtctcct cagggagtgc atccgcccca acccttaagc ttgaagaagg tgaattc
```

Genscript-FVII-026-2 DNA sequence
(SEQ ID NO: 70)
```
gaattctcag aagcacgcgt acaggctgtg ctgactcagc cgccctcggt gtcagtggcc ccaggacaga cggccaggat tacctgtggg ggaaacaaca ttggaagtaa aagtgtgcag tggtaccagc agaagccagg ccaggcccct gtgctggtcg tctatgatga tagcgaccgg ccctcaggga tccctgagcg attctctggc tccaactctg ggaacatggc caccctgacc atcagcaggg tcgaagccgg ggatgaggcc gactattact gtcaggtgtg ggatagtagt agtgatcatg tggtattcgg cggagggacc aagctgaccg tcctaggtca gcccaaggct gccccctcgg tcactctgtt cccgccgtcc gcggccgctg gtggcggtgg ctccggcgga ggtgggtccg gtggcggcgc atcaggtggg ggtggatcag gcggtggagg ttccggtggc gggggatcag acaaaactca cacatgccca ccgtgcccag cacctgaact cctgggagga ccgtcagtct tcctcttccc cccaaaaccc aaggacaccc tcatgatctc ccggaccct gaggtcacat gcgtggtggt ggacgtgagc cacgaagacc ctgaggtcaa gttcaactgg tacgtggacg gcgtggaggt tcataatgcc aagacaaagc cgcgggagga gcagtacaac agcacgtacc gtgtggtcag cgtcctcacc gtcctgcacc aggactggct gaatggcaag gagtacaagt gcaaggtctc caacaaagcc ctcccagccc ccatcgagaa aaccatctcc aaagccaaag gcagccccg agaaccacag gtgtacaccc tgcccccatc ccgcgatgag ctgaccaaga accaggtcag cctgacctgc ctggtcaaag gcttctatcc cagcgacatc gccgtggagt gggagagcaa tgggcagccg gagaacaact acaagaccac gcctcccgtg ttggactccg acggctcctt cttcctctac agcaagctca ccgtggacaa gagcaggtgg cagcagggga acgtcttctc atgctccgtg atgcatgagg
```

```
ctctgcacaa ccactacacg cagaagagcc tctccctgtc tccgggtaaa tgagaattc
```

B domain deleted FVIII amino acid sequence (SEQ ID NO: 71): Signal peptide underlined; 14 amino acid linker (containing the remaining B domain) between the HC and LC sequence is double underlined, with the S743/Q1638 fusion site indicated in bold.

```
   1  MQIELSTCFF LCLLRFCFSA TRRYYLGAVE LSWDYMQSDL GELPVDARFP
  51  PRVPKSFPFN TSVVYKKTLF VEFTDHLFNI AKPRPPWMGL LGPTIQAEVY
 101  DTVVITLKNM ASHPVSLHAV GVSYWKASEG AEYDDQTSQR EKEDDKVFPG
 151  GSHTYVWQVL KENGPMASDP LCLTYSYLSH VDLVKDLNSG LIGALLVCRE
 201  GSLAKEKTQT LHKFILLFAV FDEGKSWHSE TKNSLMQDRD AASARAWPKM
 251  HTVNGYVNRS LPGLIGCHRK SVYWHVIGMG TTPEVHSIFL EGHTFLVRNH
 301  RQASLEISPI TFLTAQTLLM DLGQFLLFCH ISSHQHDGME AYVKVDSCPE
 351  EPQLRMKNNE EAEDYDDDLT DSEMDVVRFD DDNSPSFIQI RSVAKKHPKT
 401  WVHYIAAEEE DWDYAPLVLA PDDRSYKSQY LNNGPQRIGR KYKKVRFMAY
 451  TDETFKTREA IQHESGILGP LLYGEVGDTL LIIFKNQASR PYNIYPHGIT
 501  DVRPLYSRRL PKGVKHLKDF PILPGEIFKY KWTVTVEDGP TKSDPRCLTR
 551  YYSSFVNMER DLASGLIGPL LICYKESVDQ RGNQIMSDKR NVILFSVFDE
 601  NRSWYLTENI QRFLPNPAGV QLEDPEFQAS NIMHSINGYV FDSLQLSVCL
 651  HEVAYWYILS IGAQTDFLSV FFSGYTFKHK MVYEDTLTLF PFSGETVFMS
 701  MENPGLWILG CHNSDFRNRG MTALLKVSSC DKNTGDYYED SYEDISAYLL
 751  SKNNAIEPRS FSQNPPVLKR HQREITRTTL QSDQEEIDYD DTISVEMKKE
 801  DFDIYDEDEN QSPRSFQKKT RHYFIAAVER LWDYGMSSSP HVLRNRAQSG
 851  SVPQFKKVVF QEFTDGSFTQ PLYRGELNEH LGLLGPYIRA EVEDNIMVTF
 901  RNQASRPYSF YSSLISYEED QRQGAEPRKN FVKPNETKTY FWKVQHHMAP
 951  TKDEFDCKAW AYFSDVDLEK DVHSGLIGPL LVCHTNTLNP AHGRQVTVQE
1001  FALFFTIFDE TKSWYFTENM ERNCRAPCNI QMEDPTFKEN YRFHAINGYI
1051  MDTLPGLVMA QDQRIRWYLL SMGSNENIHS IHFSGHVFTV RKKEEYKMAL
1101  YNLYPGVFET VEMLPSKAGI WRVECLIGEH LHAGMSTLFL VYSNKCQTPL
1151  GMASGHIRDF QITASGQYGQ WAPKLARLHY SGSINAWSTK EPFSWIKVDL
1201  LAPMIIHGIK TQGARQKFSS LYISQFIIMY SLDGKKWQTY RGNSTGTLMV
1251  FFGNVDSSGI KHNIFNPPII ARYIRLHPTH YSIRSTLRME LMGCDLNSCS
1301  MPLGMESKAI SDAQITASSY FTNMFATWSP SKARLHLQGR SNAWRPQVNN
1351  PKEWLQVDFQ KTMKVTGVTT QGVKSLLTSM YVKEFLISSS QDGHQWTLFF
1401  QNGKVKVFQG NQDSFTPVVN SLDPPLLTRY LRIHPQSWVH QIALRMEVLG
1451  CEAQDLY
```

Full length FVIII amino acid sequence (SEQ ID NO: 72): Signal peptide underlined

```
   1  MQIELSTCFF LCLLRFCFSA TRRYYLGAVE LSWDYMQSDL GELPVDARFP
  51  PRVPKSFPFN TSVVYKKTLF VEFTDHLFNI AKPRPPWMGL LGPTIQAEVY
 101  DTVVITLKNM ASHPVSLHAV GVSYWKASEG AEYDDQTSQR EKEDDKVFPG
 151  GSHTYVWQVL KENGPMASDP LCLTYSYLSH VDLVKDLNSG LIGALLVCRE
 201  GSLAKEKTQT LHKFILLFAV FDEGKSWHSE TKNSLMQDRD AASARAWPKM
```

```
 251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDDRSYKSQY LNNGPQRIGR KYKKVRFMAY

451 TDETFKTREA IQHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

751 SKNNAIEPRS FSQNSRHPST RQKQFNATTI PENDIEKTDP WFAHRTPMPK

801 IQNVSSSDLL MLLRQSPTPH GLSLSDLQEA KYETFSDDPS PGAIDSNNSL

851 SEMTHFRPQL HHSGDMVFTP ESGLQLRLNE KLGTTAATEL KKLDFKVSST

901 SNNLISTIPS DNLAAGTDNT SSLGPPSMPV HYDSQLDTTL FGKKSSPLTE

951 SGGPLSLSEE NNDSKLLESG LMNSQESSWG KNVSSTESGR LFKGKRAHGP

1001 ALLTKDNALF KVSISLLKTN KTSNNSATNR KTHIDGPSLL IENSPSVWQN

1051 ILESDTEFKK VTPLIHDRML MDKNATALRL NHMSNKTTSS KNMEMVQQKK

1101 EGPIPPDAQN PDMSFFKMLF LPESARWIQR THGKNSLNSG QGPSPKQLVS

1151 LGPEKSVEGQ NFLSEKNKVV VGKGEFTKDV GLKEMVFPSS RNLFLTNLDN

1201 LHENNTHNQE KKIQEEIEKK ETLIQENVVL PQIHTVTGTK NFMKNLFLLS

1251 TRQNVEGSYD GAYAPVLQDF RSLNDSTNRT KKHTAHFSKK GEEENLEGLG

1301 NQTKQIVEKY ACTTRISPNT SQQNFVTQRS KRALKQFRLP LEETELEKRI

1351 IVDDTSTQWS KNMKHLTPST LTQIDYNEKE KGAITQSPLS DCLTRSHSIP

1401 QANRSPLPIA KVSSFPSIRP IYLTRVLFQD NSSHLPAASY RKKDSGVQES

1451 SHFLQGAKKN NLSLAILTLE MTGDQREVGS LGTSATNSVT YKKVENTVLP

1501 KPDLPKTSGK VELLPKVHIY QKDLFPTETS NGSPGHLDLV EGSLLQGTEG

1551 AIKWNEANRP GKVPFLRVAT ESSAKTPSKL LDPLAWDNHY GTQIPKEEWK

1601 SQEKSPEKTA FKKKDTILSL NACESNHAIA AINEGQNKPE IEVTWAKQGR

1651 TERLCSQNPP VLKRHQREIT RTTLQSDQEE IDYDDTISVE MKKEDFDIYD

1701 EDENQSPRSF QKKTRHYFIA AVERLWDYGM SSSPHVLRNR AQSGSVPQFK

1751 KVVFQEFTDG SFTQPLYRGE LNEHLGLLGP YIRAEVEDNI MVTFRNQASR

1801 PYSFYSSLIS YEEDQRQGAE PRKNFVKPNE TKTYFWKVQH HMAPTKDEFD

1851 CKAWAYFSDV DLEKDVHSGL IGPLLVCHTN TLNPAHGRQV TVQEFALFFT

1901 IFDETKSWYF TENMERNCRA PCNIQMEDPT FKENYRFHAI NGYIMDTLPG

1951 LVMAQDQRIR WYLLSMGSNE NIHSIHFSGH VFTVRKKEEY KMALYNLYPG

2001 VFETVEMLPS KAGIWRVECL IGEHLHAGMS TLFLVYSNKC QTPLGMASGH

2051 IRDFQITASG QYGQWAPKLA RLHYSGSINA WSTKEPFSWI KVDLLAPMII

2101 HGIKTQGARQ KFSSLYISQF IIMYSLDGKK WQTYRGNSTG TLMVFFGNVD

2151 SSGIKHNIFN PPIIARYIRL HPTHYSIRST LRMELMGCDL NSCSMPLGME

2201 SKAISDAQIT ASSYFTNMFA TWSPSKARLH LQGRSNAWRP QVNNPKEWLQ
```

2251 VDFQKTMKVT GVTTQGVKSL LTSMYVKEFL ISSSQDGHQW TLFFQNGKVK

2301 VFQGNQDSFT PVVNSLDPPL LTRYLRIHPQ SWVHQIALRM EVLGCEAQDL

2351 Y

FIX amino acid sequence (SEQ ID NO: 73). Signal sequence is shown in dotted underline, propeptide is double underlined

MQRVNMIMAE SPGLITICLL GYLLSAECTV FLDHENANKI

LNRPKRYNSG KLEEFVQGNL

ERECMEEKCS FEEAREVFEN TERTTEFWKQ YVDGDQCESN

PCLNGGSCKD DINSYECWCP

FGFEGKNCEL DVTCNIKNGR CEQFCKNSAD NKVVCSCTEG

YRLAENQKSC EPAVPFPCGR

VSVSQTSKLT RAETVFPDVD YVNSTEAETI LDNITQSTQS

FNDFTRVVGG EDAKPGQFPW

QVVLNGKVDA FCGGSIVNEK WIVTAAHCVE TGVKITVVAG

EHNIEETEHT EQKRNVIRII

PHHNYNAAIN KYNHDIALLE LDEPLVLNSY VTPICIADKE

YTNIFLKFGS GYVSGWGRVF

HKGRSALVLQ YLRVPLVDRA TCLRSTKFTI YNNMFCAGFH

EGGRDSCQGD SGGPHVTEVE

GTSFLTGIIS WGEECAMKGK YGIYTKVSRY VNWIKEKTKL

T

FIX DNA sequence (SEQ ID NO: 74)
atgcagcgcg tgaacatgat catggcagaa tcaccaggcc tcatcaccat ctgccttta ggatatctac tcagtgctga atgtacagtt tttcttgatc atgaaaacgc acaaaatt ctgaatcggc caaagaggta taattcaggt aaattggaag agtttgttca agggaatcta gagagagaat gtatggaaga aaagtgtagt tttgaagaag cacgagaagt ttttgaaaac actgaaagaa caactgaatt ttggaagcag tatgttgatg gagatcagtg tgagtccaat ccatgtttaa atggcggcag ttgcaaggat gacattaatt cctatgaatg ttggtgtccc tttggatttg aaggaaagaa ctgtgaatta gatgtaacat gtaacattaa gaatggcaga tgcgagcagt tttgtaaaaa tagtgctgat aacaaggtgg tttgctcctg tactgaggga tatcgacttg cagaaaacca gaagtcctgt gaaccagcag tgccatttcc atgtggaaga gtttctgttt cacaaacttc taagctcacc cgtgctgaga ctgttttcc tgatgtggac tatgtaaatt ctactgaagc tgaaaccatt ttggataaca tcactcaaag cacccaatca tttaatgact tcactcgggt tgttggtgga gaagatgcca aaccaggtca attcccttgg caggttgttt tgaatggtaa agttgatgca ttctgtggag gctctatcgt taatgaaaaa tggattgtaa ctgctgccca ctgtgttgaa actggtgtta aaattacagt tgtcgcaggt gaacataata ttgaggagac agaacataca gagcaaaagc gaaatgtgat tcgaattatt cctcaccaca actacaatgc agctattaat aagtacaacc atgacattgc ccttctggaa ctggacgaac ccttagtgct aaacagctac gttacaccta tttgcattgc tgacaaggaa tacacgaaca tcttcctcaa atttggatct ggctatgtaa gtggctgggg aagagtcttc cacaaaggga gatcagcttt agttcttcag taccttagag ttccacttgt tgaccgagcc acatgtcttc gatctacaaa gttcaccatc tataacaaca tgttctgtgc tggcttccat gaaggaggta gagattcatg tcaaggagat agtgggggac cccatgttac tgaagtggaa gggaccagtt tcttaactgg aattattagc tggggtgaag agtgtgcaat gaaaggcaaa tatggaatat ataccaaggt atcccggtat gtcaactgga ttaaggaaaa aacaaagctc acttga FX amino acid sequence (SEQ ID NO: 75). Signal sequence is shown in dotted underline, propeptide is double underlined

MGRPLHLVLL SASLAGLLLL GESLFIRREQ ANNILARVTR ANSFLEEMKK GHLERECMEE

TCSYEEAREV FEDSDKTNEF WNKYKDGDQC ETSPCQNQGK CKDGLGEYTC TCLEGFEGKN

CELFTRKLCS LDNGDCDQFC HEEQNSVVCS CARGYTLADN GKACIPTGPY PCGKQTLERR

KRSVAQATSS SGEAPDSITW KPYDAADLDP TENPFDLLDF NQTQPERGDN NLTRIVGGQE

CKDGECPWQA LLINEENEGF CGGTILSEFY ILTAAHCLYQ AKRFKVRVGD RNTEQEEGGE

AVHEVEVVIK HNRFTKETYD FDIAVLRLKT PITFRMNVAP ACLPERDWAE STLMTQKTGI

VSGFGRTHEK GRQSTRLKML EVPYVDRNSC KLSSSFIITQ NMFCAGYDTK QEDACQGDSG

GPHVTRFKDT YFVTGIVSWG EGCARKGKYG IYTKVTAFLK WIDRSMKTRG LPKAKSHAPE

VITSSPLK

FX DNA sequence
(SEQ ID NO: 76)
```
atggggcgcc cactgcacct cgtcctgctc agtgcctccc tggctggcct cctgctgctc
ggggaaagtc tgttcatccg cagggagcag gccaacaaca tcctggcgag ggtcacgagg
gccaattcct ttcttgaaga tgaagaaaa ggacacctcg aaagagagtg catggaagag
acctgctcat acgaagaggc ccgcgaggtc tttgaggaca gcgacaagac gaatgaattc
tggaataaat acaaagatgg cgaccagtgt gagaccagtc cttgccagaa ccagggcaaa
tgtaaagacg gcctcgggga atacacctgc acctgtttag aaggattcga aggcaaaaac
tgtgaattat tcacacggaa gctctgcagc ctggacaacg gggactgtga ccagttctgc
cacgaggaac agaactctgt ggtgtgctcc tgcgcccgcg gtacaccct ggctgacaac
ggcaaggcct gcattccccac agggccctac ccctgtggga acagaccct ggaacgcagg
aagaggtcag tggcccaggc caccagcagc agcggggagg cccctgacag catcacatgg
aagccatatg atgcagccga cctggacccc accgagaacc ccttcgacct gcttgacttc
aaccagacgc agcctgagag gggcgacaac aacctcacca ggatcgtggg aggccaggaa
tgcaaggacg gggagtgtcc ctggcaggcc ctgctcatca atgaggaaaa cgagggtttc
tgtggtggaa ccattctgag cgagttctac atcctaacgg cagcccactg tctctaccaa
gccaagagat tcaaggtgag ggtagggac cggaacacgg agcaggagga gggcggtgag
gcggtgcacg aggtggaggt ggtcatcaag cacaaccggt tcacaaagga gacctatgac
ttcgacatcg ccgtgctccg gctcaagacc cccatcacct tccgcatgaa cgtggcgcct
gcctgcctcc ccgagcgtga ctgggccgag tccacgctga tgacgcagaa gacggggatt
gtgagcggct tcgggcgcac ccacgagaag ggccggcagt ccaccaggct caagatgctg
gaggtgccct acgtggaccg caacagctgc aagctgtcca gcagcttcat catcacccag
aacatgttct gtgccggcta cgacaccaag caggaggatg cctgccaggg ggacagcggg
ggcccgcacg tcacccgctt caaggacacc tacttcgtga caggcatcgt cagctgggga
gagggctgtg cccgtaaggg gaagtacggg atctacacca aggtcaccgc cttcctcaag
tggatcgaca ggtccatgaa aaccaggggc ttgcccaagg ccaagagcca tgccccggag
gtcataacgt cctctccatt aaagtga
```
DNA sequence for pSYN-FIX-053
(SEQ ID NO: 84)
```
  1 ATGCAGCGCG TGAACATGAT CATGGCAGAA TCACCAGGCC TCATCACCAT CTGCCTTTTA
 61 GGATATCTAC TCAGTGCTGA ATGTACAGGT TTGTTTCCTT TTTTAAAATA CATTGAGTAT
121 GCTTGCCTTT TAGATATAGA AATATCTGAT GCTGTCTTCT TCACTAAATT TTGATTACAT
181 GATTTGACAG CAATATTGAA GAGTCTAACA GCCAGCACGC AGGTTGGTAA GTACTGTGGG
```

-continued

```
 241 AACATCACAG ATTTTGGCTC CATGCCCTAA AGAGAAATTG GCTTTCAGAT TATTTGGATT

301 AAAAACAAAG ACTTTCTTAA GAGATGTAAA ATTTTCATGA TGTTTTCTTT TTTGCTAAAA

361 CTAAAGAATT ATTCTTTTAC ATTTCAGTTT TTCTTGATCA TGAAAACGCC AACAAAATTC

421 TGAATCGGCC AAAGAGGTAT AATTCAGGTA AATTGGAAGA GTTTGTTCAA GGGAATCTAG

481 AGAGAGAATG TATGGAAGAA AAGTGTAGTT TTGAAGAAGC ACGAGAAGTT TTTGAAAACA

541 CTGAAAGAAC AACTGAATTT TGGAAGCAGT ATGTTGATGG AGATCAGTGT GAGTCCAATC

601 CATGTTTAAA TGGCGGCAGT TGCAAGGATG ACATTAATTC CTATGAATGT TGGTGTCCCT

661 TTGGATTTGA AGGAAAGAAC TGTGAATTAG ATGTAACATG TAACATTAAG AATGGCAGAT

721 GCGAGCAGTT TTGTAAAAAT AGTGCTGATA ACAAGGTGGT TGCTCCTGT ACTGAGGGAT

781 ATCGACTTGC AGAAAACCAG AAGTCCTGTG AACCAGCAGT GCCATTTCCA TGTGGAAGAG

841 TTTCTGTTTC ACAAACTTCT AAGCTCACCC GTGCTGAGAC TGTTTTTCCT GATGTGGACT

901 ATGTAAATTC TACTGAAGCT GAAACCATTT TGGATAACAT CACTCAAAGC ACCCAATCAT

961 TTAATGACTT CACTCGGGTT GTTGGTGGAG AAGATGCCAA ACCAGGTCAA TTCCCTTGGC

1021 AGGTTGTTTT GAATGGTAAA GTTGATGCAT TCTGTGGAGG CTCTATCGTT AATGAAAAAT

1081 GGATTGTAAC TGCTGCCCAC TGTGTTGAAA CTGGTGTTAA AATTACAGTT GCTGCAGGTG

1141 AACATAATAT TGAGGAGACA GAACATACAG AGCAAAAGCG AAATGTGATT CGAATTATTC

1201 CTCACCACAA CTACAATGCA GCTATTAATA AGTACAACCA TGACATTGCC CTTCTGGAAC

1261 TGGACGAACC CTTAGTGCTA AACAGCTACG TTACACCTAT TTGCATTGCT GACAAGGAAT

1321 ACACGAACAT CTTCCTCAAA TTTGGATCTG GCTATGTAAG TGGCTGGGGA AGAGTCTTCC

1381 ACAAAGGGAG ATCAGCTTTA GTTCTTCAGT ACCTTAGAGT TCCACTTGTT GACCGAGCCA

1441 CATGTCTTCG ATCTACAAAG TTCACCATCT ATAACAACAT GTTCTGTGCT GGCTTCCATG

1501 AAGGAGGTAG AGATTCATGT CAAGGAGATA GTGGGGGACC CCATGTTACT GAAGTGGAAG

1561 GGACCAGTTT CTTAACTGGA ATTATTAGCT GGGGTGAAGA GTGTGCAATG AAAGGCAAAT

1621 ATGGAATATA TACCAAGGTG TCCCGGTATG TCAACTGGAT TAAGGAAAAA ACAAAGCTCA

1681 CTGACAAAAC TCACACATGC CCACCGTGCC CAGCTCCGGA ACTCCTGGGA GGACCGTCAG

1741 TCTTCCTCTT CCCCCCAAAA CCCAAGGACA CCCTCATGAT CTCCCGGACC CCTGAGGTCA

1801 CATGCGTGGT GGTGGACGTG AGCCACGAAG ACCCTGAGGT CAAGTTCAAC TGGTACGTGG

1861 ACGGCGTGGA GGTGCATAAT GCCAAGACAA AGCCGCGGGA GGAGCAGTAC AACAGCACGT

1921 ACCGTGTGGT CAGCGTCCTC ACCGTCCTGC ACCAGGACTG GCTGAATGGC AAGGAGTACA

1981 AGTGCAAGGT CTCCAACAAA GCCCTCCCAG CCCCCATCGA GAAAACCATC TCCAAAGCCA

2041 AAGGGCAGCC CCGAGAACCA CAGGTGTACA CCCTGCCCCC ATCCCGGGAT GAGCTGACCA

2101 AGAACCAGGT CAGCCTGACC TGCCTGGTCA AAGGCTTCTA TCCCAGCGAC ATCGCCGTGG

2161 AGTGGGAGAG CAATGGGCAG CCGGAGAACA ACTACAAGAC CACGCCTCCC GTGTTGGACT

2221 CCGACGGCTC CTTCTTCCTC TACAGCAAGC TCACCGTCGA CAAGAGCAGG TGGCAGCAGG

2281 GGAACGTCTT CTCATGCTCC GTGATGCATG AGGCTCTGCA CAACCACTAC ACGCAGAAGA

2341 GCCTCTCCCT GTCTCCGGGT AAACGGCGCC GCCGGAGCGG TGGCGGCGGA TCAGGTGGGG

2401 GTGGATCAGG CGGTGGAGGT TCCGGTGGCG GGGGATCCAG GAAGAGGAGG AAGAGGGACA

2461 AAACTCACAC ATGCCCACCG TGCCCAGCAC CGGAACTCCT GGGCGGACCG TCAGTCTTCC

2521 TCTTCCCCCC AAAACCCAAG GACACCCTCA TGATCTCCCG GACCCCTGAG GTCACATGCG

2581 TGGTGGTGGA CGTGAGCCAC GAAGACCCTG AGGTCAAGTT CAACTGGTAC GTGGACGGCG

2641 TGGAGGTGCA TAATGCCAAG ACAAAGCCGC GGGAGGAGCA GTACAACAGC ACGTACCGTG
```

-continued

```
2701 TGGTCAGCGT CCTCACCGTC CTGCACCAGG ACTGGCTGAA TGGCAAGGAG TACAAGTGCA

2761 AGGTCTCCAA CAAAGCCCTC CCAGCCCCCA TCGAGAAAAC CATCTCCAAA GCCAAGGGC

2821 AGCCCCGAGA ACCACAGGTG TACACCCTGC CCCCATCCCG GGATGAGCTG ACCAAGAACC

2881 AGGTCAGCCT GACCTGCCTG GTCAAAGGCT TCTATCCCAG CGACATCGCC GTGGAGTGGG

2941 AGAGCAATGG GCAGCCGGAG AACAACTACA AGACCACGCC TCCCGTGTTG GACTCCGACG

3001 GCTCCTTCTT CCTCTACAGC AAGCTCACCG TGGACAAGAG CAGGTGGCAG CAGGGGAACG

3061 TCTTCTCATG CTCCGTGATG CATGAGGCTC TGCACAACCA CTACACGCAG AAGAGCCTCT

3121 CCCTGTCTCC GGGTAAATGA
```

15

FIX-053 amino acid sequence (SEQ ID NO: 85). Signal sequence is shown in dotted underline, propeptide is double underlined, and linker with proprotein convertase processing sites is shown in bold

```
  1 MQRVNMIMAE SPGLITICLL GYLLSAECTV FLDHENANKI LNRPKRYNSG KLEEFVQGNL
 61 ERECMEEKCS FEEAREVFEN TERTTEFWKQ YVDGDQCESN PCLNGGSCKD DINSYECWCP
121 FGFEGKNCEL DVTCNIKNGR CEQFCKNSAD NKVVCSCTEG YRLAENQKSC EPAVPFPCGR
181 VSVSQTSKLT RAETVFPDVD YVNSTEAETI LDNITQSTQS FNDFTRVVGG EDAKPGQFPW
241 QVVLNGKVDA FCGGSIVNEK WIVTAAHCVE TGVKITVVAG EHNIEETEHT EQKRNVIRII
301 PHHNYNAAIN KYNHDIALLE LDEPLVLNSY VTPICIADKE YTNIFLKFGS GYVSGWGRVF
361 HKGRSALVLQ YLRVPLVDRA TCLRSTKFTI YNNMFCAGFH EGGRDSCQGD SGGPHVTEVE
421 GTSFLTGIIS WGEECAMKGK YGIYTKVSRY VNWIKEKTKL TDKTHTCPPC PAPELLGGPS
481 VFLFPPKPKD TLMISRTPEV TCVVVDVSHE DPEVKFNWYV DGVEVHNAKT KPREEQYNST
541 YRVVSVLTVL HQDWLNGKEY KCKVSNKALP APIEKTISKA KGQPREPQVY TLPPSRDELT
601 KNQVSLTCLV KGFYPSDIAV EWESNGQPEN NYKTTPPVLD SDGSFFLYSK LTVDKSRWQQ
661 GNVFSCSVMH EALHNHYTQK SLSLSPGKRR RRSGGGGSGG GGSGGGGSGG GGSRKRRKRD
721 KTHTCPPCPA PELLGGPSVF LFPPKPKDTL MISRTPEVTC VVVDVSHEDP EVKFNWYVDG
781 VEVHNAKTKP REEQYNSTYR VVSVLTVLHQ DWLNGKEYKC KVSNKALPAP IEKTISKAKG
841 QPREPQVYTL PPSRDELTKN QVSLTCLVKG FYPSDIAVEW ESNGQPENNY KTTPPVLDSD
901 GSFFLYSKLT VDKSRWQQGN VFSCSVMHEA LHNHYTQKSL SLSPGK*
```

DNA sequence for pSYN-FVII-064

(SEQ ID NO: 86)

```
  1 ATGGTCTCCC AGGCCCTCAG GCTCCTCTGC CTTCTGCTTG GGCTTCAGGG CTGCCTGGCT
 61 GCAGTCTTCG TAACCCAGGA GGAAGCCCAC GGCGTCCTGC ACCGGCGCCG GCGCGCCAAC
121 GCGTTCCTGG AGGAGCTGCG GCCGGGCTCC CTGGAGAGGG AGTGCAAGGA GGAGCAGTGC
181 TCCTTCGAGG AGGCCCGGGA GATCTTCAAG GACGCGGAGA GGACGAAGCT GTTCTGGATT
241 TCTTACAGTG ATGGGGACCA GTGTGCCTCA AGTCCATGCC AGAATGGGGG CTCCTGCAAG
301 GACCAGCTCC AGTCCTATAT CTGCTTCTGC CTCCCTGCCT TCGAGGGCCG GAACTGTGAG
361 ACGCACAAGG ATGACCAGCT GATCTGTGTG AACGAGAACG GCGGCTGTGA GCAGTACTGC
421 AGTGACCACA CGGGCACCAA GCGCTCCTGT CGGTGCCACG AGGGGTACTC TCTGCTGGCA
481 GACGGGGTGT CCTGCACACC CACAGTTGAA TATCCATGTG GAAAAATACC TATTCTAGAA
541 AAAAGAAATG CCAGCAAACC CCAAGGCCGA ATTGTGGGGG GCAAGGTGTG CCCCAAGGG
601 GAGTGTCCAT GGCAGGTCCT GTTGTTGGTG AATGGAGCTC AGTTGTGTGG GGGGACCCTG
```

```
 661 ATCAACACCA TCTGGGTGGT CTCCGCGGCC CACTGTTTCG ACAAAATCAA GAACTGGAGG

721 AACCTGATCG CGGTGCTGGG CGAGCACGAC CTCAGCGAGC ACGACGGGGA TGAGCAGAGC

781 CGGCGGGTGG CGCAGGTCAT CATCCCCAGC ACGTACGTCC CGGGCACCAC CAACCACGAC

841 ATCGCGCTGC TCCGCCTGCA CCAGCCCGTG GTCCTCACTG ACCATGTGGT GCCCCTCTGC

901 CTGCCCGAAC GGACGTTCTC TGAGAGGACG CTGGCCTTCG TGCGCTTCTC ATTGGTCAGC

961 GGCTGGGGCC AGCTGCTGGA CCGTGGCGCC ACGGCCCTGG AGCTCATGGT CCTCAACGTG

1021 CCCCGGCTGA TGACCCAGGA CTGCCTGCAG CAGTCACGGA AGGTGGGAGA CTCCCCAAAT

1081 ATCACGGAGT ACATGTTCTG TGCCGGCTAC TCGGATGGCA GCAAGGACTC CTGCAAGGGG

1141 GACAGTGGAG GCCCACATGC CACCCACTAC CGGGGCACGT GGTACCTGAC GGGCATCGTC

1201 AGCTGGGGCC AGGGCTGCGC AACCGTGGGC CACTTTGGGG TGTACACCAG GGTCTCCCAG

1261 TACATCGAGT GGCTGCAAAA GCTCATGCGC TCAGAGCCAC GCCCAGGAGT CCTCCTGCGA

1321 GCCCCATTTC CCGGTGGCGG TGGCTCCGGC GGAGGTGGGT CCGGTGGCGG CGGATCAGGT

1381 GGGGGTGGAT CAGGCGGTGG AGGTTCCGGT GGCGGGGGAT CCGACAAAAC TCACACATGC

1441 CCACCGTGCC CAGCTCCGGA ACTCCTGGGA GGACCGTCAG TCTTCCTCTT CCCCCCAAAA

1501 CCCAAGGACA CCCTCTACAT CACCCGGGAG CCTGAGGTCA CATGCGTGGT GGTGGACGTG

1561 AGCCACGAAG ACCCTGAGGT CAAGTTCAAC TGGTACGTGG ACGGCGTGGA GGTGCATAAT

1621 GCCAAGACAA AGCCGCGGGA GGAGCAGTAC AACAGCACGT ACCGTGTGGT CAGCGTCCTC

1681 ACCGTCCTGC ACCAGGACTG GCTGAATGGC AAGGAGTACA AGTGCAAGGT CTCCAACAAA

1741 GCCCTCCCAG CCCCCATCGA GAAAACCATC TCCAAAGCCA AGGGCAGCCC CGAGAACCA

1801 CAGGTGTACA CCCTGCCCCC ATCCCGGGAT GAGCTGACCA AGAACCAGGT CAGCCTGACC

1861 TGCCTGGTCA AAGGCTTCTA TCCCAGCGAC ATCGCCGTGG AGTGGGAGAG CAATGGGCAG

1921 CCGGAGAACA ACTACAAGAC CACGCCTCCC GTGTTGGACT CCGACGGCTC CTTCTTCCTC

1981 TACAGCAAGC TCACCGTCGA CAAGAGCAGG TGGCAGCAGG GAACGTCTT CTCATGCTCC

2041 GTGATGCATG AGGCTCTGCA CAACCACTAC ACGCAGAAGA GCCTCTCCCT GTCTCCGGGT

2101 AAACGGCGCC GCCGGAGCGG TGGCGGCGGA TCAGGTGGGG GTGGATCAGG CGGTGGAGGT

2161 TCCGGTGGCG GGGGATCCAG GAAGAGGAGG AAGAGGGACA AAACTCACAC ATGCCCACCG

2221 TGCCCAGCAC CGGAACTCCT GGGCGGACCG TCAGTCTTCC TCTTCCCCCC AAAACCCAAG

2281 GACACCCTCT ACATCACCCG GGAGCCTGAG GTCACATGCG TGGTGGTGGA CGTGAGCCAC

2341 GAAGACCCTG AGGTCAAGTT CAACTGGTAC GTGGACGGCG TGGAGGTGCA TAATGCCAAG

2401 ACAAAGCCGC GGGAGGAGCA GTACAACAGC ACGTACCGTG TGGTCAGCGT CCTCACCGTC

2461 CTGCACCAGG ACTGGCTGAA TGGCAAGGAG TACAAGTGCA AGGTCTCCAA CAAAGCCCTC

2521 CCAGCCCCCA TCGAGAAAAC CATCTCCAAA GCCAAGGGC AGCCCCGAGA ACCACAGGTG

2581 TACACCCTGC CCCCATCCCG GGATGAGCTG ACCAAGAACC AGGTCAGCCT GACCTGCCTG

2641 GTCAAAGGCT TCTATCCCAG CGACATCGCC GTGGAGTGGG AGAGCAATGG GCAGCCGGAG

2701 AACAACTACA AGACCACGCC TCCCGTGTTG GACTCCGACG GCTCCTTCTT CCTCTACAGC

2761 AAGCTCACCG TGGACAAGAG CAGGTGGCAG CAGGGGAACG TCTTCTCATG CTCCGTGATG

2821 CATGAGGCTC TGCACAACCA CTACACGCAG AAGAGCCTCT CCCTGTCTCC GGGTAAATGA
```

FVII-064 amino acid sequence (SEQ ID NO: 87). Signal sequence is shown in dotted underline, propeptide is double underlined, linker connecting FVII to Fc is underlined, and linker with proprotein convertase processing sites is shown in bold

```
  1 MVSQALRLLC LLLGLQGCLA AVFVTQEEAH GVLHRRRRAN AFLEELRPGS LERECKEEQC

61 SFEEAREIFK DAERTKLFWI SYSDGDQCAS SPCQNGGSCK DQLQSYICFC LPAFEGRNCE

121 THKDDQLICV NENGGCEQYC SDHTGTKRSC RCHEGYSLLA DGVSCTPTVE YPCGKIPILE

181 KRNASKPQGR IVGGKVCPKG ECPWQVLLLV NGAQLCGGTL INTIWVVSAA HCFDKIKNWR

241 NLIAVLGEHD LSEHDGDEQS RRVAQVIIPS TYVPGTTNHD IALLRLHQPV VLTDHVVPLC

301 LPERTFSERT LAFVRFSLVS GWGQLLDRGA TALELMVLNV PRLMTQDCLQ QSRKVGDSPN

361 ITEYMFCAGY SDGSKDSCKG DSGGPHATHY RGTWYLTGIV SWGQGCATVG HFGVYTRVSQ

421 YIEWLQKLMR SEPRPGVLLR APFPGGGGSG GGGSGGGGSG GGGSGGGGSG GGGSDKTHTC

481 PPCPAPELLG GPSVFLFPPK PKDTLYITRE PEVTCVVVDV SHEDPEVKFN WYVDGVEVHN

541 AKTKPREEQY NSTYRVVSVL TVLHQDWLNG KEYKCKVSNK ALPAPIEKTI SKAKGQPREP

601 QVYTLPPSRD ELTKNQVSLT CLVKGFYPSD IAVEWESNGQ PENNYKTTPP VLDSDGSFFL

661 YSKLTVDKSR WQQGNVFSCS VMHEALHNHY TQKSLSLSPG KRRRRSGGGG SGGGGSGGGG

721 SGGGGSRKRR KRDKTHTCPP CPAPELLGGP SVFLFPPKPK DTLYITREPE VTCVVVDVSH

781 EDPEVKFNWY VDGVEVHNAK TKPREEQYNS TYRVVSVLTV LHQDWLNGKE YKCKVSNKAL

841 PAPIEKTISK AKGQPREPQV YTLPPSRDEL TKNQVSLTCL VKGFYPSDIA VEWESNGQPE

901 NNYKTTPPVL DSDGSFFLYS KLTVDKSRWQ QGNVFSCSVM HEALHNHYTQ KSLSLSPGK*
```

DNA sequence for pSYN-FVIII-049

(SEQ ID NO: 88)

```
   1 ATGCAAATAG AGCTCTCCAC CTGCTTCTTT CTGTGCCTTT TGCGATTCTG CTTTAGTGCC

61 ACCAGAAGAT ACTACCTGGG TGCAGTGGAA CTGTCATGGG ACTATATGCA AAGTGATCTC

121 GGTGAGCTGC CTGTGGACGC AAGATTTCCT CCTAGAGTGC AAAATCTTT TCCATTCAAC

181 ACCTCAGTCG TGTACAAAAA GACTCTGTTT GTAGAATTCA CGGATCACCT TTTCAACATC

241 GCTAAGCCAA GGCCACCCTG GATGGGTCTG CTAGGTCCTA CCATCCAGGC TGAGGTTTAT

301 GATACAGTGG TCATTACACT TAAGAACATG GCTTCCCATC CTGTCAGTCT TCATGCTGTT

361 GGTGTATCCT ACTGGAAAGC TTCTGAGGGA GCTGAATATG ATGATCAGAC CAGTCAAAGG

421 GAGAAAGAAG ATGATAAAGT CTTCCCTGGT GGAAGCCATA CATATGTCTG GCAGGTCCTG

481 AAAGAGAATG GTCCAATGGC CTCTGACCCA CTGTGCCTTA CCTACTCATA TCTTTCTCAT

541 GTGGACCTGG TAAAAGACTT GAATTCAGGC CTCATTGGAG CCCTACTAGT ATGTAGAGAA

601 GGGAGTCTGG CCAAGGAAAA GACACAGACC TTGCACAAAT TTATACTACT TTTTGCTGTA

661 TTTGATGAAG GGAAAAGTTG GCACTCAGAA ACAAAGAACT CCTTGATGCA GGATAGGGAT

721 GCTGCATCTG CTCGGGCCTG GCCTAAAATG CACACAGTCA ATGGTTATGT AAACAGGTCT

781 CTGCCAGGTC TGATTGGATG CCACAGGAAA TCAGTCTATT GGCATGTGAT TGGAATGGGC

841 ACCACTCCTG AAGTGCACTC AATATTCCTC GAAGGTCACA CATTTCTTGT GAGGAACCAT

901 CGCCAGGCGT CCTTGGAAAT CTCGCCAATA ACTTTCCTTA CTGCTCAAAC ACTCTTGATG

961 GACCTTGGAC AGTTTCTACT GTTTTGTCAT ATCTCTTCCC ACCAACATGA TGGCATGGAA

1021 GCTTATGTCA AAGTAGACAG CTGTCCAGAG GAACCCCAAC TACGAATGAA AAATAATGAA

1081 GAAGCGGAAG ACTATGATGA TGATCTTACT GATTCTGAAA TGGATGTGGT CAGGTTTGAT

1141 GATGACAACT CTCCTTCCTT TATCCAAATT CGCTCAGTTG CCAAGAAGCA TCCTAAAACT
```

-continued

```
1201 TGGGTACATT ACATTGCTGC TGAAGAGGAG GACTGGGACT ATGCTCCCTT AGTCCTCGCC

1261 CCCGATGACA GAAGTTATAA AAGTCAATAT TTGAACAATG GCCCTCAGCG GATTGGTAGG

1321 AAGTACAAAA AAGTCCGATT TATGGCATAC ACAGATGAAA CCTTTAAGAC TCGTGAAGCT

1381 ATTCAGCATG AATCAGGAAT CTTGGGACCT TTACTTTATG GGAAGTTGG AGACACACTG

1441 TTGATTATAT TTAAGAATCA AGCAAGCAGA CCATATAACA TCTACCCTCA CGGAATCACT

1501 GATGTCCGTC CTTTGTATTC AAGGAGATTA CCAAAAGGTG TAAAACATTT GAAGGATTTT

1561 CCAATTCTGC CAGGAGAAAT ATTCAAATAT AAATGGACAG TGACTGTAGA AGATGGGCCA

1621 ACTAAATCAG ATCCTCGGTG CCTGACCCGC TATTACTCTA GTTTCGTTAA TATGGAGAGA

1681 GATCTAGCTT CAGGACTCAT TGGCCCTCTC CTCATCTGCT ACAAAGAATC TGTAGATCAA

1741 AGAGGAAACC AGATAATGTC AGACAAGAGG AATGTCATCC TGTTTTCTGT ATTTGATGAG

1801 AACCGAAGCT GGTACCTCAC AGAGAATATA CAACGCTTTC TCCCCAATCC AGCTGGAGTG

1861 CAGCTTGAGG ATCCAGAGTT CCAAGCCTCC AACATCATGC ACAGCATCAA TGGCTATGTT

1921 TTTGATAGTT TGCAGTTGTC AGTTTGTTTG CATGAGGTGG CATACTGGTA CATTCTAAGC

1981 ATTGGAGCAC AGACTGACTT CCTTTCTGTC TTCTTCTCTG GATATACCTT CAAACACAAA

2041 ATGGTCTATG AAGACACACT CACCCTATTC CCATTCTCAG GAGAAACTGT CTTCATGTCG

2101 ATGGAAAACC CAGGTCTATG GATTCTGGGG TGCCACAACT CAGACTTTCG GAACAGAGGC

2161 ATGACCGCCT TACTGAAGGT TTCTAGTTGT GACAAGAACA CTGGTGATTA TTACGAGGAC

2221 AGTTATGAAG ATATTTCAGC ATACTTGCTG AGTAAAAACA ATGCCATTGA ACCAAGAAGC

2281 TTCTCTCAAA ACCCACCAGT CTTGAAACGC CATCAACGGG AAATAACTCG TACTACTCTT

2341 CAGTCAGATC AAGAGGAAAT TGACTATGAT GATACCATAT CAGTTGAAAT GAAGAAGGAA

2401 GATTTTGACA TTTATGATGA GGATGAAAAT CAGAGCCCCC GCAGCTTTCA AAAGAAAACA

2461 CGACACTATT TTATTGCTGC AGTGGAGAGG CTCTGGGATT ATGGGATGAG TAGCTCCCCA

2521 CATGTTCTAA GAAACAGGGC TCAGAGTGGC AGTGTCCCTC AGTTCAAGAA AGTTGTTTTC

2581 CAGGAATTTA CTGATGGCTC CTTTACTCAG CCCTTATACC GTGGAGAACT AAATGAACAT

2641 TTGGGACTCC TGGGGCCATA TATAAGAGCA GAAGTTGAAG ATAATATCAT GGTAACTTTC

2701 AGAAATCAGG CCTCTCGTCC CTATTCCTTC TATTCTAGCC TTATTTCTTA TGAGGAAGAT

2761 CAGAGGCAAG GAGCAGAACC TAGAAAAAAC TTTGTCAAGC CTAATGAAAC CAAAACTTAC

2821 TTTTGGAAAG TGCAACATCA TATGGCACCC ACTAAAGATG AGTTTGACTG CAAAGCCTGG

2881 GCTTATTTCT CTGATGTTGA CCTGGAAAAA GATGTGCACT CAGGCCTGAT TGGACCCCTT

2941 CTGGTCTGCC ACACTAACAC ACTGAACCCT GCTCATGGGA GACAAGTGAC AGTACAGGAA

3001 TTTGCTCTGT TTTTCACCAT CTTTGATGAG ACCAAAAGCT GGTACTTCAC TGAAAATATG

3061 GAAAGAAACT GCAGGGCTCC CTGCAATATC CAGATGGAAG ATCCCACTTT TAAAGAGAAT

3121 TATCGCTTCC ATGCAATCAA TGGCTACATA ATGGATACAC TACCTGGCTT AGTAATGGCT

3181 CAGGATCAAA GGATTCGATG GTATCTGCTC AGCATGGGCA GCAATGAAAA CATCCATTCT

3241 ATTCATTTCA GTGGACATGT GTTCACTGTA CGAAAAAAAG AGGAGTATAA AATGGCACTG

3301 TACAATCTCT ATCCAGGTGT TTTTGAGACA GTGGAAATGT TACCATCCAA AGCTGGAATT

3361 TGGCGGGTGG AATGCCTTAT TGGCGAGCAT CTACATGCTG GGATGAGCAC ACTTTTTCTG

3421 GTGTACAGCA ATAAGTGTCA GACTCCCCTG GGAATGGCTT CTGGACACAT TAGAGATTTT

3481 CAGATTACAG CTTCAGGACA ATATGGACAG TGGGCCCCAA AGCTGGCCAG ACTTCATTAT

3541 TCCGGATCAA TCAATGCCTG GAGCACCAAG GAGCCCTTTT CTTGGATCAA GGTGGATCTG

3601 TTGGCACCAA TGATTATTCA CGGCATCAAG ACCCAGGGTG CCCGTCAGAA GTTCTCCAGC
```

```
3661 CTCTACATCT CTCAGTTTAT CATCATGTAT AGTCTTGATG GGAAGAAGTG GCAGACTTAT

3721 CGAGGAAATT CCACTGGAAC CTTAATGGTC TTCTTTGGCA ATGTGGATTC ATCTGGGATA

3781 AAACACAATA TTTTTAACCC TCCAATTATT GCTCGATACA TCCGTTTGCA CCCAACTCAT

3841 TATAGCATTC GCAGCACTCT TCGCATGGAG TTGATGGGCT GTGATTTAAA TAGTTGCAGC

3901 ATGCCATTGG GAATGGAGAG TAAAGCAATA TCAGATGCAC AGATTACTGC TTCATCCTAC

3961 TTTACCAATA TGTTTGCCAC CTGGTCTCCT TCAAAAGCTC GACTTCACCT CCAAGGGAGG

4021 AGTAATGCCT GGAGACCTCA GGTGAATAAT CCAAAAGAGT GGCTGCAAGT GGACTTCCAG

4081 AAGACAATGA AAGTCACAGG AGTAACTACT CAGGGAGTAA AATCTCTGCT TACCAGCATG

4141 TATGTGAAGG AGTTCCTCAT CTCCAGCAGT CAAGATGGCC ATCAGTGGAC TCTCTTTTTT

4201 CAGAATGGCA AAGTAAAGGT TTTTCAGGGA AATCAAGACT CCTTCACACC TGTGGTGAAC

4261 TCTCTAGACC CACCGTTACT GACTCGCTAC CTTCGAATTC ACCCCCAGAG TTGGGTGCAC

4321 CAGATTGCCC TGAGGATGGA GGTTCTGGGC TGCGAGGCAC AGGACCTCTA CGACAAAACT

4381 CACACATGCC CACCGTGCCC AGCACCTGAA CTCCTGGGAG GACCGTCAGT CTTCCTCTTC

4441 CCCCCAAAAC CCAAGGACAC CCTCATGATC TCCCGGACCC CTGAGGTCAC ATGCGTGGTG

4501 GTGGACGTGA GCCACGAAGA CCCTGAGGTC AAGTTCAACT GGTACGTGGA CGGCGTGGAG

4561 GTGCATAATG CCAAGACAAA GCCGCGGGAG GAGCAGTACA ACAGCACGTA CCGTGTGGTC

4621 AGCGTCCTCA CCGTCCTGCA CCAGGACTGG CTGAATGGCA AGGAGTACAA GTGCAAGGTC

4681 TCCAACAAAG CCCTCCCAGC CCCCATCGAG AAAACCATCT CCAAAGCCAA AGGGCAGCCC

4741 CGAGAACCAC AGGTGTACAC CCTGCCCCCA TCCCGCGATG AGCTGACCAA GAACCAGGTC

4801 AGCCTGACCT GCCTGGTCAA AGGCTTCTAT CCCAGCGACA TCGCCGTGGA GTGGGAGAGC

4861 AATGGGCAGC CGGAGAACAA CTACAAGACC ACGCCTCCCG TGTTGGACTC CGACGGCTCC

4921 TTCTTCCTCT ACAGCAAGCT CACCGTCGAC AAGAGCAGGT GGCAGCAGGG GAACGTCTTC

4981 TCATGCTCCG TGATGCATGA GGCTCTGCAC AACCACTACA CGCAGAAGAG CCTCTCCCTG

5041 TCTCCGGGTA ACGGCGCCG CCGGAGCGGT GGCGGCGGAT CAGGTGGGGG TGGATCAGGC

5101 GGTGGAGGTT CCGGTGGCGG GGGATCCGGC GGTGGAGGTT CCGGTGGGGG TGGATCAAGG

5161 AAGAGGAGGA AGAGGGACAA AACTCACACA TGCCCACCGT GCCCAGCTCC AGAACTCCTG

5221 GGCGGACCGT CAGTCTTCCT CTTCCCCCCA AAACCCAAGG ACACCCTCAT GATCTCCCGG

5281 ACCCCTGAGG TCACATGCGT GGTGGTGGAC GTGAGCCACG AAGACCCTGA GGTCAAGTTC

5341 AACTGGTACG TGGACGGCGT GGAGGTGCAT AATGCCAAGA CAAAGCCGCG GGAGGAGCAG

5401 TACAACAGCA CGTACCGTGT GGTCAGCGTC CTCACCGTCC TGCACCAGGA CTGGCTGAAT

5461 GGCAAGGAGT ACAAGTGCAA GGTCTCCAAC AAAGCCCTCC CAGCCCCCAT CGAGAAAACC

5521 ATCTCCAAAG CCAAAGGGCA GCCCCGAGAA CCACAGGTGT ACACCCTGCC CCCATCCCGG

5581 GATGAGCTGA CCAAGAACCA GGTCAGCCTG ACCTGCCTGG TCAAAGGCTT CTATCCCAGC

5641 GACATCGCCG TGGAGTGGGA GAGCAATGGG CAGCCGGAGA ACAACTACAA GACCACGCCT

5701 CCCGTGTTGG ACTCCGACGG CTCCTTCTTC CTCTACAGCA AGCTCACCGT GGACAAGAGC

5761 AGGTGGCAGC AGGGGAACGT CTTCTCATGC TCCGTGATGC ATGAGGCTCT GCACAACCAC

5821 TACACGCAGA AGAGCCTCTC CCTGTCTCCG GGTAAATGA
```

FVIII-049 amino acid sequence (SEQ ID NO: 89). Signal sequence is shown in dotted underline, and linker with proprotein convertase processing sites is shown in bold

```
   1 MQIELSTCFF LCLLRFCFSA TRRYYLGAVE LSWDYMQSDL GELPVDARFP PRVPKSFPFN

61 TSVVYKKTLF VEFTDHLFNI AKPRPPWMGL LGPTIQAEVY DTVVITLKNM ASHPVSLHAV

121 GVSYWKASEG AEYDDQTSQR EKEDDKVFPG GSHTYVWQVL KENGPMASDP LCLTYSYLSH

181 VDLVKDLNSG LIGALLVCRE GSLAKEKTQT LHKFILLFAV FDEGKSWHSE TKNSLMQDRD

241 AASARAWPKM HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE EPQLRMKNNE

361 EAEDYDDDLT DSEMDVVRFD DDNSPSFIQI RSVAKKHPKT WVHYIAAEEE DWDYAPLVLA

421 PDDRSYKSQY LNNGPQRIGR KYKKVRFMAY TDETFKTREA IQHESGILGP LLYGEVGDTL

481 LIIFKNQASR PYNIYPHGIT DVRPLYSRRL PKGVKHLKDF PILPGEIFKY KWTVTVEDGP

541 TKSDPRCLTR YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL HEVAYWYILS

661 IGAQTDFLSV FFSGYTFKHK MVYEDTLTLF PFSGETVFMS MENPGLWILG CHNSDFRNRG

721 MTALLKVSSC DKNTGDYYED SYEDISAYLL SKNNAIEPRS FSQNPPVLKR HQREITRTTL

781 QSDQEEIDYD DTISVEMKKE DFDIYDEDEN QSPRSFQKKT RHYFIAAVER LWDYGMSSSP

841 HVLRNRAQSG SVPQFKKVVF QEFTDGSFTQ PLYRGELNEH LGLLGPYIRA EVEDNIMVTF

901 RNQASRPYSF YSSLISYEED QRQGAEPRKN FVKPNETKTY FWKVQHHMAP TKDEFDCKAW

961 AYFSDVDLEK DVHSGLIGPL LVCHTNTLNP AHGRQVTVQE FALFFTIFDE TKSWYFTENM

1021 ERNCRAPCNI QMEDPTFKEN YRFHAINGYI MDTLPGLVMA QDQRIRWYLL SMGSNENIHS

1081 IHFSGHVFTV RKKEEYKMAL YNLYPGVFET VEMLPSKAGI WRVECLIGEH LHAGMSTLFL

1141 VYSNKCQTPL GMASGHIRDF QITASGQYGQ WAPKLARLHY SGSINAWSTK EPFSWIKVDL

1201 LAPMIIHGIK TQGARQKFSS LYISQFIIMY SLDGKKWQTY RGNSTGTLMV FFGNVDSSGI

1261 KHNIFNPPII ARYIRLHPTH YSIRSTLRME LMGCDLNSCS MPLGMESKAI SDAQITASSY

1321 FTNMFATWSP SKARLHLQGR SNAWRPQVNN PKEWLQVDFQ KTMKVTGVTT QGVKSLLTSM

1381 YVKEFLISSS QDGHQWTLFF QNGKVKVFQG NQDSFTPVVN SLDPPLLTRY LRIHPQSWVH

1441 QIALRMEVLG CEAQDLYDKT HTCPPCPAPE LLGGPSVFLF PPKPKDTLMI SRTPEVTCVV

1501 VDVSHEDPEV KFNWYVDGVE VHNAKTKPRE EQYNSTYRVV SVLTVLHQDW LNGKEYKCKV

1561 SNKALPAPIE KTISKAKGQP REPQVYTLPP SRDELTKNQV SLTCLVKGFY PSDIAVEWES

1621 NGQPENNYKT TPPVLDSDGS FFLYSKLTVD KSRWQQGNVF SCSVMHEALH NHYTQKSLSL

1681 SPGKRRRRSG GGGSGGGGSG GGGSGGGGSG GGGSGGGGSR KRRKRDKTHT CPPCPAPELL

1741 GGPSVFLFPP KPKDTLMISR TPEVTCVVVD VSHEDPEVKF NWYVDGVEVH NAKTKPREEQ

1801 YNSTYRVVSV LTVLHQDWLN GKEYKCKVSN KALPAPIEKT ISKAKGQPRE PQVYTLPPSR

1861 DELTKNQVSL TCLVKGFYPS DIAVEWESNG QPENNYKTTP PVLDSDGSFF LYSKLTVDKS

1921 RWQQGNVFSC SVMHEALHNH YTQKSLSLSP GK*
```

DNA sequence for IFN-b-018

(SEQ ID NO: 90)

```
   1 ATGACCAACA AGTGTCTCCT CCAAATTGCT CTCCTGTTGT GCTTCTCCAC TACAGCTCTT

61 TCCATGAGCT ACAACTTGCT TGGATTCCTA CAAAGAAGCA GCAATTTTCA GTGTCAGAAG

121 CTCCTGTGGC AATTGAATGG GAGGCTTGAA TATTGCCTCA AGGACAGGAT GAACTTTGAC

181 ATCCCTGAGG AGATTAAGCA GCTGCAGCAG TTCCAGAAGG AGGACGCCGC ATTGACCATC
```

-continued

```
 241 TATGAGATGC TCCAGAACAT CTTTGCTATT TTCAGACAAG ATTCATCTAG CACTGGCTGG

301 AATGAGACTA TTGTTGAGAA CCTCCTGGCT AATGTCTATC ATCAGATAAA CCATCTGAAG

361 ACAGTCCTGG AAGAAAAACT GGAGAAAGAA GATTTCACCA GGGGAAAACT CATGAGCAGT

421 CTGCACCTGA AAAGATATTA TGGGAGGATT CTGCATTACC TGAAGGCCAA GGAGTACAGT

481 CACTGTGCCT GGACCATAGT CAGAGTGGAA ATCCTAAGGA ACTTTTACTT CATTAACAGA

541 CTTACAGGTT ACCTCCGAAA CGGTGGCGGC GGCTCCGGTG AGGCGGGTC CGGCGGTGGA

601 GGGAGCGACA AAACTCACAC ATGCCCACCG TGCCCAGCTC CGGAACTCCT GGGAGGACCG

661 TCAGTCTTCC TCTTCCCCCC AAAACCCAAG GACACCCTCA TGATCTCCCG GACCCCTGAG

721 GTCACATGCG TGGTGGTGGA CGTGAGCCAC GAAGACCCTG AGGTCAAGTT CAACTGGTAC

781 GTGGACGGCG TGGAGGTGCA TAATGCCAAG ACAAAGCCGC GGGAGGAGCA GTACAACAGC

841 ACGTACCGTG TGGTCAGCGT CCTCACCGTC CTGCACCAGG ACTGGCTGAA TGGCAAGGAG

901 TACAAGTGCA AGGTCTCCAA CAAAGCCCTC CCAGCCCCCA TCGAGAAAAC CATCTCCAAA

961 GCCAAAGGGC AGCCCCGAGA ACCACAGGTG TACACCCTGC CCCCATCCCG GGATGAGCTG

1021 ACCAAGAACC AGGTCAGCCT GACCTGCCTG GTCAAAGGCT TCTATCCCAG CGACATCGCC

1081 GTGGAGTGGG AGAGCAATGG GCAGCCGGAG AACAACTACA AGACCACGCC TCCCGTGTTG

1141 GACTCCGACG GCTCCTTCTT CCTCTACAGC AAGCTCACCG TCGACAAGAG CAGGTGGCAG

1201 CAGGGGAACG TCTTCTCATG CTCCGTGATG CATGAGGCTC TGCACAACCA CTACACGCAG

1261 AAGAGCCTCT CCCTGTCTCC GGGTAAACGG CGCCGCCGGA GCGGTGGCGG CGGATCAGGT

1321 GGGGGTGGAT CAGGCGGTGG AGGTTCCGGT GGCGGGGGAT CCAGGAAGAG GAGGAAGAGG

1381 GACAAAACTC ACACATGCCC ACCGTGCCCA GCACCGGAAC TCCTGGGCGG ACCGTCAGTC

1441 TTCCTCTTCC CCCCAAAACC CAAGGACACC CTCATGATCT CCCGGACCCC TGAGGTCACA

1501 TGCGTGGTGG TGGACGTGAG CCACGAAGAC CCTGAGGTCA AGTTCAACTG GTACGTGGAC

1561 GGCGTGGAGG TGCATAATGC CAAGACAAAG CCGCGGGAGG AGCAGTACAA CAGCACGTAC

1621 CGTGTGGTCA GCGTCCTCAC CGTCCTGCAC CAGGACTGGC TGAATGGCAA GGAGTACAAG

1681 TGCAAGGTCT CCAACAAAGC CCTCCCAGCC CCCATCGAGA AAACCATCTC CAAAGCCAAA

1741 GGGCAGCCCC GAGAACCACA GGTGTACACC CTGCCCCCAT CCCGGGATGA GCTGACCAAG

1801 AACCAGGTCA GCCTGACCTG CCTGGTCAAA GGCTTCTATC CAGCGACAT CGCCGTGGAG

1861 TGGGAGAGCA ATGGGCAGCC GGAGAACAAC TACAAGACCA CGCCTCCCGT GTTGGACTCC

1921 GACGGCTCCT TCTTCCTCTA CAGCAAGCTC ACCGTGGACA AGAGCAGGTG GCAGCAGGGG

1981 AACGTCTTCT CATGCTCCGT GATGCATGAG GCTCTGCACA ACCACTACAC GCAGAAGAGC

2041 CTCTCCCTGT CTCCGGGTAA ATGA
```

IFN-b-018 amino acid sequence (SEQ ID NO: 91). Signal sequence is shown in dotted underline, linker region connecting IFN-b to Fc region is underlined, and linker with proprotein convertase processing sites is shown in bold

```
  1 MTNKCLLQIA LLLCFSTTAL SMSYNLLGFL QRSSNFQCQK LLWQLNGRLE YCLKDRMNFD

61 IPEEIKQLQQ FQKEDAALTI YEMLQNIFAI FRQDSSSTGW NETIVENLLA NVYHQINHLK

121 TVLEEKLEKE DFTRGKLMSS LHLKRYYGRI LHYLKAKEYS HCAWTIVRVE ILRNFYFINR

181 LTGYLRNGGG GSGGGGSGGG GSDKTHTCPP CPAPELLGGP SVFLFPPKPK DTLMISRTPE

241 VTCVVVDVSH EDPEVKFNWY VDGVEVHNAK TKPREEQYNS TYRVVSVLTV LHQDWLNGKE

301 YKCKVSNKAL PAPIEKTISK AKGQPREPQV YTLPPSRDEL TKNQVSLTCL VKGFYPSDIA

361 VEWESNGQPE NNYKTTPPVL DSDGSFFLYS KLTVDKSRWQ QGNVFSCSVM HEALHNHYTQ
```

```
421 KSLSLSPGKR RRRSGGGGSG GGGSGGGGSG GGGSRKRRKR DKTHTCPPCP APELLGGPSV

481 FLFPPKPKDT LMISRTPEVT CVVVDVSHED PEVKFNWYVD GVEVHNAKTK PREEQYNSTY

541 RVVSVLTVLH QDWLNGKEYK CKVSNKALPA PIEKTISKAK GQPREPQVYT LPPSRDELTK

601 NQVSLTCLVK GFYPSDIAVE WESNGQPENN YKTTPPVLDS DGSFFLYSKL TVDKSRWQQG

661 NVFSCSVMHE ALHNHYTQKS LSLSPGK*
```

This invention is further illustrated by the following examples which should not be construed as limiting. The contents of all references, patents and published patent applications cited throughout this application are incorporated herein by reference.

What is claimed is:

1. A nucleic acid molecule encoding a polypeptide, wherein the polypeptide comprises a first biologically active moiety and a second biologically active moiety, wherein the polypeptide comprises a formula selected from the group consisting of: A-F1-B-P1-L-P2-F2 and A-F1-P1-L-P2-B-F2 in linear sequence from amino to carboxy terminus,
   wherein A is the first biologically active moiety, which comprises a clotting factor, wherein the clotting factor has pro-clotting activity;
   B is the second biologically active moiety;
   P1 and P2 are enzymatic cleavage sites;
   L is a cleavable single chain Fc (cscFc) linker; and
   F1 and F2 are Fc moieties, and
   wherein the first biologically active moiety and the second biologically active moiety are different biologically active moieties.

2. The nucleic acid molecule of claim 1, wherein P1 and P2 are recognized by different enzymes.

3. The nucleic acid molecule of claim 1, wherein at least one of P1 or P2 comprises an amino acid sequence selected from: RRRR (SEQ ID NO: 40), RKRRKR (SEQ ID NO: 39), RRRRS (SEQ ID NO: 38), TQSFNDFTR (SEQ ID NO: 7), SVSQTSKLTR (SEQ ID NO: 8), DFLAEGGGVR (SEQ ID NO: 9), TTKIKPR (SEQ ID NO: 10), LVPRG (SEQ ID NO: 35), and ALRPR (SEQ ID NO: 94).

4. The nucleic acid molecule of claim 1, wherein the cscFc linker has a length of about 1 to about 50 amino acids.

5. The nucleic acid molecule of claim 1, wherein the cscFc linker comprises a gly/ser peptide.

6. A nucleic acid molecule encoding a polypeptide comprising two polypeptide chains, wherein the first polypeptide chain comprises a light chain of a clotting factor linked to a first Fc moiety and the second polypeptide chain comprises a heavy chain of the clotting factor linked to a second Fc moiety, wherein the light chain and the heavy chain associate to form an enzymatically active clotting factor.

7. The nucleic acid molecule of claim 6, wherein the clotting factor is selected from the group consisting of FVII, FVIIa, FIX, FIXa, FX, and FXa.

8. A composition comprising the nucleic acid molecule of claim 6 and a pharmaceutically acceptable carrier.

9. The nucleic acid molecule of claim 1, wherein the cscFc linker is cleavable by thrombin.

10. The nucleic acid molecule of claim 1, wherein P1 and P2 are recognized by the same enzyme.

11. A vector comprising the nucleic acid molecule of claim 1.

12. A host cell comprising the vector of claim 11, wherein the host cell expresses an enzyme which cleaves the cscFc linker.

13. The host cell of claim 12, wherein the enzyme is endogenous to the cell.

14. The host cell of claim 12, wherein the enzyme is exogenous to the cell.

* * * * *

```
                        SEQUENCE LISTING

<160> NUMBER OF SEQ ID NOS: 107

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 1

Gly Gly Gly Gly Ser Gly Gly Gly Ser Gly Gly Gly Gly Ser
1               5                   10                  15

<210> SEQ ID NO 2
<211> LENGTH: 4
<212> TYPE: PRT
<213> ORGANISM: Homo sapiens

<400> SEQUENCE: 2

Glu Leu Leu Gly
1

<210> SEQ ID NO 3
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 3
agctctcgag tcatttaccc ggagacaggg                                          30

<210> SEQ ID NO 4
<211> LENGTH: 50
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(50)
<223> OTHER INFORMATION: Any grouping of "Gly Gly Gly Gly Ser" may be
      present of absent

<400> SEQUENCE: 4

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30
```

```
Gly Gly Ser Gly Gly Gly Ser Gly Gly Gly Ser Gly Gly
        35                  40                  45

Gly Ser
    50

<210> SEQ ID NO 5
<211> LENGTH: 30
<212> TYPE: PRT
<213> ORGANISM: Artificial Sequence
<220> FEATURE:
<223> OTHER INFORMATION: Synthetic peptide

<400> SEQUENCE: 5

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20                  25                  30

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Gly Gly Gly Gly Ser Gly Gly Gly Ser Gly Gly Gly Ser Gly
1               5                   10                  15

Gly Gly Gly Ser
            20

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Thr Gln Ser Phe Asn Asp Phe Thr Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Ser Val Ser Gln Thr Ser Lys Leu Thr Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Asp Phe Leu Ala Glu Gly Gly Gly Val Arg
1               5                   10

<210> SEQ ID NO 10
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Thr Thr Lys Ile Lys Pro Arg
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide

<400> SEQUENCE: 11

Ala Leu Arg Pro Arg Val Val Gly Gly Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Pro Lys Asn Ser Ser Met Ile Ser Asn Thr Pro
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

His Gln Ser Leu Gly Thr Gln
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

His Gln Asn Leu Ser Asp Gly Lys
1               5

<210> SEQ ID NO 15
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 15
actgacgaat tctcatttac ccggagacag ggag                              34

<210> SEQ ID NO 16
<211> LENGTH: 36
<212> TYPE: DNA
```

```
<213> ORGANISM: Artificial Sequence
<220> FEATURE:
<223> OTHER INFORMATION: Synthetic polynucleotide

<400> SEQUENCE: 16
actgacctcg agttagggaa atggggctcg caggag                                    36

<210> SEQ ID NO 17
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 17
actgacgcgg ccgcgccgcc accatggaga cagac                                     35

<210> SEQ ID NO 18
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 18
cgacaagctt gccgccacca tggtctccca ggccctcagg                                40

<210> SEQ ID NO 19
<211> LENGTH: 118
<212> TYPE: DNA
<213> ORGANISM: Artificial Sequence
<220> FEATURE:
<223> OTHER INFORMATION: Synthetic polynucleotide

<400> SEQUENCE: 19
ractgacgga tccccgcca ccggaacctc caccgcctga tccaccccca cctgatccgc           60
cgccaccgga cccacctccg ccggagccac cgccacctcg gccttggggt tgctggc            118

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20
cttggctttc tctccacagg                                                      20

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
gggaatgtca acaggcaggg                                                      20

<210> SEQ ID NO 22
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 22
```
actgacctcg agttatcggc cttggggttt gctgg                                    35

<210> SEQ ID NO 23
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 23
actgacgcgg ccgcgccgcc accatggtct cccagg                                   36

<210> SEQ ID NO 24
<211> LENGTH: 8
<212> TYPE: PRT
<213> ORGANISM: Artificial Sequence
<220> FEATURE:
<223> OTHER INFORMATION: synthetic peptide

<400> SEQUENCE: 24

His Gln Asn Ile Ser Asp Gly Lys
1               5

<210> SEQ ID NO 25
<211> LENGTH: 102
<212> TYPE: DNA
<213> ORGANISM: Artificial Sequence
<220> FEATURE:
<223> OTHER INFORMATION: Synthetic polynucleotide

<400> SEQUENCE: 25
actgacaagc ttgccgccac catggagaca gacacactcc tgctatgggt actgctgctc        60
tgggttccag gttccactgg tattgtgggg ggcaaggtgt gc                           102

<210> SEQ ID NO 26
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(31)
<223> OTHER INFORMATION: Any grouping of "Gly Gly Gly Gly Ser" may be
      present or absent

<400> SEQUENCE: 26

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
            20                  25                  30

<210> SEQ ID NO 27
<211> LENGTH: 156
<212> TYPE: DNA
<213> ORGANISM: Artificial Sequence
<220> FEATURE:
<223> OTHER INFORMATION: Synthetic polynucleotide

<400> SEQUENCE: 27
aggagttccg gagctgggca cggtgggcat gtgtgagttt tgtcggatcc cccgccaccg        60
gaacctccac cgcctgatcc accccacct gatccgccgc caccggaccc acctccgccg       120
gagccaccgc caccgggaaa tggggctcgc aggagg                                  156

```
<210> SEQ ID NO 28
<211> LENGTH: 17
<212> TYPE: PRT
<213> ORGANISM: Artificial Sequence
<220> FEATURE:
<223> OTHER INFORMATION: Synthetic peptide

<400> SEQUENCE: 28

Asp Lys Thr His Thr Cys Pro Pro Cys Pro Ala Pro Glu Leu Leu Gly
1               5                   10                  15

Gly

<210> SEQ ID NO 29
<211> LENGTH: 10
<212> TYPE: PRT
<213> ORGANISM: Artificial Sequence
<220> FEATURE:
<223> OTHER INFORMATION: Synthetic peptide

<400> SEQUENCE: 29

Gly Gly Gly Gly Ser Gly Gly Gly Gly Ser
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic peptide

<400> SEQUENCE: 30

Gly Gly Gly Ser Ser Gly Gly Gly Ser Gly
1               5                   10

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
cgtcacgttg atgtccctgc                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 32
ggcacctgaa taaccgacgg                                               20

<210> SEQ ID NO 33
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 33
tttgaattct cagttggggg tgatggtgta acc                                33

<210> SEQ ID NO 34
```

```
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa is Lys or Arg

<400> SEQUENCE: 34

Arg Xaa Xaa Arg
1

<210> SEQ ID NO 35
<211> LENGTH: 5
<212> TYPE: PRT
<213> ORGANISM: Artificial Sequence
<220> FEATURE:
<223> OTHER INFORMATION: synthetic peptide

<400> SEQUENCE: 35

Leu Val Pro Arg Gly
1               5

<210> SEQ ID NO 36
<211> LENGTH: 30
<212> TYPE: PRT
<213> ORGANISM: Artificial Sequence
<220> FEATURE:
<223> OTHER INFORMATION: Synthetic peptide

<400> SEQUENCE: 36

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 37
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 37
gcgctagccg tacggccgcc accatgaaag tgaggaaata tattacttta tgc         53

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide

<400> SEQUENCE: 38

Arg Arg Arg Arg Ser
1               5

<210> SEQ ID NO 39
<211> LENGTH: 6
<212> TYPE: PRT
<213> ORGANISM: Artificial Sequence
<220> FEATURE:
```

<223> OTHER INFORMATION: Synthetic peptide

<400> SEQUENCE: 39

Arg Lys Arg Arg Lys Arg
1               5

<210> SEQ ID NO 40
<211> LENGTH: 4
<212> TYPE: PRT
<213> ORGANISM: Artificial Sequence
<220> FEATURE:
<223> OTHER INFORMATION: Synthetic peptide

<400> SEQUENCE: 40

Arg Arg Arg Arg
1

<210> SEQ ID NO 41
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 41
gggaatgtca acaggcaggg                                          20

<210> SEQ ID NO 42
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 42
cttggctttc tctccacagg c                                        21

<210> SEQ ID NO 43
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 43
cgacaagctt gccgccacca tggtctccca ggccctcagg                    40

<210> SEQ ID NO 44
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 44
cgactccgga gctgggcacg gtgggcatgt gtgagttttg tcgggaaatg gggctcgcag   60
g                                                              61

<210> SEQ ID NO 45
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 45

```
catccccagc acgtacgtcc                                               20

<210> SEQ ID NO 46
<211> LENGTH: 132
<212> TYPE: DNA
<213> ORGANISM: Artificial Sequence
<220> FEATURE:
<223> OTHER INFORMATION: Synthetic polynucleotide

<400> SEQUENCE: 46
gggcatgtgt gagttttgtc tgatccccg ccaccggaac ctccaccgcc tgatccaccc    60
ccacctgatc cgccgccacc ggacccacct ccgccggagc caccgccacc gggaaatggg   120
gctcgcagga gg                                                      132

<210> SEQ ID NO 47
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 47
gacaaaactc acacatgccc acc                                           23

<210> SEQ ID NO 48
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 48
gcagaattct catttacccg gag                                           23

<210> SEQ ID NO 49
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 49
ggtaagcttg ccgccaccat gccgaagggg aggcagaaag                         40

<210> SEQ ID NO 50
<211> LENGTH: 41
<212> TYPE: PRT
<213> ORGANISM: Artificial Sequence
<220> FEATURE:
<223> OTHER INFORMATION: Synthetic peptide

<400> SEQUENCE: 50

Arg Arg Arg Arg Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Arg Lys Arg Arg Lys Arg
            35                  40

<210> SEQ ID NO 51
<211> LENGTH: 37
<212> TYPE: DNA
<213> ORGANISM: Artificial Sequence
```

<220> FEATURE:
<223> OTHER INFORMATION: Synthetic polynucleotide

<400> SEQUENCE: 51
agtcaagctt gtcgactccg gaactcctgg gcggacc                                    37

<210> SEQ ID NO 52
<211> LENGTH: 101
<212> TYPE: DNA
<213> ORGANISM: Artificial Sequence
<220> FEATURE:
<223> OTHER INFORMATION: Synthetic polynucleotide

<400> SEQUENCE: 52
catcggatcc cccgccaccg gaacctccac cgcctgatcc accccacct gatccgccgc            60 caccgctccg gcggcgccgt ttacccggag acagggagag g                              101

<210> SEQ ID NO 53
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 53
gagttccgga gctgggcacg gtgggcatgt gtgagttttg tctgatcccc cgccaccgga          60
acctccaccg cctgatccac ccccacctga tccgccgcca ccggacccac ctccgccgga         120
gccaccgcca cctcggcctt ggggtttgct gg                                       152

<210> SEQ ID NO 54
<211> LENGTH: 82
<212> TYPE: DNA
<213> ORGANISM: Artificial Sequence
<220> FEATURE:
<223> OTHER INFORMATION: Synthetic polynucleotide

<400> SEQUENCE: 54
cagtctggat ccggcggtgg aggttccggt gggggtggat caaggaagag gaggaagagg          60
attgtggggg gcaaggtgtg cc                                                    82

<210> SEQ ID NO 55
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 55
atgtctgaat tctcatttac ccggagacag ggagagg                                    37

<210> SEQ ID NO 56
<211> LENGTH: 5
<212> TYPE: PRT
<213> ORGANISM: Artificial Sequence
<220> FEATURE:
<223> OTHER INFORMATION: Synthetic peptide

<400> SEQUENCE: 56

Gly Gly Gly Gly Ser
1               5

<210> SEQ ID NO 57
<211> LENGTH: 29

```
<212> TYPE: PRT
<213> ORGANISM: Artificial Sequence
<220> FEATURE:
<223> OTHER INFORMATION: Synthetic peptide

<400> SEQUENCE: 57

Arg Arg Arg Arg Ser Gly Gly Gly Gly Ser Gly Gly Gly Gly Ser Gly
1               5                   10                  15
Gly Gly Gly Ser Gly Gly Gly Gly Ser Arg Arg Arg Arg
            20                  25

<210> SEQ ID NO 58
<211> LENGTH: 86
<212> TYPE: DNA
<213> ORGANISM: Artificial Sequence
<220> FEATURE:
<223> OTHER INFORMATION: Synthetic polynucleotide

<400> SEQUENCE: 58
catcggatcc cccgccaccg gaacctccac cgcctgatcc accccacct gatccgccgc      60 caccttacc cggagacagg gagagg                                           86

<210> SEQ ID NO 59
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 59
cagtcttgat cagacaaaac tcacacatgc ccacc                                35

<210> SEQ ID NO 60
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 60
actgacgaat tctcatttac ccggagacag ggag                                 34

<210> SEQ ID NO 61
<211> LENGTH: 156
<212> TYPE: DNA
<213> ORGANISM: Artificial Sequence
<220> FEATURE:
<223> OTHER INFORMATION: Synthetic polynucleotide

<400> SEQUENCE: 61
aggagttccg agctgggca cggtgggcat gtgtgagttt tgtcggatcc cccgccaccg      60
gaacctccac cgcctgatcc accccacct gatccgccgc caccggaccc acctccgccg     120
gagccaccgc caccgggaaa tggggctcgc aggagg                              156

<210> SEQ ID NO 62
<211> LENGTH: 3000
<212> TYPE: DNA
<213> ORGANISM: Artificial Sequence
<220> FEATURE:
<223> OTHER INFORMATION: Synthetic construct: pSYN-FVII-024 nucleotide
      sequence

<400> SEQUENCE: 62
atggtctccc aggccctcag gctcctctgc cttctgcttg ggcttcaggg ctgcctggct      60
```

```
gcagtcttcg taacccagga ggaagcccac ggcgtcctgc accggcgccg gcgcgccaac    120
gcgttcctgg aggagctgcg gccgggctcc ctggagaggg agtgcaagga ggagcagtgc    180
tccttcgagg aggcccggga gatcttcaag gacgcggaga ggacgaagct gttctggatt    240
tcttacagtg atggggacca gtgtgcctca agtccatgcc agaatggggg ctcctgcaag    300
gaccagctcc agtcctatat ctgcttctgc ctccctgcct tcgagggccg gaactgtgag    360
acgcacaagg atgaccagct gatctgtgtg aacgagaacg gcggctgtga gcagtactgc    420
agtgaccaca cgggcaccaa gcgctcctgt cggtgccacg aggggtactc tctgctggca    480 gacgggtgt cctgcacacc cacagttgaa tatccatgtg gaaaaatacc tattctagaa    540 aaagaaatg ccagcaaacc ccaaggccga ggtggcggtg gctccggcgg aggtgggtcc    600
ggtggcggcg gatcaggtgg gggtggatca ggcggtggag gttccggtgg cggggatca    660 gacaaaactc acacatgccc accgtgccca gctccggaac tcctgggcgg accgtcagtc    720
ttcctcttcc cccaaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaccatctc caaagccaaa    1020 gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gttggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa acggcgccgc cggagcggtg gcggcggatc aggtgggggt    1380
ggatcaggcg gtggaggttc cggtggcggg ggatccggcg gtggaggttc cggtggggt    1440 ggatcaagga gaggaggaa gaggattgtg gggggcaagg tgtgcccaa agggagtgt    1500 ccatggcagg tcctgttgtt ggtgaatgga gctcagttgt gtgggggggac cctgatcaac    1560 accatctggg tggtctccgc ggcccactgt ttcgacaaaa tcaagaactg gaggaacctg    1620
atcgcggtgc tgggcgagca cgacctcagc gagcacgacg gggatgagca gagccggcgg    1680
gtggcgcagg tcatcatccc cagcacgtac gtcccgggca ccaccaacca cgacatcgcg    1740
ctgctccgcc tgcaccagcc cgtggtcctc actgaccatg tggtgccct ctgcctgccc    1800 gaacggacgt tctctgagag gacgctggcc ttcgtgcgct tctcattggt cagcggctgg    1860
ggccagctgc tggaccgtgg cgccacggcc tggagctca tggtcctcaa cgtgccccgg    1920
ctgatgaccc aggactgcct gcagcagtca cggaaggtgg agactccccc aaatatcacg    1980
gagtacatgt tctgtgccgg ctactcggat ggcagcaagg actcctgcaa gggggacagt    2040
ggaggcccac atgccaccca ctaccggggc acgtggtacc tgacgggcat cgtcagctgg    2100
ggccagggct gcgcaaccgt gggccacttt gggtgtaca ccagggtctc ccagtacatc    2160
gagtggctgc aaaagctcat gcgctcagag ccacgcccag gagtcctcct gcgagcccca    2220
tttcccggtg gcggtggctc cggcggaggt gggtccggtg gcggcggatc aggtgggggt    2280
ggatcaggcg gtggaggttc cggtggcggg ggatcagaca aaactcacac atgcccaccg    2340
tgcccagcac ctgaactcct gggaggaccg tcagtcttcc tcttcccccc aaaacccaag    2400
```

```
gacaccctca tgatctcccg gacccctgag gtcacatgcg tggtggtgga cgtgagccac    2460
gaagaccctg aggtcaagtt caactggtac gtggacggcg tggaggtgca taatgccaag    2520
acaaagccgc gggaggagca gtacaacagc acgtaccgtg tggtcagcgt cctcaccgtc    2580
ctgcaccagg actggctgaa tggcaaggag tacaagtgca aggtctccaa caaagccctc    2640
ccagccccca tcgagaaaac catctccaaa gccaagggc agccccgaga ccacaggtg     2700 tacaccctgc ccccatcccg ggatgagctg accaagaacc aggtcagcct gacctgcctg    2760
gtcaaaggct tctatcccag cgacatcgcc gtggagtggg agagcaatgg gcagccggag    2820
aacaactaca agaccacgcc tcccgtgttg gactccgacg gctccttctt cctctacagc    2880
aagctcaccg tggacaagag caggtggcag caggggaacg tcttctcatg ctccgtgatg    2940
catgaggctc tgcacaacca ctacacgcag aagagcctct ccctgtctcc gggtaaatga    3000
```

<210> SEQ ID NO 63
<211> LENGTH: 999
<212> TYPE: PRT
<213> ORGANISM: Artificial Sequence
<220> FEATURE:
<223> OTHER INFORMATION: Synthetic construct: FVII-024 amino acid
      sequence

<400> SEQUENCE: 63

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Gly
            180                 185                 190

Gly Ser Gly Gly Gly Gly Ser Gly Gly Gly Ser Gly Gly
        195                 200                 205

Gly Ser Gly Gly Gly Gly Ser Gly Gly Gly Ser Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Arg
        435                 440                 445

Arg Arg Arg Ser Gly Gly Gly Ser Gly Gly Gly Ser Gly Gly
450                 455                 460

Gly Gly Ser Gly Gly Gly Ser Gly Gly Gly Ser Gly Gly Gly
465                 470                 475                 480

Gly Ser Arg Lys Arg Arg Lys Arg Ile Val Gly Gly Lys Val Cys Pro
                485                 490                 495

Lys Gly Glu Cys Pro Trp Gln Val Leu Leu Leu Val Asn Gly Ala Gln
            500                 505                 510

Leu Cys Gly Gly Thr Leu Ile Asn Thr Ile Trp Val Val Ser Ala Ala
        515                 520                 525

His Cys Phe Asp Lys Ile Lys Asn Trp Arg Asn Leu Ile Ala Val Leu
    530                 535                 540

Gly Glu His Asp Leu Ser Glu His Asp Gly Asp Glu Gln Ser Arg Arg
545                 550                 555                 560

Val Ala Gln Val Ile Ile Pro Ser Thr Tyr Val Pro Gly Thr Thr Asn
                565                 570                 575

His Asp Ile Ala Leu Leu Arg Leu His Gln Pro Val Val Leu Thr Asp
            580                 585                 590

His Val Val Pro Leu Cys Leu Pro Glu Arg Thr Phe Ser Glu Arg Thr
        595                 600                 605

Leu Ala Phe Val Arg Phe Ser Leu Val Ser Gly Trp Gly Gln Leu Leu
    610                 615                 620

Asp Arg Gly Ala Thr Ala Leu Glu Leu Met Val Leu Asn Val Pro Arg
625                 630                 635                 640

Leu Met Thr Gln Asp Cys Leu Gln Gln Ser Arg Lys Val Gly Asp Ser
                645                 650                 655

Pro Asn Ile Thr Glu Tyr Met Phe Cys Ala Gly Tyr Ser Asp Gly Ser
            660                 665                 670

Lys Asp Ser Cys Lys Gly Asp Ser Gly Gly Pro His Ala Thr His Tyr
```

```
                675                 680                 685
Arg Gly Thr Trp Tyr Leu Thr Gly Ile Val Ser Trp Gly Gln Gly Cys
        690                 695                 700
Ala Thr Val Gly His Phe Gly Val Tyr Thr Arg Val Ser Gln Tyr Ile
705                 710                 715                 720
Glu Trp Leu Gln Lys Leu Met Arg Ser Glu Pro Arg Pro Gly Val Leu
                725                 730                 735
Leu Arg Ala Pro Phe Pro Gly Gly Gly Ser Gly Gly Gly Gly Ser
        740                 745                 750
Gly Gly Gly Gly Ser Gly Gly Gly Ser Gly Gly Gly Ser Gly
            755                 760                 765
Gly Gly Gly Ser Asp Lys Thr His Thr Cys Pro Pro Cys Pro Ala Pro
        770                 775                 780
Glu Leu Leu Gly Gly Pro Ser Val Phe Leu Phe Pro Pro Lys Pro Lys
785                 790                 795                 800
Asp Thr Leu Met Ile Ser Arg Thr Pro Glu Val Thr Cys Val Val Val
                805                 810                 815
Asp Val Ser His Glu Asp Pro Glu Val Lys Phe Asn Trp Tyr Val Asp
                820                 825                 830
Gly Val Glu Val His Asn Ala Lys Thr Lys Pro Arg Glu Glu Gln Tyr
            835                 840                 845
Asn Ser Thr Tyr Arg Val Val Ser Val Leu Thr Val Leu His Gln Asp
850                 855                 860
Trp Leu Asn Gly Lys Glu Tyr Lys Cys Lys Val Ser Asn Lys Ala Leu
865                 870                 875                 880
Pro Ala Pro Ile Glu Lys Thr Ile Ser Lys Ala Lys Gly Gln Pro Arg
                885                 890                 895
Glu Pro Gln Val Tyr Thr Leu Pro Pro Ser Arg Asp Glu Leu Thr Lys
            900                 905                 910
Asn Gln Val Ser Leu Thr Cys Leu Val Lys Gly Phe Tyr Pro Ser Asp
        915                 920                 925
Ile Ala Val Glu Trp Glu Ser Asn Gly Gln Pro Glu Asn Asn Tyr Lys
    930                 935                 940
Thr Thr Pro Pro Val Leu Asp Ser Asp Gly Ser Phe Phe Leu Tyr Ser
945                 950                 955                 960
Lys Leu Thr Val Asp Lys Ser Arg Trp Gln Gln Gly Asn Val Phe Ser
                965                 970                 975
Cys Ser Val Met His Glu Ala Leu His Asn His Tyr Thr Gln Lys Ser
                980                 985                 990
Leu Ser Leu Ser Pro Gly Lys
            995

<210> SEQ ID NO 64
<211> LENGTH: 3819
<212> TYPE: DNA
<213> ORGANISM: Artificial Sequence
<220> FEATURE:
<223> OTHER INFORMATION: Synthetic construct: pSYN-FVII-027 DNA sequence

<400> SEQUENCE: 64
atggtctccc aggccctcag gctcctctgc cttctgcttg ggcttcaggg ctgcctggct      60
gcagtcttcg taacccagga ggaagcccac ggcgtcctgc accggcgccg gcgcgccaac     120
gcgttcctgg aggagctgcg gccgggctcc ctggagaggg agtgcaagga ggagcagtgc     180
tccttcgagg aggcccggga gatcttcaag gacgcggaga ggacgaagct gttctggatt     240
```

```
tcttacagtg atggggacca gtgtgcctca agtccatgcc agaatggggg ctcctgcaag      300
gaccagctcc agtcctatat ctgcttctgc ctccctgcct tcgagggccg gaactgtgag      360
acgcacaagg atgaccagct gatctgtgtg aacgagaacg gcggctgtga gcagtactgc      420
agtgaccaca cgggcaccaa gcgctcctgt cggtgccacg aggggtactc tctgctggca      480
gacggggtgt cctgcacacc cacagttgaa tatccatgtg gaaaaatacc tattctagaa      540
aaaagaaatg ccagcaaacc ccaaggccga attgtggggg caaggtgtg ccccaaaggg       600 gagtgtccat ggcaggtcct gttgttggtg aatggagctc agttgtgtgg ggggaccctg      660
atcaacacca tctgggtggt ctccgcggcc cactgtttcg acaaaatcaa gaactggagg      720
aacctgatcg cggtgctggg cgagcacgac ctcagcgagc acgacgggga tgagcagagc      780
cggcgggtgg cgcaggtcat catccccagc acgtacgtcc cgggcaccac caaccacgac      840
atcgcgctgc tccgcctgca ccagcccgtg gtcctcactg accatgtggt gcccctctgc      900
ctgcccgaac ggacgttctc tgagaggacg ctggccttcg tgcgcttctc attggtcagc      960
ggctggggcc agctgctgga ccgtggcgcc acggccctgg agctcatggt cctcaacgtg     1020
ccccggctga tgacccagga ctgcctgcag cagtcacgga aggtgggaga ctcccccaaat     1080 atcacggagt acatgttctg tgccggctac tcggatggca gcaaggactc ctgcaagggg     1140
gacagtggag gccacatgc cacccactac cggggcacgt ggtacctgac gggcatcgtc      1200
agctggggcc agggctgcgc aaccgtgggc cactttgggg tgtacaccag gtctcccag     1260 tacatcgagt ggctgcaaaa gctcatgcgc tcagagccac gcccaggagt cctcctgcga     1320 gcccatttc cggtggcgg tggctccggc ggaggtgggt ccggtggcgg cggatcaggt       1380
gggggtggat caggcggtgg aggttccggt ggcgggggat ccgacaaaac tcacacatgc     1440
ccaccgtgcc cagctccgga actcctgggc ggaccgtcag tcttcctctt ccccccaaaa     1500
cccaaggaca ccctcatgat ctcccggacc cctgaggtca catgcgtggt ggtggacgtg     1560
agccacgaag accctgaggt caagttcaac tggtacgtgg acggcgtgga ggtgcataat     1620
gccaagacaa agccgcggga ggagcagtac aacagcacgt accgtgtggt cagcgtcctc     1680
accgtcctgc accaggactg gctgaatggc aaggagtaca gtgcaaggt ctccaacaaa      1740 gccctcccag cccccatcga gaaaaccatc tccaaagcca agggcagcc ccgagaacca     1800 caggtgtaca ccctgccccc atcccgggat gagctgacca gaaccaggt cagcctgacc     1860 tgcctggtca aaggcttcta tcccagcgac atcgccgtgg agtgggagag caatgggcag     1920
ccggagaaca actacaagac cacgcctccc gtgttggact ccgacggctc cttcttcctc     1980
tacagcaagc tcaccgtgga caagagcagg tggcagcagg ggaacgtctt ctcatgctcc     2040
gtgatgcatg aggctctgca caaccactac acgcagaaga gcctctccct gtctccgggt     2100
aaacggcgcc gccggagcgg tggcggcgga tcaggtgggg gtggatcagg cggtggaggt     2160
tccggtggcg gggatccgg cggtggaggt tccggtgggg gtggatcaag gaagaggagg      2220
aagagggcgg aagtgcagct ggtgcagtct ggagctgagg tgaataagcc tggggcctca     2280
gtgaaggtct cctgcaaggc ttctggatac accttcaccg gctactatat gcactgggtg     2340
cgacaggccc ctggacaagg gcttgagtgg atggatggaa tcaaccctaa cagtggtggc     2400
acaaactatg cacagaagtt tcagggctgg gtcaccatga ccagggacac gtccatcagc     2460
accgcctaca tggagctgag caggctgaga tctgacgaca cggccgtgta ttactgtgcg     2520
agaggccgtg cttgtgtataa ccggaacgac cggtcccca actggttcga ccctggggc     2580
```

-continued

```
caggaaccc tggtcaccgt ctcctcaggg agtgcatccg ccccaaccct taagcttgaa    2640
gaaggtgaat tctcagaagc acgcgtacag gctgtgctga ctcagccgcc ctcggtgtca    2700
gtggccccag gacagacggc caggattacc tgtgggggaa acaacattgg aagtaaaagt    2760
gtgcagtggt accagcagaa gccaggccag gcccctgtgc tggtcgtcta tgatgatagc    2820
gaccggccct cagggatccc tgagcgattc tctggctcca actctgggaa catgccacc    2880 ctgaccatca gcagggtcga agccggggat gaggccgact attactgtca ggtgtgggat    2940
agtagtagtg atcatgtggt attcggcgga gggaccaagc tgaccgtcct aggtcagccc    3000
aaggctgccc cctcggtcac tctgttcccg ccgtccgcgg ccgctggtgg cggtggctcc    3060
ggcggaggtg ggtccggtgg cggcggatca ggtggggggtg atcaggcgg tggaggttcc    3120 ggtggcgggg gatcagacaa aactcacaca tgcccaccgt gcccagcacc tgaactcctg    3180
ggaggaccgt cagtcttcct cttccccca aacccaagg acaccctcat gatctcccgg    3240
acccctgagg tcacatgcgt ggtggtggac gtgagccacg aagaccctga ggtcaagttc    3300
aactggtacg tggacggcgt ggaggtgcat aatgccaaga caaagccgcg ggaggagcag    3360
tacaacagca cgtaccgtgt ggtcagcgtc ctcaccgtcc tgcaccagga ctggctgaat    3420
ggcaaggagt acaagtgcaa ggtctccaac aaagccctcc cagcccccat cgagaaaacc    3480
atctccaaag ccaaagggca gccccgagaa ccacaggtgt acaccctgcc cccatcccgc    3540
gatgagctga ccaagaacca ggtcagcctg acctgcctgg tcaaaggctt ctatcccagc    3600
gacatcgccg tggagtggga gagcaatggg cagccggaga acaactacaa gaccacgcct    3660
cccgtgttgg actccgacgg ctccttcttc ctctacagca agctcaccgt ggacaagagc    3720
aggtggcagc aggggaacgt cttctcatgc tccgtgatgc atgaggctct gcacaaccac    3780
tacacgcaga agagcctctc cctgtctccg ggtaaatga                           3819
```

<210> SEQ ID NO 65
<211> LENGTH: 1272
<212> TYPE: PRT
<213> ORGANISM: Artificial Sequence
<220> FEATURE:
<223> OTHER INFORMATION: Synthetic construct: FVII-027 amino acid sequence

<400> SEQUENCE: 65

```
Met Val Ser Gln Ala Leu Arg Leu Leu Cys Leu Leu Leu Gly Leu Gln
1               5                  10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140
```

```
Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
            165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
            195                 200                 205

Leu Val Asn Gly Ala Gln Leu Cys Gly Gly Thr Leu Ile Asn Thr Ile
            210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
            245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
            275                 280                 285

Pro Val Val Leu Thr Asp His Val Val Pro Leu Cys Leu Pro Glu Arg
            290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
            325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
            370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
            405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
            435                 440                 445

Ser Gly Gly Gly Ser Gly Gly Gly Ser Gly Gly Gly Ser
            450                 455                 460

Gly Gly Gly Gly Ser Gly Gly Gly Ser Asp Lys Thr His Thr Cys
465                 470                 475                 480

Pro Pro Cys Pro Ala Pro Glu Leu Leu Gly Gly Pro Ser Val Phe Leu
            485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
            515                 520                 525

Phe Asn Trp Tyr Val Asp Gly Val Glu Val His Asn Ala Lys Thr Lys
            530                 535                 540

Pro Arg Glu Glu Gln Tyr Asn Ser Thr Tyr Arg Val Val Ser Val Leu
545                 550                 555                 560
```

```
Thr Val Leu His Gln Asp Trp Leu Asn Gly Lys Glu Tyr Lys Cys Lys
            565                 570                 575

Val Ser Asn Lys Ala Leu Pro Ala Pro Ile Glu Lys Thr Ile Ser Lys
        580                 585                 590

Ala Lys Gly Gln Pro Arg Glu Pro Gln Val Tyr Thr Leu Pro Pro Ser
    595                 600                 605

Arg Asp Glu Leu Thr Lys Asn Gln Val Ser Leu Thr Cys Leu Val Lys
610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Arg Arg Arg
    690                 695                 700

Arg Ser Gly Gly Gly Gly Ser Gly Gly Gly Gly Ser Gly Gly Gly Gly
705                 710                 715                 720

Ser Gly Gly Gly Gly Ser Gly Gly Gly Gly Ser Gly Gly Gly Gly Ser
                725                 730                 735

Arg Lys Arg Arg Lys Arg Ala Glu Val Gln Leu Val Gln Ser Gly Ala
            740                 745                 750

Glu Val Asn Lys Pro Gly Ala Ser Val Lys Val Ser Cys Lys Ala Ser
        755                 760                 765

Gly Tyr Thr Phe Thr Gly Tyr Tyr Met His Trp Val Arg Gln Ala Pro
    770                 775                 780

Gly Gln Gly Leu Glu Trp Met Gly Trp Ile Asn Pro Asn Ser Gly Gly
785                 790                 795                 800

Thr Asn Tyr Ala Gln Lys Phe Gln Gly Trp Val Thr Met Thr Arg Asp
                805                 810                 815

Thr Ser Ile Ser Thr Ala Tyr Met Glu Leu Ser Arg Leu Arg Ser Asp
            820                 825                 830

Asp Thr Ala Val Tyr Tyr Cys Ala Arg Gly Arg Ala Leu Tyr Asn Arg
        835                 840                 845

Asn Asp Arg Ser Pro Asn Trp Phe Asp Pro Trp Gly Gln Gly Thr Leu
    850                 855                 860

Val Thr Val Ser Ser Gly Ser Ala Ser Ala Pro Thr Leu Lys Leu Glu
865                 870                 875                 880

Glu Gly Glu Phe Ser Glu Ala Arg Val Gln Ala Val Leu Thr Gln Pro
                885                 890                 895

Pro Ser Val Ser Val Ala Pro Gly Gln Thr Ala Arg Ile Thr Cys Gly
            900                 905                 910

Gly Asn Asn Ile Gly Ser Lys Ser Val Gln Trp Tyr Gln Gln Lys Pro
        915                 920                 925

Gly Gln Ala Pro Val Leu Val Val Tyr Asp Asp Ser Asp Arg Pro Ser
    930                 935                 940

Gly Ile Pro Glu Arg Phe Ser Gly Ser Asn Ser Gly Asn Met Ala Thr
945                 950                 955                 960

Leu Thr Ile Ser Arg Val Glu Ala Gly Asp Glu Ala Asp Tyr Tyr Cys
                965                 970                 975

Gln Val Trp Asp Ser Ser Ser Asp His Val Val Phe Gly Gly Gly Thr
```

```
               980            985               990
Lys Leu Thr Val Leu Gly Gln Pro  Lys Ala Ala Pro Ser  Val Thr Leu
                 995              1000               1005

Phe Pro  Pro Ser Ala Ala Ala  Gly Gly Gly Gly Ser  Gly Gly Gly
    1010             1015                 1020

Gly Ser  Gly Gly Gly Gly Ser  Gly Gly Gly Gly Ser  Gly Gly Gly
    1025             1030                 1035

Gly Ser  Gly Gly Gly Gly Ser  Asp Lys Thr His Thr  Cys Pro Pro
    1040             1045                 1050

Cys Pro  Ala Pro Glu Leu Leu  Gly Gly Pro Ser Val  Phe Leu Phe
    1055             1060                 1065

Pro Pro  Lys Pro Lys Asp Thr  Leu Met Ile Ser Arg  Thr Pro Glu
    1070             1075                 1080

Val Thr  Cys Val Val Val Asp  Val Ser His Glu Asp  Pro Glu Val
    1085             1090                 1095

Lys Phe  Asn Trp Tyr Val Asp  Gly Val Glu Val His  Asn Ala Lys
    1100             1105                 1110

Thr Lys  Pro Arg Glu Glu Gln  Tyr Asn Ser Thr Tyr  Arg Val Val
    1115             1120                 1125

Ser Val  Leu Thr Val Leu His  Gln Asp Trp Leu Asn  Gly Lys Glu
    1130             1135                 1140

Tyr Lys  Cys Lys Val Ser Asn  Lys Ala Leu Pro Ala  Pro Ile Glu
    1145             1150                 1155

Lys Thr  Ile Ser Lys Ala Lys  Gly Gln Pro Arg Glu  Pro Gln Val
    1160             1165                 1170

Tyr Thr  Leu Pro Pro Ser Arg  Asp Glu Leu Thr Lys  Asn Gln Val
    1175             1180                 1185

Ser Leu  Thr Cys Leu Val Lys  Gly Phe Tyr Pro Ser  Asp Ile Ala
    1190             1195                 1200

Val Glu  Trp Glu Ser Asn Gly  Gln Pro Glu Asn Asn  Tyr Lys Thr
    1205             1210                 1215

Thr Pro  Pro Val Leu Asp Ser  Asp Gly Ser Phe Phe  Leu Tyr Ser
    1220             1225                 1230

Lys Leu  Thr Val Asp Lys Ser  Arg Trp Gln Gln Gly  Asn Val Phe
    1235             1240                 1245

Ser Cys  Ser Val Met His Glu  Ala Leu His Asn His  Tyr Thr Gln
    1250             1255                 1260

Lys Ser  Leu Ser Leu Ser Pro  Gly Lys
    1265             1270

<210> SEQ ID NO 66
<211> LENGTH: 3134
<212> TYPE: DNA
<213> ORGANISM: Artificial Sequence
<220> FEATURE:
<223> OTHER INFORMATION: Synthetic construct: pSYN-FIX-044 DNA sequence

<400> SEQUENCE: 66
atgcagcgcg tgaacatgat catggcagaa tcaccaggcc tcatcaccat ctgccttta      60 ggatatctac tcagtgctga atgtacaggt ttgtttcctt ttttaaaata cattgagtat     120
gcttgccttt tagatataga aatatctgat gctgtcttct tcactaaatt ttgattacat     180
gatttgacag caatattgaa gagtctaaca gccagcacgc aggttggtaa gtactgtggg     240
aacatcacag attttggctc catgcccta agagaaattg ctttcagat tatttggatt      300
```

```
aaaaacaaag actttcttaa gagatgtaaa attttcatga tgttttcttt tttgctaaaa    360
ctaaagaatt attcttttac atttcagttt ttcttgatca tgaaaacgcc aacaaaattc    420
tgaatcggcc aaagaggtat aattcaggta aattggaaga gtttgttcaa gggaatctag    480
agagagaatg tatggaagaa aagtgtagtt ttgaagaagc acgagaagtt tttgaaaaca    540
ctgaaagaac aactgaattt tggaagcagt atgttgatgg agatcagtgt gagtccaatc    600
catgtttaaa tggcggcagt tgcaaggatg acattaattc ctatgaatgt tggtgtccct    660
ttggatttga aggaaagaac tgtgaattag atgtaacatg taacattaag aatggcagat    720
gcgagcagtt ttgtaaaaat agtgctgata caaggtggt ttgctcctgt actgagggat     780
atcgacttgc agaaaaccag aagtcctgtg aaccagcagt gccatttcca tgtggaagag    840
tttctgtttc acaaacttct aagctcaccc gtgctgagac tgttttttcct gatgtggact   900 atgtaaattc tactgaagct gaaaccattt tggataacat cactcaaagc acccaatcat    960
ttaatgactt cactcgggtt gttggtggag aagatgccaa accaggtcaa ttcccttggc    1020
aggttgtttt gaatggtaaa gttgatgcat tctgtggagg ctctatcgtt aatgaaaaat    1080
ggattgtaac tgctgcccac tgtgttgaaa ctggtgttaa aattacagtt gtcgcaggtg    1140
aacataatat tgaggagaca gaacatacag agcaaaagcg aaatgtgatt cgaattattc    1200
ctcaccacaa ctacaatgca gctattaata agtacaacca tgacattgcc cttctggaac    1260
tggacgaacc cttagtgcta aacagctacg ttacacctat ttgcattgct gacaaggaat    1320
acacgaacat cttcctcaaa tttggatctg gctatgtaag tggctgggga agagtcttcc    1380
acaaagggag atcagcttta gttcttcagt accttagagt tccacttgtt gaccgagcca    1440
catgtcttcg atctacaaag ttcaccatct ataacaacat gttctgtgct ggcttccatg    1500
aaggaggtag agattcatgt caaggagata gtggggggacc ccatgttact gaagtggaag    1560
ggaccagttt cttaactgga attattagct ggggtgaaga gtgtgcaatg aaaggcaaat    1620
atggaatata taccaaggta tcccggtatg tcaactggat taaggaaaaa acaaagctca    1680
ctgacaaaac tcacacatgc ccaccgtgcc cagctccgga actcctggga ggaccgtcag    1740
tcttcctctt ccccccaaaa cccaaggaca ccctcatgat ctcccggacc cctgaggtca    1800
catgcgtggt ggtggacgtg agccacgaag accctgaggt caagttcaac tggtacgtgg    1860
acggcgtgga ggtgcataat gccaagacaa agccgcggga ggagcagtac aacagcacgt    1920
accgtgtggt cagcgtcctc accgtcctgc accaggactg gctgaatggc aaggagtaca    1980
agtgcaaggt ctccaacaaa gccctcccag cccccatcga gaaaaccatc tccaaagcca    2040
aagggcagcc ccgagaacca caggtgtaca ccctgccccc atcccgggat gagctgacca    2100
agaaccaggt cagcctgacc tgcctggtca aaggcttcta tcccagcgac atcgccgtgg    2160
agtgggagag caatgggcag ccggagaaca actacaagac cacgcctccc gtgttggact    2220
ccgacggctc cttcttcctc tacagcaagc tcaccgtgga caagagcagg tggcagcagg    2280
ggaacgtctt ctcatgctcc gtgatgcatg aggctctgca caaccactac acgcagaaga    2340
gcctctccct gtctccgggt aaacggcgcc gccggagcgg tggcggcgga tcaggtgggg    2400
gtggatcagg cggtggaggt tccggtgcg ggggatcccg ccggcggcgc gacaaaactc     2460
acacatgccc accgtgccca gcaccggaac tcctgggcgg accgtcagtc ttcctcttcc    2520
ccccaaaacc caaggacacc ctcatgatct cccggacccc tgaggtcaca tgcgtggtgg    2580
tggacgtgag ccacgaagac cctgaggtca agttcaactg gtacgtggac ggcgtggagg    2640
tgcataatgc caagacaaag ccgcgggagg agcagtacaa cagcacgtac cgtgtggtca    2700
```

-continued

```
gcgtcctcac cgtcctgcac caggactggc tgaatggcaa ggagtacaag tgcaaggtct    2760
ccaacaaagc cctcccagcc cccatcgaga aaaccatctc caaagccaaa gggcagcccc    2820
gagaaccaca ggtgtacacc ctgccccat cccgggatga gctgaccaag aaccaggtca    2880
gcctgacctg cctggtcaaa ggcttctatc ccagcgacat cgccgtggag tgggagagca    2940
atgggcagcc ggagaacaac tacaagacca cgcctcccgt gttggactcc gacggctcct    3000
tcttcctcta cagcaagctc accgtggaca agagcaggtg gcagcagggg aacgtcttct    3060
catgctccgt gatgcatgag gctctgcaca accactacac gcagaagagc ctctccctgt    3120
ctccgggtaa atga                                                      3134
```

<210> SEQ ID NO 67
<211> LENGTH: 944
<212> TYPE: PRT
<213> ORGANISM: Artificial Sequence
<220> FEATURE:
<223> OTHER INFORMATION: Synthetic construct: FIX-044 amino acid
      sequence

<400> SEQUENCE: 67

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270
```

```
Val Lys Ile Thr Val Val Ala Gly Glu His Asn Ile Glu Glu Thr Glu
            275                 280                 285
His Thr Glu Gln Lys Arg Asn Val Ile Arg Ile Ile Pro His His Asn
290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
                340                 345                 350
Val Ser Gly Trp Gly Arg Val Phe His Lys Gly Arg Ser Ala Leu Val
            355                 360                 365
Leu Gln Tyr Leu Arg Val Pro Leu Val Asp Arg Ala Thr Cys Leu Arg
370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
                420                 425                 430
Glu Glu Cys Ala Met Lys Gly Lys Tyr Gly Ile Tyr Thr Lys Val Ser
            435                 440                 445
Arg Tyr Val Asn Trp Ile Lys Glu Lys Thr Lys Leu Thr Asp Lys Thr
450                 455                 460
His Thr Cys Pro Pro Cys Pro Ala Pro Glu Leu Leu Gly Gly Pro Ser
465                 470                 475                 480
Val Phe Leu Phe Pro Pro Lys Pro Lys Asp Thr Leu Met Ile Ser Arg
                485                 490                 495
Thr Pro Glu Val Thr Cys Val Val Val Asp Val Ser His Glu Asp Pro
                500                 505                 510
Glu Val Lys Phe Asn Trp Tyr Val Asp Gly Val Glu Val His Asn Ala
            515                 520                 525
Lys Thr Lys Pro Arg Glu Glu Gln Tyr Asn Ser Thr Tyr Arg Val Val
530                 535                 540
Ser Val Leu Thr Val Leu His Gln Asp Trp Leu Asn Gly Lys Glu Tyr
545                 550                 555                 560
Lys Cys Lys Val Ser Asn Lys Ala Leu Pro Ala Pro Ile Glu Lys Thr
                565                 570                 575
Ile Ser Lys Ala Lys Gly Gln Pro Arg Glu Pro Gln Val Tyr Thr Leu
                580                 585                 590
Pro Pro Ser Arg Asp Glu Leu Thr Lys Asn Gln Val Ser Leu Thr Cys
            595                 600                 605
Leu Val Lys Gly Phe Tyr Pro Ser Asp Ile Ala Val Glu Trp Glu Ser
610                 615                 620
Asn Gly Gln Pro Glu Asn Asn Tyr Lys Thr Thr Pro Pro Val Leu Asp
625                 630                 635                 640
Ser Asp Gly Ser Phe Phe Leu Tyr Ser Lys Leu Thr Val Asp Lys Ser
                645                 650                 655
Arg Trp Gln Gln Gly Asn Val Phe Ser Cys Ser Val Met His Glu Ala
                660                 665                 670
Leu His Asn His Tyr Thr Gln Lys Ser Leu Ser Leu Ser Pro Gly Lys
            675                 680                 685
Arg Arg Arg Arg Ser Gly Gly Gly Gly Ser Gly Gly Gly Gly Ser Gly
```

```
             690             695             700
Gly Gly Gly Ser Gly Gly Gly Ser Arg Arg Arg Asp Lys Thr
705             710             715             720

His Thr Cys Pro Pro Cys Pro Ala Pro Glu Leu Leu Gly Pro Ser
                725             730             735

Val Phe Leu Phe Pro Pro Lys Pro Lys Asp Thr Leu Met Ile Ser Arg
            740             745             750

Thr Pro Glu Val Thr Cys Val Val Val Asp Val Ser His Glu Asp Pro
        755             760             765

Glu Val Lys Phe Asn Trp Tyr Val Asp Gly Val Glu Val His Asn Ala
    770             775             780

Lys Thr Lys Pro Arg Glu Glu Gln Tyr Asn Ser Thr Tyr Arg Val Val
785             790             795             800

Ser Val Leu Thr Val Leu His Gln Asp Trp Leu Asn Gly Lys Glu Tyr
                805             810             815

Lys Cys Lys Val Ser Asn Lys Ala Leu Pro Ala Pro Ile Glu Lys Thr
            820             825             830

Ile Ser Lys Ala Lys Gly Gln Pro Arg Glu Pro Gln Val Tyr Thr Leu
        835             840             845

Pro Pro Ser Arg Asp Glu Leu Thr Lys Asn Gln Val Ser Leu Thr Cys
    850             855             860

Leu Val Lys Gly Phe Tyr Pro Ser Asp Ile Ala Val Glu Trp Glu Ser
865             870             875             880

Asn Gly Gln Pro Glu Asn Asn Tyr Lys Thr Thr Pro Pro Val Leu Asp
                885             890             895

Ser Asp Gly Ser Phe Phe Leu Tyr Ser Lys Leu Thr Val Asp Lys Ser
            900             905             910

Arg Trp Gln Gln Gly Asn Val Phe Ser Cys Ser Val Met His Glu Ala
        915             920             925

Leu His Asn His Tyr Thr Gln Lys Ser Leu Ser Leu Ser Pro Gly Lys
    930             935             940

<210> SEQ ID NO 68
<211> LENGTH: 790
<212> TYPE: DNA
<213> ORGANISM: Artificial Sequence
<220> FEATURE:
<223> OTHER INFORMATION: Synthetic construct: Genscript-FIX-044 DNA
      sequence

<400> SEQUENCE: 68
tccggaactc ctgggaggac cgtcagtctt cctcttcccc ccaaaaccca aggacaccct    60
catgatctcc cggacccctg aggtcacatg cgtggtggtg gacgtgagcc acgaagaccc   120
tgaggtcaag ttcaactggt acgtggacgg cgtggaggtg cataatgcca agacaaagcc   180
gcgggaggag cagtacaaca gcacgtaccg tgtggtcagc gtcctcaccg tcctgcacca   240
ggactggctg aatggcaagg agtacaagtg caaggtctcc aacaaagccc tcccagcccc   300
catcgagaaa accatctcca aagccaaagg gcagccccga gaaccacagg tgtacaccct   360
gcccccatcc cggatgagc tgaccaagaa ccaggtcagc ctgacctgcc tggtcaaagg   420
cttctatccc agcgacatcg ccgtggagtg ggagagcaat gggcagccgg agaacaacta   480
caagaccacg cctcccgtgt tggactccga cggctccttc ttcctctaca gcaagctcac   540
cgtggacaag agcaggtggc agcaggggaa cgtcttctca tgctccgtga tgcatgaggc   600
tctgcacaac cactacacgc agaagagcct ctccctgtct ccgggtaaac ggcgccgccg   660
```

```
gagcggtggc ggcggatcag gtggggtgg atcaggcggt ggaggttccg gtggcggggg      720
atcccgccgg cggcgcgaca aaactcacac atgcccaccg tgcccagcac cggaactcct      780
gggcggaccg                                                              790
```

```
<210> SEQ ID NO 69
<211> LENGTH: 577
<212> TYPE: DNA
<213> ORGANISM: Artificial Sequence
<220> FEATURE:
<223> OTHER INFORMATION: Synthetic construct: Genscript-FVII-027-1 DNA
      sequence

<400> SEQUENCE: 69
gaagagcctc tccctgtctc cgggtaaacg gcgccgccgg agcggtggcg gcggatcagg       60
tgggggtgga tcaggcggtg gaggttccgg tggcggggga tccggcggtg gaggttccgg      120
tgggggtgga tcaaggaaga ggaggaagag ggcggaagtg cagctggtgc agtctggagc      180
tgaggtgaat aagcctgggg cctcagtgaa ggtctcctgc aaggcttctg gatacaccct      240
caccggctac tatatgcact gggtgcgaca ggcccctgga caagggcttg agtggatggg      300
atggatcaac cctaacagtg gtggcacaaa ctatgcacac aagtttcagg gctgggtcac      360
catgaccagg gacacgtcca tcagcaccgc ctacatggag ctgagcaggc tgagatctga      420
cgacacggcc gtgtattact gtgcgagagg ccgtgctttg tataaccgga acgaccggtc      480
ccccaactgg ttcgacccct ggggccaggg aaccctggtc accgtctcct cagggagtgc      540
atccgcccca acccttaagc ttgaagaagg tgaattc                                577
```

```
<210> SEQ ID NO 70
<211> LENGTH: 1179
<212> TYPE: DNA
<213> ORGANISM: Artificial Sequence
<220> FEATURE:
<223> OTHER INFORMATION: Synthetic construct: Genscript-FVII-026-2 DNA
      sequence

<400> SEQUENCE: 70
gaattctcag aagcacgcgt acaggctgtg ctgactcagc cgccctcggt gtcagtggcc       60
ccaggacaga cggccaggat tacctgtggg ggaaacaaca ttggaagtaa aagtgtgcag      120
tggtaccagc agaagccagg ccaggcccct gtgctggtcg tctatgatga tagcgaccgg      180
ccctcaggga tccctgagcg attctctggc tccaactctg ggaacatggc caccctgacc      240
atcagcaggg tcgaagccgg ggatgaggcc gactattact gtcaggtgtg ggatagtagt      300
agtgatcatg tggtattcgg cggagggacc aagctgaccg tcctaggtca gcccaaggct      360
gccccctcgg tcactctgtt cccgccgtcc gcggccgctg gtggcggtgg ctccggcgga      420
ggtgggtccg gtggcggcgg atcaggtggg ggtggatcag gcggtggagg ttccggtggc      480
gggggatcag acaaaactca cacatgccca ccgtgcccag cacctgaact cctgggagga      540
ccgtcagtct tcctcttccc cccaaaaccc aaggacaccc tcatgatctc ccggacccct      600
gaggtcacat gcgtggtggt ggacgtgagc cacgaagacc ctgaggtcaa gttcaactgg      660
tacgtggacg gcgtggaggt gcataatgcc aagacaaagc cgcgggagga gcagtacaac      720
agcacgtacc gtgtggtcag cgtcctcacc gtcctgcacc aggactggct gaatggcaag      780
gagtacaagt gcaaggtctc caacaaagcc ctcccagccc ccatcgagaa aaccatctcc      840
aaagccaaag ggcagccccg agaaccacag gtgtacaccc tgcccccatc ccgcgatgag      900
```

-continued

```
ctgaccaaga accaggtcag cctgacctgc ctggtcaaag gcttctatcc cagcgacatc    960
gccgtggagt gggagagcaa tgggcagccg gagaacaact acaagaccac gcctcccgtg   1020
ttggactccg acggctcctt cttcctctac agcaagctca ccgtggacaa gagcaggtgg   1080
cagcagggga acgtcttctc atgctccgtg atgcatgagg ctctgcacaa ccactacacg   1140
cagaagagcc tctccctgtc tccgggtaaa tgagaattc                          1179
```

<210> SEQ ID NO 71
<211> LENGTH: 1457
<212> TYPE: PRT
<213> ORGANISM: Artificial Sequence
<220> FEATURE:
<223> OTHER INFORMATION: Synthetic construct: B domain deleted FVIII amino acid sequence

<400> SEQUENCE: 71

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
```

```
            305                 310                 315                 320
Asp Leu Gly Gln Phe Leu Leu Phe Cys His Ile Ser Ser His Gln His
                    325                 330                 335

Asp Gly Met Glu Ala Tyr Val Lys Val Asp Ser Cys Pro Glu Glu Pro
                340                 345                 350

Gln Leu Arg Met Lys Asn Asn Glu Ala Glu Asp Tyr Asp Asp Asp
            355                 360                 365

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735
```

```
Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Val Leu
            755                 760             765

Lys Arg His Gln Arg Glu Ile Thr Arg Thr Thr Leu Gln Ser Asp Gln
            770                 775                 780

Glu Glu Ile Asp Tyr Asp Asp Thr Ile Ser Val Glu Met Lys Lys Glu
785             790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
            835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945             950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
            995                 1000                1005

Asp Glu  Thr Lys Ser Trp Tyr  Phe Thr Glu Asn Met   Glu Arg Asn
    1010                1015                1020

Cys Arg  Ala Pro Cys Asn Ile  Gln Met Glu Asp Pro   Thr Phe Lys
    1025                1030                1035

Glu Asn  Tyr Arg Phe His Ala  Ile Asn Gly Tyr Ile   Met Asp Thr
    1040                1045                1050

Leu Pro  Gly Leu Val Met Ala  Gln Asp Gln Arg Ile   Arg Trp Tyr
    1055                1060                1065

Leu Leu  Ser Met Gly Ser Asn  Glu Asn Ile His Ser   Ile His Phe
    1070                1075                1080

Ser Gly  His Val Phe Thr Val  Arg Lys Lys Glu Glu   Tyr Lys Met
    1085                1090                1095

Ala Leu  Tyr Asn Leu Tyr Pro  Gly Val Phe Glu Thr   Val Glu Met
    1100                1105                1110

Leu Pro  Ser Lys Ala Gly Ile  Trp Arg Val Glu Cys   Leu Ile Gly
    1115                1120                1125

Glu His  Leu His Ala Gly Met  Ser Thr Leu Phe Leu   Val Tyr Ser
    1130                1135                1140
```

-continued

```
Asn Lys  Cys Gln Thr Pro Leu  Gly Met Ala Ser Gly  His Ile Arg
    1145                 1150                 1155

Asp Phe  Gln Ile Thr Ala Ser  Gly Gln Tyr Gly Gln  Trp Ala Pro
    1160                 1165                 1170

Lys Leu  Ala Arg Leu His Tyr  Ser Gly Ser Ile Asn  Ala Trp Ser
    1175                 1180                 1185

Thr Lys  Glu Pro Phe Ser Trp  Ile Lys Val Asp Leu  Leu Ala Pro
    1190                 1195                 1200

Met Ile  Ile His Gly Ile Lys  Thr Gln Gly Ala Arg  Gln Lys Phe
    1205                 1210                 1215

Ser Ser  Leu Tyr Ile Ser Gln  Phe Ile Ile Met Tyr  Ser Leu Asp
    1220                 1225                 1230

Gly Lys  Lys Trp Gln Thr Tyr  Arg Gly Asn Ser Thr  Gly Thr Leu
    1235                 1240                 1245

Met Val  Phe Phe Gly Asn Val  Asp Ser Ser Gly Ile  Lys His Asn
    1250                 1255                 1260

Ile Phe  Asn Pro Pro Ile Ile  Ala Arg Tyr Ile Arg  Leu His Pro
    1265                 1270                 1275

Thr His  Tyr Ser Ile Arg Ser  Thr Leu Arg Met Glu  Leu Met Gly
    1280                 1285                 1290

Cys Asp  Leu Asn Ser Cys Ser  Met Pro Leu Gly Met  Glu Ser Lys
    1295                 1300                 1305

Ala Ile  Ser Asp Ala Gln Ile  Thr Ala Ser Ser Tyr  Phe Thr Asn
    1310                 1315                 1320

Met Phe  Ala Thr Trp Ser Pro  Ser Lys Ala Arg Leu  His Leu Gln
    1325                 1330                 1335

Gly Arg  Ser Asn Ala Trp Arg  Pro Gln Val Asn Asn  Pro Lys Glu
    1340                 1345                 1350

Trp Leu  Gln Val Asp Phe Gln  Lys Thr Met Lys Val  Thr Gly Val
    1355                 1360                 1365

Thr Thr  Gln Gly Val Lys Ser  Leu Leu Thr Ser Met  Tyr Val Lys
    1370                 1375                 1380

Glu Phe  Leu Ile Ser Ser Ser  Gln Asp Gly His Gln  Trp Thr Leu
    1385                 1390                 1395

Phe Phe  Gln Asn Gly Lys Val  Lys Val Phe Gln Gly  Asn Gln Asp
    1400                 1405                 1410

Ser Phe  Thr Pro Val Val Asn  Ser Leu Asp Pro Pro  Leu Leu Thr
    1415                 1420                 1425

Arg Tyr  Leu Arg Ile His Pro  Gln Ser Trp Val His  Gln Ile Ala
    1430                 1435                 1440

Leu Arg  Met Glu Val Leu Gly  Cys Glu Ala Gln Asp  Leu Tyr
    1445                 1450                 1455
```

<210> SEQ ID NO 72
<211> LENGTH: 2351
<212> TYPE: PRT
<213> ORGANISM: Artificial Sequence
<220> FEATURE:
<223> OTHER INFORMATION: Synthetic construct: Full length FVIII amino acid sequence

<400> SEQUENCE: 72

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30
```

```
Trp Asp Tyr Met Gln Ser Asp Leu Gly Glu Leu Pro Val Asp Ala Arg
         35                  40                  45

Phe Pro Pro Arg Val Pro Lys Ser Phe Pro Phe Asn Thr Ser Val Val
 50                  55                  60

Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
                115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
        210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
        435                 440                 445
```

```
Ala Tyr Thr Asp Glu Thr Phe Lys Thr Arg Glu Ala Ile Gln His Glu
            450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                    485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
            515                 520                 525
Lys Tyr Lys Trp Thr Val Thr Val Glu Asp Gly Pro Thr Lys Ser Asp
530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                    565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
            595                 600                 605
Asn Ile Gln Arg Phe Leu Pro Asn Pro Ala Gly Val Gln Leu Glu Asp
            610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                    645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                    725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
            755                 760                 765
Ser Thr Arg Gln Lys Gln Phe Asn Ala Thr Thr Ile Pro Glu Asn Asp
770                 775                 780
Ile Glu Lys Thr Asp Pro Trp Phe Ala His Arg Thr Pro Met Pro Lys
785                 790                 795                 800
Ile Gln Asn Val Ser Ser Ser Asp Leu Leu Met Leu Leu Arg Gln Ser
                    805                 810                 815
Pro Thr Pro His Gly Leu Ser Leu Ser Asp Leu Gln Glu Ala Lys Tyr
            820                 825                 830
Glu Thr Phe Ser Asp Asp Pro Ser Pro Gly Ala Ile Asp Ser Asn Asn
            835                 840                 845
Ser Leu Ser Glu Met Thr His Phe Arg Pro Gln Leu His His Ser Gly
850                 855                 860
Asp Met Val Phe Thr Pro Glu Ser Gly Leu Gln Leu Arg Leu Asn Glu
```

```
865                 870                 875                 880
Lys Leu Gly Thr Thr Ala Ala Thr Glu Leu Lys Lys Leu Asp Phe Lys
                885                 890                 895
Val Ser Ser Thr Ser Asn Asn Leu Ile Ser Thr Ile Pro Ser Asp Asn
                900                 905                 910
Leu Ala Ala Gly Thr Asp Asn Thr Ser Ser Leu Gly Pro Ser Met
                915                 920                 925
Pro Val His Tyr Asp Ser Gln Leu Asp Thr Thr Leu Phe Gly Lys Lys
    930                 935                 940
Ser Ser Pro Leu Thr Glu Ser Gly Gly Pro Leu Ser Leu Ser Glu Glu
945                 950                 955                 960
Asn Asn Asp Ser Lys Leu Leu Glu Ser Gly Leu Met Asn Ser Gln Glu
                965                 970                 975
Ser Ser Trp Gly Lys Asn Val Ser Thr Glu Ser Gly Arg Leu Phe
                980                 985                 990
Lys Gly Lys Arg Ala His Gly Pro Ala Leu Leu Thr Lys Asp Asn Ala
                995                 1000                1005
Leu Phe Lys Val Ser Ile Ser Leu Leu Lys Thr Asn Lys Thr Ser
    1010                1015                1020
Asn Asn Ser Ala Thr Asn Arg Lys Thr His Ile Asp Gly Pro Ser
    1025                1030                1035
Leu Leu Ile Glu Asn Ser Pro Ser Val Trp Gln Asn Ile Leu Glu
    1040                1045                1050
Ser Asp Thr Glu Phe Lys Lys Val Thr Pro Leu Ile His Asp Arg
    1055                1060                1065
Met Leu Met Asp Lys Asn Ala Thr Ala Leu Arg Leu Asn His Met
    1070                1075                1080
Ser Asn Lys Thr Thr Ser Ser Lys Asn Met Glu Met Val Gln Gln
    1085                1090                1095
Lys Lys Glu Gly Pro Ile Pro Pro Asp Ala Gln Asn Pro Asp Met
    1100                1105                1110
Ser Phe Phe Lys Met Leu Phe Leu Pro Glu Ser Ala Arg Trp Ile
    1115                1120                1125
Gln Arg Thr His Gly Lys Asn Ser Leu Asn Ser Gly Gln Gly Pro
    1130                1135                1140
Ser Pro Lys Gln Leu Val Ser Leu Gly Pro Glu Lys Ser Val Glu
    1145                1150                1155
Gly Gln Asn Phe Leu Ser Glu Lys Asn Lys Val Val Val Gly Lys
    1160                1165                1170
Gly Glu Phe Thr Lys Asp Val Gly Leu Lys Glu Met Val Phe Pro
    1175                1180                1185
Ser Ser Arg Asn Leu Phe Leu Thr Asn Leu Asp Asn Leu His Glu
    1190                1195                1200
Asn Asn Thr His Asn Gln Glu Lys Lys Ile Gln Glu Glu Ile Glu
    1205                1210                1215
Lys Lys Glu Thr Leu Ile Gln Glu Asn Val Val Leu Pro Gln Ile
    1220                1225                1230
His Thr Val Thr Gly Thr Lys Asn Phe Met Lys Asn Leu Phe Leu
    1235                1240                1245
Leu Ser Thr Arg Gln Asn Val Glu Gly Ser Tyr Asp Gly Ala Tyr
    1250                1255                1260
Ala Pro Val Leu Gln Asp Phe Arg Ser Leu Asn Asp Ser Thr Asn
    1265                1270                1275
```

-continued

```
Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305

Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
    1325                1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Pro Gln Ala Asn Arg Ser Pro Leu Pro Ile Ala Lys Val Ser
    1400                1405                1410

Ser Phe Pro Ser Ile Arg Pro Ile Tyr Leu Thr Arg Val Leu Phe
    1415                1420                1425

Gln Asp Asn Ser Ser His Leu Pro Ala Ala Ser Tyr Arg Lys Lys
    1430                1435                1440

Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665
```

-continued

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Arg Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Cys Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980

Val Arg Lys Lys Glu Glu Tyr Lys Met Ala Leu Tyr Asn Leu Tyr
1985                1990                1995

Pro Gly Val Phe Glu Thr Val Glu Met Leu Pro Ser Lys Ala Gly
2000                2005                2010

Ile Trp Arg Val Glu Cys Leu Ile Gly Glu His Leu His Ala Gly
2015                2020                2025

Met Ser Thr Leu Phe Leu Val Tyr Ser Asn Lys Cys Gln Thr Pro
2030                2035                2040

Leu Gly Met Ala Ser Gly His Ile Arg Asp Phe Gln Ile Thr Ala
2045                2050                2055

Ser Gly Gln Tyr Gly Gln Trp Ala Pro Lys Leu Ala Arg Leu His

```
              2060                2065                2070

Tyr Ser Gly Ser Ile Asn Ala Trp Ser Thr Lys Glu Pro Phe Ser
        2075                2080                2085

Trp Ile Lys Val Asp Leu Leu Ala Pro Met Ile Ile His Gly Ile
        2090                2095                2100

Lys Thr Gln Gly Ala Arg Gln Lys Phe Ser Ser Leu Tyr Ile Ser
        2105                2110                2115

Gln Phe Ile Ile Met Tyr Ser Leu Asp Gly Lys Lys Trp Gln Thr
        2120                2125                2130

Tyr Arg Gly Asn Ser Thr Gly Thr Leu Met Val Phe Phe Gly Asn
        2135                2140                2145

Val Asp Ser Ser Gly Ile Lys His Asn Ile Phe Asn Pro Pro Ile
        2150                2155                2160

Ile Ala Arg Tyr Ile Arg Leu His Pro Thr His Tyr Ser Ile Arg
        2165                2170                2175

Ser Thr Leu Arg Met Glu Leu Met Gly Cys Asp Leu Asn Ser Cys
        2180                2185                2190

Ser Met Pro Leu Gly Met Glu Ser Lys Ala Ile Ser Asp Ala Gln
        2195                2200                2205

Ile Thr Ala Ser Ser Tyr Phe Thr Asn Met Phe Ala Thr Trp Ser
        2210                2215                2220

Pro Ser Lys Ala Arg Leu His Leu Gln Gly Arg Ser Asn Ala Trp
        2225                2230                2235

Arg Pro Gln Val Asn Asn Pro Lys Glu Trp Leu Gln Val Asp Phe
        2240                2245                2250

Gln Lys Thr Met Lys Val Thr Gly Val Thr Thr Gln Gly Val Lys
        2255                2260                2265

Ser Leu Leu Thr Ser Met Tyr Val Lys Glu Phe Leu Ile Ser Ser
        2270                2275                2280

Ser Gln Asp Gly His Gln Trp Thr Leu Phe Phe Gln Asn Gly Lys
        2285                2290                2295

Val Lys Val Phe Gln Gly Asn Gln Asp Ser Phe Thr Pro Val Val
        2300                2305                2310

Asn Ser Leu Asp Pro Pro Leu Leu Thr Arg Tyr Leu Arg Ile His
        2315                2320                2325

Pro Gln Ser Trp Val His Gln Ile Ala Leu Arg Met Glu Val Leu
        2330                2335                2340

Gly Cys Glu Ala Gln Asp Leu Tyr
        2345                2350

<210> SEQ ID NO 73
<211> LENGTH: 461
<212> TYPE: PRT
<213> ORGANISM: Artificial Sequence
<220> FEATURE:
<223> OTHER INFORMATION: Synthetic construct: FIX amino acid sequence

<400> SEQUENCE: 73

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
```

```
            50                  55                  60
Met Glu Glu Lys Cys Ser Phe Glu Ala Arg Glu Val Phe Glu Asn
 65                  70                  75                  80

Thr Glu Arg Thr Thr Glu Phe Trp Lys Gln Tyr Val Asp Gly Asp Gln
                     85                  90                  95

Cys Glu Ser Asn Pro Cys Leu Asn Gly Ser Cys Lys Asp Asp Ile
                100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
                195                 200                 205

Thr Ile Leu Asp Asn Ile Thr Gln Ser Thr Gln Ser Phe Asn Asp Phe
                    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
                260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Ile Pro His His Asn
        290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
                420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
450                 455                 460
```

<210> SEQ ID NO 74

<211> LENGTH: 1384
<212> TYPE: DNA
<213> ORGANISM: Artificial Sequence
<220> FEATURE:
<223> OTHER INFORMATION: Synthetic construct: FIX DNA sequence

<400> SEQUENCE: 74

```
atgcagcgcg tgaacatgat catggcagaa tcaccaggcc tcatcaccat ctgccttta      60
ggatatctac tcagtgctga atgtacagtt tttcttgatc atgaaaacgc acaaaattct    120
gaatcggcca agaggtata attcaggtaa attggaagag tttgttcaag ggaatctaga     180
gagagaatgt atggaagaaa agtgtagttt gaagaagca cgagaagttt ttgaaaacac     240
tgaaagaaca actgaatttt ggaagcagta tgttgatgga gatcagtgtg agtccaatcc   300
atgtttaaat ggcggcagtt gcaaggatga cattaattcc tatgaatgtt ggtgtccctt    360
tggatttgaa ggaaagaact gtgaattaga tgtaacatgt aacattaaga atggcagatg    420
cgagcagttt tgtaaaaata tgctgataa caaggtggtt tgctcctgta ctgagggata    480
tcgacttgca gaaaaccaga agtcctgtga accagcagtc ccatttccat gtggaagagt    540
ttctgtttca caaacttcta agctcacccg tgctgagact gttttttcctg atgtggacta   600
tgtaaattct actgaagctg aaaccatttt ggataacatc actcaaagca cccaatcatt    660
taatgacttc actcggggttg ttggtggaga agatgccaaa ccaggtcaat tcccttggca    720
ggttgttttg aatggtaaag ttgatgcatt ctgtggaggc tctatcgtta tgaaaaatg     780
gattgtaact gctgcccact gtgttgaaac tggtgttaaa attacagttg tcgcaggtga    840
acataatatt gaggagacag aacatacaga gcaaaagcga atgtgattc gaattattcc    900
tcaccacaac tacaatgcag ctattaataa gtacaaccat gacattgccc ttctggaact    960
ggacgaaccc ttagtgctaa acagctacgt tacacctatt tgcattgctg acaaggaata   1020
cacgaacatc ttcctcaaat ttggatctgg ctatgtaagt ggctggggaa gagtcttcca   1080
caaagggaga tcagctttag ttcttcagta ccttagagtt ccacttgttg accgagccac   1140
atgtcttcga tctacaaagt tcaccatcta taacaacatg ttctgtgctg cttccatga    1200
aggaggtaga gattcatgtc aaggagatag tggggaccc catgttactg aagtggaagg    1260
gaccagttt ttaactggaa ttattagctg gggtgaagag tgtgcaatga aaggcaaata    1320
tggaatatat accaaggta cccggtatgt caactggatt aaggaaaaaa caaagctcac    1380
ttga                                                                1384
```

<210> SEQ ID NO 75
<211> LENGTH: 488
<212> TYPE: PRT
<213> ORGANISM: Artificial Sequence
<220> FEATURE:
<223> OTHER INFORMATION: Synthetic construct: FX amino acid sequence

<400> SEQUENCE: 75

```
Met Gly Arg Pro Leu His Leu Val Leu Leu Ser Ala Ser Leu Ala Gly
  1               5                  10                  15

Leu Leu Leu Leu Gly Glu Ser Leu Phe Ile Arg Arg Glu Gln Ala Asn
             20                  25                  30

Asn Ile Leu Ala Arg Val Thr Arg Ala Asn Ser Phe Leu Glu Glu Met
         35                  40                  45

Lys Lys Gly His Leu Glu Arg Glu Cys Met Glu Glu Thr Cys Ser Tyr
     50                  55                  60

Glu Glu Ala Arg Glu Val Phe Glu Asp Ser Asp Lys Thr Asn Glu Phe
```

```
            65                  70                  75                  80
Trp Asn Lys Tyr Lys Asp Gly Asp Gln Cys Glu Thr Ser Pro Cys Gln
                    85                  90                  95

Asn Gln Gly Lys Cys Lys Asp Gly Leu Gly Glu Tyr Thr Cys Thr Cys
                100                 105                 110

Leu Glu Gly Phe Glu Gly Lys Asn Cys Glu Leu Phe Thr Arg Lys Leu
                115                 120                 125

Cys Ser Leu Asp Asn Gly Asp Cys Asp Gln Phe Cys His Glu Glu Gln
            130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
                180                 185                 190

Glu Ala Pro Asp Ser Ile Thr Trp Lys Pro Tyr Asp Ala Ala Asp Leu
            195                 200                 205

Asp Pro Thr Glu Asn Pro Phe Asp Leu Leu Asp Phe Asn Gln Thr Gln
        210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
                260                 265                 270

Thr Ala Ala His Cys Leu Tyr Gln Ala Lys Arg Phe Lys Val Arg Val
            275                 280                 285

Gly Asp Arg Asn Thr Glu Gln Glu Glu Gly Gly Glu Ala Val His Glu
        290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
                340                 345                 350

Leu Met Thr Gln Lys Thr Gly Ile Val Ser Gly Phe Gly Arg Thr His
            355                 360                 365

Glu Lys Gly Arg Gln Ser Thr Arg Leu Lys Met Leu Glu Val Pro Tyr
        370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
        450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485
```

```
<210> SEQ ID NO 76
<211> LENGTH: 1467
<212> TYPE: DNA
<213> ORGANISM: Artificial Sequence
<220> FEATURE:
<223> OTHER INFORMATION: Synthetic construct: FX DNA sequence

<400> SEQUENCE: 76
atggggcgcc cactgcacct cgtcctgctc agtgcctccc tggctggcct cctgctgctc      60
ggggaaagtc tgttcatccg cagggagcag gccaacaaca tcctggcgag ggtcacgagg     120
gccaattcct ttcttgaaga gatgaagaaa ggacacctcg aaagagagtg catggaagag     180
acctgctcat acgaagaggc ccgcgaggtc tttgaggaca gcgacaagac gaatgaattc     240
tggaataaat acaaagatgg cgaccagtgt gagaccagtc cttgccagaa ccagggcaaa     300
tgtaaagacg gcctcgggga atacacctgc acctgtttag aaggattcga aggcaaaaac     360
tgtgaattat tcacacggaa gctctgcagc ctggacaacg gggactgtga ccagttctgc     420
cacgaggaac agaactctgt ggtgtgctcc tgcgcccgcg gtacaccct ggctgacaac     480 ggcaaggcct gcattccac agggccctac ccctgtggga acagaccct ggaacgcagg     540 aagaggtcag tggcccaggc caccagcagc agcggggagg cccctgacag catcacatgg     600
aagccatatg atgcagccga cctggacccc accgagaacc ccttcgacct gcttgacttc     660
aaccagacgc agcctgagag gggcgacaac aacctcacca ggatcgtggg aggccaggaa     720
tgcaaggacg gggagtgtcc ctggcaggcc ctgctcatca atgaggaaaa cgagggtttc     780
tgtggtggaa ccattctgag cgagttctac atcctaacgg cagcccactg tctctaccaa     840
gccaagagat tcaaggtgag ggtaggggac cggaacacgg agcaggagga gggcggtgag     900
gcggtgcacg aggtggaggt ggtcatcaag cacaaccggt tcacaaagga gacctatgac     960
ttcgacatcg ccgtgctccg gctcaagacc cccatcacct tccgcatgaa cgtggcgcct    1020
gcctgcctcc ccgagcgtga ctgggccgag tccacgctga tgacgcagaa gacggggatt    1080
gtgagcggct tcgggcgcac ccacgagaag ggccggcagt ccaccaggct caagatgctg    1140
gaggtgccct acgtggaccg caacagctgc aagctgtcca gcagcttcat catcacccag    1200
aacatgttct gtgccggcta cgacaccaag caggaggatg cctgccaggg ggacagcggg    1260
ggcccgcacg tcacccgctt caaggacacc tacttcgtga caggcatcgt cagctgggga    1320
gagggctgtg cccgtaaggg gaagtacggg atctacacca aggtcaccgc cttcctcaag    1380
tggatcgaca ggtccatgaa aaccaggggc ttgcccaagg ccaagagcca tgccccggag    1440
gtcataacgt cctctccatt aaagtga                                          1467

<210> SEQ ID NO 77
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 77
cgttgggatc ggagtccatg c                                                 21

<210> SEQ ID NO 78
<211> LENGTH: 21
<212> TYPE: DNA
<213> ORGANISM: Artificial Sequence
<220> FEATURE:
```

<223> OTHER INFORMATION: Synthetic polynucleotide

<400> SEQUENCE: 78
gcatggactc cgatcccaac g                                        21

<210> SEQ ID NO 79
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 79
gcgaattccg gtccgtcatt gcctagggct cgagagtttt ttaggagtgt ttggatcag    59

<210> SEQ ID NO 80
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 80
ggaggatgta gatctttgtg atcaatagc                                29

<210> SEQ ID NO 81
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 81
gctattgatc acaaagatct acatcctcc                                29

<210> SEQ ID NO 82
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 82
ggtgaattct cactcaggca ggtgtgaggg cagc                          34

<210> SEQ ID NO 83
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 83
gccaggccac atgactactc cgc                                      23

<210> SEQ ID NO 84
<211> LENGTH: 3140
<212> TYPE: DNA
<213> ORGANISM: Artificial Sequence
<220> FEATURE:
<223> OTHER INFORMATION: Synthetic construct: DNA sequence for
      pSYN-FIX-053

<400> SEQUENCE: 84
atgcagcgcg tgaacatgat catggcagaa tcaccaggcc tcatcaccat ctgccttta   60

```
ggatatctac tcagtgctga atgtacaggt ttgtttcctt ttttaaaata cattgagtat    120
gcttgccttt tagatataga aatatctgat gctgtcttct tcactaaatt ttgattacat    180
gatttgacag caatattgaa gagtctaaca gccagcacgc aggttggtaa gtactgtggg    240
aacatcacag attttggctc catgccctaa agagaaattg gctttcagat tatttggatt    300
aaaaacaaag actttcttaa gagatgtaaa attttcatga tgttttcttt tttgctaaaa    360
ctaaagaatt attcttttac atttcagttt ttcttgatca tgaaaacgcc aacaaaattc    420
tgaatcggcc aaagaggtat aattcaggta aattggaaga gtttgttcaa gggaatctag    480
agagagaatg tatggaagaa aagtgtagtt ttgaagaagc acgagaagtt tttgaaaaca    540
ctgaaagaac aactgaattt tggaagcagt atgttgatgg agatcagtgt gagtccaatc    600 catgttttaaa tggcggcagt tgcaaggatg acattaattc ctatgaatgt tggtgtccct    660
ttggatttga aggaaagaac tgtgaattag atgtaacatg taacattaag aatggcagat    720
gcgagcagtt ttgtaaaaat agtgctgata caaggtggt ttgctcctgt actgagggat    780
atcgacttgc agaaaaccag aagtcctgtg aaccagcagt gccatttcca tgtggaagag    840
tttctgtttc acaaacttct aagctcaccc gtgctgagac tgttttttcct gatgtggact    900 atgtaaattc tactgaagct gaaaccattt tggataacat cactcaaagc acccaatcat    960
ttaatgactt cactcgggtt gttggtggag aagatgccaa accaggtcaa ttcccttggc   1020
aggttgtttt gaatggtaaa gttgatgcat tctgtggagg ctctatcgtt aatgaaaaat   1080
ggattgtaac tgctgcccac tgtgttgaaa ctggtgttaa aattacagtt gtcgcaggtg   1140
aacataatat tgaggagaca gaacatacag agcaaaagcg aaatgtgatt cgaattattc   1200
ctcaccacaa ctacaatgca gctattaata agtacaacca tgacattgcc cttctggaac   1260
tggacgaacc cttagtgcta aacagctacg ttacacctat ttgcattgct gacaaggaat   1320
acacgaacat cttcctcaaa tttggatctg gctatgtaag tggctgggga agagtcttcc   1380
acaaagggag atcagcttta gttcttcagt accttagagt tccacttgtt gaccgagcca   1440
catgtcttcg atctacaaag ttcaccatct ataacaacat gttctgtgct ggcttccatg   1500
aaggaggtag agattcatgt caaggagata gtgggggacc ccatgttact gaagtggaag   1560
ggaccagttt cttaactgga attattagct ggggtgaaga gtgtgcaatg aaaggcaaat   1620
atggaatata taccaaggtg tcccggtatg tcaactggat taaggaaaaa acaaagctca   1680
ctgacaaaac tcacacatgc ccaccgtgcc cagctccgga actcctggga ggaccgtcag   1740
tcttcctctt ccccccaaaa cccaaggaca ccctcatgat ctcccggacc cctgaggtca   1800
catgcgtggt ggtggacgtg agccacgaag accctgaggt caagttcaac tggtacgtgg   1860
acggcgtgga ggtgcataat gccaagacaa agccgcggga ggagcagtac aacagcacgt   1920
accgtgtggt cagcgtcctc accgtcctgc accaggactg gctgaatggc aaggagtaca   1980
agtgcaaggt ctccaacaaa gccctcccag cccccatcga gaaaaccatc tccaaagcca   2040
aagggcagcc ccgagaacca caggtgtaca ccctgccccc atcccgggat gagctgacca   2100
agaaccaggt cagcctgacc tgcctggtca aaggcttcta tcccagcgac atcgccgtgg   2160
agtgggagag caatgggcag ccggagaaca actacaagac cacgcctccc gtgttggact   2220
ccgacggctc cttcttcctc tacagcaagc tcaccgtcga caagagcagg tggcagcagg   2280
ggaacgtctt ctcatgctcc gtgatgcatg aggctctgca caaccactac acgcagaaga   2340
gcctctccct gtctccgggt aaacggcgcc gccgagcgg tggcggcgga tcaggtgggg   2400
gtggatcagg cggtggaggt tccggtggcg ggggatccag gaagaggagg aagagggaca   2460
```

-continued

```
aaactcacac atgcccaccg tgcccagcac cggaactcct gggcggaccg tcagtcttcc    2520 tcttccccc aaaacccaag dacaccctca tgatctcccg daccctgag gtcacatgcg     2580 tggtggtgga cgtgagccac gaagaccctg aggtcaagtt caactggtac gtggacggcg    2640
tggaggtgca taatgccaag acaaagccgc gggaggagca gtacaacagc acgtaccgtg    2700
tggtcagcgt cctcaccgtc ctgcaccagg actggctgaa tggcaaggag tacaagtgca    2760
aggtctccaa caaagccctc ccagccccca tcgagaaaac catctccaaa gccaagggc     2820 agccccgaga accacaggtg tacaccctgc cccatcccg ggatgagctg accaagaacc     2880
aggtcagcct gacctgcctg gtcaaaggct tctatcccag cgacatcgcc gtggagtggg    2940
agagcaatgg gcagccggag aacaactaca agaccacgcc tcccgtgttg gactccgacg    3000
gctccttctt cctctacagc aagctcaccg tggacaagag caggtggcag caggggaacg    3060
tcttctcatg ctccgtgatg catgaggctc tgcacaacca ctacacgcag aagagcctct    3120
ccctgtctcc gggtaaatga                                                3140
```

<210> SEQ ID NO 85
<211> LENGTH: 946
<212> TYPE: PRT
<213> ORGANISM: Artificial Sequence
<220> FEATURE:
<223> OTHER INFORMATION: Synthetic construct: FIX-053 amino acid sequence

<400> SEQUENCE: 85

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
```

-continued

```
               225                 230                 235                 240
        Gln Val Val Leu Asn Gly Lys Val Asp Ala Phe Cys Gly Gly Ser Ile
                        245                 250                 255
        Val Asn Glu Lys Trp Ile Val Thr Ala Ala His Cys Val Glu Thr Gly
                        260                 265                 270
        Val Lys Ile Thr Val Val Ala Gly Glu His Asn Ile Glu Glu Thr Glu
                        275                 280                 285
        His Thr Glu Gln Lys Arg Asn Val Ile Arg Ile Pro His His Asn
                        290                 295                 300
        Tyr Asn Ala Ala Ile Asn Lys Tyr Asn His Asp Ile Ala Leu Leu Glu
        305                 310                 315                 320
        Leu Asp Glu Pro Leu Val Leu Asn Ser Tyr Val Thr Pro Ile Cys Ile
                        325                 330                 335
        Ala Asp Lys Glu Tyr Thr Asn Ile Phe Leu Lys Phe Gly Ser Gly Tyr
                        340                 345                 350
        Val Ser Gly Trp Gly Arg Val Phe His Lys Gly Arg Ser Ala Leu Val
                        355                 360                 365
        Leu Gln Tyr Leu Arg Val Pro Leu Val Asp Arg Ala Thr Cys Leu Arg
                        370                 375                 380
        Ser Thr Lys Phe Thr Ile Tyr Asn Asn Met Phe Cys Ala Gly Phe His
        385                 390                 395                 400
        Glu Gly Gly Arg Asp Ser Cys Gln Gly Asp Ser Gly Gly Pro His Val
                        405                 410                 415
        Thr Glu Val Glu Gly Thr Ser Phe Leu Thr Gly Ile Ile Ser Trp Gly
                        420                 425                 430
        Glu Glu Cys Ala Met Lys Gly Lys Tyr Gly Ile Tyr Thr Lys Val Ser
                        435                 440                 445
        Arg Tyr Val Asn Trp Ile Lys Glu Lys Thr Lys Leu Thr Asp Lys Thr
                        450                 455                 460
        His Thr Cys Pro Pro Cys Pro Ala Pro Glu Leu Leu Gly Gly Pro Ser
        465                 470                 475                 480
        Val Phe Leu Phe Pro Pro Lys Pro Lys Asp Thr Leu Met Ile Ser Arg
                        485                 490                 495
        Thr Pro Glu Val Thr Cys Val Val Val Asp Val Ser His Glu Asp Pro
                        500                 505                 510
        Glu Val Lys Phe Asn Trp Tyr Val Asp Gly Val Glu Val His Asn Ala
                        515                 520                 525
        Lys Thr Lys Pro Arg Glu Glu Gln Tyr Asn Ser Thr Tyr Arg Val Val
                        530                 535                 540
        Ser Val Leu Thr Val Leu His Gln Asp Trp Leu Asn Gly Lys Glu Tyr
        545                 550                 555                 560
        Lys Cys Lys Val Ser Asn Lys Ala Leu Pro Ala Pro Ile Glu Lys Thr
                        565                 570                 575
        Ile Ser Lys Ala Lys Gly Gln Pro Arg Glu Pro Gln Val Tyr Thr Leu
                        580                 585                 590
        Pro Pro Ser Arg Asp Glu Leu Thr Lys Asn Gln Val Ser Leu Thr Cys
                        595                 600                 605
        Leu Val Lys Gly Phe Tyr Pro Ser Asp Ile Ala Val Glu Trp Glu Ser
                        610                 615                 620
        Asn Gly Gln Pro Glu Asn Asn Tyr Lys Thr Thr Pro Pro Val Leu Asp
        625                 630                 635                 640
        Ser Asp Gly Ser Phe Phe Leu Tyr Ser Lys Leu Thr Val Asp Lys Ser
                        645                 650                 655
```

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

Arg Arg Arg Arg Ser Gly Gly Gly Gly Ser Gly Gly Gly Gly Ser Gly
690                 695                 700

Gly Gly Ser Gly Gly Gly Gly Ser Arg Lys Arg Arg Lys Arg Asp
705                 710                 715                 720

Lys Thr His Thr Cys Pro Pro Cys Pro Ala Pro Glu Leu Leu Gly Gly
                725                 730                 735

Pro Ser Val Phe Leu Phe Pro Pro Lys Pro Lys Asp Thr Leu Met Ile
            740                 745                 750

Ser Arg Thr Pro Glu Val Thr Cys Val Val Val Asp Val Ser His Glu
        755                 760                 765

Asp Pro Glu Val Lys Phe Asn Trp Tyr Val Asp Gly Val Glu Val His
    770                 775                 780

Asn Ala Lys Thr Lys Pro Arg Glu Glu Gln Tyr Asn Ser Thr Tyr Arg
785                 790                 795                 800

Val Val Ser Val Leu Thr Val Leu His Gln Asp Trp Leu Asn Gly Lys
                805                 810                 815

Glu Tyr Lys Cys Lys Val Ser Asn Lys Ala Leu Pro Ala Pro Ile Glu
            820                 825                 830

Lys Thr Ile Ser Lys Ala Lys Gly Gln Pro Arg Glu Pro Gln Val Tyr
        835                 840                 845

Thr Leu Pro Pro Ser Arg Asp Glu Leu Thr Lys Asn Gln Val Ser Leu
    850                 855                 860

Thr Cys Leu Val Lys Gly Phe Tyr Pro Ser Asp Ile Ala Val Glu Trp
865                 870                 875                 880

Glu Ser Asn Gly Gln Pro Glu Asn Asn Tyr Lys Thr Thr Pro Pro Val
                885                 890                 895

Leu Asp Ser Asp Gly Ser Phe Phe Leu Tyr Ser Lys Leu Thr Val Asp
            900                 905                 910

Lys Ser Arg Trp Gln Gln Gly Asn Val Phe Ser Cys Ser Val Met His
        915                 920                 925

Glu Ala Leu His Asn His Tyr Thr Gln Lys Ser Leu Ser Leu Ser Pro
    930                 935                 940

Gly Lys
945

<210> SEQ ID NO 86
<211> LENGTH: 2880
<212> TYPE: DNA
<213> ORGANISM: Artificial Sequence
<220> FEATURE:
<223> OTHER INFORMATION: Synthetic construct: DNA sequence for
      pSYN-FVII-064

<400> SEQUENCE: 86
atggtctccc aggccctcag gctcctctgc cttctgcttg gcttcagggg ctgcctggct        60
gcagtcttcg taacccagga ggaagcccac ggcgtcctgc accggcgccg cgcgccaac       120 gcgttcctgg aggagctgcg gccgggctcc ctggagaggg agtgcaagga ggagcagtgc      180
tccttcgagg aggcccggga gatcttcaag gacgcggaga ggacgaagct gttctggatt      240
tcttacagtg atggggacca gtgtgcctca agtccatgcc agaatggggg ctcctgcaag      300

```
gaccagctcc agtcctatat ctgcttctgc ctccctgcct tcgagggccg gaactgtgag    360
acgcacaagg atgaccagct gatctgtgtg aacgagaacg gcggctgtga gcagtactgc    420
agtgaccaca cgggcaccaa gcgctcctgt cggtgccacg aggggtactc tctgctggca    480
gacgggtgt cctgcacacc cacagttgaa tatccatgtg gaaaatacc tattctagaa       540
aaagaaatg ccagcaaacc caaggccga attgtggggg gcaaggtgtg ccccaagggg       600
gagtgtccat ggcaggtcct gttgttggtg aatggagctc agttgtgtgg ggggaccctg    660
atcaacacca tctgggtggt ctccgcggcc cactgtttcg acaaaatcaa gaactggagg    720
aacctgatcg cggtgctggg cgagcacgac ctcagcgagc acgacgggga tgagcagagc    780
cggcgggtgg cgcaggtcat catccccagc acgtacgtcc cggcaccac caaccacgac     840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg   1020
ccccggctga tgacccagga ctgcctgcag cagtcacgga aggtgggaga ctccccaaat   1080
atcacggagt acatgttctg tgccggctac tcggatggca gcaaggactc ctgcaagggg   1140
gacagtggag gcccacatgc cacccactac cggggcacgt ggtacctgac gggcatcgtc   1200
agctggggcc agggctgcgc aaccgtgggc cactttgggg tgtacaccag gtctcccag    1260
tacatcgagt ggctgcaaaa gctcatgcgc tcagagccac gcccaggagt cctcctgcga   1320
gccccatttc ccggtggcgg tggctccggc ggaggtgggt ccggtggcgg cggatcaggt   1380
gggggtggat caggcggtgg aggttccggt ggcggggat ccgacaaaac tcacacatgc    1440
ccaccgtgcc cagctccgga actcctggga ggaccgtcag tcttcctctt ccccccaaaa   1500
cccaaggaca cctctacat cacccggag cctgaggtca catgcgtggt ggtggacgtg      1560
agccacgaag accctgaggt caagttcaac tggtacgtgg acggcgtgga ggtgcataat   1620
gccaagacaa agccgcggga ggagcagtac aacagcacgt accgtgtggt cagcgtcctc   1680
accgtcctgc accaggactg gctgaatggc aaggagtaca agtgcaaggt ctccaacaaa   1740
gccctcccag cccccatcga gaaaaccatc tccaaagcca aagggcagcc ccgagaacca   1800
caggtgtaca ccctgccccc atcccgggat gagctgacca agaaccaggt cagcctgacc   1860
tgcctggtca aaggcttcta tcccagcgac atcgccgtgg agtgggagag caatgggcag   1920
ccggagaaca actacaagac cacgcctccc gtgttggact ccgacggctc cttcttcctc   1980
tacagcaagc tcaccgtcga caagagcagg tggcagcagg ggaacgtctt ctcatgctcc   2040
gtgatgcatg aggctctgca caaccactac acgcagaaga gcctctccct gtctccgggt   2100
aaacggcgcc gccggagcgg tggcggcgga tcaggtgggg gtggatcagg cggtggaggt   2160
tccggtggcg ggggatccag gaagaggagg aagagggaca aaactcacac atgcccaccg   2220
tgcccagcac cggaactcct gggcggaccg tcagtcttcc tcttcccccc aaaacccaag   2280
gacaccctct acatcacccg ggagcctgag gtcacatgcg tggtggtgga cgtgagccac   2340
gaagaccctg aggtcaagtt caactggtac gtggacggcg tggaggtgca taatgccaag   2400
acaaagccgc gggaggagca gtacaacagc acgtaccgtg tggtcagcgt cctcaccgtc   2460
ctgcaccagg actggctgaa tggcaaggag tacaagtgca aggtctccaa caaagccctc   2520
ccagccccca tcgagaaaac catctccaaa gccaagggc agcccgaga accacaggtg      2580
tacaccctgc cccatcccg ggatgagctg accaagaacc aggtcagcct gacctgcctg     2640
gtcaaaggct tctatcccag cgacatcgcc gtggagtggg agagcaatgg gcagccggag   2700
```

-continued

```
aacaactaca agaccacgcc tcccgtgttg gactccgacg gctccttctt cctctacagc   2760
aagctcaccg tggacaagag caggtggcag caggggaacg tcttctcatg ctccgtgatg   2820
catgaggctc tgcacaacca ctacacgcag aagagcctct ccctgtctcc gggtaaatga   2880
```

<210> SEQ ID NO 87
<211> LENGTH: 959
<212> TYPE: PRT
<213> ORGANISM: Artificial Sequence
<220> FEATURE:
<223> OTHER INFORMATION: Synthetic construct: FVII-064 amino acid sequence

<400> SEQUENCE: 87

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
```

```
                    325                 330                 335
    Val Leu Asn Val Pro Arg Leu Met Thr Gln Asp Cys Leu Gln Gln Ser
                340                 345                 350

Arg Lys Val Gly Asp Ser Pro Asn Ile Thr Glu Tyr Met Phe Cys Ala
                355                 360                 365

Gly Tyr Ser Asp Gly Ser Lys Asp Ser Cys Lys Gly Asp Ser Gly Gly
                370                 375                 380

Pro His Ala Thr His Tyr Arg Gly Thr Trp Tyr Leu Thr Gly Ile Val
    385                 390                 395                 400

Ser Trp Gly Gln Gly Cys Ala Thr Val Gly His Phe Gly Val Tyr Thr
                    405                 410                 415

Arg Val Ser Gln Tyr Ile Glu Trp Leu Gln Lys Leu Met Arg Ser Glu
                420                 425                 430

Pro Arg Pro Gly Val Leu Leu Arg Ala Pro Phe Pro Gly Gly Gly Gly
                435                 440                 445

Ser Gly Gly Gly Ser Gly Gly Gly Ser Gly Gly Gly Gly Ser
    450                 455                 460

Gly Gly Gly Gly Ser Gly Gly Gly Ser Asp Lys Thr His Thr Cys
    465                 470                 475                 480

Pro Pro Cys Pro Ala Pro Glu Leu Leu Gly Gly Pro Ser Val Phe Leu
                    485                 490                 495

Phe Pro Pro Lys Pro Lys Asp Thr Leu Tyr Ile Thr Arg Glu Pro Glu
                500                 505                 510

Val Thr Cys Val Val Val Asp Val Ser His Glu Asp Pro Glu Val Lys
                515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
    545                 550                 555                 560

Thr Val Leu His Gln Asp Trp Leu Asn Gly Lys Glu Tyr Lys Cys Lys
                    565                 570                 575

Val Ser Asn Lys Ala Leu Pro Ala Pro Ile Glu Lys Thr Ile Ser Lys
                580                 585                 590

Ala Lys Gly Gln Pro Arg Glu Pro Gln Val Tyr Thr Leu Pro Pro Ser
                595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
    625                 630                 635                 640

Pro Glu Asn Asn Tyr Lys Thr Thr Pro Pro Val Leu Asp Ser Asp Gly
                    645                 650                 655

Ser Phe Phe Leu Tyr Ser Lys Leu Thr Val Asp Lys Ser Arg Trp Gln
                660                 665                 670

Gln Gly Asn Val Phe Ser Cys Ser Val Met His Glu Ala Leu His Asn
                675                 680                 685

His Tyr Thr Gln Lys Ser Leu Ser Leu Ser Pro Gly Lys Arg Arg Arg
    690                 695                 700

Arg Ser Gly Gly Gly Gly Ser Gly Gly Gly Gly Ser Gly Gly Gly Gly
    705                 710                 715                 720

Ser Gly Gly Gly Gly Ser Arg Lys Arg Arg Lys Arg Asp Lys Thr His
                    725                 730                 735

Thr Cys Pro Pro Cys Pro Ala Pro Glu Leu Leu Gly Gly Pro Ser Val
                740                 745                 750
```

```
Phe Leu Phe Pro Pro Lys Pro Lys Asp Thr Leu Tyr Ile Thr Arg Glu
        755                 760                 765
Pro Glu Val Thr Cys Val Val Val Asp Val Ser His Glu Asp Pro Glu
770                 775                 780
Val Lys Phe Asn Trp Tyr Val Asp Gly Val Glu Val His Asn Ala Lys
785                 790                 795                 800
Thr Lys Pro Arg Glu Glu Gln Tyr Asn Ser Thr Tyr Arg Val Val Ser
            805                 810                 815
Val Leu Thr Val Leu His Gln Asp Trp Leu Asn Gly Lys Glu Tyr Lys
        820                 825                 830
Cys Lys Val Ser Asn Lys Ala Leu Pro Ala Pro Ile Glu Lys Thr Ile
        835                 840                 845
Ser Lys Ala Lys Gly Gln Pro Arg Glu Pro Gln Val Tyr Thr Leu Pro
850                 855                 860
Pro Ser Arg Asp Glu Leu Thr Lys Asn Gln Val Ser Leu Thr Cys Leu
865                 870                 875                 880
Val Lys Gly Phe Tyr Pro Ser Asp Ile Ala Val Glu Trp Glu Ser Asn
            885                 890                 895
Gly Gln Pro Glu Asn Asn Tyr Lys Thr Thr Pro Pro Val Leu Asp Ser
        900                 905                 910
Asp Gly Ser Phe Phe Leu Tyr Ser Lys Leu Thr Val Asp Lys Ser Arg
        915                 920                 925
Trp Gln Gln Gly Asn Val Phe Ser Cys Ser Val Met His Glu Ala Leu
930                 935                 940
His Asn His Tyr Thr Gln Lys Ser Leu Ser Leu Ser Pro Gly Lys
945                 950                 955

<210> SEQ ID NO 88
<211> LENGTH: 5859
<212> TYPE: DNA
<213> ORGANISM: Artificial Sequence
<220> FEATURE:
<223> OTHER INFORMATION: Synthetic construct: DNA sequence for
      pSYN-FVIII-049

<400> SEQUENCE: 88
```

| | | | | | |
|---|---|---|---|---|---|
| atgcaaatag | agctctccac | ctgcttcttt | ctgtgccttt | tgcgattctg | ctttagtgcc | 60 |
| accagaagat | actacctggg | tgcagtggaa | ctgtcatggg | actatatgca | aagtgatctc | 120 |
| ggtgagctgc | ctgtggacgc | aagatttcct | cctagagtgc | caaaatcttt | tccattcaac | 180 |
| acctcagtcg | tgtacaaaaa | gactctgttt | gtagaattca | cggatcacct | tttcaacatc | 240 |
| gctaagccaa | ggccaccctg | gatgggtctg | ctaggtccta | ccatccaggc | tgaggtttat | 300 |
| gatacagtgt | cattacact | taagaacatg | gcttcccatc | ctgtcagtct | tcatgctgtt | 360 |
| ggtgtatcct | actggaaagc | ttctgaggga | gctgaatatg | atgatcagac | cagtcaaagg | 420 |
| gagaaagaag | atgataaagt | cttccctggt | ggaagccata | catatgtctg | gcaggtcctg | 480 |
| aaagagaatg | gtccaatggc | ctctgaccca | ctgtgcctta | cctactcata | tctttctcat | 540 |
| gtggacctgg | taaaagactt | gaattcaggc | ctcattggag | ccctactagt | atgtagagaa | 600 |
| gggagtctgg | ccaaggaaaa | gacacagacc | ttgcacaaat | ttatactact | ttttgctgta | 660 |
| tttgatgaag | ggaaaagttg | gcactcagaa | acaaagaact | ccttgatgca | ggatagggat | 720 |
| gctgcatctg | ctcgggcctg | gcctaaaatg | cacacagtca | atggttatgt | aaacaggtct | 780 |
| ctgccaggtc | tgattggatg | ccacaggaaa | tcagtctatt | ggcatgtgat | tggaatgggc | 840 |

```
accactcctg aagtgcactc aatattcctc gaaggtcaca catttcttgt gaggaaccat   900
cgccaggcgt ccttggaaat ctcgccaata actttcctta ctgctcaaac actcttgatg   960
gaccttggac agtttctact gttttgtcat atctcttccc accaacatga tggcatggaa  1020
gcttatgtca aagtagacag ctgtccagag gaaccccaac tacgaatgaa aaataatgaa  1080
gaagcggaag actatgatga tgatcttact gattctgaaa tggatgtggt caggtttgat  1140
gatgacaact ctccttcctt tatccaaatt cgctcagttg ccaagaagca tcctaaaact  1200
tgggtacatt acattgctgc tgaagaggag gactgggact atgctcccct agtcctcgcc  1260
cccgatgaca gaagttataa aagtcaatat ttgaacaatg gccctcagcg gattggtagg  1320
aagtacaaaa aagtccgatt tatggcatac acagatgaaa cctttaagac tcgtgaagct  1380
attcagcatg aatcaggaat cttgggacct ttactttatg gggaagttgg agacacactg  1440
ttgattatat ttaagaatca agcaagcaga ccatataaca tctaccctca cggaatcact  1500
gatgtccgtc ctttgtattc aaggagatta ccaaaaggtg taaaacattt gaaggatttt  1560
ccaattctgc caggagaaat attcaaatat aaatggacag tgactgtaga agatgggcca  1620
actaaatcag atcctcggtg cctgacccgc tattactcta gtttcgttaa tatggagaga  1680
gatctagctt caggactcat tggccctctc ctcatctgct acaaagaatc tgtagatcaa  1740
agaggaaacc agataatgtc agacaagagg aatgtcatcc tgttttctgt atttgatgag  1800
aaccgaagct ggtacctcac agagaatata caacgctttc tccccaatcc agctggagtg  1860
cagcttgagg atccagagtt ccaagcctcc aacatcatgc acagcatcaa tggctatgtt  1920
tttgatagtt tgcagttgtc agtttgtttg catgaggtgg catactggta cattctaagc  1980
attggagcac agactgactt cctttctgtc ttcttctctg gatataccct caaacacaaa  2040
atggtctatg aagacacact caccctattc ccattctcag gagaaactgt cttcatgtcg  2100
atggaaaacc caggtctatg gattctgggg tgccacaact cagactttcg gaacagaggc  2160
atgaccgcct tactgaaggt ttctagttgt gacaagaaca ctggtgatta ttacgaggac  2220
agttatgaag atatttcagc atacttgctg agtaaaaaca atgccattga accaagaagc  2280
ttctctcaaa acccaccagt cttgaaacgc catcaacggg aaataactcg tactactctt  2340
cagtcagatc aagaggaaat tgactatgat gataccatat cagttgaaat gaagaaggaa  2400
gattttgaca tttatgatga ggatgaaaat cagagccccc gcagctttca aaagaaaaca  2460
cgacactatt ttattgctgc agtggagagg ctctgggatt atgggatgag tagctcccca  2520
catgttctaa gaaacagggc tcagagtggc agtgtccctc agttcaagaa agttgttttc  2580
caggaatttta ctgatggctc ctttactcag cccttatacc gtggagaact aaatgaacat  2640
ttgggactcc tggggccata tataagagca gaagttgaag ataatatcat ggtaactttc  2700
agaaatcagg cctctcgtcc ctattccttc tattctagcc ttatttctta tgaggaagat  2760
cagaggcaag gagcagaacc tagaaaaaac tttgtcaagc ctaatgaaac caaaacttac  2820
ttttggaaag tgcaacatca tatggcaccc actaaagatg agtttgactg caaagcctgg  2880
gcttatttct ctgatgttga cctggaaaaa gatgtgcact caggcctgat tggacccctt  2940
ctggtctgcc acactaacac actgaaccct gctcatggga caagtgac agtacaggaa   3000
tttgctctgt ttttcaccat ctttgatgag accaaaagct ggtacttcac tgaaaatatg  3060
gaaagaaact gcagggctcc ctgcaatatc cagatggaag atcccacttt taaagagaat  3120
tatcgcttcc atgcaatcaa tggctacata atggatacac tacctggctt agtaatggct  3180
caggatcaaa ggattcgatg gtatctgctc agcatgggca gcaatgaaaa catccattct  3240
```

```
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac actttttctg    3420
gtgtacagca ataagtgtca gactcccctg ggaatggctt ctggacacat tagagatttt    3480
cagattacag cttcaggaca atatggacag tgggccccaa agctggccag acttcattat    3540
tccggatcaa tcaatgcctg gagcaccaag gagccctttt cttggatcaa ggtggatctg    3600
ttggcaccaa tgattattca cggcatcaag acccaggtgt cccgtcagaa gttctccagc    3660
ctctacatct ctcagtttat catcatgtat agtcttgatg gaagaagtg gcagacttat    3720
cgaggaaatt ccactggaac cttaatggtc ttctttggca atgtggattc atctgggata    3780
aaacacaata ttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga aagtcacagg agtaactact cagggagtaa aatctctgct taccagcatg    4140
tatgtgaagg agttcctcat ctccagcagt caagatggcc atcagtggac tctctttttt    4200
cagaatggca agtaaaggt ttttcaggga aatcaagact ccttcacacc tgtggtgaac    4260
tctctagacc caccgttact gactcgctac cttcgaattc accccagag ttgggtgcac    4320
cagattgccc tgaggatgga ggttctgggc tgcgaggcac aggacctcta cgacaaaact    4380
cacacatgcc caccgtgccc agcacctgaa ctcctgggag gaccgtcagt cttcctcttc    4440
cccccaaaac ccaaggacac cctcatgatc tcccggaccc ctgaggtcac atgcgtggtg    4500
gtggacgtga gccacgaaga ccctgaggtc aagttcaact ggtacgtgga cggcgtggag    4560
gtgcataatg ccaagacaaa gccgcgggag gagcagtaca acagcacgta ccgtgtggtc    4620
agcgtcctca ccgtcctgca ccaggactgg ctgaatggca aggagtacaa gtgcaaggtc    4680
tccaacaaag ccctcccagc ccccatcgag aaaaccatct ccaaagccaa agggcagccc    4740
cgagaaccac aggtgtacac cctgccccca tcccgcgatg agctgaccaa gaaccaggtc    4800
agcctgacct gcctggtcaa aggcttctat cccagcgaca tcgccgtgga gtgggagagc    4860
aatgggcagc cggagaacaa ctacaagacc acgcctcccg tgttggactc cgacggctcc    4920
ttcttcctct acagcaagct caccgtcgac aagagcaggt ggcagcaggg gaacgtcttc    4980
tcatgctccg tgatgcatga ggctctgcac aaccactaca cgcagaagag cctctccctg    5040
tctccgggta aacggcgccg ccggagcggt ggcggcggat caggtggggg tggatcaggc    5100
ggtggaggtt ccggtggcgg gggatccggc ggtggaggtt ccggtggggg tggatcaagg    5160
aagaggagga agaggacaa aactcacaca tgcccaccgt gcccagctcc agaactcctg    5220
ggcggaccgt cagtcttcct cttcccccca aaacccaagg acaccctcat gatctcccgg    5280
accctgaggt cacatgcgt ggtggtggac gtgagccacg aagaccctga ggtcaagttc    5340
aactggtacg tggacggcgt ggaggtgcat aatgccaaga caaagccgcg ggaggagcag    5400
tacaacagca cgtaccgtgt ggtcagcgtc ctcaccgtcc tgcaccagga ctggctgaat    5460
ggcaaggagt acaagtgcaa ggtctccaac aaagccctcc cagcccccat cgagaaaacc    5520
atctccaaag ccaaagggca gccccgagaa ccacaggtgt acaccctgcc cccatcccgg    5580
```

```
gatgagctga ccaagaacca ggtcagcctg acctgcctgg tcaaaggctt ctatcccagc    5640
gacatcgccg tggagtggga gagcaatggg cagccggaga caactacaa gaccacgcct     5700 cccgtgttgg actccgacgg ctccttcttc ctctacagca agctcaccgt ggacaagagc    5760
aggtggcagc aggggaacgt cttctcatgc tccgtgatgc atgaggctct gcacaaccac    5820
tacacgcaga agagcctctc cctgtctccg ggtaaatga                           5859
```

<210> SEQ ID NO 89
<211> LENGTH: 1952
<212> TYPE: PRT
<213> ORGANISM: Artificial Sequence
<220> FEATURE:
<223> OTHER INFORMATION: Synthetic construct: FVIII-049 amino acid sequence

<400> SEQUENCE: 89

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
```

```
                305                 310                 315                 320
           Asp Leu Gly Gln Phe Leu Leu Phe Cys His Ile Ser Ser His Gln His
                       325                 330                 335

Asp Gly Met Glu Ala Tyr Val Lys Val Asp Ser Cys Pro Glu Glu Pro
                       340                 345                 350

Gln Leu Arg Met Lys Asn Asn Glu Ala Glu Asp Tyr Asp Asp Asp
                       355                 360                 365

Leu Thr Asp Ser Glu Met Asp Val Val Arg Phe Asp Asp Asn Ser
                       370                 375                 380

Pro Ser Phe Ile Gln Ile Arg Ser Val Ala Lys Lys His Pro Lys Thr
           385                 390                 395                 400

Trp Val His Tyr Ile Ala Ala Glu Glu Asp Trp Asp Tyr Ala Pro
                       405                 410                 415

Leu Val Leu Ala Pro Asp Arg Ser Tyr Lys Ser Gln Tyr Leu Asn
                       420                 425                 430

Asn Gly Pro Gln Arg Ile Gly Arg Lys Tyr Lys Lys Val Arg Phe Met
                       435                 440                 445

Ala Tyr Thr Asp Glu Thr Phe Lys Thr Arg Glu Ala Ile Gln His Glu
                       450                 455                 460

Ser Gly Ile Leu Gly Pro Leu Leu Tyr Gly Glu Val Gly Asp Thr Leu
           465                 470                 475                 480

Leu Ile Ile Phe Lys Asn Gln Ala Ser Arg Pro Tyr Asn Ile Tyr Pro
                       485                 490                 495

His Gly Ile Thr Asp Val Arg Pro Leu Tyr Ser Arg Arg Leu Pro Lys
                       500                 505                 510

Gly Val Lys His Leu Lys Asp Phe Pro Ile Leu Pro Gly Glu Ile Phe
                       515                 520                 525

Lys Tyr Lys Trp Thr Val Thr Val Glu Asp Gly Pro Thr Lys Ser Asp
                       530                 535                 540

Pro Arg Cys Leu Thr Arg Tyr Tyr Ser Ser Phe Val Asn Met Glu Arg
           545                 550                 555                 560

Asp Leu Ala Ser Gly Leu Ile Gly Pro Leu Leu Ile Cys Tyr Lys Glu
                       565                 570                 575

Ser Val Asp Gln Arg Gly Asn Gln Ile Met Ser Asp Lys Arg Asn Val
                       580                 585                 590

Ile Leu Phe Ser Val Phe Asp Glu Asn Arg Ser Trp Tyr Leu Thr Glu
                       595                 600                 605

Asn Ile Gln Arg Phe Leu Pro Asn Pro Ala Gly Val Gln Leu Glu Asp
                       610                 615                 620

Pro Glu Phe Gln Ala Ser Asn Ile Met His Ser Ile Asn Gly Tyr Val
           625                 630                 635                 640

Phe Asp Ser Leu Gln Leu Ser Val Cys Leu His Glu Val Ala Tyr Trp
                       645                 650                 655

Tyr Ile Leu Ser Ile Gly Ala Gln Thr Asp Phe Leu Ser Val Phe Phe
                       660                 665                 670

Ser Gly Tyr Thr Phe Lys His Lys Met Val Tyr Glu Asp Thr Leu Thr
                       675                 680                 685

Leu Phe Pro Phe Ser Gly Glu Thr Val Phe Met Ser Met Glu Asn Pro
                       690                 695                 700

Gly Leu Trp Ile Leu Gly Cys His Asn Ser Asp Phe Arg Asn Arg Gly
           705                 710                 715                 720

Met Thr Ala Leu Leu Lys Val Ser Ser Cys Asp Lys Asn Thr Gly Asp
                       725                 730                 735
```

```
Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Val Leu
            755                 760                 765

Lys Arg His Gln Arg Glu Ile Thr Arg Thr Thr Leu Gln Ser Asp Gln
            770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
            835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
            1010                1015                1020

Cys Arg Ala Pro Cys Asn Ile Gln Met Glu Asp Pro Thr Phe Lys
            1025                1030                1035

Glu Asn Tyr Arg Phe His Ala Ile Asn Gly Tyr Ile Met Asp Thr
            1040                1045                1050

Leu Pro Gly Leu Val Met Ala Gln Asp Gln Arg Ile Arg Trp Tyr
            1055                1060                1065

Leu Leu Ser Met Gly Ser Asn Glu Asn Ile His Ser Ile His Phe
            1070                1075                1080

Ser Gly His Val Phe Thr Val Arg Lys Lys Glu Glu Tyr Lys Met
            1085                1090                1095

Ala Leu Tyr Asn Leu Tyr Pro Gly Val Phe Glu Thr Val Glu Met
            1100                1105                1110

Leu Pro Ser Lys Ala Gly Ile Trp Arg Val Glu Cys Leu Ile Gly
            1115                1120                1125

Glu His Leu His Ala Gly Met Ser Thr Leu Phe Leu Val Tyr Ser
            1130                1135                1140
```

```
Asn Lys Cys Gln Thr Pro Leu Gly Met Ala Ser Gly His Ile Arg
1145                1150                1155

Asp Phe Gln Ile Thr Ala Ser Gly Gln Tyr Gly Gln Trp Ala Pro
1160                1165                1170

Lys Leu Ala Arg Leu His Tyr Ser Gly Ser Ile Asn Ala Trp Ser
1175                1180                1185

Thr Lys Glu Pro Phe Ser Trp Ile Lys Val Asp Leu Leu Ala Pro
1190                1195                1200

Met Ile Ile His Gly Ile Lys Thr Gln Gly Ala Arg Gln Lys Phe
1205                1210                1215

Ser Ser Leu Tyr Ile Ser Gln Phe Ile Ile Met Tyr Ser Leu Asp
1220                1225                1230

Gly Lys Lys Trp Gln Thr Tyr Arg Gly Asn Ser Thr Gly Thr Leu
1235                1240                1245

Met Val Phe Phe Gly Asn Val Asp Ser Ser Gly Ile Lys His Asn
1250                1255                1260

Ile Phe Asn Pro Pro Ile Ile Ala Arg Tyr Ile Arg Leu His Pro
1265                1270                1275

Thr His Tyr Ser Ile Arg Ser Thr Leu Arg Met Glu Leu Met Gly
1280                1285                1290

Cys Asp Leu Asn Ser Cys Ser Met Pro Leu Gly Met Glu Ser Lys
1295                1300                1305

Ala Ile Ser Asp Ala Gln Ile Thr Ala Ser Ser Tyr Phe Thr Asn
1310                1315                1320

Met Phe Ala Thr Trp Ser Pro Ser Lys Ala Arg Leu His Leu Gln
1325                1330                1335

Gly Arg Ser Asn Ala Trp Arg Pro Gln Val Asn Asn Pro Lys Glu
1340                1345                1350

Trp Leu Gln Val Asp Phe Gln Lys Thr Met Lys Val Thr Gly Val
1355                1360                1365

Thr Thr Gln Gly Val Lys Ser Leu Leu Thr Ser Met Tyr Val Lys
1370                1375                1380

Glu Phe Leu Ile Ser Ser Ser Gln Asp Gly His Gln Trp Thr Leu
1385                1390                1395

Phe Phe Gln Asn Gly Lys Val Lys Val Phe Gln Gly Asn Gln Asp
1400                1405                1410

Ser Phe Thr Pro Val Val Asn Ser Leu Asp Pro Pro Leu Leu Thr
1415                1420                1425

Arg Tyr Leu Arg Ile His Pro Gln Ser Trp Val His Gln Ile Ala
1430                1435                1440

Leu Arg Met Glu Val Leu Gly Cys Glu Ala Gln Asp Leu Tyr Asp
1445                1450                1455

Lys Thr His Thr Cys Pro Pro Cys Pro Ala Pro Glu Leu Leu Gly
1460                1465                1470

Gly Pro Ser Val Phe Leu Phe Pro Pro Lys Pro Lys Asp Thr Leu
1475                1480                1485

Met Ile Ser Arg Thr Pro Glu Val Thr Cys Val Val Val Asp Val
1490                1495                1500

Ser His Glu Asp Pro Glu Val Lys Phe Asn Trp Tyr Val Asp Gly
1505                1510                1515

Val Glu Val His Asn Ala Lys Thr Lys Pro Arg Glu Glu Gln Tyr
1520                1525                1530

Asn Ser Thr Tyr Arg Val Val Ser Val Leu Thr Val Leu His Gln
```

```
                1535                1540                1545

Asp Trp Leu Asn Gly Lys Glu Tyr Lys Cys Lys Val Ser Asn Lys
            1550                1555                1560

Ala Leu Pro Ala Pro Ile Glu Lys Thr Ile Ser Lys Ala Lys Gly
            1565                1570                1575

Gln Pro Arg Glu Pro Gln Val Tyr Thr Leu Pro Pro Ser Arg Asp
            1580                1585                1590

Glu Leu Thr Lys Asn Gln Val Ser Leu Thr Cys Leu Val Lys Gly
            1595                1600                1605

Phe Tyr Pro Ser Asp Ile Ala Val Glu Trp Glu Ser Asn Gly Gln
            1610                1615                1620

Pro Glu Asn Asn Tyr Lys Thr Thr Pro Pro Val Leu Asp Ser Asp
            1625                1630                1635

Gly Ser Phe Phe Leu Tyr Ser Lys Leu Thr Val Asp Lys Ser Arg
            1640                1645                1650

Trp Gln Gln Gly Asn Val Phe Ser Cys Ser Val Met His Glu Ala
            1655                1660                1665

Leu His Asn His Tyr Thr Gln Lys Ser Leu Ser Leu Ser Pro Gly
            1670                1675                1680

Lys Arg Arg Arg Ser Gly Gly Gly Ser Gly Gly Gly
            1685                1690                1695

Ser Gly Gly Gly Ser Gly Gly Gly Ser Gly Gly Gly
            1700                1705                1710

Ser Gly Gly Gly Ser Arg Lys Arg Lys Arg Asp Lys Thr
            1715                1720                1725

His Thr Cys Pro Pro Cys Pro Ala Pro Glu Leu Leu Gly Gly Pro
            1730                1735                1740

Ser Val Phe Leu Phe Pro Pro Lys Pro Lys Asp Thr Leu Met Ile
            1745                1750                1755

Ser Arg Thr Pro Glu Val Thr Cys Val Val Val Asp Val Ser His
            1760                1765                1770

Glu Asp Pro Glu Val Lys Phe Asn Trp Tyr Val Asp Gly Val Glu
            1775                1780                1785

Val His Asn Ala Lys Thr Lys Pro Arg Glu Glu Gln Tyr Asn Ser
            1790                1795                1800

Thr Tyr Arg Val Val Ser Val Leu Thr Val Leu His Gln Asp Trp
            1805                1810                1815

Leu Asn Gly Lys Glu Tyr Lys Cys Lys Val Ser Asn Lys Ala Leu
            1820                1825                1830

Pro Ala Pro Ile Glu Lys Thr Ile Ser Lys Ala Lys Gly Gln Pro
            1835                1840                1845

Arg Glu Pro Gln Val Tyr Thr Leu Pro Pro Ser Arg Asp Glu Leu
            1850                1855                1860

Thr Lys Asn Gln Val Ser Leu Thr Cys Leu Val Lys Gly Phe Tyr
            1865                1870                1875

Pro Ser Asp Ile Ala Val Glu Trp Glu Ser Asn Gly Gln Pro Glu
            1880                1885                1890

Asn Asn Tyr Lys Thr Thr Pro Pro Val Leu Asp Ser Asp Gly Ser
            1895                1900                1905

Phe Phe Leu Tyr Ser Lys Leu Thr Val Asp Lys Ser Arg Trp Gln
            1910                1915                1920

Gln Gly Asn Val Phe Ser Cys Ser Val Met His Glu Ala Leu His
            1925                1930                1935
```

Asn His Tyr Thr Gln Lys Ser Leu Ser Leu Ser Pro Gly Lys
    1940                1945            1950

<210> SEQ ID NO 90
<211> LENGTH: 2064
<212> TYPE: DNA
<213> ORGANISM: Artificial Sequence
<220> FEATURE:
<223> OTHER INFORMATION: Synthetic construct: DNA sequence for IFN-b-018

<400> SEQUENCE: 90

| | | | | | |
|---|---|---|---|---|---|
| atgaccaaca | agtgtctcct | ccaaattgct | ctcctgttgt | gcttctccac | tacagctctt | 60 |
| tccatgagct | acaacttgct | tggattccta | caaagaagca | gcaattttca | gtgtcagaag | 120 |
| ctcctgtggc | aattgaatgg | gaggcttgaa | tattgcctca | aggacaggat | gaactttgac | 180 |
| atccctgagg | agattaagca | gctgcagcag | ttccagaagg | aggacgccgc | attgaccatc | 240 |
| tatgagatgc | tccagaacat | ctttgctatt | ttcagacaag | attcatctag | cactggctgg | 300 |
| aatgagacta | ttgttgagaa | cctcctggct | aatgtctatc | atcagataaa | ccatctgaag | 360 |
| acagtcctgg | aagaaaaact | ggagaaagaa | gatttcacca | ggggaaaact | catgagcagt | 420 |
| ctgcacctga | aagatattta | tgggaggatt | ctgcattacc | tgaaggccaa | ggagtacagt | 480 |
| cactgtgcct | ggaccatagt | cagagtggaa | atcctaagga | acttttactt | cattaacaga | 540 |
| cttacaggtt | acctccgaaa | cggtggcggc | ggctccggtg | aggcgggtc | cggcggtgga | 600 |
| gggagcgaca | aaactcacac | atgcccaccg | tgcccagctc | cggaactcct | gggaggaccg | 660 |
| tcagtcttcc | tcttcccccc | aaaacccaag | gacaccctca | tgatctcccg | gaccctgag | 720 |
| gtcacatgcg | tggtggtgga | cgtgagccac | gaagaccctg | aggtcaagtt | caactggtac | 780 |
| gtggacggcg | tggaggtgca | taatgccaag | acaaagccgc | gggaggagca | gtacaacagc | 840 |
| acgtaccgtg | tggtcagcgt | cctcaccgtc | ctgcaccagg | actggctgaa | tggcaaggag | 900 |
| tacaagtgca | aggtctccaa | caaagccctc | ccagccccca | tcgagaaaac | catctccaaa | 960 |
| gccaaagggc | agccccgaga | accacaggtg | tacaccctgc | ccccatcccg | ggatgagctg | 1020 |
| accaagaacc | aggtcagcct | gacctgcctg | gtcaaaggct | tctatcccag | cgacatcgcc | 1080 |
| gtggagtggg | agagcaatgg | gcagccggag | aacaactaca | agaccacgcc | tcccgtgttg | 1140 |
| gactccgacg | gctccttctt | cctctacagc | aagctcaccg | tggacaagag | caggtggcag | 1200 |
| caggggaacg | tcttctcatg | ctccgtgatg | catgaggctc | tgcacaacca | ctacacgcag | 1260 |
| aagagcctct | ccctgtctcc | gggtaaacgg | cgccgccgga | gcggtggcgg | cggatcaggt | 1320 |
| ggggtggat | caggcggtgg | aggttccggt | ggcggggat | ccaggaagag | gaggaagagg | 1380 |
| gacaaaactc | acacatgccc | accgtgccca | gcaccggaac | tcctgggcgg | accgtcagtc | 1440 |
| ttcctcttcc | ccccaaaacc | caaggacacc | ctcatgatct | cccggacccc | tgaggtcaca | 1500 |
| tgcgtggtgg | tggacgtgag | ccacgaagac | cctgaggtca | agttcaactg | gtacgtggac | 1560 |
| ggcgtggagg | tgcataatgc | caagacaaag | ccgcgggagg | agcagtacaa | cagcacgtac | 1620 |
| cgtgtggtca | gcgtcctcac | cgtcctgcac | caggactggc | tgaatggcaa | ggagtacaag | 1680 |
| tgcaaggtct | ccaacaaagc | cctcccagcc | ccatcgaga | aaaccatctc | caaagccaaa | 1740 |
| gggcagcccc | gagaaccaca | ggtgtacacc | ctgcccccat | cccgggatga | gctgaccaag | 1800 |
| aaccaggtca | gcctgacctg | cctggtcaaa | ggcttctatc | ccagcgacat | cgccgtggag | 1860 |
| tgggagagca | atgggcagcc | ggagaacaac | tacaagacca | cgcctcccgt | gttggactcc | 1920 |
| gacggctcct | tcttcctcta | cagcaagctc | accgtggaca | agagcaggtg | gcagcagggg | 1980 |

```
aacgtcttct catgctccgt gatgcatgag gctctgcaca accactacac gcagaagagc    2040 ctctcccctgt ctccgggtaa atga                                          2064
```

<210> SEQ ID NO 91
<211> LENGTH: 687
<212> TYPE: PRT
<213> ORGANISM: Artificial Sequence
<220> FEATURE:
<223> OTHER INFORMATION: Synthetic construct: IFN-b-018 amino acid
      sequence

<400> SEQUENCE: 91

```
Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Gly Gly Gly Gly Ser
            180                 185                 190

Gly Gly Gly Gly Ser Gly Gly Gly Ser Asp Lys Thr His Thr Cys
        195                 200                 205

Pro Pro Cys Pro Ala Pro Glu Leu Leu Gly Gly Pro Ser Val Phe Leu
    210                 215                 220

Phe Pro Pro Lys Pro Lys Asp Thr Leu Met Ile Ser Arg Thr Pro Glu
225                 230                 235                 240

Val Thr Cys Val Val Val Asp Val Ser His Glu Asp Pro Glu Val Lys
                245                 250                 255

Phe Asn Trp Tyr Val Asp Gly Val Glu Val His Asn Ala Lys Thr Lys
            260                 265                 270

Pro Arg Glu Glu Gln Tyr Asn Ser Thr Tyr Arg Val Val Ser Val Leu
        275                 280                 285

Thr Val Leu His Gln Asp Trp Leu Asn Gly Lys Glu Tyr Lys Cys Lys
    290                 295                 300

Val Ser Asn Lys Ala Leu Pro Ala Pro Ile Glu Lys Thr Ile Ser Lys
305                 310                 315                 320

Ala Lys Gly Gln Pro Arg Glu Pro Gln Val Tyr Thr Leu Pro Pro Ser
                325                 330                 335
```

```
Arg Asp Glu Leu Thr Lys Asn Gln Val Ser Leu Thr Cys Leu Val Lys
                340                 345                 350
Gly Phe Tyr Pro Ser Asp Ile Ala Val Glu Trp Glu Ser Asn Gly Gln
            355                 360                 365
Pro Glu Asn Asn Tyr Lys Thr Thr Pro Pro Val Leu Asp Ser Asp Gly
        370                 375                 380
Ser Phe Phe Leu Tyr Ser Lys Leu Thr Val Asp Lys Ser Arg Trp Gln
385                 390                 395                 400
Gln Gly Asn Val Phe Ser Cys Ser Val Met His Glu Ala Leu His Asn
                405                 410                 415
His Tyr Thr Gln Lys Ser Leu Ser Leu Ser Pro Gly Lys Arg Arg Arg
            420                 425                 430
Arg Ser Gly Gly Gly Ser Gly Gly Gly Ser Gly Gly Gly
        435                 440                 445
Ser Gly Gly Gly Ser Arg Lys Arg Lys Arg Asp Lys Thr His
    450                 455                 460
Thr Cys Pro Pro Cys Pro Ala Pro Glu Leu Leu Gly Gly Pro Ser Val
465                 470                 475                 480
Phe Leu Phe Pro Pro Lys Pro Lys Asp Thr Leu Met Ile Ser Arg Thr
                485                 490                 495
Pro Glu Val Thr Cys Val Val Val Asp Val Ser His Glu Asp Pro Glu
            500                 505                 510
Val Lys Phe Asn Trp Tyr Val Asp Gly Val Glu Val His Asn Ala Lys
        515                 520                 525
Thr Lys Pro Arg Glu Glu Gln Tyr Asn Ser Thr Tyr Arg Val Val Ser
530                 535                 540
Val Leu Thr Val Leu His Gln Asp Trp Leu Asn Gly Lys Glu Tyr Lys
545                 550                 555                 560
Cys Lys Val Ser Asn Lys Ala Leu Pro Ala Pro Ile Glu Lys Thr Ile
                565                 570                 575
Ser Lys Ala Lys Gly Gln Pro Arg Glu Pro Gln Val Tyr Thr Leu Pro
            580                 585                 590
Pro Ser Arg Asp Glu Leu Thr Lys Asn Gln Val Ser Leu Thr Cys Leu
        595                 600                 605
Val Lys Gly Phe Tyr Pro Ser Asp Ile Ala Val Glu Trp Glu Ser Asn
610                 615                 620
Gly Gln Pro Glu Asn Asn Tyr Lys Thr Thr Pro Pro Val Leu Asp Ser
625                 630                 635                 640
Asp Gly Ser Phe Phe Leu Tyr Ser Lys Leu Thr Val Asp Lys Ser Arg
                645                 650                 655
Trp Gln Gln Gly Asn Val Phe Ser Cys Ser Val Met His Glu Ala Leu
            660                 665                 670
His Asn His Tyr Thr Gln Lys Ser Leu Ser Leu Ser Pro Gly Lys
        675                 680                 685

<210> SEQ ID NO 92
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 92
gttttcaatc tctaggaccc actcgcc                                            27
```

```
<210> SEQ ID NO 93
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 93
ggtaagcttg ccatggagct gaggccctgg ttgc                                 34

<210> SEQ ID NO 94
<211> LENGTH: 5
<212> TYPE: PRT
<213> ORGANISM: Artificial Sequence
<220> FEATURE:
<223> OTHER INFORMATION: Synthetic peptide

<400> SEQUENCE: 94

Ala Leu Arg Pro Arg
1               5

<210> SEQ ID NO 95
<211> LENGTH: 2739
<212> TYPE: DNA
<213> ORGANISM: Artificial Sequence
<220> FEATURE:
<223> OTHER INFORMATION: Synthetic Construct

<400> SEQUENCE: 95
atgggctggg ggagccgctg ctgctgcccg ggacgtttgg acctgctgtg cgtgctggcg      60
ctgctcgggg gctgcctgct ccccgtgtgt cggacgcgcg tctacaccaa ccactgggca     120
gtcaaaatcg ccgggggctt cccggaggcc aaccgtatcg ccagcaagta cggattcatc     180
aacataggac agatagggggc cctgaaggac tactaccact tctaccatag caggacgatt     240
aaaaggtcag ttatctcgag cagagggacc cacagtttca tttcaatgga accaaaggtg     300
gaatggatcc aacagcaagt ggtaaaaaag cggacaaaga gggattatga cttcagtcgt     360
gcccagtcta cctatttcaa tgatcccaag tggcccagta tgtggtatat gcactgcagt     420
gacaatacac atccctgcca gtctgacatg aatatcgaag gagcctggaa gagaggctac     480
acgggaaaga acattgtggt cactatcctg gatgacggaa ttgagagaac ccatccagat     540
ctgatgcaaa actacgatgc tctggcaagt gcgacgtga atgggaatga cttggaccca     600
atgcctcgtt atgatgcaag caacgagaac aagcatggga ctcgctgtgc tggagaagtg     660
gcagccgctg caaacaattc gcactgcaca gtcggaattg cttttaacgc caagatcgga     720
ggagtgcgaa tgctggacgg agatgtcacg gacatggttg aagcaaaatc agttagcttc     780 aaccccagc acgtgcacat ttacagcgcc agctgggggc cggatgatga tggcaagact     840
gtggacggac cagccccct cacccggcaa gcctttgaaa acggcgttag aatggggcgg     900
agaggcctcg gctctgtgtt tgtttgggca tctggaaatg gtggaaggag caaagaccac     960
tgctcctgtg atggctacac caacagcatc tacaccatct ccatcagcag cactgcagaa    1020
agcggaaaga accttggta cctggaagag tgttcatcca cgctggccac aacctacagc    1080 agcgggggagt cctacgataa gaaaatcatc actacagatc tgaggcagcg ttgcacggac    1140
aaccacactg ggacgtcagc ctcagccccc atggctgcag catcattgc gctggccctg    1200 gaagccaatc cgtttctgac ctggagagac gtacagcatg ttattgtcag gacttcccgt    1260
gcgggacatt tgaacgctaa tgactggaaa accaatgctg ctggttttaa ggtgagccat    1320
ctttatggat ttggactgat ggacgcagaa gccatggtga tggaggcaga gaagtggacc    1380
```

```
accgttcccc ggcagcacgt gtgtgtggag agcacagacc gacaaatcaa gacaatccgc   1440
cctaacagtg cagtgcgctc catctacaaa gcctcaggct gctcagataa ccccaaccgc   1500
catgtcaact acctggagca cgtcgttgtg cgcatcacca tcacccaccc caggagagga   1560
gacctggcca tctacctgac ctcgccctct ggaactaggt ctcagctttt ggccaacagg   1620
ctatttgatc actccatgga aggattcaaa aactgggagt tcatgaccat tcattgctgg   1680
ggagaaagag ctgctggtga ctgggtcctt gaagtttatg atactccctc tcagctaagg   1740
aactttaaga ctccaggtaa attgaaagaa tggtctttgg tcctctacgg cacctccgtg   1800
cagccatatt caccaaccaa tgaatttccg aaagtggaac ggttccgcta tagccgagtt   1860
gaagacccca cagacgacta tggcacagag gattatgcag gtccctgcga ccctgagtgc   1920
agtgaggttg gctgtgacgg gccaggacca gaccactgca atgactgttt gcactactac   1980
tacaagctga aaacaatac caggatctgt gtctccagct gcccccctgg ccactaccac   2040
gccgacaaga gcgctgcag gaagtgtgcc cccaactgtg agtcctgctt tgggagccat   2100
ggtgaccaat gcatgtcctg caaatatgga tactttctga atgaagaaac caacagctgt   2160
gttactcact gccctgatgg gtcatatcag gataccaaga aaaatctttg ccggaaatgc   2220
agtgaaaact gcaagacatg tactgaattc cataactgta cagaatgtag ggatgggtta   2280
agcctgcagg gatcccggtg ctctgtctcc tgtgaagatg gacggtattt caacggccag   2340
gactgccagc cctgccaccg cttctgcgcc acttgtgctg gggcaggagc tgatgggtgc   2400
attaactgca cagagggcta cttcatggag gatgggagat gcgtgcagag ctgtagtatc   2460
agctattact ttgaccactc ttcagagaat ggatacaaat cctgcaaaaa atgtgatatc   2520
agttgtttga cgtgcaatgg cccaggattc aagaactgta caagctgccc tagtgggtat   2580
ctcttagact taggaatgtg tcaaatggga gccatttgca aggatgcaac ggaagagtcc   2640
tgggcggaag gaggcttctg tatgcttgtg aaaaagaaca atctgtgcca acggaaggtt   2700
cttcaacaac tttgctgcaa aacatgtaca tttcaaggc                         2739
```

<210> SEQ ID NO 96
<211> LENGTH: 8
<212> TYPE: PRT
<213> ORGANISM: Artificial Sequence
<220> FEATURE:
<223> OTHER INFORMATION: Synthetic peptide

<400> SEQUENCE: 96

Val Ile Ser Ser His Leu Gly Gln
1               5

<210> SEQ ID NO 97
<211> LENGTH: 21
<212> TYPE: PRT
<213> ORGANISM: Artificial Sequence
<220> FEATURE:
<223> OTHER INFORMATION: Synthetic peptide

<400> SEQUENCE: 97

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 98
<211> LENGTH: 12

```
<212> TYPE: PRT
<213> ORGANISM: Artificial Sequence
<220> FEATURE:
<223> OTHER INFORMATION: Synthetic peptide

<400> SEQUENCE: 98

Leu Gln Gln Ser Arg Lys Val Gly Asp Ser Pro Asn
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Synthetic peptide

<400> SEQUENCE: 99

Glu Ala Ser Tyr Pro Gly Lys
1               5

<210> SEQ ID NO 100
<211> LENGTH: 4
<212> TYPE: PRT
<213> ORGANISM: Artificial Sequence
<220> FEATURE:
<223> OTHER INFORMATION: Synthetic peptide

<400> SEQUENCE: 100

Arg Ala Gly Arg
1

<210> SEQ ID NO 101
<211> LENGTH: 4
<212> TYPE: PRT
<213> ORGANISM: Artificial Sequence
<220> FEATURE:
<223> OTHER INFORMATION: Synthetic peptide

<400> SEQUENCE: 101

Arg Ser Lys Arg
1

<210> SEQ ID NO 102
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 102
atctacacca tctccatcag cagc                                              24

<210> SEQ ID NO 103
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 103
aaggcggccg ctcagccttg aaatgtacat gttttgc                                37

<210> SEQ ID NO 104
<211> LENGTH: 18
<212> TYPE: DNA
<213> ORGANISM: Artificial Sequence
<220> FEATURE:
```

```
<223> OTHER INFORMATION: Synthetic polynucleotide

<400> SEQUENCE: 104
agcgagggag cagcgagg                                                 18

<210> SEQ ID NO 105
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 105
ggtagttgac atggcggttg g                                             21

<210> SEQ ID NO 106
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 106
cagcgactta agccaccatg ggctggggga gccg                               34

<210> SEQ ID NO 107
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 107
gtaggttgtg gccagcgtgg                                               20
```